(12) United States Patent
Christensen et al.

(10) Patent No.: US 11,761,014 B2
(45) Date of Patent: Sep. 19, 2023

(54) NUCLEOTIDE SEQUENCES AND POLYPEPTIDES ENCODED THEREBY USEFUL FOR MODIFYING PLANT CHARACTERISTICS IN RESPONSE TO COLD

(71) Applicant: Ceres, Inc., Thousands Oaks, CA (US)

(72) Inventors: Cory Christensen, Simi Valley, CA (US); Jack Okamuro, Oak Park, CA (US); Shing Kwok, Woodland Hills, CA (US); Roger Pennell, Malibu, CA (US)

(73) Assignee: Ceres, Inc., Thousand Oaks, CA (US)

( * ) Notice: Subject to any disclaimer, the term of this patent is extended or adjusted under 35 U.S.C. 154(b) by 89 days.

(21) Appl. No.: 17/314,977

(22) Filed: May 7, 2021

(65) Prior Publication Data

US 2021/0388371 A1    Dec. 16, 2021

Related U.S. Application Data

(60) Division of application No. 16/719,390, filed on Dec. 18, 2019, now Pat. No. 11,034,973, which is a division of application No. 16/275,659, filed on Feb. 14, 2019, now Pat. No. 10,696,979, which is a division of application No. 15/362,633, filed on Nov. 28, 2016, now Pat. No. 10,240,166, which is a division of application No. 11/779,266, filed on Jul. 17, 2007, now abandoned, which is a continuation-in-part of application No. 11/778,060, filed on Jul. 15, 2007, now abandoned, which is a continuation-in-part of application No. 11/248,547, filed on Oct. 12, 2005, now Pat. No. 7,244,879.

(51) Int. Cl.
| | |
|---|---|
| *C12N 15/82* | (2006.01) |
| *C07K 14/415* | (2006.01) |
| *A01H 1/02* | (2006.01) |
| *C12Q 1/6895* | (2018.01) |

(52) U.S. Cl.
CPC ........... *C12N 15/8273* (2013.01); *A01H 1/02* (2013.01); *C07K 14/415* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | | |
|---|---|---|---|---|
| 5,990,387 | A * | 11/1999 | Tomes | C12N 15/8207 800/278 |
| 7,244,879 | B2 | 7/2007 | Christensen et al. | |
| 10,240,166 | B2 | 3/2019 | Christensen et al. | |
| 10,508,284 | B2 | 12/2019 | Christensen et al. | |
| 10,696,979 | B2 | 6/2020 | Christensen et al. | |
| 11,021,714 | B2 | 6/2021 | Christensen et al. | |
| 11,034,973 | B2 | 6/2021 | Christensen et al. | |
| 11,459,580 | B2 | 10/2022 | Christensen et al. | |
| 2004/0031072 | A1 | 2/2004 | La Rosa et al. | |
| 2006/0107345 | A1 | 5/2006 | Alexandrov et al. | |
| 2006/0150283 | A1 | 7/2006 | Alexandrov et al. | |
| 2009/0094717 | A1 | 4/2009 | Troukhan et al. | |
| 2009/0241208 | A1 | 9/2009 | Christensen et al. | |
| 2009/0265275 | A1 | 10/2009 | Alexandrov et al. | |
| 2009/0265815 | A1 | 10/2009 | Alexandrov et al. | |
| 2010/0083407 | A1 | 4/2010 | Feldmann et al. | |
| 2013/0042367 | A1 | 2/2013 | Nadzan et al. | |
| 2015/0259699 | A1 | 9/2015 | Nadzan et al. | |
| 2016/0369294 | A9 * | 12/2016 | Nadzan | C12N 15/8201 |
| 2018/0223303 | A1 | 8/2018 | Alexandrov et al. | |
| 2019/0241902 | A1 | 8/2019 | Christensen et al. | |
| 2019/0276836 | A1 | 9/2019 | Christensen et al. | |
| 2020/0109412 | A1 | 4/2020 | Christensen et al. | |
| 2020/0255853 | A1 | 8/2020 | Ceres et al. | |
| 2021/0324400 | A1 | 10/2021 | Christensen et al. | |

FOREIGN PATENT DOCUMENTS

| | | | | |
|---|---|---|---|---|
| EP | 1033405 A2 * | 9/2000 | | C07H 21/04 |
| ER | 1033405 | 9/2000 | | |
| WO | WO 9902687 | 1/1999 | | |
| WO | WO 2004035798 | 4/2004 | | |

OTHER PUBLICATIONS

Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495, 1994).*
Thornton et al. (Nature structural Biology, structural genomics supplement, Nov. 2000).*
Keskin et al. (Protein Science, 13:1043-1055, 2004).*
Seki et al. (NCBI, GenBank Sequence Accession No. AK118678.1, pp. 1-2, Published Dec. 6, 2002).*
Didierjean et al. (Planta, 199:1-8, 1996).*
U.S. Appl. No. 17/314,977, filed May 7, 2021, Christensen et al.
Didierjean et al., Heavy-metal-responsive genes in maize: identification and comparison of their expression upon various forms of abiotic stress, Planta 199:1-8, 1996.
GenBank Accession No. AK118678.1, dated Feb. 14, 2004.
Kim et al., "Molecular cloning of low temperature-inducible ribosomal proteins from soybean," *Journal of Experimental Botany* 55:1153-1155, 2004.
Lu et al., "*Arabidopsis* Mutants Deficient in Diacylglycerol Acyltransferase Display Increased Sensitivity to Abscisic Acid, Sugards, and Osmotic Stress during Germination and Seedling Development," *Plant Physiology* 129:1352-1358, 2002.

(Continued)

*Primary Examiner* — Vinod Kumar
(74) *Attorney, Agent, or Firm* — DENTONS US LLP

(57) ABSTRACT

Methods and materials for modulating cold tolerance levels in plants are disclosed. For example, nucleic acids encoding cold tolerance-modulating polypeptides are disclosed as well as methods for using such nucleic acids to transform plant cells. Also disclosed are plants having increased levels of cold tolerance and plant products produced from plants having increased cold tolerance levels.

9 Claims, 8 Drawing Sheets

Specification includes a Sequence Listing.

(56) References Cited

OTHER PUBLICATIONS

Ngo et al., "Computational Complexity, Protein Structure Prediction, and the Levinthal Pradox," *The Protein Folding Problem and Tertiary Structure Prediction*, K. Merz and S. Le Grand (eds.), pp. 492-495, 1994.

Guo et al., "Protein tolerance to random amino acid change," *PNAS* 101:9205-9210, 2004.

GenBank Accession No. AY117196, dated Sep. 18, 2002.

Keskin et al., "A new, structurally nonredundant, diverse data set of protein-protein interfaces and its implications," *Protein Science* 13:1043-1055, 2004.

Thornton et al., "From structure to function: Approaches and limitations," *Nature Structural Biology, Structural Gemonics Supplement*, Nov. 2000.

Wells, "Additivity of Mutational Effects in Proteins," *Biochemistry* 29:8509-8517, 1990.

Seki, et al., (NCBI, GenBank Accession No. AK118678.1, pp. 1-2, Published Dec. 6, 2002).

USPTO: Notice of Allowance and Fee(s) Due regarding U.S. Appl. No. 16/275,629, dated Aug. 2, 2019.

USPTO: Office Action regarding U.S. Appl. No. 16/275,659, dated Dec. 19, 2019.

Response to Office Action regarding U.S. Appl. No. 16/275,659, dated Feb. 4, 2020.

Supplemental Response to Office Action regarding U.S. Appl. No. 16/275,659, dated Feb. 11, 2020.

USPTO: Notice of Allowance regarding U.S. Appl. No. 16/275,659 dated Feb. 28, 2020.

* cited by examiner

FIGURE 2

| SEQ ID | Sequence | Pos |
|---|---|---|
| SEQ-ID-NO-17-CLONE-839727 | MSAAE---GA VVFSEEKEAL VLKSWAIMKK DSANLGLRFF LKIFEIAPSA | 47 |
| SEQ-ID-NO-16-CLONE-1554560 | MALAEADDGA VVFGEEQEAL VLKSWAVMKK DAANLGLRFF LKVFEIAPSA | 50 |
| SEQ-ID-NO-60-CLONE-1802327 | MALAE---GN VIFGEEQEAL VLKSWALMKK DSADLGLRFF LKIFEIAPSA | 47 |
| SEQ-ID-NO-9-CLONE-30469-FL | -MESE---GK IVFTEEQEAL VVKSWSVMKK NSADLGLKLF IKIFEIAPTT | 46 |
| SEQ-ID-NO-10-GI-30909306 | -MESE---GK IVFTEEQEAL VVKSWSVMKK NSADLGLKLF IKIFEIAPTA | 46 |
| SEQ-ID-NO-13-CLONE-546001 | -MTTTLERG-- -FSEEEQEAL VVKSWNVMKK NSGELGLKFF LKIFEIAPSA | 46 |
| SEQ-ID-NO-70-CLONE-1916866 | MAIYE---GK --VFTEEQEAL VVKSWTVMKK NAAELGLKFF LKIFEIAPSA | 46 |

| SEQ ID | Sequence | Pos |
|---|---|---|
| SEQ-ID-NO-17-CLONE-839727 | RQMFPFLRDS DVPLETNPKL KTHAVSVFVM TCEAAAQLRK AGKITVRETT | 97 |
| SEQ-ID-NO-16-CLONE-1554560 | KQMFSFLRDS DVPLEKNPKL KTHAMSVFVM TCEAAAQLRK AGKVTVRETT | 100 |
| SEQ-ID-NO-60-CLONE-1802327 | KQMFSFLRDS DVPLEKNPKL KNHAMSVFVM TCEAAAQLRK AGKVTVRETT | 97 |
| SEQ-ID-NO-9-CLONE-30469-FL | KKMFSFLRDS PIPAEQNPKL KPHAMSVFVM CCESAVQLRK AGKVTVRETT | 96 |
| SEQ-ID-NO-10-GI-30909306 | QKLFSFLRDS PIPAEQNPKL KPHAVSVFVM CCESAVQLRK TGKVTVKETT | 96 |
| SEQ-ID-NO-13-CLONE-546001 | KKLFSFLRDS TMPLEQNPKL KPHAMSVFVM TCDSAVQLRK AGKVTVRESN | 96 |
| SEQ-ID-NO-70-CLONE-1916866 | KKLFSFLRDS NVPLEQNTKL KPHAMSVFVM TCESAVQLRK AGKVTVRESN | 96 |

| SEQ ID | Sequence | Pos |
|---|---|---|
| SEQ-ID-NO-17-CLONE-839727 | LKRLGGTHLK YGVADGHFEV TRFALLETIK EALPADMWGP EMRNAWGEAY | 147 |
| SEQ-ID-NO-16-CLONE-1554560 | LKRLGATHLR YGVADGHFEV TGFALLETIK EALPADMWSL EMKKAWAEAY | 150 |
| SEQ-ID-NO-60-CLONE-1802327 | LKRLGATHFK YGVADGHFEV TRFALLETIK EALPADMWSL EMKNAWSEAY | 147 |
| SEQ-ID-NO-9-CLONE-30469-FL | LKRLGASHSK YGVDEHFEV AKYALLETIK EAVP-EMWSP EMKVAWGQAY | 145 |
| SEQ-ID-NO-10-GI-30909306 | LKRLGANHSK YGVDEHFEV TKYALLETIK EAVP-EMWSP EMKSAWGQAY | 145 |
| SEQ-ID-NO-13-CLONE-546001 | LKKLGATHFR TGVANEHFEV TKFALLETIK EAVP-EMWSP AMKNAWGEAY | 145 |
| SEQ-ID-NO-70-CLONE-1916866 | LKKLGATHFK YGVDEHFEV TKFALLETIK EAVP-DMWSD EMKNAWGEAY | 145 |

| SEQ ID | Sequence | Pos |
|---|---|---|
| SEQ-ID-NO-17-CLONE-839727 | DQLVAAIKQE MKPSE---- | 162 |
| SEQ-ID-NO-16-CLONE-1554560 | SQLVAAIKRE MKPDA---- | 165 |
| SEQ-ID-NO-60-CLONE-1802327 | NQLVAAIKQE MKPAA---- | 162 |
| SEQ-ID-NO-9-CLONE-30469-FL | DHLVAAIKAE MNLSN---- | 160 |
| SEQ-ID-NO-10-GI-30909306 | DHLVAAIKSE MKPSH---- | 160 |
| SEQ-ID-NO-13-CLONE-546001 | DQLVDAIKSE MKPPSS--- | 161 |
| SEQ-ID-NO-70-CLONE-1916866 | DRLVAAIKIE MKACSQAA | 163 |

FIGURE 3

| SEQ ID | Sequence | Length |
|---|---|---|
| SEQ-ID-NO-221-CLONE-839727-T | MSAAE---GA VVFSEEKEAL VLKSWAI MKK DSANLGLRFF LKIFEIAPSA | 47 |
| SEQ-ID-NO-207-CLONE-1554560-T | MALAEADDGA VVFGEEQEAL VLKSWAVMKK DAANLGLRFF LKVFEIAPSA | 50 |
| SEQ-ID-NO-208-CLONE-1802327-T | MALAE---GN VIFGEEQEAL VLKSWALMKK DSADLGLRFF LKIFEIAPSA | 47 |
| SEQ-ID-NO-7-CLONE-30469 | MESE---GK IVFTEEQEAL VVKSWSVMKK NSAELGLKLF IKIFEIAPTA | 46 |
| SEQ-ID-NO-227-GI-30909306-T | MESE---GK LVFTEEQEAL VVKSWSVMKK NSADLGLKLF IKIFEIAPTA | 46 |
| SEQ-ID-NO-219-CLONE-546001-T | MTIT---LE RGFSEEQEAL VVKSWNVMKK NSCELGLKFF LKIFEIAPSA | 46 |
| SEQ-ID-NO-212-CLONE-1916866-T | MATY---EG KVFTEEQEAL VVKSWTVMKK NAAELGLKFF LKIFEIAPSA | 46 |

| SEQ ID | Sequence | Length |
|---|---|---|
| SEQ-ID-NO-221-CLONE-839727-T | RQMFPFLRDS DVPLEINPKL KTHAVSVFVM -- | 77 |
| SEQ-ID-NO-207-CLONE-1554560-T | KQMFSFLRDS DVPLEKNPKL KTHAMSVFVM -- | 80 |
| SEQ-ID-NO-208-CLONE-1802327-T | KQMFSFLRDS DVPLEKNPKL KNHAMSVFVM -- | 77 |
| SEQ-ID-NO-7-CLONE-30469 | KKMFSFLRDS PIPAEQNPKL KPHAMSVFVM YN | 78 |
| SEQ-ID-NO-227-GI-30909306-T | KKLFSFLRDS PIPAEQNPKL KPHAVSVFVM -- | 76 |
| SEQ-ID-NO-219-CLONE-546001-T | QKLFSFLRDS TVPLEQNPKL KPHAVSVFVM -- | 76 |
| SEQ-ID-NO-212-CLONE-1916866-T | KKLFSFLRDS NVPLEQNTKL KPHAMSVFVM -- | 76 |

FIGURE 4

| | | | | | | |
|---|---|---|---|---|---|---|
| SEQ-ID-NO-20-CLONE-271922 | MA KRT KK V GI | VGKYGT RYGA | SI RKQI KKME | VSQHSKYFCE | FCGKY G VKRK | 50 |
| SEQ-ID-NO-54-CLONE-1627907 | MT KRT KKAGI | VGKYGT RYGA | SLRKQI KKME | VSQHAKYFCE | FCGKYAVKRQ | 50 |
| SEQ-ID-NO-25-CLONE-664936 | MT KRT KKAGI | VGKYGT RYGA | SLRKQI KKME | VSQHSKFFCE | FCGKYAVKRK | 50 |
| SEQ-ID-NO-28-CLONE-632613 | MT KRT KKAGI | VGKYGT RYGA | SLRKQI KKME | VSQHSKYFCE | FCGKFAVKRK | 50 |
| SEQ-ID-NO-29-CLONE-1390976 | MT KRT KKAGI | VGKYGT RYGA | SLRKQI KKME | VSQHSKYFCE | FCGKFAVKRK | 50 |
| SEQ-ID-NO-58-CLONE-1783890 | MT KRT KKAGI | VGKYGT RYGA | SLRKQI KKME | VSQHSKYFCE | FCGKFAVKRK | 50 |

| | | | | | | |
|---|---|---|---|---|---|---|
| SEQ-ID-NO-20-CLONE-271922 | AVGI WGCKDC | GKVKAGGAYT | MNT ASAVTVR | STI RRL REQI | E G | 92 |
| SEQ-ID-NO-54-CLONE-1627907 | AVGI WGCKDC | GKVKAGGAYT | LNT ASAVTVR | STI RRL REQT | E S | 92 |
| SEQ-ID-NO-25-CLONE-664936 | AVGI WGCKDC | GKVKAGGAYT | LNT ASAVTVR | STI RRL REQT | E G | 92 |
| SEQ-ID-NO-28-CLONE-632613 | AVGI WGCKDC | GKVKAGGAYT | MNT ASAVTVR | STI RRL REQT | E A | 92 |
| SEQ-ID-NO-29-CLONE-1390976 | AVGI WGCKDC | GKVKAGGAYT | MNT ASAVTVR | STI RRL REQT | E A | 92 |
| SEQ-ID-NO-58-CLONE-1783890 | AVGI WGCKDC | GKVKAGGAYT | MNT ASAVTVR | STI RRL REQT | E A | 92 |

FIGURE 5

| SEQ-ID | 1-50 | 51-100 | 101-150 | 151-200 |
|---|---|---|---|---|
| SEQ-ID-NO-34-CLONE-2403-FL | MQIFVKTLTG KTITLEVESS DTIDNVKAKI QDKEGIPPDQ QRLIFAGKQL | EDGRTLADYN QKESTLHLV LRLRGGTMIK VKTLTGKEIE IDIEPTDTID | RIKERVEEKE GIPPVQQRLI YAGKQLADDK TAKDYAIEGG SVLHLVLALR |
| SEQ-ID-NO-35-CLONE-1482731 | MQIFVKTLTG KTITLEVESS DTIDNVKSKI QDKEGIPPDQ QRLIFAGKQL | EDGRTLADYN QKESTLHLV LRLRGGTMIK VKTLTGKEIE IDIEPTDTID | RIKERVEEKE GIPPVQQRLI YAGKQLADDK TAKDYNIEGG SVLHLVLALR |
| SEQ-ID-NO-36-CLONE-522921 | MQIFVKTLTG KTITLEVESS DTIDNVKAKI QDKEGIPPDQ QRLIFAGKQL | EDGRTLADYN QKESTLHLV LRLRGGTMIK VKTLTGKEIE IDIEPTDTID | RIKERVEEKE GIPPVQQRLI YAGKQLADDK TAKEYNIEGG SVLHLVLALR |
| SEQ-ID-NO-37-CLONE-1036726 | MQIFVKTLTG KTITLEVESS DTIDNVKAKI QDKEGIPPDQ QRLIFAGKQL | EDGRTLADYN QKESTLHLV LRLRGGTMIK VKTLTGKEIF IDIEPTDTID | RIKERVEEKE GIPPVQQRLI YAGKQLADDK XKDYNIEGG SVSA |
| SEQ-ID-NO-68-CLONE-1884696 | MQIFVKTLTG KTITLEVESS DTIDNVKAKI QDKEGIPPDQ QRLIFAGKQL | EDGRTLADYN QKESTLHLV LRLRGGMQL VKTLTGKTIT LEVESSDTID | NVKAKIQDKE GIPPDQQRLI FAGKQLEDGR TLADYNIQKD STLHVLRLR |
| SEQ-ID-NO-80-CLONE-2034916 | MQIFVKTLTG KTITLEVESS DTIDNVKAKI QDKEGIPPDQ QRLIFAGKQL | EDGRTLADYN QKESTLHLV LRLRGGMQLT VKTLTGKTIT LEVESSDTID | NVKVKIQDKE GIPPDQQRLI FAGKQLEDGR TLADYNIQKE STLHVLRLR |

| SEQ-ID | 201- | end |
|---|---|---|
| SEQ-ID-NO-34-CLONE-2403-FL | GGL | 154 L |
| SEQ-ID-NO-35-CLONE-1482731 | GGS | 154 D |
| SEQ-ID-NO-36-CLONE-522921 | GGT | 154 Y |
| SEQ-ID-NO-37-CLONE-1036726 | -SG | 147 S |
| SEQ-ID-NO-68-CLONE-1884696 | GG- | 153 F |
| SEQ-ID-NO-80-CLONE-2034916 | GGMQIFVKTL TGKTITLEVE SSDTIDNVKA KIQDKEGIPP DQQRLIFAGK QLEDGRTLAD YNI | 213 |

FIGURE 6

| | | | | | |
|---|---|---|---|---|---|
| SEQ-ID-NO-40-CLONE-2403 | MQI FVKTLTG | KTI TLEVESS | DTI DNVKAKI | QDK | 33 |
| SEQ-ID-NO-205-CLONE-1036726-T | MQI FVKTLTG | KTI TLEVESS | DTI DNVKAKI | QDK | 33 |
| SEQ-ID-NO-211-CLONE-1884696-T | MQI FVKTLTG | KTI TLEVESS | DTI DNVKAKI | QDK | 33 |
| SEQ-ID-NO-213-CLONE-1950105-T | MQI FVKTLTG | KTI TLEVESS | DTI DNVKAKI | QDK | 33 |
| SEQ-ID-NO-218-CLONE-522921-T | MQI FVKTLTG | KTI TLEVESS | DTI DNVKAKI | QDK | 33 |
| SEQ-ID-NO-206-CLONE-1482731-T | MQI FVKTLTG | KTI TLEVESS | DTI DNVKSKI | QDK | 33 |

FIGURE 7

(Sequence alignment figure)

Figure 7 continued

| SEQ ID | | | | | | | |
|---|---|---|---|---|---|---|---|
| SEQ-ID-NO-46-CLONE-1055099 | VESWSGGGP | --- | --- | RAPARARSA | ARAGTAKEGE | EDCRSYCGSS | 144 |
| SEQ-ID-NO-56-CLONE-1761125 | VESSSGPRGA | PRAAAA | --- | AAPRIRRRS | VKKPRPAAPD | DCHSDCASS | 151 |
| SEQ-ID-NO-83-GI-1255550159 | VESSSGPRGP | RPAA | --- | TAAAVPRRR | VPRPAPPAPD | AGCHSDCASS | 143 |
| SEQ-ID-NO-45-CLONE-273307 | VESFSGARP- | --- | --- | -RPVLPP-R | FP-PPSI-PD | GDCRHSDCGSS | 158 |
| SEQ-ID-NO-62-CLONE-1838364 | VESFSGPRPA | QPPQKSAD | --- | -FAMVSTRKY | YPRPPPLVPE | -DCHSDCDSS | 183 |
| SEQ-ID-NO-50-CLONE-1240330 | VESFSGPRPP | TTTTTTTT | --- | ATPFLTATRR | YPRTPPLVPE | -DCRSDCDSS | 177 |
| SEQ-ID-NO-42-CLONE-674166 | VESFSGPRAA | VPA | --- | TAPVATGRR | YPRTPPVI PE | -DCHSDCDSS | 163 |
| SEQ-ID-NO-86-GI-56384582 | VESFCGPRPV | RPPM | --- | PPSAVIGRR | YPRTPPVAPG | -DCHSDCDSS | 164 |
| SEQ-ID-NO-48-ANNOT-1441430 | VESFSGPRPP | QPTTTT | --- | KSGNGPRRS | HPRPPVVPE | -DCHSDCDSS | 171 |
| SEQ-ID-NO-87-GI-57012880 | VESFSGPRPP | PAPR | --- | -QQTTASSRK | MTRSPPVVPD | -DCRSDCDSS | 171 |
| SEQ-ID-NO-44-CLONE-975572 | VKSCSGVRPA | SS | --- | SVAKAAIKR | YPRTPPVAPE | -DCRSDCDSS | 166 |
| SEQ-ID-NO-84-GI-15223609 | VESFSGPRPT | --- | --- | TMKPATTKR | YPRTPPVVPE | -DCHSDCDSS | 176 |

| | | | | | | | |
|---|---|---|---|---|---|---|---|
| SEQ-ID-NO-46-CLONE-1055099 | SSVLE | EGADDA | AAS | RSPLPFDLNM | PPPQECAL--- | | 177 |
| SEQ-ID-NO-56-CLONE-1761125 | ASV-VD | DGDDAS | TV-- | RSRAPFDLNV | PAPVDCDH--- | | 182 |
| SEQ-ID-NO-83-GI-1255550159 | ASV-VD | DADDAS | TVR | SRVAAFDLNL | PFPLDRDH--- | | 175 |
| SEQ-ID-NO-45-CLONE-273307 | ASV-VD | DDCTDA | AAS | PFPLPFDLNL | -PPGGGAGV--- | | 194 |
| SEQ-ID-NO-62-CLONE-1838364 | ASV-VD | DGDAL | SSC | RKITLPFDLNF | -PPLDEDG--- | | 214 |
| SEQ-ID-NO-50-CLONE-1240330 | SSV-VD | DGDDN | VSS | RDPLPFDLNA | -LPFDDAA--- | | 210 |
| SEQ-ID-NO-42-CLONE-674166 | SSV-VD | DGECDN | VAS | REPLPFDLNA | LPLDDAD--- | | 197 |
| SEQ-ID-NO-86-GI-56384582 | SSV-VD | DADDN | AASSTMLSFK | RQPLPFDLNF | -PPLEEGD--- | | 202 |
| SEQ-ID-NO-48-ANNOT-1441430 | SSV-VD | DRDVAS | SLC | RKPLPFDLNF | -PPLDQVD--- | | 205 |
| SEQ-ID-NO-87-GI-57012880 | SSV-VDHGDC | EKENDNDN | TAS | RKPLEFDLNL | -PPMDDAG--- | | 214 |
| SEQ-ID-NO-44-CLONE-975572 | SSV-VE | DGXDA | SSS | KPPFEFDLNF | XPLDGVD--- | | 200 |
| SEQ-ID-NO-84-GI-15223609 | SSV-D | DDDIA | SSS | NPPFQFDLNF | -PPLDCVD--- | | 210 |

| | | | | | |
|---|---|---|---|---|---|
| SEQ-ID-NO-46-CLONE-1055099 | ---DAEADQM | TCRYDTLR | --- | --- | 194 |
| SEQ-ID-NO-56-CLONE-1761125 | ---ALDL | -C---TELRL | --- | --- | 192 |
| SEQ-ID-NO-83-GI-1255550159 | ---VDL | -C---TDLRL | --- | --- | 184 |
| SEQ-ID-NO-45-CLONE-273307 | GFYADEEDEL | RL---TALRL | --- | --- | 211 |
| SEQ-ID-NO-62-CLONE-1838364 | ---RSPM | YC-FMSLAM | PVMNDDDRLL | DLFFFFKKC | 246 |
| SEQ-ID-NO-50-CLONE-1240330 | ---ADDL | RR---TALCL | --- | --- | 222 |
| SEQ-ID-NO-42-CLONE-674166 | ---VATDDL | FC---TVLCL | --- | --- | 210 |
| SEQ-ID-NO-86-GI-56384582 | -VANGLGEDL | HC---TLLCL | --- | --- | 218 |
| SEQ-ID-NO-48-ANNOT-1441430 | ---LCGSG | -DDL---TALCL | --- | --- | 219 |
| SEQ-ID-NO-87-GI-57012880 | ---ADDL | HC---TALCL | --- | --- | 225 |
| SEQ-ID-NO-44-CLONE-975572 | -LFVGA-DDX | XC---TDLXL | --- | --- | 215 |
| SEQ-ID-NO-84-GI-15223609 | -LFNGA-DDL | HC---TDLRL | --- | --- | 225 |

SEQUENCE LISTING

```
<160> NUMBER OF SEQ ID NOS: 229

<210> SEQ ID NO 1
<211> LENGTH: 828
<212> TYPE: DNA
<213> ORGANISM: Arabidopsis thaliana
<220> FEATURE:
<221> NAME/KEY: misc_feature
<223> OTHER INFORMATION: Ceres CLONE ID no. 30087
<220> FEATURE:
<221> NAME/KEY: misc_feature
<223> OTHER INFORMATION: Ceres SEED LINE ID no. ME01451
<220> FEATURE:
<221> NAME/KEY: misc_feature
<223> OTHER INFORMATION: Encodes the protein at SEQ ID NO: 2

<400> SEQUENCE: 1 aactttctc tcccactctt tcttttacta ctctcacaca tatctctgtc tatatatcac      60
tttacataaa ccactattcc acacacaaac acacatagcc atggcctctt ctttctcttc    120
acaagccttc ttcttgctca cattgtctat ggttttaatt cctttctctt tagctcaagc    180
tcccatgatg gctccttctg gctcaatgtc catgccgcct atgtctagcg gcggtggaag    240
ctcggttcct cctccagtga tgtctccgat gccaatgatg actccaccac ctatgcctat    300
gactccatca cccatgccca tgactccacc acctatgcct atggctccac caccaatgcc    360
catggcttca ccaccaatga tgccaatgac tccatctaca agcccaagcc cattaacagt    420
tccggatatg ccttcgccgc cgatgccatc cggaatggaa tcttcaccct ctccaggacc    480
catgccaccg gcaatggcgg cttcgccgga ttcgggagct ttcaatgtta gaaacaacgt    540
cgtaacactt tcatgcgttg ttggagttgt tgcagctcat tttctcctcg tttgaaatga    600
ttattgaatt ggtcagcctc gatcgttttc ttgtaattta ctttcatatt ttttttccct    660
caaattatta gtggtcatca ttttataata tttgagtttg tgtttgatgt acgattcaga    720
catttgtttg cattatgtgc ttaataagtt tatcgttgac tctacttgaa gagagacttt    780
```
gtgtgtgatg taaatttctt ctatctatgg aacattgcat tcgtagcc                    828

<210> SEQ ID NO 2
<211> LENGTH: 164
<212> TYPE: PRT
<213> ORGANISM: Arabidopsis thaliana
<220> FEATURE:
<221> NAME/KEY: misc_feature
<223> OTHER INFORMATION: Ceres CLONE ID no. 30087
<220> FEATURE:
<221> NAME/KEY: misc_feature
<223> OTHER INFORMATION: Ceres SEED LINE ID no. ME01451

<400> SEQUENCE: 2

Met Ala Ser Ser Phe Ser Ser Gln Ala Phe Leu Leu Thr Leu Ser
1               5                   10                  15

Met Val Leu Ile Pro Phe Ser Leu Ala Gln Ala Pro Met Met Ala Pro
            20                  25                  30

Ser Gly Ser Met Ser Met Pro Pro Met Ser Ser Gly Gly Gly Ser Ser
        35                  40                  45

Val Pro Pro Val Met Ser Pro Met Pro Met Met Thr Pro Pro Pro
50                  55                  60

Met Pro Met Thr Pro Ser Pro Met Pro Met Thr Pro Pro Pro Met Pro
65                  70                  75                  80

Met Ala Pro Pro Met Pro Met Ala Ser Pro Pro Met Met Pro Met
            85                  90                  95

Thr Pro Ser Thr Ser Pro Ser Pro Leu Thr Val Pro Asp Met Pro Ser
            100                 105                 110

Pro Pro Met Pro Ser Gly Met Glu Ser Ser Pro Ser Pro Gly Pro Met
        115                 120                 125

Pro Pro Ala Met Ala Ala Ser Pro Asp Ser Gly Ala Phe Asn Val Arg
    130                 135                 140

Asn Asn Val Val Thr Leu Ser Cys Val Val Gly Val Val Ala Ala His
145                 150                 155                 160

Phe Leu Leu Val

<210> SEQ ID NO 3
<211> LENGTH: 155
<212> TYPE: PRT
<213> ORGANISM: Brassica napus
<220> FEATURE:
<221> NAME/KEY: misc_feature
<223> OTHER INFORMATION: Ceres CLONE ID no. 947579
<220> FEATURE:
<221> NAME/KEY: misc_feature
<223> OTHER INFORMATION: Functional homolog of Ceres Clone ID no. 30087
      given in SEQ ID NO: 2

<400> SEQUENCE: 3

Met Ala Ala Ser Gln Ala Phe Leu Leu Leu Thr Leu Ser Met Ala Leu
1               5                   10                  15

Val His Phe Ser Leu Ala Gln Ser Pro Met Met Ala Pro Ser Gly Ser
            20                  25                  30

Met Ser Met Pro Pro Met Pro Ser Gly Gly Ser Pro Met Pro Met Met
        35                  40                  45

Thr Pro Pro Pro Met Pro Met Met Thr Pro Pro Pro Met Ala Met Ala
    50                  55                  60

Pro Pro Pro Met Pro Met Thr Pro Pro Pro Met Pro Met Ala Pro Met
65                  70                  75                  80

Pro Met Thr Pro Ser Ser Ser Pro Met Ser Pro Pro Thr Thr Met Ala

```
                    85                  90                  95

Pro Ser Pro Glu Thr Val Pro Asp Met Ala Ser Pro Met Met Pro
            100                 105                 110

Gly Met Glu Ser Ser Pro Ser Pro Gly Pro Met Pro Pro Ala Met Ala
        115                 120                 125

Ser Pro Asp Ser Gly Ala Phe Asn Val Arg Asn Asp Val Val Ala Ile
130                 135                 140

Ser Phe Leu Val Ala Ala His Leu Leu Leu Val
145                 150                 155

<210> SEQ ID NO 4
<211> LENGTH: 152
<212> TYPE: PRT
<213> ORGANISM: Brassica napus
<220> FEATURE:
<221> NAME/KEY: misc_feature
<223> OTHER INFORMATION: Public GI no. 62526422
<220> FEATURE:
<221> NAME/KEY: misc_feature
<223> OTHER INFORMATION: Functional homolog of Ceres Clone ID no. 30087
      given in SEQ ID NO: 2

<400> SEQUENCE: 4

Met Ala Leu Ser His Pro Met Thr Ile Phe Ser Leu Phe Leu Thr Phe
1               5                   10                  15

Leu Ala Leu Thr Ala Ala Gln Ser Pro Met Met Ala Pro Thr Met Pro
            20                  25                  30

Pro Ser Thr Met Ser Met Pro Pro Thr Thr Ser Thr Thr Thr Pro Pro
        35                  40                  45

Pro Met Ser Ser Met Ser Pro Pro Ser Ala Met Ser Pro Thr Pro
    50                  55                  60

Ser Thr Met Ser Pro Pro Met Ser Pro Thr Pro Ser Met Ser
65                  70                  75                  80

Pro Met Gly Pro Met Thr Pro Thr Met Ser Pro Met Asp Ser Pro Pro
                85                  90                  95

Ala Pro Ala Gly Pro Gly Met Ala Pro Gly Met Ser Thr Pro Gly Pro
            100                 105                 110

Ala Pro Gly Pro Met Gly Gly Glu Ser Met Ala Ser Pro Pro Pro Ser
        115                 120                 125

Ser Gly Phe Val His Gly Ile Ser Ile Ser Met Ala Met Val Ala Ile
    130                 135                 140

Ile Gly Ser Val Ala Leu Phe Phe
145                 150

<210> SEQ ID NO 5
<211> LENGTH: 150
<212> TYPE: PRT
<213> ORGANISM: Parthenium argentatum
<220> FEATURE:
<221> NAME/KEY: misc_feature
<223> OTHER INFORMATION: Ceres CLONE ID no. 1606506
<220> FEATURE:
<221> NAME/KEY: misc_feature
<223> OTHER INFORMATION: Functional homolog of Ceres Clone ID no. 30087
      given in SEQ ID NO: 2

<400> SEQUENCE: 5

Met Ala Val Ser Arg Tyr Ile Ile Leu Leu Leu Ser Phe Thr Tyr Leu
1               5                   10                  15

Ala Ala Phe Ser Thr Ala Gln Ala Pro Ser Met Ser Pro Met Met Met
            20                  25                  30
```

```
Pro Met Ala Pro Pro Pro Ser Thr Met Pro Met Thr Pro Pro Ser
            35                  40                  45
Thr Met Pro Met Thr Pro Pro Pro Thr Pro Met Thr Met Thr Pro Pro
 50                  55                  60
Pro Met Met Met Pro Met Thr Pro Pro Pro Met Pro Gly Thr Pro
 65                  70                  75                  80
Pro Met Thr Met Pro Met Gly Pro Pro Pro Met Met Pro Met Ser
                 85                  90                  95
Pro Gly Pro Ser Met Met Pro Ala Ser Pro Pro Ser Pro Met Gly Pro
                100                 105                 110
Ser Met Ala Pro Glu Pro Ala Thr Met Ser Pro Gly Pro Ser Met Thr
                115                 120                 125
Pro Ala Glu Thr Pro Ala Ser Gly Ala Ile Met Gln Tyr Ser Ser Ile
130                 135                 140
Thr Met Leu Gly Ile Val
145                 150
```

```
<210> SEQ ID NO 6
<211> LENGTH: 586
<212> TYPE: DNA
<213> ORGANISM: Artificial Sequence
<220> FEATURE:
<223> OTHER INFORMATION: Ceres CLONE ID no. 30469
<220> FEATURE:
<221> NAME/KEY: misc_feature
<223> OTHER INFORMATION: Ceres SEED LINE ID no. ME02779
<220> FEATURE:
<221> NAME/KEY: misc_feature
<223> OTHER INFORMATION: Encodes the protein at SEQ ID NO: 7

<400> SEQUENCE: 6
aaaagatcta caaaacagag agttgtatac tttaaatcat ttagaggttg tgaaatatta      60
tggagagtga aggaaagatt gtgttcacag aagagcaaga ggctcttgta gtgaagtctt     120
ggagtgtcat gaagaaaaac tcagctgaat taggtctcaa actcttcatc aagatctttg     180
agattgcacc aacaacgaag aagatgttct ctttcttgag agactcacca attcctgctg     240
agcaaaatcc aaagctcaag cctcacgcaa tgtctgtttt tgtcatgtac aactgaggaa     300
aacagggaaa gttacggtga gggagactac tttgaagaga cttggagcca gccattctaa     360
atacggtgtc gttgacgaac actttgaggt ggccaagtat gcattgttgg agacgataaa     420
ggaggcagtg ccggagatgt ggtcaccgga gatgaaggtg gcttggggtc aggcttatga     480
tcaccttgtt gctgccatta agctgaaat gaatctttcc aactaaaaaa tcatatacta     540
ttatatagtt gtaaacttgt aataaatatt tcattttgaa ttgttc                    586
```

```
<210> SEQ ID NO 7
<211> LENGTH: 78
<212> TYPE: PRT
<213> ORGANISM: Artificial Sequence
<220> FEATURE:
<223> OTHER INFORMATION: Ceres CLONE ID no. 30469
<220> FEATURE:
<221> NAME/KEY: misc_feature
<223> OTHER INFORMATION: Ceres SEED LINE ID no. ME02779
<220> FEATURE:
<221> NAME/KEY: misc_feature
<222> LOCATION: (13)..(74)
<223> OTHER INFORMATION: Pfam Name: Globin
      Pfam Description: Globin

<400> SEQUENCE: 7
```

```
Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Glu Leu Gly
            20                  25                  30

Leu Lys Leu Phe Ile Lys Ile Phe Glu Ile Ala Pro Thr Thr Lys Lys
        35                  40                  45

Met Phe Ser Phe Leu Arg Asp Ser Pro Ile Pro Ala Glu Gln Asn Pro
    50                  55                  60

Lys Leu Lys Pro His Ala Met Ser Val Phe Val Met Tyr Asn
65                  70                  75
```

<210> SEQ ID NO 8
<211> LENGTH: 483
<212> TYPE: DNA
<213> ORGANISM: Arabidopsis thaliana
<220> FEATURE:
<221> NAME/KEY: misc_feature
<223> OTHER INFORMATION: Ceres CLONE ID no. 30469_FL
<220> FEATURE:
<221> NAME/KEY: misc_feature
<223> OTHER INFORMATION: Encodes the protein at SEQ ID NO: 9

<400> SEQUENCE: 8

```
atggagagtg aaggaaagat tgtgttcaca gaagagcaag aggctcttgt agtgaagtct    60
tggagtgtca tgaagaaaaa ctcagctgaa ttaggtctca aactcttcat caagatcttt   120
gagattgcac caacaacgaa gaagatgttc tctttcttga gagactcacc aattcctgct   180
gagcaaaatc caaagctcaa gcctcacgca atgtctgttt ttgtcatgtg ttgtgaatca   240
gcagtacaac tgaggaaaac agggaaagtt acggtgaggg agactacttt gaagagactt   300
ggagccagcc attctaaata cggtgtcgtt gacgaacact tgaggtggc caagtatgca    360
ttgttggaga cgataaagga ggcagtgccg gagatgtggt caccggagat gaaggtggct   420
tggggtcagg cttatgatca ccttgttgct gccattaaag ctgaaatgaa tctttccaac   480
taa                                                                483
```

<210> SEQ ID NO 9
<211> LENGTH: 160
<212> TYPE: PRT
<213> ORGANISM: Arabidopsis thaliana
<220> FEATURE:
<221> NAME/KEY: misc_feature
<223> OTHER INFORMATION: Ceres CLONE ID no. 30469_FL
<220> FEATURE:
<221> NAME/KEY: misc_feature
<222> LOCATION: (13)..(152)
<223> OTHER INFORMATION: Pfam Name: Globin
    Pfam Description: Globin
<220> FEATURE:
<221> NAME/KEY: misc_feature
<223> OTHER INFORMATION: Functional homolog of Ceres Clone ID no. 30469
    given in SEQ ID NO: 7

<400> SEQUENCE: 9

```
Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Glu Leu Gly
            20                  25                  30

Leu Lys Leu Phe Ile Lys Ile Phe Glu Ile Ala Pro Thr Thr Lys Lys
        35                  40                  45

Met Phe Ser Phe Leu Arg Asp Ser Pro Ile Pro Ala Glu Gln Asn Pro
    50                  55                  60
```

-continued

```
Lys Leu Lys Pro His Ala Met Ser Val Phe Val Met Cys Cys Glu Ser
 65                  70                  75                  80

Ala Val Gln Leu Arg Lys Thr Gly Lys Val Thr Val Arg Glu Thr Thr
                 85                  90                  95

Leu Lys Arg Leu Gly Ala Ser His Ser Lys Tyr Gly Val Val Asp Glu
            100                 105                 110

His Phe Glu Val Ala Lys Tyr Ala Leu Leu Glu Thr Ile Lys Glu Ala
        115                 120                 125

Val Pro Glu Met Trp Ser Pro Glu Met Lys Val Ala Trp Gly Gln Ala
    130                 135                 140

Tyr Asp His Leu Val Ala Ala Ile Lys Ala Glu Met Asn Leu Ser Asn
145                 150                 155                 160
```

<210> SEQ ID NO 10
<211> LENGTH: 160
<212> TYPE: PRT
<213> ORGANISM: Raphanus sativus
<220> FEATURE:
<221> NAME/KEY: misc_feature
<223> OTHER INFORMATION: Public GI no. 30909306
<220> FEATURE:
<221> NAME/KEY: misc_feature
<222> LOCATION: (13)..(152)
<223> OTHER INFORMATION: Pfam Name: Globin
    Pfam Description: Globin
<220> FEATURE:
<221> NAME/KEY: misc_feature
<223> OTHER INFORMATION: Functional homolog of Ceres Clone ID no. 30469
    given in SEQ ID NO: 7

<400> SEQUENCE: 10

```
Met Glu Ser Glu Gly Lys Ile Val Phe Thr Glu Glu Gln Glu Ala Leu
  1               5                  10                  15

Val Val Lys Ser Trp Ser Val Met Lys Lys Asn Ser Ala Asp Leu Gly
             20                  25                  30

Leu Lys Leu Phe Ile Lys Ile Phe Glu Ile Ala Pro Thr Ala Lys Lys
         35                  40                  45

Leu Phe Ser Phe Leu Arg Asp Ser Pro Ile Pro Ala Glu Gln Asn Pro
     50                  55                  60

Lys Leu Lys Pro His Ala Met Ser Val Phe Val Met Cys Cys Glu Ser
 65                  70                  75                  80

Ala Ala Gln Leu Arg Lys Thr Gly Lys Val Thr Val Lys Glu Thr Thr
                 85                  90                  95

Leu Lys Arg Leu Gly Ala Asn His Ser Lys Tyr Gly Val Val Asp Glu
            100                 105                 110

His Phe Glu Val Thr Lys Tyr Ala Leu Leu Glu Thr Ile Lys Glu Ala
        115                 120                 125

Val Pro Glu Met Trp Ser Pro Glu Met Lys Ser Ala Trp Gly Gln Ala
    130                 135                 140

Tyr Asp His Leu Val Ala Ala Ile Lys Ala Glu Met Lys Pro Ser His
145                 150                 155                 160
```

<210> SEQ ID NO 11
<211> LENGTH: 158
<212> TYPE: PRT
<213> ORGANISM: Arabidopsis thaliana
<220> FEATURE:
<221> NAME/KEY: misc_feature
<223> OTHER INFORMATION: Public GI no. 37903656
<220> FEATURE:
<221> NAME/KEY: misc_feature
<222> LOCATION: (10)..(149)

```
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 11

Met Glu Gly Lys Val Phe Thr Glu Glu Gln Glu Thr Leu Val Val Lys
1               5                   10                  15

Ser Trp Gly Val Met Lys Lys Asn Ala Glu Leu Gly Leu Lys Phe
            20                  25                  30

Phe Leu Lys Ile Phe Glu Ile Ala Pro Ser Ala Gln Lys Leu Phe Ser
            35                  40                  45

Phe Leu Arg Asp Ser Asp Ile Pro Leu Glu Lys Asn Pro Lys Leu Lys
        50                  55                  60

Pro His Ala Met Ser Val Phe Val Met Thr Cys Glu Ser Ala Val Gln
65                  70                  75                  80

Leu Arg Lys Ala Gly Lys Val Thr Val Arg Glu Ser Thr Leu Lys Arg
                85                  90                  95

Leu Gly Gly Val His Phe Lys Ser Gly Val Val Asp Glu His Tyr Glu
            100                 105                 110

Val Thr Lys Phe Ala Leu Leu Glu Thr Ile Lys Glu Ala Leu Pro Glu
        115                 120                 125

Met Trp Ser Pro Glu Met Lys Asn Ala Trp Gly Glu Ala Tyr Asp Gln
130                 135                 140

Leu Val Ala Ala Ile Lys Ser Glu Met Lys Pro Pro Leu Asn
145                 150                 155

<210> SEQ ID NO 12
<211> LENGTH: 163
<212> TYPE: PRT
<213> ORGANISM: Arabidopsis thaliana
<220> FEATURE:
<221> NAME/KEY: misc_feature
<223> OTHER INFORMATION: Public GI no. 15824736
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 12

Met Ala Thr Tyr Glu Gly Lys Val Phe Thr Glu Glu Gln Glu Ala Leu
1               5                   10                  15

Val Val Lys Ser Trp Thr Val Met Lys Lys Thr Ala Glu Leu Gly
            20                  25                  30

Leu Lys Phe Phe Leu Lys Ile Phe Glu Ile Ala Pro Ser Ala Lys Lys
            35                  40                  45

Leu Phe Ser Phe Leu Arg Asp Ser Asn Val Pro Leu Glu Gln Asn Thr
        50                  55                  60

Lys Leu Lys Pro His Ala Met Ser Val Phe Val Met Thr Cys Glu Ser
65                  70                  75                  80

Ala Val Gln Leu Arg Lys Ala Gly Lys Val Thr Val Arg Glu Ser Asn
                85                  90                  95

Leu Lys Lys Leu Gly Ala Thr His Phe Lys Tyr Gly Val Val Asp Glu
            100                 105                 110
```

```
His Phe Glu Val Thr Lys Phe Ala Leu Leu Glu Thr Ile Lys Glu Ala
        115                 120                 125

Val Pro Asp Met Trp Ser Glu Met Lys Asn Ala Trp Gly Glu Ala
    130                 135                 140

Tyr Asp Arg Leu Val Ala Ala Ile Lys Ile Glu Met Lys Ala Cys Ser
145                 150                 155                 160

Gln Ala Ala

<210> SEQ ID NO 13
<211> LENGTH: 161
<212> TYPE: PRT
<213> ORGANISM: Glycine max
<220> FEATURE:
<221> NAME/KEY: misc_feature
<223> OTHER INFORMATION: Ceres CLONE ID no. 546001
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 13

Met Thr Thr Thr Leu Glu Arg Gly Phe Ser Glu Glu Gln Glu Ala Leu
1               5                   10                  15

Val Val Lys Ser Trp Asn Val Met Lys Lys Asn Ser Gly Glu Leu Gly
            20                  25                  30

Leu Lys Phe Phe Leu Lys Ile Phe Glu Ile Ala Pro Ser Ala Gln Lys
        35                  40                  45

Leu Phe Ser Phe Leu Arg Asp Ser Thr Val Pro Leu Glu Gln Asn Pro
    50                  55                  60

Lys Leu Lys Pro His Ala Val Ser Val Phe Val Met Thr Cys Asp Ser
65                  70                  75                  80

Ala Val Gln Leu Arg Lys Ala Gly Lys Val Thr Val Arg Glu Ser Asn
                85                  90                  95

Leu Lys Lys Leu Gly Ala Thr His Phe Arg Thr Gly Val Ala Asn Glu
            100                 105                 110

His Phe Glu Val Thr Lys Phe Ala Leu Leu Glu Thr Ile Lys Glu Ala
        115                 120                 125

Val Pro Glu Met Trp Ser Pro Ala Met Lys Asn Ala Trp Gly Glu Ala
    130                 135                 140

Tyr Asp Gln Leu Val Asp Ala Ile Lys Ser Glu Met Lys Pro Pro Ser
145                 150                 155                 160

Ser

<210> SEQ ID NO 14
<211> LENGTH: 160
<212> TYPE: PRT
<213> ORGANISM: Glycine max
<220> FEATURE:
<221> NAME/KEY: misc_feature
<223> OTHER INFORMATION: Public GI no. 11095158
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
```

<223> OTHER INFORMATION: Functional homolog of Ceres Clone ID no. 30469
      given in SEQ ID NO: 7

<400> SEQUENCE: 14

Met Gly Thr Leu Asp Thr Lys Gly Phe Thr Glu Glu Gln Glu Ala Leu
1               5                   10                  15

Val Val Lys Ser Trp Asn Ala Met Lys Lys Asn Ser Ala Glu Leu Gly
            20                  25                  30

Leu Lys Leu Phe Leu Lys Ile Phe Glu Ile Ala Pro Ser Ala Gln Lys
        35                  40                  45

Leu Phe Ser Phe Leu Lys Asp Ser Lys Val Pro Leu Glu Gln Asn Thr
    50                  55                  60

Lys Leu Lys Pro His Ala Met Ser Val Phe Leu Met Thr Cys Glu Ser
65                  70                  75                  80

Ala Val Gln Leu Arg Lys Ser Gly Lys Val Thr Val Arg Glu Ser Ser
                85                  90                  95

Leu Lys Lys Leu Gly Ala Asn His Phe Lys Tyr Gly Val Val Asp Glu
            100                 105                 110

His Phe Glu Val Thr Lys Phe Ala Leu Leu Glu Thr Ile Lys Glu Ala
        115                 120                 125

Val Pro Glu Met Trp Ser Pro Ala Met Lys Asn Ala Trp Gly Glu Ala
    130                 135                 140

Tyr Asp Gln Leu Val Asn Ala Ile Lys Ser Glu Met Lys Pro Ser Ser
145                 150                 155                 160

<210> SEQ ID NO 15
<211> LENGTH: 152
<212> TYPE: PRT
<213> ORGANISM: Glycine max
<220> FEATURE:
<221> NAME/KEY: misc_feature
<223> OTHER INFORMATION: Public GI no. 12963875
<220> FEATURE:
<221> NAME/KEY: misc_feature
<222> LOCATION: (8)..(147)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 15

Met Ser Ser Phe Ser Glu Glu Gln Glu Ala Leu Val Val Lys Ser Trp
1               5                   10                  15

Gly Ser Met Lys Lys Asp Ala Gly Glu Trp Gly Leu Lys Phe Phe Leu
            20                  25                  30

Lys Ile Phe Glu Ile Ala Pro Ser Ala Lys Lys Met Phe Ser Phe Leu
        35                  40                  45

Lys Asp Ser Asn Val Pro Leu Asp Gln Asn Pro Lys Leu Lys Ile His
    50                  55                  60

Ala Lys Ser Val Leu Val Met Thr Cys Glu Ala Ala Val Gln Leu Arg
65                  70                  75                  80

Lys Ala Gly Lys Val Val Val Arg Asp Ser Thr Leu Lys Lys Ile Gly
                85                  90                  95

Ala Thr His Phe Lys Tyr Gly Val Val Asp Glu His Phe Glu Val Thr
            100                 105                 110

Lys Tyr Ala Leu Leu Glu Thr Ile Lys Glu Ala Ser Gln Glu Met Trp
        115                 120                 125

```
Ser Val Glu Met Lys Asn Ala Trp Gly Glu Ala Tyr Asp Gln Leu Val
    130                 135                 140

Ser Ala Ile Lys Thr Glu Met Lys
145                 150

<210> SEQ ID NO 16
<211> LENGTH: 165
<212> TYPE: PRT
<213> ORGANISM: Zea mays
<220> FEATURE:
<221> NAME/KEY: misc_feature
<223> OTHER INFORMATION: Ceres CLONE ID no. 1554560
<220> FEATURE:
<221> NAME/KEY: misc_feature
<222> LOCATION: (17)..(157)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 16

Met Ala Leu Ala Glu Ala Asp Asp Gly Ala Val Val Phe Gly Glu Glu
1               5                   10                  15

Gln Glu Ala Leu Val Leu Lys Ser Trp Ala Val Met Lys Lys Asp Ala
            20                  25                  30

Ala Asn Leu Gly Leu Arg Phe Phe Leu Lys Val Phe Glu Ile Ala Pro
        35                  40                  45

Ser Ala Lys Gln Met Phe Ser Phe Leu Arg Asp Ser Asp Val Pro Leu
    50                  55                  60

Glu Lys Asn Pro Lys Leu Lys Thr His Ala Met Ser Val Phe Val Met
65                  70                  75                  80

Thr Cys Glu Ala Ala Gln Leu Arg Lys Ala Gly Lys Val Thr Val
                85                  90                  95

Arg Glu Thr Thr Leu Lys Arg Leu Gly Ala Thr His Leu Arg Tyr Gly
                100                 105                 110

Val Ala Asp Gly His Phe Glu Val Thr Gly Phe Ala Leu Leu Glu Thr
            115                 120                 125

Ile Lys Glu Ala Leu Pro Ala Asp Met Trp Ser Leu Glu Met Lys Lys
    130                 135                 140

Ala Trp Ala Glu Ala Tyr Ser Gln Leu Val Ala Ala Ile Lys Arg Glu
145                 150                 155                 160

Met Lys Pro Asp Ala
                165

<210> SEQ ID NO 17
<211> LENGTH: 162
<212> TYPE: PRT
<213> ORGANISM: Triticum aestivum
<220> FEATURE:
<221> NAME/KEY: misc_feature
<223> OTHER INFORMATION: Ceres CLONE ID no. 839727
<220> FEATURE:
<221> NAME/KEY: misc_feature
<222> LOCATION: (14)..(154)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 17
```

```
Met Ser Ala Ala Glu Gly Ala Val Val Phe Ser Glu Glu Lys Glu Ala
1               5                   10                  15

Leu Val Leu Lys Ser Trp Ala Ile Met Lys Lys Asp Ser Ala Asn Leu
            20                  25                  30

Gly Leu Arg Phe Phe Leu Lys Ile Phe Glu Ile Ala Pro Ser Ala Arg
            35                  40                  45

Gln Met Phe Pro Phe Leu Arg Asp Ser Asp Val Pro Leu Glu Thr Asn
    50                  55                  60

Pro Lys Leu Lys Thr His Ala Val Ser Val Phe Val Met Thr Cys Glu
65              70                  75                  80

Ala Ala Ala Gln Leu Arg Lys Ala Gly Lys Ile Thr Val Arg Glu Thr
                85                  90                  95

Thr Leu Lys Arg Leu Gly Gly Thr His Leu Lys Tyr Gly Val Ala Asp
            100                 105                 110

Gly His Phe Glu Val Thr Arg Phe Ala Leu Leu Glu Thr Ile Lys Glu
            115                 120                 125

Ala Leu Pro Ala Asp Met Trp Gly Pro Glu Met Arg Asn Ala Trp Gly
    130                 135                 140

Glu Ala Tyr Asp Gln Leu Val Ala Ala Ile Lys Gln Glu Met Lys Pro
145             150                 155                 160

Ser Glu

<210> SEQ ID NO 18
<211> LENGTH: 169
<212> TYPE: PRT
<213> ORGANISM: Triticum aestivum
<220> FEATURE:
<221> NAME/KEY: misc_feature
<223> OTHER INFORMATION: Public GI no. 14701800
<220> FEATURE:
<221> NAME/KEY: misc_feature
<222> LOCATION: (21)..(161)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 18

Met Ala Leu Val Glu Gly Asn Asn Gly Val Ser Gly Gly Ala Val Ser
1               5                   10                  15

Phe Ser Glu Glu Gln Glu Ala Leu Val Leu Lys Ser Trp Ala Ile Met
            20                  25                  30

Lys Lys Asp Ser Ala Asn Ile Gly Leu Arg Phe Phe Leu Lys Ile Phe
            35                  40                  45

Glu Val Ala Pro Ser Ala Ser Gln Met Phe Ser Phe Leu Arg Asn Ser
    50                  55                  60

Asp Val Pro Leu Glu Lys Asn Pro Lys Leu Lys Thr His Ala Met Ser
65              70                  75                  80

Val Phe Val Met Thr Cys Glu Ala Ala Ala Gln Leu Arg Lys Ala Gly
                85                  90                  95

Lys Val Thr Val Arg Asp Thr Thr Leu Lys Arg Leu Gly Ala Thr His
            100                 105                 110

Phe Lys Tyr Gly Val Gly Asp Ala His Phe Glu Val Thr Arg Phe Ala
            115                 120                 125

Leu Leu Glu Thr Ile Lys Glu Ala Val Pro Val Asp Met Trp Ser Pro
    130                 135                 140
```

Ala Met Lys Ser Ala Trp Ser Glu Ala Tyr Asn Gln Leu Val Ala Ala
145                 150                 155                 160

Ile Lys Gln Glu Met Lys Pro Ala Glu
                165

<210> SEQ ID NO 19
<211> LENGTH: 416
<212> TYPE: DNA
<213> ORGANISM: Arabidopsis thaliana
<220> FEATURE:
<221> NAME/KEY: misc_feature
<223> OTHER INFORMATION: Ceres CLONE ID no. 271922
<220> FEATURE:
<221> NAME/KEY: misc_feature
<223> OTHER INFORMATION: Ceres SEED LINE ID no. ME03944
<220> FEATURE:
<221> NAME/KEY: misc_feature
<223> OTHER INFORMATION: Encodes the protein at SEQ ID NO: 20

<400> SEQUENCE: 19
gctcattagg gtttctcatc tacgacggcg tggtgttcct ccttcctgct ctgaaaaatg      60
gcgaagagaa cgaagaaggt tggaatcgtc ggcaaatacg gaacacgtta tggtgcgagt     120
atcaggaagc agattaagaa gatggaggtc agccagcaca gcaagtactt ctgtgagttc     180
tgtggcaagt acggagtgaa gcgaaaggct gttggtatct ggggttgcaa ggattgtggc     240
aaggtcaagg caggtggtgc ttacacaatg aacaccgcca gtgcggtcac tgttagaagc     300
acgatcagaa ggttgaggga gcagatcgag ggttaaaagt ctgctggctt tttatatttg     360
gtttccttgt tttgacaatt taagttttgc atcaacagtg agaacatgtt ttgatt         416

<210> SEQ ID NO 20
<211> LENGTH: 92
<212> TYPE: PRT
<213> ORGANISM: Arabidopsis thaliana
<220> FEATURE:
<221> NAME/KEY: misc_feature
<223> OTHER INFORMATION: Ceres CLONE ID no. 271922
<220> FEATURE:
<221> NAME/KEY: misc_feature
<223> OTHER INFORMATION: Ceres SEED LINE ID no. ME03944
<220> FEATURE:
<221> NAME/KEY: misc_feature
<222> LOCATION: (2)..(91)
<223> OTHER INFORMATION: Pfam Name: Ribosomal_L37ae;
      Pfam Description: Ribosomal L37ae protein family

<400> SEQUENCE: 20

Met Ala Lys Arg Thr Lys Lys Val Gly Ile Val Gly Lys Tyr Gly Thr
1               5                   10                  15

Arg Tyr Gly Ala Ser Ile Arg Lys Gln Ile Lys Lys Met Glu Val Ser
                20                  25                  30

Gln His Ser Lys Tyr Phe Cys Glu Phe Cys Gly Lys Tyr Gly Val Lys
            35                  40                  45

Arg Lys Ala Val Gly Ile Trp Gly Cys Lys Asp Cys Gly Lys Val Lys
        50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Ile Glu Gly
                85                  90

<210> SEQ ID NO 21
<211> LENGTH: 92
<212> TYPE: PRT
<213> ORGANISM: Arabidopsis thaliana

```
<220> FEATURE:
<221> NAME/KEY: misc_feature
<223> OTHER INFORMATION: Public GI no. 4090257
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no.
      271922 given in SEQ ID NO: 20

<400> SEQUENCE: 21
```

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Phe Phe Cys Glu Phe Cys Gly Lys Phe Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Leu Asn Thr Pro Ser Ala Val Thr Val Arg
65                  70                  75                  80

Ser Thr Ile Arg Arg Leu Arg Glu Gln Thr Glu Gly
                85                  90

```
<210> SEQ ID NO 22
<211> LENGTH: 92
<212> TYPE: PRT
<213> ORGANISM: Arabidopsis thaliana
<220> FEATURE:
<221> NAME/KEY: misc_feature
<223> OTHER INFORMATION: Public GI no. 4741896
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no.
      271922 given in SEQ ID NO: 20

<400> SEQUENCE: 22
```

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Tyr Phe Cys Glu Phe Cys Gly Lys Tyr Ala Val Lys
        35                  40                  45

Arg Lys Ala Val Gly Ile Trp Gly Cys Lys Ala Cys Gly Lys Val Lys
    50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Ser
                85                  90

```
<210> SEQ ID NO 23
<211> LENGTH: 92
<212> TYPE: PRT
<213> ORGANISM: Arabidopsis thaliana
<220> FEATURE:
<221> NAME/KEY: misc_feature
<223> OTHER INFORMATION: Ceres CLONE ID no. 36046
```

-continued

```
<220> FEATURE:
<221> NAME/KEY: misc_feature
<222> LOCATION: (2)..(91)
<223> OTHER INFORMATION: Pfam Name: Ribosomal_L37ae
     Pfam Description: Ribosomal L37ae protein family
<220> FEATURE:
<221> NAME/KEY: misc_feature
<222> LOCATION: (45)..(45)
<223> OTHER INFORMATION: Xaa is any aa, unknown, or other
<220> FEATURE:
<221> NAME/KEY: misc_feature
<222> LOCATION: (49)..(49)
<223> OTHER INFORMATION: Xaa is any aa, unknown, or other
<220> FEATURE:
<221> NAME/KEY: misc_feature
<223> OTHER INFORMATION: Functional homolog of Ceres Clone ID no.
     271922 given in SEQ ID NO: 20

<400> SEQUENCE: 23

Met Ala Lys Arg Thr Lys Lys Val Gly Ile Val Gly Lys Tyr Gly Thr
1               5                   10                  15

Arg Tyr Gly Ala Ser Ile Arg Lys Gln Ile Lys Lys Met Glu Val Ser
            20                  25                  30

Gln His Ser Lys Tyr Phe Cys Glu Phe Cys Gly Lys Xaa Gly Val Lys
        35                  40                  45

Xaa Lys Ala Val Gly Ile Trp Gly Cys Lys Asp Cys Gly Lys Val Lys
50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Ile Glu Gly
                85                  90

<210> SEQ ID NO 24
<211> LENGTH: 92
<212> TYPE: PRT
<213> ORGANISM: Arabidopsis thaliana
<220> FEATURE:
<221> NAME/KEY: misc_feature
<223> OTHER INFORMATION: Public GI no. 6016699
<220> FEATURE:
<221> NAME/KEY: misc_feature
<222> LOCATION: (2)..(91)
<223> OTHER INFORMATION: Pfam Name: Ribosomal_L37ae
     Pfam Description: Ribosomal L37ae protein family
<220> FEATURE:
<221> NAME/KEY: misc_feature
<223> OTHER INFORMATION: Functional homolog of Ceres Clone ID no.
     271922 given in SEQ ID NO: 20

<400> SEQUENCE: 24

Met Thr Lys Arg Thr Lys Lys Ala Arg Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Asn Lys Tyr Phe Cys Glu Phe Cys Gly Lys Tyr Ser Val Lys
        35                  40                  45

Arg Lys Val Val Gly Ile Trp Gly Cys Lys Asp Cys Gly Lys Val Lys
50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ser
                85                  90

<210> SEQ ID NO 25
<211> LENGTH: 92
```

```
<212> TYPE: PRT
<213> ORGANISM: Glycine max
<220> FEATURE:
<221> NAME/KEY: misc_feature
<223> OTHER INFORMATION: Ceres CLONE ID no. 664936
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no.
      271922 given in SEQ ID NO: 20

<400> SEQUENCE: 25

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Phe Phe Cys Glu Phe Cys Gly Lys Tyr Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Gly
                85                  90

<210> SEQ ID NO 26
<211> LENGTH: 92
<212> TYPE: PRT
<213> ORGANISM: Glycine max
<220> FEATURE:
<221> NAME/KEY: misc_feature
<223> OTHER INFORMATION: Ceres CLONE ID no. 658438
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no.
      271922 given in SEQ ID NO: 20

<400> SEQUENCE: 26

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Tyr Phe Cys Glu Phe Cys Gly Lys Phe Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90

<210> SEQ ID NO 27
<211> LENGTH: 92
<212> TYPE: PRT
<213> ORGANISM: Glycine max
<220> FEATURE:
```

```
<221> NAME/KEY: misc_feature
<223> OTHER INFORMATION: Ceres CLONE ID no. 1049262
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no.
      271922 given in SEQ ID NO: 20

<400> SEQUENCE: 27

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
                20                  25                  30

Gln His Ser Lys Phe Phe Cys Glu Phe Cys Gly Lys Tyr Ala Val Lys
            35                  40                  45

Arg Lys Ala Val Gly Ile Trp Gly Cys Lys Asp Cys Gly Lys Val Lys
    50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Ser
                85                  90

<210> SEQ ID NO 28
<211> LENGTH: 92
<212> TYPE: PRT
<213> ORGANISM: Triticum aestivum
<220> FEATURE:
<221> NAME/KEY: misc_feature
<223> OTHER INFORMATION: Ceres CLONE ID no. 632613
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no.
      271922 given in SEQ ID NO: 20

<400> SEQUENCE: 28

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
                20                  25                  30

Gln His Ser Lys Tyr Phe Cys Glu Phe Cys Gly Lys Phe Ala Val Lys
            35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90

<210> SEQ ID NO 29
<211> LENGTH: 92
<212> TYPE: PRT
<213> ORGANISM: Zea mays
<220> FEATURE:
<221> NAME/KEY: misc_feature
<223> OTHER INFORMATION: Ceres CLONE ID no. 1390976
<220> FEATURE:
```

```
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no.
      271922 given in SEQ ID NO: 20

<400> SEQUENCE: 29
```

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
                20                  25                  30

Gln His Ser Lys Tyr Phe Cys Glu Phe Cys Gly Lys Phe Ala Val Lys
            35                  40                  45

Arg Lys Ala Val Gly Ile Trp Gly Cys Lys Asp Cys Gly Lys Val Lys
        50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90

```
<210> SEQ ID NO 30
<211> LENGTH: 92
<212> TYPE: PRT
<213> ORGANISM: Zea mays
<220> FEATURE:
<221> NAME/KEY: misc_feature
<223> OTHER INFORMATION: Ceres CLONE ID no. 1457185
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no.
      271922 given in SEQ ID NO: 20

<400> SEQUENCE: 30
```

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
                20                  25                  30

Gln His Ser Lys Tyr Phe Cys Glu Phe Cys Gly Lys Phe Ala Val Lys
            35                  40                  45

Arg Lys Ala Val Gly Ile Trp Gly Cys Lys Asp Cys Gly Lys Val Lys
        50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90

```
<210> SEQ ID NO 31
<211> LENGTH: 92
<212> TYPE: PRT
<213> ORGANISM: Zea mays
<220> FEATURE:
<221> NAME/KEY: misc_feature
<223> OTHER INFORMATION: Public GI no. 56202147
<220> FEATURE:
<221> NAME/KEY: misc_feature
<222> LOCATION: (2)..(91)
<223> OTHER INFORMATION: Pfam Name: Ribosomal_L37ae
```

```
            Pfam Description: Ribosomal L37ae protein family
<220> FEATURE:
<221> NAME/KEY: misc_feature
<223> OTHER INFORMATION: Functional homolog of Ceres Clone ID no.
      271922 given in SEQ ID NO: 20

<400> SEQUENCE: 31

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Tyr Phe Cys Glu Phe Cys Gly Lys Phe Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90

<210> SEQ ID NO 32
<211> LENGTH: 92
<212> TYPE: PRT
<213> ORGANISM: Zea mays
<220> FEATURE:
<221> NAME/KEY: misc_feature
<223> OTHER INFORMATION: Public GI no. 58578274
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no.
      271922 given in SEQ ID NO: 20

<400> SEQUENCE: 32

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Glu Tyr Phe Cys Glu Phe Cys Gly Lys Tyr Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Ser
                85                  90

<210> SEQ ID NO 33
<211> LENGTH: 632
<212> TYPE: DNA
<213> ORGANISM: Arabidopsis thaliana
<220> FEATURE:
<221> NAME/KEY: misc_feature
<223> OTHER INFORMATION: Ceres CLONE ID no. 2403_FL
<220> FEATURE:
<221> NAME/KEY: misc_feature
<223> OTHER INFORMATION: Encodes the protein at SEQ ID NO: 34

<400> SEQUENCE: 33
attccccatc gcacagaccc gcctaagaat ccgagagaga agaagagata atgcagatct    60
```

-continued

```
tcgtcaaaac cctcaccggc aaaactataa ccctagaggt tgagagcagc gacaccatcg    120
acaatgttaa agccaaaatc caggacaaat agggcatacc acctgatcaa cagaggctga    180
tttttgctgg taagcaattg gaagatggcc ggaccttagc tgactacaac atccagaaag    240
agtctactct tcatcttgtc ctcaggctca gaggtggaac catgatcaag gtgaagacac    300
tcactggaaa agaaatcgag attgatatcg aaccaaccga cactattgat cggatcaaag    360
aacgtgttga agagaaagaa ggcatccctc ctgttcaaca aaggctcatc tatgccggaa    420
aacagcttgc tgatgacaaa acggccaaag attatgcgat agagggaggc tctgttcttc    480
atttggttct tgctcttagg ggtggtcttc tctgatctga ataaataagc ttttcaacaa    540
acatctttcc cctcactatt gtcctccttt tgtggaattc atgacacaca aaaattgcta    600
tgggaaattg gaatattatg atgttttttc tc                                   632
```

<210> SEQ ID NO 34
<211> LENGTH: 154
<212> TYPE: PRT
<213> ORGANISM: Arabidopsis thaliana
    220>
<221> NAME/KEY: misc_feature
<223> OTHER INFORMATION: Ceres CLONE ID no. 2403_FL
<220> FEATURE:
<221> NAME/KEY: misc_feature
<222> LOCATION: (1)..(74)
<223> OTHER INFORMATION: Pfam Name: ubiquitin
    Pfam Description: Ubiquitin family
<220> FEATURE:
<221> NAME/KEY: misc_feature
<222> LOCATION: (77)..(150)
<223> OTHER INFORMATION: Pfam Name: ubiquitin
    Pfam Description: Ubiquitin family
<220> FEATURE:
<221> NAME/KEY: misc_feature
<223> OTHER INFORMATION: Functional homolog of Ceres Clone ID no. 2403
    given in SEQ ID NO: 40

<400> SEQUENCE: 34

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Thr Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Ala Lys Asp Tyr Ala Ile Glu Gly Gly Ser Val Leu His
    130                 135                 140

Leu Val Leu Ala Leu Arg Gly Gly Leu Leu
145                 150

<210> SEQ ID NO 35
<211> LENGTH: 154

```
<212> TYPE: PRT
<213> ORGANISM: Zea mays
<220> FEATURE:
<221> NAME/KEY: misc_feature
<223> OTHER INFORMATION: Ceres CLONE ID no. 1482731
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 35

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Thr Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Ala Lys Asp Tyr Asn Ile Glu Gly Gly Ser Val Leu His
    130                 135                 140

Leu Val Leu Ala Leu Arg Gly Gly Ser Asp
145                 150

<210> SEQ ID NO 36
<211> LENGTH: 154
<212> TYPE: PRT
<213> ORGANISM: Glycine max
<220> FEATURE:
<221> NAME/KEY: misc_feature
<223> OTHER INFORMATION: Ceres CLONE ID no. 522921
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 36

Met Gln Ile Phe Val Lys Thr Leu Thr Gly Lys Thr Ile Thr Leu Glu
1               5                   10                  15
```

```
Val Glu Ser Ser Asp Thr Ile Asp Asn Val Lys Ala Lys Ile Gln Asp
             20                  25                  30

Lys Glu Gly Ile Pro Pro Asp Gln Gln Arg Leu Ile Phe Ala Gly Lys
         35                  40                  45

Gln Leu Glu Asp Gly Arg Thr Leu Ala Asp Tyr Asn Ile Gln Lys Glu
 50                  55                  60

Ser Thr Leu His Leu Val Leu Arg Leu Arg Gly Gly Thr Met Ile Lys
 65                  70                  75                  80

Val Lys Thr Leu Thr Gly Lys Glu Ile Glu Ile Asp Ile Glu Pro Thr
                 85                  90                  95

Asp Thr Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Ala Lys Glu Tyr Asn Ile Glu Gly Gly Ser Val Leu His
    130                 135                 140

Leu Val Leu Ala Leu Arg Gly Gly Thr Tyr
145                 150

<210> SEQ ID NO 37
<211> LENGTH: 147
<212> TYPE: PRT
<213> ORGANISM: Brassica napus
<220> FEATURE:
<221> NAME/KEY: misc_feature
<223> OTHER INFORMATION: Ceres CLONE ID no. 1036726
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(142)
<223> OTHER INFORMATION: Pfam Name: ubiquitin
      Pfam Description: Ubiquitin family
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 37

Met Gln Ile Phe Val Lys Thr Leu Thr Gly Lys Thr Ile Thr Leu Glu
1               5                  10                  15

Val Glu Ser Ser Asp Thr Ile Asp Asn Val Lys Ala Lys Ile Gln Asp
             20                  25                  30

Lys Glu Gly Ile Pro Pro Asp Gln Gln Arg Leu Ile Phe Ala Gly Lys
         35                  40                  45

Gln Leu Glu Asp Gly Arg Thr Leu Ala Asp Tyr Asn Ile Gln Lys Glu
 50                  55                  60

Ser Thr Leu His Leu Val Leu Arg Leu Arg Gly Gly Thr Met Ile Lys
 65                  70                  75                  80

Val Lys Thr Leu Thr Gly Lys Glu Ile Glu Ile Asp Ile Glu Pro Thr
                 85                  90                  95

Asp Thr Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
```

```
                115                 120                 125
Asp Lys Thr Xaa Lys Asp Tyr Asn Ile Glu Gly Gly Ser Val Ser Ala
        130                 135                 140

Ser Gly Ser
145

<210> SEQ ID NO 38
<211> LENGTH: 153
<212> TYPE: PRT
<213> ORGANISM: Glycine max
<220> FEATURE:
<221> NAME/KEY: misc_feature
<223> OTHER INFORMATION: Ceres CLONE ID no. 513071
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<222> LOCATION: (146)..(146)
<223> OTHER INFORMATION: Xaa can be any naturally occurring amino acid
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 38

Met Gln Ile Phe Val Lys Thr Leu Thr Gly Lys Thr Ile Thr Leu Glu
1               5                   10                  15

Val Glu Ser Ser Asp Thr Val Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Ser Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Ala Lys Asp Tyr Asn Ile Glu Gly Gly Ser Val Leu His
    130                 135                 140

Leu Xaa Leu Ala Leu Arg Gly Gly Tyr
145                 150

<210> SEQ ID NO 39
<211> LENGTH: 620
<212> TYPE: DNA
<213> ORGANISM: Artificial Sequence
<220> FEATURE:
<223> OTHER INFORMATION: Ceres CLONE ID no. 2403
<220> FEATURE:
<221> NAME/KEY: misc_feature
<223> OTHER INFORMATION: Ceres SEED LINE ID no. ME05304
<220> FEATURE:
<221> NAME/KEY: misc_feature
```

<223> OTHER INFORMATION: Encodes the protein at SEQ ID NO: 40

<400> SEQUENCE: 39

```
attccccatc gcacagaccc ccctaagaat ccgagagaga agaagagata atgcagatct      60
tcgtcaaaac cctcaccggc aaaactataa ccctagaagt tgagagcagc gacaccatcg     120
acaatgttaa agccaaaatc caggacaaag agggcatacc acctgatcaa cagaggctga     180
ttttgctgg taagcaattg gaagatggcc ggaccttagc tgattacaac atccagaaag      240
agtctactct tcatcttgtc ctcaggctca gaggtggaac catgatcaag gtgaagacac     300
tcactggaaa agaaatcgag attgatatcg aaccaaccga cactattgat cggatcaaag     360
aacgtgttga agagaaagaa ggcatccctc ctgttcaaca aaggctcata tatgccggaa     420
aacagcttgc tgatgacaaa acggccaaag attatgcgat agagggaggc tctgttcttc     480
atttggttct tgctcttagg ggtggtcttc tctgatctta ataaataagc ttttcaacaa     540
acatcttttc cctcactatt gtcctcctta tgtggaattc atgacacacc aaaattgcta     600
tgggaaattg gaatattatg                                                  620
```

<210> SEQ ID NO 40
<211> LENGTH: 33
<212> TYPE: PRT
<213> ORGANISM: Artificial Sequence
<220> FEATURE:
<223> OTHER INFORMATION: Ceres CLONE ID no. 2403
<220> FEATURE:
<221> NAME/KEY: misc_feature
<223> OTHER INFORMATION: Ceres SEED LINE ID no. ME05304
<220> FEATURE:
<221> NAME/KEY: misc_feature
<222> LOCATION: (1)..(33)
<223> OTHER INFORMATION: Pfam Name: ubiquitin
      Pfam Description: Ubiquitin family

<400> SEQUENCE: 40

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys
```

<210> SEQ ID NO 41
<211> LENGTH: 1106
<212> TYPE: DNA
<213> ORGANISM: Glycine max
<220> FEATURE:
<221> NAME/KEY: misc_feature
<223> OTHER INFORMATION: Ceres CLONE ID no. 674166
<220> FEATURE:
<221> NAME/KEY: misc_feature
<223> OTHER INFORMATION: Ceres SEED LINE ID no. ME03186
<220> FEATURE:
<221> NAME/KEY: misc_feature
<223> OTHER INFORMATION: Encodes the protein at SEQ ID NO: 42

<400> SEQUENCE: 41

```
atatttttgt gtagatgaag atcaacaaga gaaggtgttg ttgtgagttg tgttgttatg      60
gtaccttcct tcaaccacaa aacctctctc cctctaccac ccattctctt ctctctctct     120
ctctcccgtc ctccatctct caccttctca atctcttcac caccaccatc atcatcatta     180
tcttctccaa tctctataac ctcgaaatcc ctcaaaacct ctccctcaaa ccaaatgaaa     240
tgaccctttt gtgagaacat tttttccccc ttaagaaaag gtcaaaggct gcaactttt     300
```

```
cttaaccaat ctcacatttt tttatttttc aacgtatttt ggccaggttt ggttttctgg      360
gttgtcttgg aattcaaaaa agattccaac tttgaagatg ggtaggggtg gaaccgccgc      420
ggcggcggcg gaggtcgccg aacccggttt aaggccggtt tatttcaaag aacagcgata      480 tagggggcgtc agaaaaagac cgtggggccg gttcgctgcc gaaatcagag acccttttgaa     540 gaaagccagg gtttggctcg gaacctttga caccgccgag gaggcggcgc gtgcctacga      600
cacggcggcg agaaccctcc ggggaccaaa ggcgaagacc aatttccctc tttctccgcc      660
gttctaccat cccgatccat tttccgatca ccggcacttc gccaacaccg gcgaagattt      720
ccacgatcac cggcgaccaa catccagtgg catgagcagc accgtagagt ccttcagcgg      780 ccccccgtgct gccgtgccgg cgacagcgcc ggtggccacc ggccggagat atccccggac      840 gccaccgtt atccccgagg actgccgcag cgactgcgat tcgtcgtcct ccgtcgttga      900
cgacggcgaa ggcgacaacg tggcgtcgtc gttcccgcga gaaccgttgc cgtttgatct      960
aaacgcgttg ccgttagacg atgctgacgt ggcaaccgat gatctgttct gcaccgttct     1020
ttgcctctga tgagaaaaaa tgaaaaaacg gaacgaaatg atgtatttgg ttcgttgacg     1080
gaattattat tattttttc tttctt                                            1106
```

<210> SEQ ID NO 42
<211> LENGTH: 210
<212> TYPE: PRT
<213> ORGANISM: Glycine max
<220> FEATURE:
<221> NAME/KEY: misc_feature
<223> OTHER INFORMATION: Ceres CLONE ID no. 674166
<220> FEATURE:
<221> NAME/KEY: misc_feature
<223> OTHER INFORMATION: Ceres SEED LINE ID no. ME03186
<220> FEATURE:
<221> NAME/KEY: misc_feature
<222> LOCATION: (26)..(89)
<223> OTHER INFORMATION: Pfam Name: AP2
    Pfam Description: AP2 domain
<220> FEATURE:
<221> NAME/KEY: misc_feature
<222> LOCATION: (26)..(89)
<223> OTHER INFORMATION: Pfam Name: AP2;
    Pfam Description: AP2 domain

<400> SEQUENCE: 42

Met Gly Arg Gly Gly Thr Ala Ala Ala Ala Glu Val Ala Glu Pro
1               5                   10                  15

Gly Leu Arg Pro Val Tyr Phe Lys Glu Gln Arg Tyr Arg Gly Val Arg
            20                  25                  30

Lys Arg Pro Trp Gly Arg Phe Ala Ala Glu Ile Arg Asp Pro Leu Lys
        35                  40                  45

Lys Ala Arg Val Trp Leu Gly Thr Phe Asp Thr Ala Glu Glu Ala Ala
    50                  55                  60

Arg Ala Tyr Asp Thr Ala Ala Arg Thr Leu Arg Gly Pro Lys Ala Lys
65                  70                  75                  80

Thr Asn Phe Pro Leu Ser Pro Pro Phe Tyr His Pro Asp Pro Phe Ser
                85                  90                  95

Asp His Arg His Phe Ala Asn Thr Gly Glu Asp Phe His Asp His Arg
            100                 105                 110

Arg Pro Thr Ser Ser Gly Met Ser Ser Thr Val Glu Ser Phe Ser Gly
        115                 120                 125

Pro Arg Ala Ala Val Pro Ala Thr Ala Pro Val Ala Thr Gly Arg Arg
    130                 135                 140

```
Tyr Pro Arg Thr Pro Pro Val Ile Pro Glu Asp Cys Arg Ser Asp Cys
145                 150                 155                 160

Asp Ser Ser Ser Val Val Asp Asp Gly Glu Gly Asp Asn Val Ala
            165                 170                 175

Ser Ser Phe Pro Arg Glu Pro Leu Pro Phe Asp Leu Asn Ala Leu Pro
            180                 185                 190

Leu Asp Asp Ala Asp Val Ala Thr Asp Asp Leu Phe Cys Thr Val Leu
            195                 200                 205

Cys Leu
    210

<210> SEQ ID NO 43
<211> LENGTH: 225
<212> TYPE: PRT
<213> ORGANISM: Glycine max
<220> FEATURE:
<221> NAME/KEY: misc_feature
<223> OTHER INFORMATION: Public GI no. 12322345
<220> FEATURE:
<221> NAME/KEY: misc_feature
<222> LOCATION: (26)..(89)
<223> OTHER INFORMATION: Pfam Name: AP2
      Pfam Description: AP2 domain
<220> FEATURE:
<221> NAME/KEY: misc_feature
<223> OTHER INFORMATION: Functional homolog of Ceres Clone ID no. 674166
      given in SEQ ID NO: 42

<400> SEQUENCE: 43

Met Arg Arg Gly Arg Gly Ser Ser Ala Val Ala Gly Pro Thr Val Val
1               5                   10                  15

Ala Ala Ile Asn Gly Ser Val Lys Glu Ile Arg Phe Arg Gly Val Arg
            20                  25                  30

Lys Arg Pro Trp Gly Arg Phe Ala Ala Glu Ile Arg Asp Pro Trp Lys
            35                  40                  45

Lys Ala Arg Val Trp Leu Gly Thr Phe Asp Ser Ala Glu Glu Ala Ala
    50                  55                  60

Arg Ala Tyr Asp Ser Ala Ala Arg Asn Leu Arg Gly Pro Lys Ala Lys
65                  70                  75                  80

Thr Asn Phe Pro Ile Asp Ser Ser Pro Pro Pro Asn Leu Arg
                85                  90                  95

Phe Asn Gln Ile Arg Asn Gln Asn Gln Asn Val Asp Pro Phe Met
                100                 105                 110

Asp His Arg Leu Phe Thr Asp His Gln Gln Gln Phe Pro Ile Val Asn
            115                 120                 125

Arg Pro Thr Ser Ser Ser Met Ser Ser Thr Val Glu Ser Phe Ser Gly
130                 135                 140

Pro Arg Pro Thr Thr Met Lys Pro Ala Thr Thr Lys Arg Tyr Pro Arg
145                 150                 155                 160

Thr Pro Pro Val Val Pro Glu Asp Cys His Ser Asp Cys Asp Ser Ser
            165                 170                 175

Ser Ser Val Ile Asp Asp Asp Asp Ile Ala Ser Ser Ser Arg Arg
            180                 185                 190

Arg Asn Pro Pro Phe Gln Phe Asp Leu Asn Phe Pro Pro Leu Asp Cys
            195                 200                 205

Val Asp Leu Phe Asn Gly Ala Asp Asp Leu His Cys Thr Asp Leu Arg
    210                 215                 220

Leu
225
```

```
<210> SEQ ID NO 44
<211> LENGTH: 215
<212> TYPE: PRT
<213> ORGANISM: Brassica napus
<220> FEATURE:
<221> NAME/KEY: misc_feature
<223> OTHER INFORMATION: Ceres CLONE ID no. 975672
<220> FEATURE:
<221> NAME/KEY: misc_feature
<222> LOCATION: (21)..(84)
<223> OTHER INFORMATION: Pfam Name: AP2
      Pfam Description: AP2 domain
<220> FEATURE:
<221> NAME/KEY: misc_feature
<222> LOCATION: (174)..(174)
<223> OTHER INFORMATION: Xaa is any aa, unknown, or other
<220> FEATURE:
<221> NAME/KEY: misc_feature
<222> LOCATION: (194)..(194)
<223> OTHER INFORMATION: Xaa is any aa, unknown, or other
<220> FEATURE:
<221> NAME/KEY: misc_feature
<222> LOCATION: (208)..(208)
<223> OTHER INFORMATION: Xaa is any aa, unknown, or other
<220> FEATURE:
<221> NAME/KEY: misc_feature
<222> LOCATION: (209)..(209)
<223> OTHER INFORMATION: Xaa is any aa, unknown, or other
<220> FEATURE:
<221> NAME/KEY: misc_feature
<222> LOCATION: (214)..(214)
<223> OTHER INFORMATION: Xaa is any aa, unknown, or other
<220> FEATURE:
<221> NAME/KEY: misc_feature
<223> OTHER INFORMATION: Functional homolog of Ceres Clone ID no. 674166
      given in SEQ ID NO: 42

<400> SEQUENCE: 44

Met Arg Lys Gly Arg Gly Ser Ser Ala Val Pro Pro Ala Leu Pro Gly
1               5                   10                  15

Ser Val Lys Glu Pro Arg Tyr Arg Gly Val Arg Lys Arg Pro Trp Gly
            20                  25                  30

Arg Phe Ala Ala Glu Ile Arg Asp Pro Leu Lys Lys Ser Arg Val Trp
        35                  40                  45

Leu Gly Thr Phe Asp Ser Ala Glu Glu Ala Ala Arg Ala Tyr Asp Ala
    50                  55                  60

Ala Ala Arg Asn Leu Arg Gly Pro Lys Ala Lys Thr Asn Phe Gln Ile
65                  70                  75                  80

Asp Cys Ser Pro Ser Ser Pro Leu Gln Pro Leu His His Arg Asn Gln
                85                  90                  95

Ile Asp Pro Phe Met Asp His Arg Leu Tyr Gly Gly Glu Gln Glu Val
            100                 105                 110

Val Ile Ile Ser Arg Pro Ala Ser Ser Ser Met Ser Ser Thr Val Lys
        115                 120                 125

Ser Cys Ser Gly Val Arg Pro Ala Ser Ser Val Ala Lys Ala Ala
    130                 135                 140

Thr Lys Arg Tyr Pro Arg Thr Pro Val Ala Pro Glu Asp Cys Arg
145                 150                 155                 160

Ser Asp Cys Asp Ser Ser Ser Val Val Glu Asp Gly Xaa Asp Ile
                165                 170                 175

Ala Ser Ser Ser Ser Arg Arg Lys Pro Pro Phe Glu Phe Asp Leu Asn
            180                 185                 190

Phe Xaa Pro Leu Asp Gly Val Asp Leu Phe Val Gly Ala Asp Asp Xaa
        195                 200                 205
```

```
Xaa Cys Thr Asp Leu Xaa Leu
    210             215

<210> SEQ ID NO 45
<211> LENGTH: 211
<212> TYPE: PRT
<213> ORGANISM: Zea mays
<220> FEATURE:
<221> NAME/KEY: misc_feature
<223> OTHER INFORMATION: Ceres CLONE ID no. 273307
<220> FEATURE:
<221> NAME/KEY: misc_feature
<222> LOCATION: (17)..(80)
<223> OTHER INFORMATION: Pfam Name: AP2
      Pfam Description: AP2 domain
<220> FEATURE:
<221> NAME/KEY: misc_feature
<223> OTHER INFORMATION: Functional homolog of Ceres Clone ID no. 674166
      given in SEQ ID NO: 42

<400> SEQUENCE: 45

Met Arg Arg Arg Gly Val Ala Ala Asp Ala Asp Gly Asp Val Glu
1               5                   10                  15

Leu Arg Phe Arg Gly Val Arg Lys Arg Pro Trp Gly Arg Tyr Ala Ala
            20                  25                  30

Glu Ile Arg Asp Pro Ala Lys Lys Ala Arg Val Trp Leu Gly Thr Phe
        35                  40                  45

Asp Ser Ala Glu Asp Ala Ala Arg Ala Tyr Asp Ala Ala Ala Arg Met
    50                  55                  60

Leu Arg Gly Pro Lys Ala Arg Thr Asn Phe Pro Leu Pro Ala Ala Ala
65                  70                  75                  80

Ala Leu His His Pro His Met Pro Ala Ala Ala Ala Ala Ala Ala Pro
                85                  90                  95

Pro Tyr Thr Thr Tyr Pro Thr Ala Thr Gly Val Val Ser Thr Pro Pro
            100                 105                 110

Val Ala Arg Pro Ala Cys Ser Ser Leu Ser Ser Thr Val Glu Ser Phe
        115                 120                 125

Ser Gly Ala Arg Pro Arg Pro Val Leu Pro Pro Arg Phe Pro Pro Pro
    130                 135                 140

Ser Ile Pro Asp Gly Asp Cys Arg Ser Asp Cys Gly Ser Ser Ala Ser
145                 150                 155                 160

Val Val Asp Asp Asp Cys Thr Asp Ala Ala Ala Ser Ala Ser Cys Pro
                165                 170                 175

Phe Pro Leu Pro Phe Asp Leu Asn Leu Pro Pro Gly Gly Gly Gly Ala
            180                 185                 190

Gly Val Gly Phe Tyr Ala Asp Glu Glu Asp Glu Leu Arg Leu Thr Ala
        195                 200                 205

Leu Arg Leu
    210

<210> SEQ ID NO 46
<211> LENGTH: 194
<212> TYPE: PRT
<213> ORGANISM: Triticum aestivum
<220> FEATURE:
<221> NAME/KEY: misc_feature
<223> OTHER INFORMATION: Ceres CLONE ID no. 1055099
<220> FEATURE:
<221> NAME/KEY: misc_feature
<222> LOCATION: (20)..(83)
<223> OTHER INFORMATION: Pfam Name: AP2
      Pfam Description: AP2 domain
```

```
<220> FEATURE:
<221> NAME/KEY: misc_feature
<223> OTHER INFORMATION: Functional homolog of Ceres Clone ID no. 674166
      given in SEQ ID NO: 42

<400> SEQUENCE: 46
```

Met Arg Lys Ala Arg Pro Pro Gln Pro Gln Pro Gln Pro Ser Gln Gln
1               5                   10                  15

Ser Pro Glu Ile Arg Tyr Arg Gly Val Arg Lys Arg Pro Ser Gly Arg
            20                  25                  30

Tyr Ala Ala Glu Ile Arg Asp Pro Ala Lys Lys Thr Pro Ile Trp Leu
        35                  40                  45

Gly Thr Phe Asp Cys Ala Glu Asp Ala Ala Arg Ala Tyr Asp Ser Ala
    50                  55                  60

Ala Arg Ser Leu Arg Gly Pro Thr Ala Arg Thr Asn Phe Pro Pro Ser
65                  70                  75                  80

Ser Ala Thr Gln Pro Pro Arg Pro Pro Pro Ala Ala Ala
                85                  90                  95

Ala Ala Ala Thr Ser Ser Gln Ser Ser Thr Val Glu Ser Trp Ser Gly
            100                 105                 110

Gly Gly Pro Arg Ala Pro Ala Arg Ala Arg Ser Ala Ala Arg Ala Gly
            115                 120                 125

Thr Ala Lys Glu Gly Glu Glu Asp Cys Arg Ser Tyr Cys Gly Ser Ser
        130                 135                 140

Ser Ser Val Leu Leu Glu Glu Gly Ala Asp Asp Ala Ala Ala Ser Arg
145                 150                 155                 160

Ser Pro Leu Pro Phe Asp Leu Asn Met Pro Pro Pro Gln Glu Gly Ala
                165                 170                 175

Leu Asp Ala Glu Ala Asp Gln Met Thr Cys Arg Tyr Asp Thr Leu Leu
            180                 185                 190

Arg Leu

```
<210> SEQ ID NO 47
<211> LENGTH: 660
<212> TYPE: DNA
<213> ORGANISM: Populus balsamifera subsp. trichocarpa
<220> FEATURE:
<221> NAME/KEY: misc_feature
<223> OTHER INFORMATION: Ceres ANNOT ID no.1441430
<220> FEATURE:
<221> NAME/KEY: misc_feature
<223> OTHER INFORMATION: Encodes the protein at SEQ ID NO: 48

<400> SEQUENCE: 47
atggggagaa caagaacaac aacaaaacag gctgttgacc caaatggatc tgcaacccaa      60
aatatgttag taattgcaaa agagcccaga tacagaggag tacgaaagag accatgggga     120
agattcgctg cggagattag agatccctgg aaaaagacca gagtttggct gggcaccttc     180
gactctgcag aggatgcagc gcgtgcctac gatgcggctg ctcgcaccct ccgcggagca     240
aaggccaaga caaactttcc tatctccaca acgaaccagt tattcaatca tcaaaatcaa     300
aaccaaagcc caaccgatcc cttcttggat caccacagta taaatcccca aagacccaca     360
tctagcagtt tgagcagtac agtggagtct ttcagcggtc ctaggcctcc gcagccaaca     420
acaacaacaa aatcgggaaa tgggccgagg agatctcatc cacggatccc accggttgtt     480
ccagaagatt gtcatagcga ttgcgattca tcttcttcgg tggttgatga cagagatgtc     540
gcatccgctg cttcttcttt gtgccgcaag cctttgcctt cgatctaaa tttcccaccg      600
```
ttggaccagg ttgacttggg ctctggtgat gatctccact gcactgcttt atgcctttga    660

<210> SEQ ID NO 48
<211> LENGTH: 219
<212> TYPE: PRT
<213> ORGANISM: Populus balsamifera subsp. trichocarpa
<220> FEATURE:
<221> NAME/KEY: misc_feature
<223> OTHER INFORMATION: Ceres ANNOT ID no. 1441430
<220> FEATURE:
<221> NAME/KEY: misc_feature
<222> LOCATION: (29)..(92)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 48

Met Gly Arg Thr Arg Thr Thr Lys Gln Ala Val Asp Pro Asn Gly
1               5                   10                  15

Ser Ala Thr Gln Asn Met Leu Val Ile Ala Lys Glu Pro Arg Tyr Arg
            20                  25                  30

Gly Val Arg Lys Arg Pro Trp Gly Arg Phe Ala Ala Glu Ile Arg Asp
        35                  40                  45

Pro Trp Lys Lys Thr Arg Val Trp Leu Gly Thr Phe Asp Ser Ala Glu
    50                  55                  60

Asp Ala Ala Arg Ala Tyr Asp Ala Ala Arg Thr Leu Arg Gly Ala
65                  70                  75                  80

Lys Ala Lys Thr Asn Phe Pro Ile Ser Thr Thr Asn Gln Leu Phe Asn
                85                  90                  95

His Gln Asn Gln Asn Gln Ser Pro Thr Asp Pro Phe Leu Asp His His
            100                 105                 110

Ser Ile Asn Pro Gln Arg Pro Thr Ser Ser Ser Leu Ser Ser Thr Val
        115                 120                 125

Glu Ser Phe Ser Gly Pro Arg Pro Pro Gln Pro Thr Thr Thr Thr Lys
    130                 135                 140

Ser Gly Asn Gly Pro Arg Arg Ser His Pro Arg Ile Pro Pro Val Val
145                 150                 155                 160

Pro Glu Asp Cys His Ser Asp Cys Asp Ser Ser Ser Val Val Asp
                165                 170                 175

Asp Arg Asp Val Ala Ser Ala Ala Ser Ser Leu Cys Arg Lys Pro Leu
            180                 185                 190

Pro Phe Asp Leu Asn Phe Pro Pro Leu Asp Gln Val Asp Leu Gly Ser
        195                 200                 205

Gly Asp Asp Leu His Cys Thr Ala Leu Cys Leu
    210                 215

<210> SEQ ID NO 49
<211> LENGTH: 985
<212> TYPE: DNA
<213> ORGANISM: Glycine max
<220> FEATURE:
<221> NAME/KEY: misc_feature
<223> OTHER INFORMATION: Ceres CLONE ID no.1240330
<220> FEATURE:
<221> NAME/KEY: misc_feature
<223> OTHER INFORMATION: Encodes the protein at SEQ ID NO: 50

<400> SEQUENCE: 49
attattcctc ttccatctct attctccata acacccacca caccacttgt gaaaaacctc    60

-continued

```
attaatatca cacactgaca tgtatctctg agctccaatc caatacaaga ccacaccttg    120
tcgtgtcgga cgaaccttgg tgtctgtttt ttttttttt tcattatttt ctccgaagag      180
atgaggaagg gcagaggtgg aggcgcctcg gcggcggcgg tggatgtgaa cggatccatt    240
ttaaaggagc ctcggtaccg gggcgtgagg aagagaccgt gggggagatt cgccgcggag    300
atcagagacc cgttgaagaa agccagggtt tggttgggaa ccttcgattc tgccgaggat    360
gctgctcgtg cctacgacgc cgccgctcgg actctccgag gtcccaaggc caaaacaaat    420 ttccccctc tctcaccttt ttgctatcca caccccacca ccgatccttt cttctacact     480
ggtttccacg atcaacacca ccaccacaac aacaacaacc ttaacaaccc tcaaagaccc    540
acttcaagtg gcatgagtag caccgttgag tccttcagtg ggccccgccc tcccaccacc    600
accactacca ccacaaccac aactgcgacg ccgttttga ctgctacgcg agataccccg     660
cgcactcccc ctcttgtccc tgaagactgc cacagtgact gcgactcttc ctcctccgtc    720
gttgacgacg gcgacgacaa catcgtttcg tcgtcgtttc gacctccctt gccgtttgat    780
ctcaacgcgc tgccgtttga tgatgctgcc gcggatgatg atctacgccg caccgcgctt    840
tgtctctgat gatgattatc gtgcgatgat gatttttaat ttctcatttt tttacttgat    900
ttttttgtta ttgctatgca gaagaaatat atatttaaaa tgatgatcag atgtaagatt    960 atggtaaatat gatcttaatt ctgtg                                         985
```

<210> SEQ ID NO 50
<211> LENGTH: 222
<212> TYPE: PRT
<213> ORGANISM: Glycine max
<220> FEATURE:
<221> NAME/KEY: misc_feature
<223> OTHER INFORMATION: Ceres CLONE ID no. 1240330
<220> FEATURE:
<221> NAME/KEY: misc_feature
<222> LOCATION: (24)..(87)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 50

```
Met Arg Lys Gly Arg Gly Gly Ala Ser Ala Ala Val Asp Val
1               5                   10                  15

Asn Gly Ser Ile Leu Lys Glu Pro Arg Tyr Arg Gly Val Arg Lys Arg
            20                  25                  30

Pro Trp Gly Arg Phe Ala Ala Glu Ile Arg Asp Pro Leu Lys Lys Ala
        35                  40                  45

Arg Val Trp Leu Gly Thr Phe Asp Ser Ala Glu Asp Ala Ala Arg Ala
    50                  55                  60

Tyr Asp Ala Ala Ala Arg Thr Leu Arg Gly Pro Lys Ala Lys Thr Asn
65                  70                  75                  80

Phe Pro Pro Leu Ser Pro Phe Cys Tyr Pro His Pro Thr Thr Asp Pro
                85                  90                  95

Phe Phe Tyr Thr Gly Phe His Asp Gln His His His Asn Asn Asn
            100                 105                 110

Asn Leu Asn Asn Pro Gln Arg Pro Thr Ser Ser Gly Met Ser Ser Thr
        115                 120                 125

Val Glu Ser Phe Ser Gly Pro Arg Pro Thr Thr Thr Thr Thr
    130                 135                 140
```

```
Thr Thr Thr Thr Ala Thr Pro Phe Leu Thr Ala Thr Arg Arg Tyr Pro
145                 150                 155                 160

Arg Thr Pro Pro Leu Val Pro Glu Asp Cys His Ser Asp Cys Asp Ser
            165                 170                 175

Ser Ser Ser Val Val Asp Asp Gly Asp Asp Asn Ile Val Ser Ser Ser
        180                 185                 190

Phe Arg Pro Pro Leu Pro Phe Asp Leu Asn Ala Leu Pro Phe Asp Asp
    195                 200                 205

Ala Ala Ala Asp Asp Asp Leu Arg Arg Thr Ala Leu Cys Leu
    210                 215                 220

<210> SEQ ID NO 51
<211> LENGTH: 726
<212> TYPE: DNA
<213> ORGANISM: Zea mays
<220> FEATURE:
<221> NAME/KEY: misc_feature
<223> OTHER INFORMATION: Ceres CLONE ID no.1382611
<220> FEATURE:
<221> NAME/KEY: misc_feature
<223> OTHER INFORMATION: Encodes the protein at SEQ ID NO: 52

<400> SEQUENCE: 51
acttttctct cccattcttt tacaactcac gttgcacagc cttttttctct atatattact    60 tgacataaac tactattcac aacacaaaca cacacataac catggcctct tcttcacaag   120
ctttcctttt gctcacattg tctatggttt tagttcattt ctctttagct caatctccca   180
tgatggctcc ttctggctcc atgtccatgc cgccaatgcc tagcggcggc tctccaatgc   240
caatgatgac tccaccacct atgccaatga tgactccacc acctatggct atggctccac   300
cacctatgcc tatgactcca ccaccaatgc ccatggctcc gatgccaatg actccatctt   360
caagtccaat gagcccacca actactatgg ccccaagtcc agaaacagtc cctgatatgg   420
cttcgccacc gatgatgcca ggaatggatt cttctcctcc tccgggaccc atgccaccgg   480
caatggcctc tccagattcc ggagcattca atgtaagaaa cgacgtcgta gcaatttcgt   540
tccttgttgc agctcatttg ctcctagttt gagattatta ttaaattggc cagcgtcgtg   600
tttgtgtaat ttactttcat ttttttctcg agccattaat tttcatgttt tatcatatat   660
ttgggtttgt gtttgatatg gtacgattca gacatttgtt tgcttaataa gtttatcgtt   720
gactct                                                              726

<210> SEQ ID NO 52
<211> LENGTH: 156
<212> TYPE: PRT
<213> ORGANISM: Zea mays
<220> FEATURE:
<221> NAME/KEY: misc_feature
<223> OTHER INFORMATION: Ceres CLONE ID no. 1382611
<220> FEATURE:
<221> NAME/KEY: misc_feature
<223> OTHER INFORMATION: Functional Homolog of Ceres CLONE ID no. 30087
      Given in SEQ ID NO: 2

<400> SEQUENCE: 52

Met Ala Ser Ser Ser Gln Ala Phe Leu Leu Leu Thr Leu Ser Met Val
1               5                   10                  15

Leu Val His Phe Ser Leu Ala Gln Ser Pro Met Met Ala Pro Ser Gly
            20                  25                  30

Ser Met Ser Met Pro Pro Met Pro Ser Gly Gly Ser Pro Met Pro Met
        35                  40                  45
```

Met Thr Pro Pro Pro Met Pro Met Met Thr Pro Pro Pro Met Ala Met
50                  55                      60

Ala Pro Pro Pro Met Pro Met Thr Pro Pro Pro Met Pro Met Ala Pro
65                  70                      75                      80

Met Pro Met Thr Pro Ser Ser Ser Pro Met Ser Pro Pro Thr Thr Met
                85                      90                      95

Ala Pro Ser Pro Glu Thr Val Pro Asp Met Ala Ser Pro Pro Met Met
            100                     105                     110

Pro Gly Met Asp Ser Ser Pro Ser Pro Gly Pro Met Pro Pro Ala Met
            115                     120                     125

Ala Ser Pro Asp Ser Gly Ala Phe Asn Val Arg Asn Asp Val Val Ala
            130                     135                     140

Ile Ser Phe Leu Val Ala Ala His Leu Leu Leu Val
145                 150                     155

<210> SEQ ID NO 53
<211> LENGTH: 580
<212> TYPE: DNA
<213> ORGANISM: Papaver somniferum
<220> FEATURE:
<221> NAME/KEY: misc_feature
<223> OTHER INFORMATION: Ceres CLONE ID no.1627907
<220> FEATURE:
<221> NAME/KEY: misc_feature
<223> OTHER INFORMATION: Encodes the protein at SEQ ID NO: 54

<400> SEQUENCE: 53
gcagaagcac aaggtaagat tgaaggagga gaccggaact cttcttcgcc aaaaccctag       60
ttcgagctca ccaacaacaa tctttcgcaa tgactaagcg taccaagaag gccggaattg      120
tgggtaaata tggtaccaga tatggagctt cattaaggaa acagattaag aagatggaag      180
tgagtcagca tgcaaagtac ttctgtgagt tctgcggaaa gtacgctgtg aagagacagg      240
ctgttggaat ctggggatgc aaggattgtg gcaaagttaa agctggtggt gcttacactt      300
tgaacaccgc cagtgccgtg acagttagaa gcaccattag aaggttgagg gagcaaactg      360
aatcttagat tgatctcgtt atctatattt tgtattttgg tactgggtga gaggtaccat      420
cagagctaat ttagtgttta tcaccttttc tggtcttcaa gaactagtta gtcattttgt      480
tattcagaga tttttgataa tgtctagtat cttacatttg tgagcagact atttctttgt      540
ttcaaattat ggagttctga tgaatcttat atttattctc                            580

<210> SEQ ID NO 54
<211> LENGTH: 92
<212> TYPE: PRT
<213> ORGANISM: Papaver somniferum
<220> FEATURE:
<221> NAME/KEY: misc_feature
<223> OTHER INFORMATION: Ceres CLONE ID no. 1627907
<220> FEATURE:
<221> NAME/KEY: misc_feature
<222> LOCATION: (2)..(91)
<223> OTHER INFORMATION: Pfam Name: Ribosomal_L37ae
    Pfam Description: Ribosomal L37ae protein family
<220> FEATURE:
<221> NAME/KEY: misc_feature
<223> OTHER INFORMATION: Functional Homolog of Ceres CLONE ID no. 271922
    Given in SEQ ID NO: 20

<400> SEQUENCE: 54

Met Thr Lys Arg Thr Lys Lys Ala Gly Ile Val Gly Lys Tyr Gly Thr
1               5                   10                  15

```
Arg Tyr Gly Ala Ser Leu Arg Lys Gln Ile Lys Lys Met Glu Val Ser
                20                  25                  30

Gln His Ala Lys Tyr Phe Cys Glu Phe Cys Gly Lys Tyr Ala Val Lys
            35                  40                  45

Arg Gln Ala Val Gly Ile Trp Gly Cys Lys Asp Cys Gly Lys Val Lys
        50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Ser
                85                  90

<210> SEQ ID NO 55
<211> LENGTH: 983
<212> TYPE: DNA
<213> ORGANISM: Panicum virgatum
<220> FEATURE:
<221> NAME/KEY: misc_feature
<223> OTHER INFORMATION: Ceres CLONE ID no.1761125
<220> FEATURE:
<221> NAME/KEY: misc_feature
<223> OTHER INFORMATION: Encodes the protein at SEQ ID NO: 56

<400> SEQUENCE: 55
accagaccac accacaccac accgcgtcca catcctcccg cgcttctccg ctcagcccgc      60
gcgtttccgc tgaggaggga tagccgcgcg gcgcgtcgag gggtttgtct ttgatcgggt     120
agctgaggct gagcgggcgg ggcaggatga tgcgcgacac ggcggccgtg gccgtggcgg     180
cgccgcggta caggggcgtg cggaagcggc cgtggggccg gttcgcggcg gagatccgcg     240
acccggcgaa gcgcgcgcgc gtctggctcg gcaccttcga ctccgccgag gccgcggcgc     300
gcgcctacga cgtcgccgcg cggacccctgc gcggcccgct cgccaggacc aacttccccct     360 gcgcctcctc ccgcctcccg ctgccctccc gccaccaagg cggctgtggc ggcggcctcg     420
tcgcgccgcc gccgccgcg ccgacgtgca gctccagctc caccgtcgag tcctccagcg     480
gaccccgagg ggcgcccagg gctgctgcgg cggcggcgcc tcgaattcgg aggcggtcgg     540
tgaaaaagcc gcggccggca gcgccgcgaca tcgactgcca cagcgactgc gcctcgtcgg     600
cctccgtcgt ggacgacggc gacgacgcct ccacggtccg gtcgcgcgcg ccgttcgacc     660
tcaacgtccc ggctccggtg gacggtgacc acgccctcga cctctgcacg gagctgcggc     720
tctgagcaat atgatcctcg aacaacaaca acagcaaaac attgaaggcg attttccccc     780
ggtcttcttt tcctgactaa attctgatat gatcaatatg ctcgagagtt ctcgtttct     840 ttaacgcctc ttgtatttgg atctgctacc atcttctctg cccattctat ttgtacacca     900
gataacatgt aagatgttca cgaattaaca catatctttt cttaaaaaaa tgaattaaca     960
cggaaaaaaa aaaaaaaaaa aaa                                             983

<210> SEQ ID NO 56
<211> LENGTH: 192
<212> TYPE: PRT
<213> ORGANISM: Panicum virgatum
<220> FEATURE:
<221> NAME/KEY: misc_feature
<223> OTHER INFORMATION: Ceres CLONE ID no. 1761125
<220> FEATURE:
<221> NAME/KEY: misc_feature
<222> LOCATION: (13)..(76)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
```

Given in SEQ ID NO: 42

<400> SEQUENCE: 56

```
Met Met Arg Asp Thr Ala Ala Val Ala Val Ala Ala Pro Arg Tyr Arg
1               5                   10                  15

Gly Val Arg Lys Arg Pro Trp Gly Arg Phe Ala Ala Glu Ile Arg Asp
            20                  25                  30

Pro Ala Lys Arg Ala Arg Val Trp Leu Gly Thr Phe Asp Ser Ala Glu
        35                  40                  45

Ala Ala Ala Arg Ala Tyr Asp Val Ala Ala Arg Thr Leu Arg Gly Pro
    50                  55                  60

Leu Ala Arg Thr Asn Phe Pro Cys Ala Ser Ser Arg Leu Pro Leu Pro
65                  70                  75                  80

Ser Arg His Gln Gly Gly Cys Gly Gly Gly Leu Val Ala Pro Pro
                85                  90                  95

Ala Ala Pro Thr Cys Ser Ser Ser Thr Val Glu Ser Ser Ser Gly
            100                 105                 110

Pro Arg Gly Ala Pro Arg Ala Ala Ala Ala Ala Pro Arg Ile Arg
            115                 120                 125

Arg Arg Ser Val Lys Lys Pro Arg Pro Ala Ala Pro Asp Ile Asp Cys
130                 135                 140

His Ser Asp Cys Ala Ser Ser Ala Ser Val Val Asp Asp Gly Asp Asp
145                 150                 155                 160

Ala Ser Thr Val Arg Ser Arg Ala Pro Phe Asp Leu Asn Val Pro Ala
                165                 170                 175

Pro Val Asp Gly Asp His Ala Leu Asp Leu Cys Thr Glu Leu Arg Leu
            180                 185                 190
```

<210> SEQ ID NO 57
<211> LENGTH: 594
<212> TYPE: DNA
<213> ORGANISM: Panicum virgatum
<220> FEATURE:
<221> NAME/KEY: misc_feature
<223> OTHER INFORMATION: Ceres CLONE ID no.1783890
<220> FEATURE:
<221> NAME/KEY: misc_feature
<223> OTHER INFORMATION: Encodes the protein at SEQ ID NO: 58

<400> SEQUENCE: 57

```
gagccctacc cgcacccgcg ccgccgccgc cccgcgcccc gtcgccgcag acgactccgc    60
cccgtcgccg cgatgacgaa gcgcaccaag aaggccggaa tcgtcggcaa atatggaact   120
aggtatggtg ctagcttgcg taagcaaatc aagaagatgg aggtgtctca gcactccaag   180
tacttctgcg agttctgtgg aaagtttgct gtgaaaagga aagcagttgg aatctgggga   240
tgcaaggact gcgggaaggt taaggctggt ggtgcttaca ccatgaacac tgctagtgca   300
gtcaccgtca ggagcacaat ccgtcgcttg agggagcaga ctgaagcata atcggagctc   360
ttctctgcag tagtcctgtg cttttttgtac cgtctaagac atatggctgt ttggcctaag   420
aacattcatg aatattctgg ttatgcttaa ggatatcaaa aattatggtg ctaaaatttg   480
tacttcgttg ctgttgcaaa gttgacctgt cttgatccat tcataatgta gaatttcctc   540
atggttctta tctccagttt gctactcttt ggccaaaaaa aaaaaaaaaa aaaa          594
```

<210> SEQ ID NO 58
<211> LENGTH: 92
<212> TYPE: PRT
<213> ORGANISM: Panicum virgatum

```
<220> FEATURE:
<221> NAME/KEY: misc_feature
<223> OTHER INFORMATION: Ceres CLONE ID no. 1783890
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional Homolog of Ceres CLONE ID no. 271922
      Given in SEQ ID NO: 20

<400> SEQUENCE: 58

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
                20                  25                  30

Gln His Ser Lys Tyr Phe Cys Glu Phe Cys Gly Lys Phe Ala Val Lys
            35                  40                  45

Arg Lys Ala Val Gly Ile Trp Gly Cys Lys Asp Cys Gly Lys Val Lys
        50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90

<210> SEQ ID NO 59
<211> LENGTH: 880
<212> TYPE: DNA
<213> ORGANISM: Panicum virgatum
<220> FEATURE:
<221> NAME/KEY: misc_feature
<223> OTHER INFORMATION: Ceres CLONE ID no.1802327
<220> FEATURE:
<221> NAME/KEY: misc_feature
<223> OTHER INFORMATION: Encodes the protein at SEQ ID NO: 60

<400> SEQUENCE: 59
acacagatac attcgtcgat ccaccactgt ccagtgcttg gcggttacgc acgcacgcac    60
acagatagga ttatctttta ctacaccaac tcaccaagat actagcaagc cgaatcgaca   120
aacaagcagc aggaagagga ggcatggcgc tcgcggaggg gaacgtcatc ttcggcgagg   180
agcaggaggc gctggtgctc aagtcgtggg ccctcatgaa gaaggactcg gccgacctcg   240
gcctccgctt cttcctcaag atcttcgaga tcgcgccgtc ggcgaagcag atgttctcgt   300
tcctgcgcga ctccgacgtg ccgctcgaga agaaccccaa gctcaagaac cacgccatgt   360
ccgtcttcgt catgacctgc gaggcggcgg cgcagctacg gaaggccggg aaggtcaccg   420
tcagggagac gacgctcaag cggctggcg ccacgcactt caagtacggc gtcgccgacg   480
gccacttcga ggtgacgagg ttcgcgctgc tggagacgat aaaggaggcg cttcccgccg   540
acatgtggag cctggagatg aagaacgcct ggagcgaggc ttacaaccag ctggtggcgg   600
ccatcaagca ggagatgaag cctgccgcat gatgctgctg ctgctactga gatgaagcct   660
gcccgcatga tgctgctgct gctactcggc ctccgcgctg agttccccct acgatgcacc   720
accatctcca aattcttcat cgctgttttt ttttttttgc tgttttgact tgtattgtgc   780
attttccaaa tctctcgatg gagacaagtg tgatgactaa ttttttgagag catgtatata   840 tgttgtgatg agcattgaat aaaaaaaaaa aaaaaaaaa                          880

<210> SEQ ID NO 60
```

```
<211> LENGTH: 162
<212> TYPE: PRT
<213> ORGANISM: Panicum virgatum
<220> FEATURE:
<221> NAME/KEY: misc_feature
<223> OTHER INFORMATION: Ceres CLONE ID no. 1802327
<220> FEATURE:
<221> NAME/KEY: misc_feature
<222> LOCATION: (14)..(154)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 60
```

Met Ala Leu Ala Glu Gly Asn Val Ile Phe Gly Glu Glu Gln Glu Ala
1               5                  10                  15

Leu Val Leu Lys Ser Trp Ala Leu Met Lys Lys Asp Ser Ala Asp Leu
            20                  25                  30

Gly Leu Arg Phe Phe Leu Lys Ile Phe Glu Ile Ala Pro Ser Ala Lys
        35                  40                  45

Gln Met Phe Ser Phe Leu Arg Asp Ser Asp Val Pro Leu Glu Lys Asn
    50                  55                  60

Pro Lys Leu Lys Asn His Ala Met Ser Val Phe Val Met Thr Cys Glu
65                  70                  75                  80

Ala Ala Ala Gln Leu Arg Lys Ala Gly Lys Val Thr Val Arg Glu Thr
                85                  90                  95

Thr Leu Lys Arg Leu Gly Ala Thr His Phe Lys Tyr Gly Val Ala Asp
            100                 105                 110

Gly His Phe Glu Val Thr Arg Phe Ala Leu Leu Glu Thr Ile Lys Glu
        115                 120                 125

Ala Leu Pro Ala Asp Met Trp Ser Leu Glu Met Lys Asn Ala Trp Ser
130                 135                 140

Glu Ala Tyr Asn Gln Leu Val Ala Ala Ile Lys Gln Glu Met Lys Pro
145                 150                 155                 160

Ala Ala

```
<210> SEQ ID NO 61
<211> LENGTH: 1017
<212> TYPE: DNA
<213> ORGANISM: Gossypium hirsutum
<220> FEATURE:
<221> NAME/KEY: misc_feature
<223> OTHER INFORMATION: Ceres CLONE ID no.1838364
<220> FEATURE:
<221> NAME/KEY: misc_feature
<223> OTHER INFORMATION: Encodes the protein at SEQ ID NO: 62

<400> SEQUENCE: 61
cctgcccatt tccatcttcc ttctttcctt cctctttcct ttgtcttctt gctttatctt     60 cccttatct tcaatctttt ctgttctgtt ttttcttag attcataggt aagttcgttt     120
tggttggctt gattatttcc tcacttccct tcttttttgg ttcatcgtga tcttttcatc    180 aaccccttt gattgttata tagattgtta ctattctttt aatctttaa atattttttt     240 tccatgagga gagggagagg tgccgcagct gcaaacgccg tagctaggag accggcactg    300
caacccagcg gatctattaa agagccgaga tacagaggtg ttagaaaaag gccatggggc    360
agattcgcgg ccgagattcg agacccttgg aagaagacca gggtctggtt agggacgttc    420
gactcggccg aagaagccgc tcgagcctac gatacggcgg cgaggacgct ccgtggaccc    480
```

```
aaagctaaaa caaatttccc cataaattct tcaaatatcc cggcttttcc tttcgaaacc      540
aatcatcacc acaacgaagg gttcatcgac caacgccggt tatatccgat gggcgaattt      600
catgaccccg aagtgaatcc acagagaccc acgaggagta gcatgagtag cacggtggag      660
tcgtttagtg gacccagacc ggcccaacca ccgcaaaagt cggcggactt cgcggtggtt      720
tcgactagga agtactatcc gaggccgccg ccagtagagc cagaggattg tcatagtgac      780
tgtgattcat catcgtcggt ggttgatgat ggggatatcg cgttgtcttc ttgtcggaaa      840
actttgcctt tcgatctcaa ttttccaccc ttggatgaag atggaagatc tccagtgtac      900
tgctttatgt ctttgatcgc gatgccggtg atgaatgatg atgatcgatt attggatctc      960 ttttctttt ttaaaaaatg ttagctttt taagcggaaa aaaaaaaaaa aaaaaa         1017
```

<210> SEQ ID NO 62
<211> LENGTH: 246
<212> TYPE: PRT
<213> ORGANISM: Gossypium hirsutum
<220> FEATURE:
<221> NAME/KEY: misc_feature
<223> OTHER INFORMATION: Ceres CLONE ID no. 1838364
<220> FEATURE:
<221> NAME/KEY: misc_feature
<222> LOCATION: (28)..(91)
<223> OTHER INFORMATION: Pfam Name: AP2
    Pfam Description: AP2 domain
<220> FEATURE:
<221> NAME/KEY: misc_feature
<223> OTHER INFORMATION: Functional Homolog of Ceres CLONE ID no. 674166
    Given in SEQ ID NO: 42

<400> SEQUENCE: 62

```
Met Arg Arg Gly Arg Gly Ala Ala Ala Ala Asn Ala Val Ala Arg
1               5                   10                  15

Pro Ala Leu Gln Pro Ser Gly Ser Ile Lys Glu Pro Arg Tyr Arg Gly
                20                  25                  30

Val Arg Lys Arg Pro Trp Gly Arg Phe Ala Ala Glu Ile Arg Asp Pro
            35                  40                  45

Trp Lys Lys Thr Arg Val Trp Leu Gly Thr Phe Asp Ser Ala Glu Glu
    50                  55                  60

Ala Ala Arg Ala Tyr Asp Thr Ala Ala Arg Thr Leu Arg Gly Pro Lys
65                  70                  75                  80

Ala Lys Thr Asn Phe Pro Ile Asn Ser Ser Asn Ile Pro Ala Phe Pro
                85                  90                  95

Phe Glu Thr Asn His His His Asn Glu Gly Phe Ile Asp Gln Arg Arg
                100                 105                 110

Leu Tyr Pro Met Gly Glu Phe His Asp Pro Glu Val Asn Pro Gln Arg
            115                 120                 125

Pro Thr Arg Ser Ser Met Ser Ser Thr Val Glu Ser Phe Ser Gly Pro
    130                 135                 140

Arg Pro Ala Gln Pro Pro Gln Lys Ser Ala Asp Phe Ala Val Val Ser
145                 150                 155                 160

Thr Arg Lys Tyr Tyr Pro Arg Pro Pro Val Glu Pro Glu Asp Cys
                165                 170                 175

His Ser Asp Cys Asp Ser Ser Ser Val Val Asp Ala Gly Asp Ile
                180                 185                 190

Ala Leu Ser Ser Cys Arg Lys Thr Leu Pro Phe Asp Leu Asn Phe Pro
            195                 200                 205

Pro Leu Asp Glu Asp Gly Arg Ser Pro Val Tyr Cys Phe Met Ser Leu
```

```
                    210                 215                 220
Ile Ala Met Pro Val Met Asn Asp Asp Asp Arg Leu Leu Asp Leu Phe
225                 230                 235                 240

Phe Phe Phe Lys Lys Cys
                245

<210> SEQ ID NO 63
<211> LENGTH: 708
<212> TYPE: DNA
<213> ORGANISM: Panicum virgatum
<220> FEATURE:
<221> NAME/KEY: misc_feature
<223> OTHER INFORMATION: Ceres CLONE ID no.1876458
<220> FEATURE:
<221> NAME/KEY: misc_feature
<223> OTHER INFORMATION: Encodes the protein at SEQ ID NO: 64

<400> SEQUENCE: 63
acacagatac attcgtcgat ccaccactgt ccagtgcttg gcggttacgc acgcacgcac     60
acagatagga ttatctttta ctacaccaac tcaccaagat actagcaagc cgaatcgaca    120
aacaagcagc aggaagagga ggcatggcgc tcgcggaggg gaacgtcatc ttcggcgagg    180
agcaggaggc gctggtgctc aagtcgtggg ccctcatgaa gaaggactcg gccgacctcg    240
gcctccgctt cttcctcaag atcttcgaga tcgcgccgtc ggcgaagcag atgttctcgt    300
tcctgcgcga ctccgacgtg ccgctcgaga gaaccccaa gctcaagacc cacgccatgt    360
ccgtcttcgt catgacctgc gaggcggcgg cgcagctacg gaaggccggg aaggtcaccg    420
tcagggagac gacgctcaag cggctgggcg ccacgcactt caagtacggc gtcgccgacg    480
gccacttcga ggtgacgagg ttcgcgctgc tggagacgat aaaggaggcg cttcccgccg    540
acatgtggag cctggagatg aagtacgcct ggagcgaggc ttacaaccag cttgtggcgg    600
ccatcaagca ggagatgaag cctgccgcat gatgctgctg ctgctactcg gcctccgcgc    660
tgagttcccc ctacgatgca ccaccatctc caaattcttc atcgctgt                 708

<210> SEQ ID NO 64
<211> LENGTH: 162
<212> TYPE: PRT
<213> ORGANISM: Panicum virgatum
<220> FEATURE:
<221> NAME/KEY: misc_feature
<223> OTHER INFORMATION: Ceres CLONE ID no. 1876458
<220> FEATURE:
<221> NAME/KEY: misc_feature
<222> LOCATION: (14)..(154)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 64

Met Ala Leu Ala Glu Gly Asn Val Ile Phe Gly Glu Glu Gln Glu Ala
1               5                   10                  15

Leu Val Leu Lys Ser Trp Ala Leu Met Lys Lys Asp Ser Ala Asp Leu
                20                  25                  30

Gly Leu Arg Phe Phe Leu Lys Ile Phe Glu Ile Ala Pro Ser Ala Lys
            35                  40                  45

Gln Met Phe Ser Phe Leu Arg Asp Ser Asp Val Pro Leu Glu Lys Asn
        50                  55                  60

Pro Lys Leu Lys Thr His Ala Met Ser Val Phe Val Met Thr Cys Glu
```

```
                65                  70                  75                  80
Ala Ala Ala Gln Leu Arg Lys Ala Gly Lys Val Thr Val Arg Glu Thr
                    85                  90                  95

Thr Leu Lys Arg Leu Gly Ala Thr His Phe Lys Tyr Gly Val Ala Asp
            100                 105                 110

Gly His Phe Glu Val Thr Arg Phe Ala Leu Leu Glu Thr Ile Lys Glu
        115                 120                 125

Ala Leu Pro Ala Asp Met Trp Ser Leu Glu Met Lys Tyr Ala Trp Ser
130                 135                 140

Glu Ala Tyr Asn Gln Leu Val Ala Ala Ile Lys Gln Glu Met Lys Pro
145                 150                 155                 160

Ala Ala
```

<210> SEQ ID NO 65
<211> LENGTH: 712
<212> TYPE: DNA
<213> ORGANISM: Panicum virgatum
<220> FEATURE:
<221> NAME/KEY: misc_feature
<223> OTHER INFORMATION: Ceres CLONE ID no.1879148
<220> FEATURE:
<221> NAME/KEY: misc_feature
<223> OTHER INFORMATION: Encodes the protein at SEQ ID NO: 66

<400> SEQUENCE: 65

```
acacagatac attcgtcgat ccaccactgt ccagtgctcg gctcggttac gcacgcacgc    60
acacaaattg tagtacctgt gttttacacc accaaagata ctagcaagcc gagtcgacaa   120
acaaagcagc aggaagaggc atggcgctcg ctgacgggaa cggcgcggcc atcttcggcg   180
aggagcagga ggcgctggtg ctcaagtcgt gggccctcat gaagaaggac tcggccgacc   240
tcggcctccg cttcttcctc aagatcttcg agatcgcgcc gtcggcgaag cagatgttct   300
cgttcctgcg cgactccgac gtgccgctgg agaagaaccc caagctcaag acccacgcca   360
tgtccgtctt cgtcatgacc tgcgaggcgg cagcgcagct acggaaggcc gggaaggtca   420
ccgtcaggga cgacgcgctc aagcggctgg gcgcaacgca cttcaagtac ggcgtcgccg   480
acggccactt cgaggtgaca aggttcgcgc tgctggagac gataaaggag gcgcttcccg   540
ccgacatgtg gagcctggag atgaagaacg cctggagcga ggcttacaac cagctcgtgg   600
cggccatcaa gcaggagatg aagcctgctg catgatgctg catgctgcta catactcggc   660
ctccgagttc ccctacgat gcaccaccat ctccaagttc ttcatcgcta tt            712
```

<210> SEQ ID NO 66
<211> LENGTH: 164
<212> TYPE: PRT
<213> ORGANISM: Panicum virgatum
<220> FEATURE:
<221> NAME/KEY: misc_feature
<223> OTHER INFORMATION: Ceres CLONE ID no. 1879148
<220> FEATURE:
<221> NAME/KEY: misc_feature
<222> LOCATION: (16)..(156)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 66

```
Met Ala Leu Ala Asp Gly Asn Gly Ala Ala Ile Phe Gly Glu Glu Gln
1               5                   10                  15
```

```
Glu Ala Leu Val Leu Lys Ser Trp Ala Leu Met Lys Lys Asp Ser Ala
             20                  25                  30

Asp Leu Gly Leu Arg Phe Phe Leu Lys Ile Phe Glu Ile Ala Pro Ser
         35                  40                  45

Ala Lys Gln Met Phe Ser Phe Leu Arg Asp Ser Asp Val Pro Leu Glu
     50                  55                  60

Lys Asn Pro Lys Leu Lys Thr His Ala Met Ser Val Phe Val Met Thr
 65                  70                  75                  80

Cys Glu Ala Ala Ala Gln Leu Arg Lys Ala Gly Lys Val Thr Val Arg
                 85                  90                  95

Glu Thr Thr Leu Lys Arg Leu Gly Ala Thr His Phe Lys Tyr Gly Val
                100                 105                 110

Ala Asp Gly His Phe Glu Val Thr Arg Phe Ala Leu Leu Glu Thr Ile
            115                 120                 125

Lys Glu Ala Leu Pro Ala Asp Met Trp Ser Leu Glu Met Lys Asn Ala
130                 135                 140

Trp Ser Glu Ala Tyr Asn Gln Leu Val Ala Ala Ile Lys Gln Glu Met
145                 150                 155                 160

Lys Pro Ala Ala

<210> SEQ ID NO 67
<211> LENGTH: 1129
<212> TYPE: DNA
<213> ORGANISM: Gossypium hirsutum
<220> FEATURE:
<221> NAME/KEY: misc_feature
<223> OTHER INFORMATION: Ceres CLONE ID no.1884696
<220> FEATURE:
<221> NAME/KEY: misc_feature
<223> OTHER INFORMATION: Encodes the protein at SEQ ID NO: 68

<400> SEQUENCE: 67
atccgccccc atttgttcgc tctgtatatt gaactttct ttctcgattt tctctttgaa      60
caaaaatgat gaagatcttc aaccagactc tcaccggcaa gactatcacg ctcgaggtcg    120
agagctccga caccatcgaa ggcgccaaca ccattctcca agatggaggg agcctccctc    180
cttaccgaac ccgactgatc ttcgccggac aacagcttga ggacggactg accttgtgcg    240
attacaacat cttaaaggag gtcaactctc cacctcttcc tccggttgcg cggtgggatg    300
cttaccttcc ggaggacctt gaccggcaat accatcactc tccaggtcta aagcgccgac    360
tcgatcaagt tcgttcacgc taacatccaa gactaggaag gcgtcccccc ataccaacta    420
cgactctgct tcgaccgaaa acaacttgaa gacggccgta ccttggccga ctacaacatc    480
cagaaggagt caacgctcca tcttgtcctt cgtttgcgtg gcgggatgca aatcttcgtt    540
aagacgctta cgggaaagac gatcactctc gaggtcgaga gctctgacac gatcgacaac    600
gtgaaagcca aaatccaaga caaggaaggc atcccgccag accagcaacg tctcatcttc    660
gccggaaagc aactcgagga cgggcggact ttagccgatt acaatatcca gaaggaatcg    720
actcttcatc tggtcctgcg tcttggaggt gggatgcaga tcttcgtcaa gactttgacc    780
ggtaagacga ttactttaga agtggagagc tcggatacga ttgataacgt gaaagcgaag    840
attcaggaca agaaggaat ccaccagat cagcaaggt tgattttgc tgggaaacaa    900 ctggaagacg gaaggacttt ggctgattac aatattcaaa aggattccac tcttcacctt    960
gttcttcgtc ttcgtggtgg gttctaagcc ttaaggtctc ccttaatgtg ggttttctgg   1020
ttttacgtga aggactgtgc cctgtaatgg ccttttaaat aatttctagt ctttgtttac   1080
```
cggttgcatc tatgtatggt ttctcttaga atggaattag catatttac            1129

<210> SEQ ID NO 68
<211> LENGTH: 153
<212> TYPE: PRT
<213> ORGANISM: Gossypium hirsutum
<220> FEATURE:
<221> NAME/KEY: misc_feature
<223> OTHER INFORMATION: Ceres CLONE ID no. 1884696
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional Homolog of Ceres CLONE ID no. 2403
      Given in SEQ ID NO: 40

<400> SEQUENCE: 68

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Gly Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Asp Ser Thr Leu His
    130                 135                 140

Leu Val Leu Arg Leu Arg Gly Gly Phe
145                 150

<210> SEQ ID NO 69
<211> LENGTH: 679
<212> TYPE: DNA
<213> ORGANISM: Gossypium hirsutum
<220> FEATURE:
<221> NAME/KEY: misc_feature
<223> OTHER INFORMATION: Ceres CLONE ID no.1916866
<220> FEATURE:
<221> NAME/KEY: misc_feature
<223> OTHER INFORMATION: Encodes the protein at SEQ ID NO: 70

<400> SEQUENCE: 69
aaatcaaata cctactgcaa ttaaaatccc ggaattactt aaacaacaat ggctacctat            60
gaaggtaaag ttttcactga agaacaagaa gctttggtgg tcaagtcatg gactgtaatg           120
aagaagaacg cagctgaatt gggtcttaaa ttcttcttga agatatttga gattgcacca           180
tcagccaaga aactattctc attcttgaga gactccaatg ttccattgga gcaaaacaca           240

```
aagctgaagc cccatgccat gtctgtcttt gtcatgacat gtgaatctgc agtgcaactg    300
cgtaaagcag gcaaagttac agtgagggaa tcaaatttga agaaattagg agctacccat    360
tttaagtatg gggtagttga tgaacatttt gaggtaacaa aatttgctct tttggagacc    420
ataaaagaag cagtaccaga tatgtggtca gatgagatga agaatgcatg gggtgaagcc    480
tatgatcgtt tggtcgcagc cattaaaata gaaatgaagg catgctcaca agctgcatga    540
tttcacaagt tccctacatt attgcttgtt aattttgggt ccaataagat tgaaagtttt    600
caatcattta aacatgtaat gtaacatagc tattgctcat cactactgtt ttttccccct    660
agtttgtttg ctcctgttc                                                 679
```

<210> SEQ ID NO 70
<211> LENGTH: 163
<212> TYPE: PRT
<213> ORGANISM: Gossypium hirsutum
<220> FEATURE:
<221> NAME/KEY: misc_feature
<223> OTHER INFORMATION: Ceres CLONE ID no. 1916866
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 70

Met Ala Thr Tyr Glu Gly Lys Val Phe Thr Glu Glu Gln Glu Ala Leu
1               5                   10                  15

Val Val Lys Ser Trp Thr Val Met Lys Lys Asn Ala Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met Thr Cys Glu Ser
65                  70                  75                  80

Ala Val Gln Leu Arg Lys Ala Gly Lys Val Thr Val Arg Glu Ser Asn
                85                  90                  95

Leu Lys Lys Leu Gly Ala Thr His Phe Lys Tyr Gly Val Val Asp Glu
            100                 105                 110

His Phe Glu Val Thr Lys Phe Ala Leu Leu Glu Thr Ile Lys Glu Ala
        115                 120                 125

Val Pro Asp Met Trp Ser Asp Glu Met Lys Asn Ala Trp Gly Glu Ala
    130                 135                 140

Tyr Asp Arg Leu Val Ala Ala Ile Lys Ile Glu Met Lys Ala Cys Ser
145                 150                 155                 160

Gln Ala Ala

<210> SEQ ID NO 71
<211> LENGTH: 1003
<212> TYPE: DNA
<213> ORGANISM: Panicum virgatum
<220> FEATURE:
<221> NAME/KEY: misc_feature
<223> OTHER INFORMATION: Ceres CLONE ID no.1950105
<220> FEATURE:
<221> NAME/KEY: misc_feature
<223> OTHER INFORMATION: Encodes the protein at SEQ ID NO: 72

<400> SEQUENCE: 71

```
atcgccacaa gttcgcgatc tctcgatttc acaaatcgcc gagaagaccc gagcagagaa      60
gttccctccg atcgccttgc caagatgcag atctttgtga agacactcac tggcaagact     120
atcacccttg aggtggagtc ttctgacaca attgacaatg tcaaggcaaa gatccaggac     180
aaggaaggga ttcctccaga ccagcagcgc cttatcttcg ctggcaagca gcttgaggat     240
ggccgtacac ttgcagatta caacattcag aaggagtcca cactgcacct tgtcctcagg     300
ctgcgtggag gcatgcagat tttcgtgaag accctcactg caagacgat caccctggag      360
gtggagtcat ctgacaccat cgacaatgtg aaggcaaaga tccaggacaa ggagggcatc     420
cccctgacc agcagcgcct catctttgca ggcaagcagt tggaggatgg gcgaactctg      480
gctgactaya atatccagaa agaatcmacc ctgcacctsg tsctccgcct gcgtggtgga     540
atgcagatct ttgtgaagac gcttaccggc aagaccatca ccttggaggt ggagtcttcg     600
gacaccatcg acaatgtgaa ggcgaagatt caggacaagg agggcattcc tccggaccag     660
crgcgcctca tctttgctgg caagcagcta gaggacgggc gtaccctggc ggattacaac     720
atccagaagg agtccaccct ccaccttgtc ctgcgcctcc gtggtggttt ctgagcctag     780
tgctcctgag ttgccttttg tcgttatggt caacctctgg tttaagtcgt gtgaactctc     840
tgcattgcgt tgctagtgtc tggttgtggt tgtaataaga acatgaagaa catgttgctg     900
tggatcacat gacttttttt ttttgaaccg gaagatcaca tgactttcat ggctttaagt     960
tcctgaactc tgaaatctgg accccctttt aagctctgaa ctc                      1003
```

<210> SEQ ID NO 72
<211> LENGTH: 229
<212> TYPE: PRT
<213> ORGANISM: Panicum virgatum
<220> FEATURE:
<221> NAME/KEY: misc_feature
<223> OTHER INFORMATION: Ceres CLONE ID no. 1950105
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<222> LOCATION: (153)..(226)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional Homolog of Ceres CLONE ID no. 2403
      Given in SEQ ID NO: 40
<220> FEATURE:
<221> NAME/KEY: misc_feature
<222> LOCATION: (135)..(135)
<223> OTHER INFORMATION: Xaa is any aa, unknown, or other
<220> FEATURE:
<221> NAME/KEY: misc_feature
<222> LOCATION: (141)..(141)
<223> OTHER INFORMATION: Xaa is any aa, unknown, or other
<220> FEATURE:
<221> NAME/KEY: misc_feature
<222> LOCATION: (145)..(145)
<223> OTHER INFORMATION: Xaa is any aa, unknown, or other
<220> FEATURE:
<221> NAME/KEY: misc_feature

```
<222> LOCATION: (146)..(146)
<223> OTHER INFORMATION: Xaa is any aa, unknown, or other
<220> FEATURE:
<221> NAME/KEY: misc_feature
<222> LOCATION: (193)..(193)
<223> OTHER INFORMATION: Xaa is any aa, unknown, or other

<400> SEQUENCE: 72
```

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Met Gln Ile Phe
65              70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Xaa Asn Ile Gln Lys Glu Xaa Thr Leu His
    130                 135                 140

Xaa Xaa Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
                165                 170                 175

Asn Val Lys Ala Lys Ile Gln Asp Lys Glu Gly Ile Pro Pro Asp Gln
            180                 185                 190

Xaa Arg Leu Ile Phe Ala Gly Lys Gln Leu Glu Asp Gly Arg Thr Leu
        195                 200                 205

Ala Asp Tyr Asn Ile Gln Lys Glu Ser Thr Leu His Leu Val Leu Arg
    210                 215                 220

Leu Arg Gly Gly Phe
225

```
<210> SEQ ID NO 73
<211> LENGTH: 724
<212> TYPE: DNA
<213> ORGANISM: Panicum virgatum
<220> FEATURE:
<221> NAME/KEY: misc_feature
<223> OTHER INFORMATION: Ceres CLONE ID no.1990746
<220> FEATURE:
<221> NAME/KEY: misc_feature
<222> LOCATION: (623)..(623)
<223> OTHER INFORMATION: n is a, c, t, g, unknown, or other
<220> FEATURE:
<221> NAME/KEY: misc_feature
<222> LOCATION: (624)..(624)
<223> OTHER INFORMATION: n is a, c, t, g, unknown, or other
<220> FEATURE:
<221> NAME/KEY: misc_feature
<222> LOCATION: (625)..(625)
<223> OTHER INFORMATION: n is a, c, t, g, unknown, or other
<220> FEATURE:
<221> NAME/KEY: misc_feature
<223> OTHER INFORMATION: Encodes the protein at SEQ ID NO: 74

<400> SEQUENCE: 73
```

-continued

```
acacagatac actcgtcgat ccaccagacc accactgtcc agtgctcggc tcggttacgc      60
acgcacgcac acaaatagga gtacctgttt tacaccacca agatactagc aagcccaagc     120
cgagtcgaca aacaagcagc aggaagaggc atggcgctcg cggaggggaa cggcgcggcc     180
atcttcggcg aggaacagga ggcgctggtg ctcaagtcgt gggccctcat gaagaaggac     240
tcggccgacc tcggcctccg cttcttcctc aagatcttcg agatcgcgcc gtcggcgaag     300
cagatgttct cgttcctgcg cgactccgac gtgccgctgg agaagaaccc caagctcaag     360
acccacgcca tgtccgtctt cgtcatgacc tgcgaggcgg cagtgcagct acggaaggcc     420
gggaaggtca ccgtcaggga gacgacgctc aagcggctgg gcgcaacgca cttcaagtac     480
ggcgtcgccg acggccactt cgaggtgaca aggttcgcgc tgctggagac gataaaggag     540
gcgcttcccg ccgacatgtg gagcctggag atgaagaacg cctggagcga ggcttacaac     600
cagctcgtgg cggccatcaa gcnnnagatg aagcctgccg catgatgctg catgctgcta     660
catactcggc ctccgagtcc cccctacgat gcaccaccat ctcccagttc ttcatcgcta     720
tttt                                                                  724
```

<210> SEQ ID NO 74
<211> LENGTH: 164
<212> TYPE: PRT
<213> ORGANISM: Panicum virgatum
<220> FEATURE:
<221> NAME/KEY: misc_feature
<223> OTHER INFORMATION: Ceres CLONE ID no. 1990746
<220> FEATURE:
<221> NAME/KEY: misc_feature
<222> LOCATION: (16)..(156)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7
<220> FEATURE:
<221> NAME/KEY: misc_feature
<222> LOCATION: (158)..(158)
<223> OTHER INFORMATION: Xaa is any aa, unknown, or other
<220> FEATURE:
<221> NAME/KEY: misc_feature
<222> LOCATION: (159)..(159)
<223> OTHER INFORMATION: Xaa is any aa, unknown, or other

<400> SEQUENCE: 74

```
Met Ala Leu Ala Glu Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met Thr
65                  70                  75                  80

Cys Glu Ala Ala Val Gln Leu Arg Lys Ala Gly Lys Val Thr Val Arg
                85                  90                  95

Glu Thr Thr Leu Lys Arg Leu Gly Ala Thr His Phe Lys Tyr Gly Val
            100                 105                 110

Ala Asp Gly His Phe Glu Val Thr Arg Phe Ala Leu Leu Glu Thr Ile
        115                 120                 125
```

-continued

```
Lys Glu Ala Leu Pro Ala Asp Met Trp Ser Leu Glu Met Lys Asn Ala
        130                 135                 140

Trp Ser Glu Ala Tyr Asn Gln Leu Val Ala Ala Ile Lys Xaa Xaa Met
145                 150                 155                 160

Lys Pro Ala Ala

<210> SEQ ID NO 75
<211> LENGTH: 696
<212> TYPE: DNA
<213> ORGANISM: Panicum virgatum
<220> FEATURE:
<221> NAME/KEY: misc_feature
<223> OTHER INFORMATION: Ceres CLONE ID no.2007485
<220> FEATURE:
<221> NAME/KEY: misc_feature
<223> OTHER INFORMATION: Encodes the protein at SEQ ID NO: 76

<400> SEQUENCE: 75
agagcagggg gatggaagaa aataaactac tggccaaacc ctagccgagc cccgggtccg      60
ctcaccgcct tcccaccccc ccacccaccc acctgccccc ccccccccc cgccctcgcc     120 gtccgcgatg cgccgggcga agccgccgca gccgcagccg tcgccgtcgc cggagatccg     180
gtaccgcggc gtgcggaggc ggccatcggg gcgctacgcc gccgagatcc gggacccggc     240
caagaagacc ccgatctggc tcggcacctt cgactccgcc gaggccgccg cgcgcgccta     300
cgacgccgcc gcccgatccc tccgcgggcc caccgcccgc accaacttcc ccagcgccgc     360 ggccccgcg ccgcggcaca gcaggccccc cgccccctcc gccgccgcgc aggcggctgc     420
cgcggcggca gcgccacgt ccagccacag cagcaccata gagtcgtgga gcgacggcgc     480
gacccgcgcc gcgctggcgc gtagcgctgc ctccgtcctg gcgcgcagcg ccgctccgac     540
ggaggaggaa gacgaggact gccgcagcta ctgcggatcc tcgtcgtccg tcctctgcga     600
agacactggg ggcgacgatg cggccgcctc ccgcgcgccc ctgccgttcg atctgaacct     660
gccgccgcct catgacgcgg cctccgagac cgatca                              696

<210> SEQ ID NO 76
<211> LENGTH: 201
<212> TYPE: PRT
<213> ORGANISM: Panicum virgatum
<220> FEATURE:
<221> NAME/KEY: misc_feature
<223> OTHER INFORMATION: Ceres CLONE ID no. 2007485
<220> FEATURE:
<221> NAME/KEY: misc_feature
<222> LOCATION: (17)..(80)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 76

Met Arg Arg Ala Lys Pro Pro Gln Pro Gln Pro Ser Pro Ser Pro Glu
1               5                   10                  15

Ile Arg Tyr Arg Gly Val Arg Arg Pro Ser Gly Arg Tyr Ala Ala
            20                  25                  30

Glu Ile Arg Asp Pro Ala Lys Lys Thr Pro Ile Trp Leu Gly Thr Phe
        35                  40                  45

Asp Ser Ala Glu Ala Ala Ala Arg Ala Tyr Asp Ala Ala Ala Arg Ser
    50                  55                  60

Leu Arg Gly Pro Thr Ala Arg Thr Asn Phe Pro Ser Ala Ala Ala Pro
```

```
            65                  70                  75                  80
Ala Pro Arg His Ser Arg Pro Ala Pro Ser Ala Ala Gln Ala
                    85                  90                  95

Ala Ala Ala Ala Ala Ala Thr Ser Ser His Ser Ser Thr Ile Glu
            100                 105                 110

Ser Trp Ser Asp Gly Ala Thr Arg Ala Ala Leu Ala Arg Ser Ala Ala
                115                 120                 125

Ser Val Leu Ala Arg Ser Ala Ala Pro Thr Glu Glu Glu Asp Glu Asp
            130                 135                 140

Cys Arg Ser Tyr Cys Gly Ser Ser Ser Val Leu Cys Glu Asp Thr
145                 150                 155                 160

Gly Gly Asp Asp Ala Ala Ala Ser Arg Ala Pro Leu Pro Phe Asp Leu
                165                 170                 175

Asn Leu Pro Pro Pro His Asp Ala Ala Ser Glu Thr Asp Gln Met Gly
                180                 185                 190

Ala Arg Tyr Asp Thr Leu Leu Arg Leu
                195                 200

<210> SEQ ID NO 77
<211> LENGTH: 698
<212> TYPE: DNA
<213> ORGANISM: Panicum virgatum
<220> FEATURE:
<221> NAME/KEY: misc_feature
<223> OTHER INFORMATION: Ceres CLONE ID no.2033803
<220> FEATURE:
<221> NAME/KEY: misc_feature
<223> OTHER INFORMATION: Encodes the protein at SEQ ID NO: 78

<400> SEQUENCE: 77
acacagatac attcgtcgat ccaccagacc accactgtcc agtgctcggc tcggttacgc      60
acgcacgcac acaaatagga gtacctgttt tacaccaaga tactagcaag cccaagccga     120
gtcgacaaac aagcagcagg aagaggcatg gcgctcgcgg aggggaacgg cgcggccatc     180
ttcggcgagg agcaggaggc gctggtgctc aagtcgtggg ccctcatgaa gaaggactcg     240
gccgacctcg gctccgcttc ttcctcaag atcttcgaga tcgcgccgtc ggcgaagcag      300
atgttctcgt tcctgcgcga ctccgacgtg ccgctggaga agaaccccaa gctcaagacc     360
cacgccatgt ccgtcttcgt catgacctgc gaggcggcag cgcagctacg gaaggccggg     420
aaggtcaccg tcagggagac gacgctcaag cggctgggcg caacgcactt caagtacggc     480
gtcgccgacg gccacttcga ggtgacaagg ttcgcgcttc ccgccgactt gtggagcctg     540
gagatgaaga acgcctggag cgaggcttac aaccagctcg tggcggccat caagcaggag     600
atgaagcctg ccgcatgatg ctgcatgctg ctacatactc ggcctccgag ttccccctac     660
gatgcaccac catctccaag ttctttcatt gtcttgtg                             698

<210> SEQ ID NO 78
<211> LENGTH: 156
<212> TYPE: PRT
<213> ORGANISM: Panicum virgatum
<220> FEATURE:
<221> NAME/KEY: misc_feature
<223> OTHER INFORMATION: Ceres CLONE ID no. 2033803
<220> FEATURE:
<221> NAME/KEY: misc_feature
<222> LOCATION: (16)..(148)
<223> OTHER INFORMATION: Pfam Name: Globin
      Pfam Description: Globin
<220> FEATURE:
<221> NAME/KEY: misc_feature
```

<223> OTHER INFORMATION: Functional homolog of Ceres Clone ID no. 30469
      given in SEQ ID NO: 7

<400> SEQUENCE: 78

Met Ala Leu Ala Glu Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met Thr
65                  70                  75                  80

Cys Glu Ala Ala Ala Gln Leu Arg Lys Ala Gly Lys Val Thr Val Arg
                85                  90                  95

Glu Thr Thr Leu Lys Arg Leu Gly Ala Thr His Phe Lys Tyr Gly Val
            100                 105                 110

Ala Asp Gly His Phe Glu Val Thr Arg Phe Ala Leu Pro Ala Asp Leu
        115                 120                 125

Trp Ser Leu Glu Met Lys Asn Ala Trp Ser Glu Ala Tyr Asn Gln Leu
    130                 135                 140

Val Ala Ala Ile Lys Gln Glu Met Lys Pro Ala Ala
145                 150                 155

<210> SEQ ID NO 79
<211> LENGTH: 724
<212> TYPE: DNA
<213> ORGANISM: Panicum virgatum
<220> FEATURE:
<221> NAME/KEY: misc_feature
<223> OTHER INFORMATION: Ceres CLONE ID no.2034916
<220> FEATURE:
<221> NAME/KEY: misc_feature
<223> OTHER INFORMATION: Encodes the protein at SEQ ID NO: 80

<400> SEQUENCE: 79
aatccaatct cccccgatcc ccaatcgcga attccctct ccggcaggcg aagcaatcga      60
ggggcaccct ttcatctcgt caagatgcag atctttgtga agaccctcac tggtaagacc    120
atcaccctcg aggttgagtc ctcggatacc attgacaacg tcaaggctaa atccaggac     180 aaggagggga tccctccgga ccagcagcgc ctcatctttg ccggcaagca gctcgaagat    240
gggaggacgc ttgctgacta caacatccag aaggagtcca cctccacct cgtgctcagg    300 ctcaggggtg gtatgcagat ctttgtcaag actctcaccg gcaagacgat tactcttgag    360
gttgagtcct cggacacgat cgacaatgta aggtgaaga tccaagacaa ggaggggatc     420
ccaccggacc agcagcgcct catctttgcc ggcaagcagc tcgaggatgg ccgcactctg    480
gctgactaca acattcagaa agagtcgacc cttcaccttg tgctcaggct gaggggaggc    540
atgcaaatat ttgtcaagac tctgactggc aagaccatca cgcttgaggt ggagtcgtct    600
gacaccattg ataatgtgaa ggcgaagatc caagacaagg agggcatccc gccggaccag    660
cagcgcctga tctttgccgg taagcagctg gaggatggtc gtaccctggc agactataat    720
attc                                                                  724

<210> SEQ ID NO 80
<211> LENGTH: 213
<212> TYPE: PRT

```
<213> ORGANISM: Panicum virgatum
<220> FEATURE:
<221> NAME/KEY: misc_feature
<223> OTHER INFORMATION: Ceres CLONE ID no. 2034916
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<222> LOCATION: (153)..(213)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional Homolog of Ceres CLONE ID no. 2403
      Given in SEQ ID NO: 40

<400> SEQUENCE: 80

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Val Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Glu Ser Thr Leu His
    130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
                165                 170                 175

Asn Val Lys Ala Lys Ile Gln Asp Lys Glu Gly Ile Pro Pro Asp Gln
            180                 185                 190

Gln Arg Leu Ile Phe Ala Gly Lys Gln Leu Glu Asp Gly Arg Thr Leu
        195                 200                 205

Ala Asp Tyr Asn Ile
    210

<210> SEQ ID NO 81
<211> LENGTH: 1194
<212> TYPE: DNA
<213> ORGANISM: Glycine max
<220> FEATURE:
<221> NAME/KEY: misc_feature
<223> OTHER INFORMATION: Ceres CLONE ID no.651581
<220> FEATURE:
<221> NAME/KEY: misc_feature
<222> LOCATION: (678)..(678)
```

```
<223> OTHER INFORMATION: n is a, c, t, g, unknown, or other
<220> FEATURE:
<221> NAME/KEY: misc_feature
<222> LOCATION: (679)..(679)
<223> OTHER INFORMATION: n is a, c, t, g, unknown, or other
<220> FEATURE:
<221> NAME/KEY: misc_feature
<223> OTHER INFORMATION: Encodes the protein at SEQ ID NO: 82

<400> SEQUENCE: 81
gtgtagttga aggagcagaa gaagaagaag agaaggtggt accgccttca attctctttt       60
tctctctcca tttctcatcc tcatcatctt attattcctc ttccatctct attctccata      120
acacccacca caccacttgt gaaaaacctc attaatatca cacactgaca tgtatctctg      180
agctccaatc caatacaaga ccacaccttg tcgtgtcgga cgaaccttgg tgtctgtttt      240
tttttttttt tttcattatt ttctccgaag agatgaggaa gggcaraggt ggaggcgcct      300
cggcggcggc ggtggatgtg aacggatcca ttttaaagga gcctcggtac cggggcgtga      360
ggaagagacc gtgggggaga ttcgccgcgg agatcagaga cccgttgaag aaagccaggg      420
tttggttggg aaccttcaat tctgccgagg atgctgctcg tgcctacrac gccgccgctc      480
ggactctccg aggtcccaag gccaaaacaa atttccccccc tctctcacct ttttgctatc      540
cacaccccac caccgatcct ttcttstaca ctggtttcca cgatcaacac caccaccaca      600
acaacaacaa cctcaacaac cctcaaagac ccacttcaag tggcatgagt agcmccgttg      660
agtccttcag tgggcccnnc ccttttttccc ccaccaccac cmctaccacc acaaccacaa      720
ctgcgacgcc gttttttgact gctacgcgga gatacccgcg cactccccct cttgtccctg      780
aagactgcca cagtgactgc gactcttcct cctccgtcgt tgacgacggc gacgacaaca      840
tcgtttcgtc gtcgtttcga cctcccttgc cgtttgatct caacgcgctg ccgtttgatg      900
atgctgccgc ggatgatgat ctacgccgca ccgcgctttg tctctgatga tgattatcgt      960
gcgatgatga ttttttaattt ctcatttttt tacttgattt ttttgttatt gctatgcaga     1020
agaaatatat atttaaaatg atgatcagat gtaagattat ggtaatatga tcttaattct     1080
gtgagaggaa gattccgtgt tggttatatt ttcttctttt tattatttt ttaaacattt     1140 ttatttagaa ggaaatattg aatgaaaaga aaaagagaa agtaattatg atcg            1194

<210> SEQ ID NO 82
<211> LENGTH: 224
<212> TYPE: PRT
<213> ORGANISM: Glycine max
<220> FEATURE:
<221> NAME/KEY: misc_feature
<223> OTHER INFORMATION: Ceres CLONE ID no. 651581
<220> FEATURE:
<221> NAME/KEY: misc_feature
<222> LOCATION: (24)..(87)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42
<220> FEATURE:
<221> NAME/KEY: misc_feature
<222> LOCATION: (137)..(137)
<223> OTHER INFORMATION: Xaa is any aa, unknown, or other

<400> SEQUENCE: 82

Met Arg Lys Gly Arg Gly Gly Ala Ser Ala Ala Ala Val Asp Val
1               5                   10                  15

Asn Gly Ser Ile Leu Lys Glu Pro Arg Tyr Arg Gly Val Arg Lys Arg
```

```
                    20                  25                  30
Pro Trp Gly Arg Phe Ala Ala Glu Ile Arg Asp Pro Leu Lys Lys Ala
            35                  40                  45

Arg Val Trp Leu Gly Thr Phe Asn Ser Ala Glu Asp Ala Ala Arg Ala
        50                  55                  60

Tyr Asp Ala Ala Ala Arg Thr Leu Arg Gly Pro Lys Ala Lys Thr Asn
 65                  70                  75                  80

Phe Pro Pro Leu Ser Pro Phe Cys Tyr Pro His Pro Thr Thr Asp Pro
                85                  90                  95

Phe Phe Tyr Thr Gly Phe His Asp Gln His His His Asn Asn Asn
                100                 105                 110

Asn Leu Asn Asn Pro Gln Arg Pro Thr Ser Ser Gly Met Ser Ser Thr
            115                 120                 125

Val Glu Ser Phe Ser Gly Pro Arg Xaa Phe Ser Pro Thr Thr Thr Thr
        130                 135                 140

Thr Thr Thr Thr Thr Thr Ala Thr Pro Phe Leu Thr Ala Thr Arg Arg
145                 150                 155                 160

Tyr Pro Arg Thr Pro Pro Leu Val Pro Glu Asp Cys His Ser Asp Cys
                165                 170                 175

Asp Ser Ser Ser Val Val Asp Asp Gly Asp Asp Asn Ile Val Ser
            180                 185                 190

Ser Ser Phe Arg Pro Pro Leu Pro Phe Asp Leu Asn Ala Leu Pro Phe
        195                 200                 205

Asp Asp Ala Ala Ala Asp Asp Asp Leu Arg Arg Thr Ala Leu Cys Leu
    210                 215                 220

<210> SEQ ID NO 83
<211> LENGTH: 184
<212> TYPE: PRT
<213> ORGANISM: Oryza sativa subsp. indica
<220> FEATURE:
<221> NAME/KEY: misc_feature
<223> OTHER INFORMATION: Public GI ID no. 125550159
<220> FEATURE:
<221> NAME/KEY: misc_feature
<222> LOCATION: (7)..(70)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 83

Met Cys Glu Ala Ala Ala Pro Arg Tyr Arg Gly Val Arg Lys Arg Pro
 1               5                  10                  15

Trp Gly Arg Phe Ala Ala Glu Ile Arg Asp Pro Ala Lys Arg Ala Arg
            20                  25                  30

Val Trp Leu Gly Thr Tyr Asp Ser Ala Glu Ala Ala Ala Arg Ala Tyr
        35                  40                  45

Asp Val Ala Ala Arg Asn Leu Arg Gly Pro Leu Ala Arg Thr Asn Phe
    50                  55                  60

Pro Leu Val Ser Ser Leu Pro Leu Pro Ser Pro His Tyr His Leu Pro
65                  70                  75                  80

Gly Lys Ala Ala Ala Ala Pro Pro Val Ala Gly Pro Ala Cys Ser
                85                  90                  95

Ala Ser Ser Thr Val Glu Ser Ser Gly Pro Arg Gly Pro Arg Pro
                100                 105                 110
```

```
Ala Ala Thr Ala Ala Ala Val Pro Arg Arg Val Pro Arg Pro Ala
            115                 120                 125

Pro Pro Ala Pro Asp Ala Gly Cys His Ser Asp Cys Ala Ser Ser Ala
    130                 135                 140

Ser Val Val Asp Asp Ala Asp Asp Ala Ser Thr Val Arg Ser Arg Val
145                 150                 155                 160

Ala Ala Phe Asp Leu Asn Leu Pro Pro Leu Asp Arg Asp His Val
                165                 170                 175

Asp Leu Cys Thr Asp Leu Arg Leu
            180

<210> SEQ ID NO 84
<211> LENGTH: 225
<212> TYPE: PRT
<213> ORGANISM: Arabidopsis thaliana
<220> FEATURE:
<221> NAME/KEY: misc_feature
<223> OTHER INFORMATION: Public GI ID no. 15223609
<220> FEATURE:
<221> NAME/KEY: misc_feature
<222> LOCATION: (26)..(89)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 84

Met Arg Arg Gly Arg Gly Ser Ser Ala Val Ala Gly Pro Thr Val Val
1               5                   10                  15

Ala Ala Ile Asn Gly Ser Val Lys Glu Ile Arg Phe Arg Gly Val Arg
            20                  25                  30

Lys Arg Pro Trp Gly Arg Phe Ala Ala Glu Ile Arg Asp Pro Trp Lys
        35                  40                  45

Lys Ala Arg Val Trp Leu Gly Thr Phe Asp Ser Ala Glu Glu Ala Ala
    50                  55                  60

Arg Ala Tyr Asp Ser Ala Ala Arg Asn Leu Arg Gly Pro Lys Ala Lys
65                  70                  75                  80

Thr Asn Phe Pro Ile Asp Ser Ser Ser Pro Pro Pro Asn Leu Arg
                85                  90                  95

Phe Asn Gln Ile Arg Asn Gln Asn Gln Asn Val Asp Pro Phe Met
                100                 105                 110

Asp His Arg Leu Phe Thr Asp His Gln Gln Gln Phe Pro Ile Val Asn
            115                 120                 125

Arg Pro Thr Ser Ser Ser Met Ser Ser Thr Val Glu Ser Phe Ser Gly
    130                 135                 140

Pro Arg Pro Thr Thr Met Lys Pro Ala Thr Thr Lys Arg Tyr Pro Arg
145                 150                 155                 160

Thr Pro Pro Val Val Pro Glu Asp Cys His Ser Asp Cys Asp Ser Ser
                165                 170                 175

Ser Ser Val Ile Asp Asp Asp Asp Ile Ala Ser Ser Ser Arg Arg
                180                 185                 190

Arg Asn Pro Pro Phe Gln Phe Asp Leu Asn Phe Pro Pro Leu Asp Cys
        195                 200                 205

Val Asp Leu Phe Asn Gly Ala Asp Asp Leu His Cys Thr Asp Leu Arg
    210                 215                 220

Leu
225
```

-continued

<210> SEQ ID NO 85
<211> LENGTH: 164
<212> TYPE: PRT
<213> ORGANISM: Arabidopsis thaliana
<220> FEATURE:
<221> NAME/KEY: misc_feature
<223> OTHER INFORMATION: Public GI ID no. 30683885
<220> FEATURE:
<221> NAME/KEY: misc_feature
<223> OTHER INFORMATION: Functional Homolog of Ceres CLONE ID no. 30087
     Given in SEQ ID NO: 2

<400> SEQUENCE: 85

Met Ala Ser Ser Phe Ser Ser Gln Ala Phe Phe Leu Leu Thr Leu Ser
1               5                   10                  15

Met Val Leu Ile Pro Phe Ser Leu Ala Gln Ala Pro Met Met Ala Pro
            20                  25                  30

Ser Gly Ser Met Ser Met Pro Pro Met Ser Gly Gly Gly Ser Ser
        35                  40                  45

Val Pro Pro Val Met Ser Pro Met Pro Met Thr Pro Pro Pro
    50                  55                  60

Met Pro Met Thr Pro Pro Pro Met Pro Met Thr Pro Pro Pro Met Pro
65                  70                  75                  80

Met Ala Pro Pro Pro Met Pro Met Ala Ser Pro Pro Met Met Pro Met
                85                  90                  95

Thr Pro Ser Thr Ser Pro Ser Pro Leu Thr Val Pro Asp Met Pro Ser
            100                 105                 110

Pro Pro Met Pro Ser Gly Met Glu Ser Ser Pro Ser Pro Gly Pro Met
        115                 120                 125

Pro Pro Ala Met Ala Ala Ser Pro Asp Ser Gly Ala Phe Asn Val Arg
    130                 135                 140

Asn Asn Val Val Thr Leu Ser Cys Val Val Gly Val Val Ala Ala His
145                 150                 155                 160

Phe Leu Leu Val

<210> SEQ ID NO 86
<211> LENGTH: 218
<212> TYPE: PRT
<213> ORGANISM: Pisum sativum
<220> FEATURE:
<221> NAME/KEY: misc_feature
<223> OTHER INFORMATION: Public GI ID no. 56384582
<220> FEATURE:
<221> NAME/KEY: misc_feature
<222> LOCATION: (21)..(84)
<223> OTHER INFORMATION: Pfam Name: AP2
     Pfam Description: AP2 domain
<220> FEATURE:
<221> NAME/KEY: misc_feature
<223> OTHER INFORMATION: Functional Homolog of Ceres CLONE ID no. 674166
     Given in SEQ ID NO: 42

<400> SEQUENCE: 86

Met Gly Arg Gly Gly Ala Thr Thr Ala Ala Ala Val Glu Pro Val
1               5                   10                  15

Phe Phe Lys Glu Pro Arg Tyr Arg Gly Val Arg Lys Arg Pro Trp Gly
            20                  25                  30

Arg Phe Ala Ala Glu Ile Arg Asp Pro Leu Lys Lys Ala Arg Val Trp
        35                  40                  45

Leu Gly Thr Phe Asp Thr Ala Glu Glu Ala Ala Arg Ala Tyr Asp Thr
    50                  55                  60

```
Ala Ala Arg Asn Leu Arg Gly Pro Lys Ala Lys Thr Asn Phe Pro Leu
 65                  70                  75                  80

Ala Gln Pro Phe Tyr Gln Asn Pro Glu Ala Gly Asn Pro Phe Gly Glu
                 85                  90                  95

Leu Arg Phe Tyr Ala Gly Gly Ala Gly Glu Gly Phe Gln Asp His Arg
            100                 105                 110

Arg Pro Thr Ser Ser Gly Met Ser Ser Thr Val Glu Ser Phe Gly Gly
        115                 120                 125

Pro Arg Pro Val Arg Pro Met Pro Pro Ser Ala Val Thr Gly Arg
130                 135                 140

Arg Tyr Pro Arg Thr Pro Pro Val Ala Pro Gly Asp Cys Arg Ser Asp
145                 150                 155                 160

Cys Asp Ser Ser Ser Val Val Asp Asp Ala Asp Asn Asp Asn Ala
                165                 170                 175

Ala Ser Ser Thr Met Leu Ser Phe Lys Arg Gln Pro Leu Pro Phe Asp
                180                 185                 190

Leu Asn Ala Pro Pro Leu Glu Glu Gly Asp Val Ala Asn Gly Leu Gly
            195                 200                 205

Glu Asp Leu His Cys Thr Leu Leu Cys Leu
210                 215
```

<210> SEQ ID NO 87
<211> LENGTH: 225
<212> TYPE: PRT
<213> ORGANISM: Nicotiana tabacum
<220> FEATURE:
<221> NAME/KEY: misc_feature
<223> OTHER INFORMATION: Public GI ID no. 57012880
<220> FEATURE:
<221> NAME/KEY: misc_feature
<222> LOCATION: (26)..(89)
<223> OTHER INFORMATION: Pfam Name: AP2
    Pfam Description: AP2 domain
<220> FEATURE:
<221> NAME/KEY: misc_feature
<223> OTHER INFORMATION: Functional Homolog of Ceres CLONE ID no. 674166
    Given in SEQ ID NO: 42

<400> SEQUENCE: 87

```
Met Arg Arg Gly Arg Ala Ala Ala Pro Ala Pro Val Thr Gly Glu
  1               5                  10                  15

Pro Asn Gly Ser Gly Gly Ser Lys Glu Ile Arg Phe Arg Gly Val Arg
                 20                  25                  30

Lys Arg Pro Trp Gly Arg Phe Ala Ala Glu Ile Arg Asp Pro Trp Lys
             35                  40                  45

Lys Thr Arg Val Trp Leu Gly Thr Phe Asp Ser Ala Glu Asp Ala Ala
 50                  55                  60

Arg Ala Tyr Asp Ala Ala Ala Arg Ala Leu Arg Gly Pro Lys Ala Lys
 65                  70                  75                  80

Thr Asn Phe Pro Leu Pro Tyr Ala His His Gln Phe Asn Gln Gly
                 85                  90                  95

His Asn Pro Asn Asn Asp Pro Phe Val Asp Ser Arg Phe Tyr Pro Gln
            100                 105                 110

Asp Asn Pro Ile Ile Ser Gln Arg Pro Thr Ser Ser Met Ser Ser
        115                 120                 125

Thr Val Glu Ser Phe Ser Gly Pro Arg Pro Pro Ala Pro Arg Gln
130                 135                 140

Gln Thr Thr Ala Ser Ser Arg Lys Tyr Thr Arg Ser Pro Pro Val Val
```

-continued

```
                145                 150                 155                 160
Pro Asp Asp Cys His Ser Asp Cys Asp Ser Ser Ser Val Val Asp
                    165                 170                 175

His Gly Asp Cys Glu Lys Glu Asn Asp Asn Asp Asn Asp Asn Ile Ala
                    180                 185                 190

Ser Ser Ser Phe Arg Lys Pro Leu Leu Phe Asp Leu Asn Leu Pro Pro
                    195                 200                 205

Pro Met Asp Asp Ala Gly Ala Asp Asp Leu His Cys Thr Ala Leu Cys
                    210                 215                 220

Leu
225

<210> SEQ ID NO 88
<211> LENGTH: 163
<212> TYPE: PRT
<213> ORGANISM: Gossypium hirsutum
<220> FEATURE:
<221> NAME/KEY: misc_feature
<223> OTHER INFORMATION: Public GI ID no. 62548111
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 88

Met Ala Thr Tyr Glu Gly Lys Val Phe Thr Glu Glu Gln Glu Ala Leu
1               5                   10                  15

Val Val Lys Ser Trp Thr Val Met Lys Lys Asn Ala Ala Glu Leu Gly
                    20                  25                  30

Leu Lys Phe Phe Leu Lys Ile Phe Glu Ile Ala Pro Ser Ala Lys Lys
                35                  40                  45

Leu Phe Ser Phe Leu Arg Asp Ser Asn Val Pro Leu Glu Gln Asn Thr
            50                  55                  60

Lys Leu Lys Pro His Ala Met Ser Val Phe Val Met Thr Cys Glu Ser
65                  70                  75                  80

Ala Val Gln Leu Arg Lys Ala Gly Lys Val Thr Val Arg Glu Ser Asn
                    85                  90                  95

Leu Lys Lys Leu Gly Ala Thr His Phe Lys Tyr Gly Val Val Asp Glu
                100                 105                 110

His Phe Glu Val Thr Lys Phe Ala Leu Leu Glu Thr Ile Lys Glu Ala
            115                 120                 125

Val Pro Asp Met Trp Ser Asp Glu Met Lys Asn Ala Trp Gly Glu Ala
        130                 135                 140

Tyr Asp Arg Leu Val Ala Ala Ile Lys Ile Glu Met Lys Ala Cys Ser
145                 150                 155                 160

Leu Ala Ala

<210> SEQ ID NO 89
<211> LENGTH: 153
<212> TYPE: PRT
<213> ORGANISM: Gossypium hirsutum
<220> FEATURE:
<221> NAME/KEY: misc_feature
<223> OTHER INFORMATION: Ceres CLONE ID no. 100021733
<220> FEATURE:
<221> NAME/KEY: misc_feature
```

```
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional Homolog of Ceres CLONE ID no. 2403
      Given in SEQ ID NO: 40

<400> SEQUENCE: 89

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Glu Ser Thr Leu His
    130                 135                 140

Leu Val Leu Arg Leu Arg Gly Gly Phe
145                 150

<210> SEQ ID NO 90
<211> LENGTH: 775
<212> TYPE: DNA
<213> ORGANISM: Brassica napus
<220> FEATURE:
<221> NAME/KEY: misc_feature
<223> OTHER INFORMATION: Ceres CLONE ID no. 947579
<220> FEATURE:
<221> NAME/KEY: misc_feature
<223> OTHER INFORMATION: Encodes the protein at SEQ ID NO: 3

<400> SEQUENCE: 90
ctctctagat cttggatcac tcggacgaca tgtgttggat cccagtgcac tggccctgcc      60
agcctactca aaaaaacswt samttttckc tcccattstt tkacractca tcgttggcac     120
wtcctwcttt ctstatatat tacttgacat wawcyrctmt ycacmwcaca wacacacacw     180
taaccatggc cagcttcaca wgctttcctt ttgctcacat tgyctatggc tttagytcat     240
ytctctttag ctcwatctcc catgatggct ccttctggct ccatgtccat gscgckchat     300
gccatagcgg cggctctcca atgccaatga tgactccacc acctatgcca atgatgactc     360
cmccgcctat ggctatggct ccaccaccta tgcctatgac tccaccacca atgcccatgg     420
ctccgatgcc aatgactcca tcttcaagtc caatgagccc accaactact atggccccaa     480
gtccagaaac agtccctgat atggcttcgc caccgatgat gccgggaatg gagtcttctc     540
cttctccggg acccatgcca ccggcaatgg cctctccaga ttccggagca ttcaatgtaa     600
```

| | |
|---|---|
| gaaacgacgt cgtagcaatt tcgttccttg ttgcagctca tttgctccta gtttgagatt | 660 |
| attattaaat tggccagcgt cgtgttgtgt aatttacttt cattttttct cgagccatta | 720 |
| gttttcatgt tttatcatat atttgggttt gtgtttgata tggtacgatt cagmc | 775 |

```
<210> SEQ ID NO 91
<211> LENGTH: 1032
<212> TYPE: DNA
<213> ORGANISM: Arabidopsis thaliana
<220> FEATURE:
<221> NAME/KEY: misc_feature
<223> OTHER INFORMATION: Ceres CLONE ID no. 36046
<220> FEATURE:
<221> NAME/KEY: misc_feature
<223> OTHER INFORMATION: Encodes the protein at SEQ ID NO: 23

<400> SEQUENCE: 91
```

| | |
|---|---|
| gctcattagg gtttctcatc tacggcgtgg tgttcctcct tcctgctctg aaaaatggcg | 60 |
| aagagaacga agaaggttgg aatcgtcggc aaatacggaa cacgttatgg tgcgagtatc | 120 |
| aggaagcaga ttaagaagat ggaggtcagc cagcacagca agtacttctg tgagttctgt | 180 |
| ggcaagtacg gagtgaagcg aaaggctgtt ggtatctggg gttgcaagga ttgtggcaag | 240 |
| gtcaaggcag gtggtgctta cacaatgaac accgccagtg cggtcactgt tagaagcacg | 300 |
| atcagaaggt tgagggagca gatcgagggt taaaagtctg ctgaggaaga tgctgagaca | 360 |
| gtatacgctt gtatcgactt ggtatcaacg ataatacaga ggaagctgag gaagatcaag | 420 |
| gagaaggact cagaccatgg aaggcacatg aaaggtttca acagattgaa ggtaagggaa | 480 |
| ccagtgattg agccggttgt ggaggatgtt gaggacagta ctgactcgag cgtaggagaa | 540 |
| gaagaagaag aggatgattt gatcaaggag attgtccgta ccaagacttt cgagatgcca | 600 |
| ccattgactg tcgctgaggc agtcgagcag ctggaactag tcagtcacga cttctatggc | 660 |
| ttccaaaatg aaaactggtg agataaacat agtgtacaag agaaagaag gaggttacgg | 720 |
| tctgataatc ccaaagaaag acgggaaggc cgagaaggtt gagccgcttc caaccgagca | 780 |
| attgaatgaa cactctttcg ccgagtagac tgcctctgca cacaccaaaa ccgataagct | 840 |
| catctctcct tacagtttac ctgtgtagga gttagggttc ttgaataaac aatgcaacaa | 900 |
| agattgtaga agtcagtgta cataaaaaaa tggccaacca ctctttgtta cttttgtggt | 960 |
| gaaaaggaag atcttaattc tctttccatc agatgatagc aatacatttt ttcataaaca | 1020 |
| agaatgttac at | 1032 |

```
<210> SEQ ID NO 92
<211> LENGTH: 492
<212> TYPE: DNA
<213> ORGANISM: Parthenium argentatum
<220> FEATURE:
<221> NAME/KEY: misc_feature
<223> OTHER INFORMATION: Ceres CLONE ID no. 1606506
<220> FEATURE:
<221> NAME/KEY: misc_feature
<223> OTHER INFORMATION: Encodes the protein at SEQ ID NO: 5

<400> SEQUENCE: 92
```

| | |
|---|---|
| atctagcttc aaccttttt tcctctcact actcaattca atatggctgt ctcacgttac | 60 |
| attatcctac tcttatcctt cacctacttg gctgccttct ccaccgctca agctccatca | 120 |
| atgtcaccaa tgatgatgcc catggcacca ccaccatcga cgatgcccat gacaccacca | 180 |
| ccatcgacga tgcccatgac accaccacca acgcccatga ccatgacacc accaccaatg | 240 |
| atgatgccca tgacaccacc accaatgccc atggggacac caccaatgac aatgcccatg | 300 |

-continued

| | |
|---|---|
| ggaccgccac caatgatgat gcccatgagc ccaggaccat ccatgatgcc agcctccccg | 360 |
| ccatcaccca tgggaccgtc catggcacct gaaccagcta ccatgtcgcc tggaccctcc | 420 |
| atgacgcctg ctgagacacc agccagtggc gctatcatgc agtattctag catcactatg | 480 |
| ttgggcattg tg | 492 |

<210> SEQ ID NO 93
<211> LENGTH: 970
<212> TYPE: DNA
<213> ORGANISM: Glycine max
<220> FEATURE:
<221> NAME/KEY: misc_feature
<223> OTHER INFORMATION: Ceres CLONE ID no. 546001
<220> FEATURE:
<221> NAME/KEY: misc_feature
<223> OTHER INFORMATION: Encodes the protein at SEQ ID NO: 13

<400> SEQUENCE: 93

| | |
|---|---|
| agatataatc gaaaaaaatt actgtttgga tatattccac tatttagaaa gcaaaatgga | 60 |
| ctacgaaaac ttgagtaaca aggtaagcca cacaaatggg aatgactccc cattacaatg | 120 |
| aagggccaac ttcattttca atgaatccca ctataaaaac tttagcaatg caaaagctaa | 180 |
| aacatcaacc atttcctcat ccactttcac tggaatcaca atcctgaaac aaaaacatct | 240 |
| tagcatttaa catactacta gacaacatga ccaccacatt ggaaagaggt ttctcggaag | 300 |
| agcaagaagc tctggtggtg aagtcatgga atgtcatgaa gaagaattct ggagagttgg | 360 |
| gtctcaagtt tttcttgaaa atatttgaga ttgctccatc agctcagaaa ttgttctcat | 420 |
| tcttgagaga ttcaacggtt cctttggagc aaaatcccaa gctcaagccc catgccgtgt | 480 |
| ctgtctttgt aatgacctgt gattcagcag ttcagctgcg gaaggccggg aaagtcactg | 540 |
| tcagagaatc aaacttgaaa aaattaggtg ctacccattt tagaaccggc gtagcaaacg | 600 |
| agcatttcga ggtgacaaag tttgcactgt tggagaccat aaaagaagct gtaccagaaa | 660 |
| tgtggtcacc ggctatgaag aatgcatggg agaagcttta tgatcagctg gtcgatgcca | 720 |
| ttaaatctga aatgaaacca ccctcctctt agactccagt ttaagcagtt cctttccttc | 780 |
| cctctcaatt ctcaaattgt tatattaata aaagtgagaa agtttaggct tgtgctttta | 840 |
| ttttgtgtga atgtaatata ctttgtgtac gtagacttgg ctattgggag ttgctaggtt | 900 |
| gggaagtgtt tcgcattcaa caattctgta gttgaaggtg attaaatgaa ttatagctat | 960 |
| ttgtttcttc | 970 |

<210> SEQ ID NO 94
<211> LENGTH: 604
<212> TYPE: DNA
<213> ORGANISM: Zea mays
<220> FEATURE:
<221> NAME/KEY: misc_feature
<223> OTHER INFORMATION: Ceres CLONE ID no. 1554560
<220> FEATURE:
<221> NAME/KEY: misc_feature
<223> OTHER INFORMATION: Encodes the protein at SEQ ID NO: 16

<400> SEQUENCE: 94

| | |
|---|---|
| tcgtatccac ccaacctccc actgtaaaaa agagcagcgg aacgtgcgtg catccatcca | 60 |
| attccaatcc cagtcccaat cccaccagtg tccagtgctc ggggaaccga cacagctcct | 120 |
| cagcagagaa gccagcccga tcagcagaca gcaggcatgg cgctcgcgga ggccgacgac | 180 |
| ggcgcggtgg tcttcggcga ggagcaggag gcgctggtgc tcaagtcgtg ggccgtcatg | 240 |

```
aagaaggacg ccgccaacct gggcctccgc ttcttcctca aggtcttcga gatcgcgccg    300
tcggcgaagc agatgttctc gttcctgcgc gactccgacg tgccgctaga gaagaacccc    360
aagctcaaga cgcacgccat gtccgtcttc gtcatgacct gcgaggcggc ggcgcagctc    420
cgcaaggccg ggaaggtcac cgtgagggag accacgctca gaggctgggc gccacgcac     480 ttgaggtacg gcgtcgcaga tggacacttc gaggtgacgg ggttcgcgct gcttgagacg    540
atcaaggagg cgctccccgc tgacatgtgg agcctcgaga tgaagaaagc ctgggccgag    600
gcct                                                                 604

<210> SEQ ID NO 95
<211> LENGTH: 846
<212> TYPE: DNA
<213> ORGANISM: Triticum aestivum
<220> FEATURE:
<221> NAME/KEY: misc_feature
<223> OTHER INFORMATION: Ceres CLONE ID no. 839727
<220> FEATURE:
<221> NAME/KEY: misc_feature
<223> OTHER INFORMATION: Encodes the protein at SEQ ID NO: 17

<400> SEQUENCE: 95
acgccgtccg tttctggctc atcaggaggt ccaaaggccg cgcaagtcga cctatataag     60
cgcctccgct ccagcttggg atcaaatcac gaccaacacg taccggatct tgaccgaccg    120
aaccattcag tgctcgcgct cactcacgca tcatagccaa gttaagcggg aaggaaggaa    180
ggaaggaagc catgtctgcc gcggagggag ccgtcgtgtt cagcgaggag aaggaggcgc    240
tggtgctcaa gtcatgggcc atcatgaaga aggattccgc caaccttggg ctccgcttct    300
tcctcaagat cttcgagatc gcgccgtcgg cgaggcagat gttcccgttc ctgcgcgact    360
ccgacgtgcc gctggagacc aaccccaagc tcaagaccca cgccgtgtcc gtcttcgtca    420
tgacgtgcga ggctgctgcg cagctgcgga aagccgggaa gatcaccgtc agggagacca    480
ccctgaagag gctgggcggc acgcacttga atacggcgt ggcagatggc cactttgagg    540
tgacgcggtt cgctctgctc gagacgatca aggaggcgct tccggcggac atgtggggc     600 cggagatgag gaacgcgtgg ggcgaggcct acgaccaact ggtcgcggcc atcaagcaag    660
agatgaagcc ctctgagtag ctcatccatt gtactcatat catatgccac gcaacttccg    720
tccatatccg tccaactttc gttgcttgac cggttcactc atgtcaccat attgtgtttg    780
tattgtgtgt ttacgtgtac taacgcatat tgtaaaatgg gcattcaata aggaacaaa    840 ttgtgc                                                               846

<210> SEQ ID NO 96
<211> LENGTH: 440
<212> TYPE: DNA
<213> ORGANISM: Glycine max
<220> FEATURE:
<221> NAME/KEY: misc_feature
<223> OTHER INFORMATION: Ceres CLONE ID no. 664936
<220> FEATURE:
<221> NAME/KEY: misc_feature
<223> OTHER INFORMATION: Encodes the protein at SEQ ID NO: 25

<400> SEQUENCE: 96
ctcttgtctt agtctaataa acaacacgga cgcagagcct tcgatccaga aaccatgact     60
aagagaacga agaaggcagg cattgtcgga aaatatggta cccgatatgg tgctagtttg    120
cggaagcaga ttaagaagat ggaagttagt cagcatagca aattcttttg tgaatttgt     180 gggaagtatg ctgtgaagag gaaggctgtg ggaatatggg gatgcaagga ttgtggtaaa    240
```

```
gtgaaagctg gcggtgccta cactttgaat actgcaagtg ctgtcactgt gcgcagcacc    300
atccggaggt tgagggaaca aaccgagggt tgagcttttt ggttgatgtt agattttgag    360
caaattaact ggagaaatga ttcgtttttg tttaggaagc tgtattgttt caacttacaa    420
tgcagtgtga attgctttcg                                                440
```

<210> SEQ ID NO 97
<211> LENGTH: 463
<212> TYPE: DNA
<213> ORGANISM: Glycine max
<220> FEATURE:
<221> NAME/KEY: misc_feature
<223> OTHER INFORMATION: Ceres CLONE ID no. 658438
<220> FEATURE:
<221> NAME/KEY: misc_feature
<223> OTHER INFORMATION: Encodes the protein at SEQ ID NO: 26

<400> SEQUENCE: 97

```
atatawcttg actctccgca attccctgtc tcckccgccg cagcttccgt ctcccggatt     60
tcgccgcctg ccgcakccgc agcagctcgc cgsccacgcs tcctayccgt cgacgagatg    120
acgaascgca ccaagaaggc tggaattgtc ggcaaatatg gtacccgtta tggtgccagt    180
ttgcgtaagc agatcargaa gatggaggtg tctcagcact ccaagtactt ckgtgagttc    240
tgtgggaagt ttgctgtgaa gaggaaagsa gttggaattt ggggatgcaa tggactgtgg    300
gaaggwsaag gaaaccttcg ccwkaaaccg tgagctcgaa gtgmggtcca ctccaggwgg    360
gccatgctcg gggccttggg swgcagtctt ccccgaagct attgtyccgc aacggggtca    420
agtttggaga agctgtgtgg ttcaaggccg ggtcccagat ctt                      463
```

<210> SEQ ID NO 98
<211> LENGTH: 458
<212> TYPE: DNA
<213> ORGANISM: Glycine max
<220> FEATURE:
<221> NAME/KEY: misc_feature
<223> OTHER INFORMATION: Ceres CLONE ID no. 1049262
<220> FEATURE:
<221> NAME/KEY: misc_feature
<223> OTHER INFORMATION: Encodes the protein at SEQ ID NO: 27
<220> FEATURE:
<221> NAME/KEY: misc_feature
<222> LOCATION: (224)..(224)
<223> OTHER INFORMATION: n is a, c, t, g, unknown, or other

<400> SEQUENCE: 98

```
aacaaaccct cgttcacggt tcaacttcag cagccgcgcc tctaacttgt agcagcgata     60
cctcttctct tatcactaaa aaatgaccaa gagaaccaag aaggccggta ttgttggaaa    120
atacggcacc cgatatggtg ctagtttaag gaagcaaatc aagaagatgg aagttagtca    180
gcacagtaaa ttcttttgtg agttctgtgg aaagtacgct gttnagagga aggccgtggg    240
tatttggggc tgcaaagatt gtggaaaagt gaaggctgga ggtgcttaca cattgaatac    300
tgcgagtgct gtcactgtcc ggagcaccat tcggaggctg agagagcaga ctgagagttg    360
aaagcagttt acacttttca tttgtttcca aagcttattt taaaattatc atacaatttt    420
ggcaggtcta tgttaggaat attagtaatg tgctactt                            458
```

<210> SEQ ID NO 99
<211> LENGTH: 600
<212> TYPE: DNA
<213> ORGANISM: Triticum aestivum
<220> FEATURE:

<221> NAME/KEY: misc_feature
<223> OTHER INFORMATION: Ceres CLONE ID no. 632613
<220> FEATURE:
<221> NAME/KEY: misc_feature
<223> OTHER INFORMATION: Encodes the protein at SEQ ID NO: 28

<400> SEQUENCE: 99

```
ctcaaaaccc taggcttcca tatataactt gactctccac aattccctgt ctccgccgcc      60
gcagctttcg tctcccggat ttcgccgccg cagccgctca ccgccacgc ctcctacccg      120
tcgacgagat gacgaagcgc accaagaagg ctggtattgt cggcaaatat ggtacccgtt     180
atggtgccag tttgcgtaag cagatcaaga agatggaggt gtctcagcac tccaagtact     240
tctgtgagtt ctgtgggaag tttgctgtga agaggaaagc agttggaatt tggggatgca     300
aggactgtgg gaaggtgaag gctggcggtg cttacactat gaacactgcc agtgcggtca     360
ctgtcaggag cactatccgt cgtttgaggg agcagactga agcataagtt gctactagtg     420
ttttgtccta gtgaatcatc tgggatttcg cagtttagac gatactttgg attcagttcc     480
attggctgtt tagtcaagga ttatctttgt acttggtgcg atgatgttct gttatgttat     540
tctcccaccc ttttgttgcc tgattccact ctgatttact gtggattctg atttgccttc     600
```

<210> SEQ ID NO 100
<211> LENGTH: 546
<212> TYPE: DNA
<213> ORGANISM: Zea mays
<220> FEATURE:
<221> NAME/KEY: misc_feature
<223> OTHER INFORMATION: Ceres CLONE ID no. 1390976
<220> FEATURE:
<221> NAME/KEY: misc_feature
<223> OTHER INFORMATION: Encodes the protein at SEQ ID NO: 29

<400> SEQUENCE: 100

```
aagcatccac aattccacat aacctcgccc gcgccgcctc ccccacgaga cgccttcttg      60
ctctcgcttc cggtgacgcc cgccacttcc tcccgacga gatgacgaaa cgcaccaaga     120
aggcaggaat cgttggcaaa tatggtacca ggtatggtgc cagtttacgt aaacagatca     180
agaagatgga ggtctcgcag cactccaaat acttctgtga gttctgtggc aagtttgccg     240
tgaagaggaa agcagttggt atctggggat gcaaggactg tgggaaggtt aaggccggtg     300
gcgcctacac aatgaacact gctagtgcgg tcactgtgag aagcacaatc cggcgcctgc     360
gggagcagac cgaagcatga ttgcgggcag cttgaaaagg agtacctgga tttttgtagt     420
tcagccaaga gccgtgaacc attttgcctt tttagctaaa tgaacaagaa atgtttatct     480
atctgtagtg accactttgt actcatggtt tgtcatgcta aattgatggt atgcactatg     540
caatgc                                                                546
```

<210> SEQ ID NO 101
<211> LENGTH: 550
<212> TYPE: DNA
<213> ORGANISM: Zea mays
<220> FEATURE:
<221> NAME/KEY: misc_feature
<223> OTHER INFORMATION: Ceres CLONE ID no. 1457185
<220> FEATURE:
<221> NAME/KEY: misc_feature
<223> OTHER INFORMATION: Encodes the protein at SEQ ID NO: 30

<400> SEQUENCE: 101

```
atatataact tgactctccg caattccctg tctccgccgc cgcagcttcc gtctcccgga      60
tttcgccgcc gccgcagccg cagcagctcg ccgcccacgc ctcctacccg tcgacgagat    120
```

```
gacgaagcgc accaagaagg ctggaattgt cggcaaatat ggtacccgtt atggtgccag      180
tttgcgtaag cagatcaaga agatggaggt gtctcagcac tccaagtact tctgtgagtt      240
ctgtgggaag tttgctgtga agaggaaagc agttggaatt tggggatgca aggactgtgg      300
gaaggtgaag gctggcggtg cttacaccat gaacactgcc agtgcggtca ctgtcaggag      360
cactatccgt cgcttgaggg agcagactga agcataagtt gctactagtg ttttgtccta      420
gtgaatcatc tgggattttg cagtttagac gatactttgg attcagttct gttggctgtt      480
tagtcaagga ttatctttgt acttggtgcg atgatgttct gttatgttat ctctcaccc       540 ttttttttgcc                                                            550

<210> SEQ ID NO 102
<211> LENGTH: 668
<212> TYPE: DNA
<213> ORGANISM: Zea mays
<220> FEATURE:
<221> NAME/KEY: misc_feature
<223> OTHER INFORMATION: Ceres CLONE ID no. 1482731
<220> FEATURE:
<221> NAME/KEY: misc_feature
<223> OTHER INFORMATION: Encodes the protein at SEQ ID NO: 35

<400> SEQUENCE: 102
aaaaattcat tgatcgaaaa aaagaaaaaa gaaagaaaag aaaagatgca gatcttcgtg       60
aaaaccttga ccggcaaaac cataacccta gaggttgaaa gcagcgacac catcgacaat      120
gtcaaatcca aaatccagga caaagagggg ataccacctg atcaacagag gctcatcttt      180
gctgggaaac aacttgagga tggtcgaacg ctagctgact acaacattca gaaagagtcc      240
actcttcact tggttctgag gcttaggggt gggaccatga tcaaggtcaa gactctcact      300
ggtaaagaaa tcgaaattga tatcgaacct accgatacta ttgaccggat caaggaacgt      360
gttgaggaga aagaaggcat ccctcctgtt caacaaggc tcatctatgc tgggaaacag       420
ctagctgatg acaaaacggc aaaggactac aacatagagg gaggctctgt tcttcatctg      480
gtccttgctc tcaggggtgg ttctgactaa ataactattt gctctagagt tcctttcaat      540
ggctttggtt ggttgaatcc atgagacaaa gtgaatacaa tttggatttc gtgctttggt      600
tactatgatg ctatttcagc tggtttggat caatttacca aaaaaaaaa aaaaaaaaa        660 aaaaaaag                                                              668

<210> SEQ ID NO 103
<211> LENGTH: 752
<212> TYPE: DNA
<213> ORGANISM: Glycine max
<220> FEATURE:
<221> NAME/KEY: misc_feature
<223> OTHER INFORMATION: Ceres CLONE ID no. 522921
<220> FEATURE:
<221> NAME/KEY: misc_feature
<223> OTHER INFORMATION: Encodes the protein at SEQ ID NO: 36
<220> FEATURE:
<221> NAME/KEY: misc_feature
<222> LOCATION: (639)..(639)
<223> OTHER INFORMATION: n is a, c, t, g, unknown, or other
<220> FEATURE:
<221> NAME/KEY: misc_feature
<222> LOCATION: (674)..(674)
<223> OTHER INFORMATION: n is a, c, t, g, unknown, or other
<220> FEATURE:
<221> NAME/KEY: misc_feature
<222> LOCATION: (690)..(690)
<223> OTHER INFORMATION: n is a, c, t, g, unknown, or other
<220> FEATURE:
```

```
<221> NAME/KEY: misc_feature
<222> LOCATION: (697)..(697)
<223> OTHER INFORMATION: n is a, c, t, g, unknown, or other
<220> FEATURE:
<221> NAME/KEY: misc_feature
<222> LOCATION: (700)..(700)
<223> OTHER INFORMATION: n is a, c, t, g, unknown, or other
<220> FEATURE:
<221> NAME/KEY: misc_feature
<222> LOCATION: (714)..(714)
<223> OTHER INFORMATION: n is a, c, t, g, unknown, or other

<400> SEQUENCE: 103
aattacaaat acaaatacga ataccettct ctctcacaca aaacactagt ccctcccttc      60
ttccttgtct cttctcttc tcaacaacat gcagatcttc gtcaagactt tgactggcaa      120
gaccatcacc ctcgaggtcg agagtagcga caccatcgac aacgtcaagg ccaagatcca     180
ggacaaggaa ggtatccctc ctgaccagca gagtttgatt tttgctggta agcagctgga     240
agatggtcgc actcttgctg attataacat acaaaaggaa tcaacacttc acttggtctt     300
gaggctcagg ggaggaacca tgattaaagt gaagactcta actggaaaag aaattgaaat     360
tgacattgag ccaactgata caatcgaccg gatcaaggaa cgcgttgaag aaaaagaggg     420
aattccacct gtgcagcaga gactcatata tgcaggtaaa cagcttgctg atgacaaaac     480
agctaaagag tacaacattg agggtggttc tgtacttcac ttggtgcttg cattgagggg     540
tggtacttat tagtgtagat gccatatcag aacccaaaga catgaaagga agctctattc     600
ctgccccgtc tctctgaaga catcattgtt cttttatgng cttggttttt gtaattgtgg     660
ctactattgg tggncagtaa ctcagtatcn ttttagntgn atgctattta aaancctaa     720 ggtgggcctt tatatgaata tctgaaccaa tg                                  752

<210> SEQ ID NO 104
<211> LENGTH: 484
<212> TYPE: DNA
<213> ORGANISM: Brassica napus
<220> FEATURE:
<221> NAME/KEY: misc_feature
<223> OTHER INFORMATION: Ceres CLONE ID no. 1036726
<220> FEATURE:
<221> NAME/KEY: misc_feature
<223> OTHER INFORMATION: Encodes the protein at SEQ ID NO: 37

<400> SEQUENCE: 104
gaaatcaaat aaaaaaatct ttaagcaaga aaagaaagaa aatgcagatc ttcgtcaaaa      60
ccctgacggg gaaaaccata accctggagg ttgaaagcag cgacaccatc gacaatgtca     120
aagccaaaat ccaggacaaa gaaggaatac cgccggatca gcagaggctg atcttcgctg     180
ggaagcaact agaagacggt agaacccttg cggactacaa catccagaaa gagtccactc     240
ttcacttggt cttgaggctt aggggtggca ccatgatcaa ggtcaagact ctcactggca     300
aagaaatcga gattgacatc gaacctaccg acaccattga tcgcatcaag gagcgtgttg     360
aggagaaaga aggcatccct cctgttcaac agaggctcat ctacgctgga aaacagctag     420
ctgatgacaa gacggcmaaa gactacaaca tcgagggagg ctctgtttct gcatctggtt     480
cttg                                                                 484

<210> SEQ ID NO 105
<211> LENGTH: 580
<212> TYPE: DNA
<213> ORGANISM: Glycine max
<220> FEATURE:
<221> NAME/KEY: misc_feature
```

<223> OTHER INFORMATION: Ceres CLONE ID no. 513071
<220> FEATURE:
<221> NAME/KEY: misc_feature
<223> OTHER INFORMATION: Encodes the protein at SEQ ID NO: 38
<220> FEATURE:
<221> NAME/KEY: misc_feature
<222> LOCATION: (543)..(543)
<223> OTHER INFORMATION: n is a, c, t, g, unknown, or other

<400> SEQUENCE: 105

| | | | | | |
|---|---|---|---|---|---|
| aagaaaaagg | aaattttctt | gggcgttctt | cggcttcgtt | gtcacaaggt | tcgagttcgt | 60 |
| caccgtctag | tacgactgtg | cgagggagga | agaggcgagg | agaagatgca | gatcttcgtg | 120 |
| aagaccctga | cggggaagac | catcaccctc | gaggtggaga | gcagcgacac | cgtcgacaac | 180 |
| gtcaaagcca | aaatccagga | caaggaaggg | attccccag | atcaacagcg | actgatattc | 240 |
| gctggcaagc | agctggagga | tggacgcacg | ctggctgact | acaacatcca | aaaggagtca | 300 |
| actcttcatt | tggtcctcag | gcttaggggt | ggaaccatga | tcaaggtcaa | aactctcact | 360 |
| gggaaagaga | tcgagatcga | cattgaaccc | actgactcga | ttgacaggat | caaggagcgt | 420 |
| gttgaagaga | agaaggcat | tcctcccgtg | cagcaaaggc | tcatctatgc | tggtaagcag | 480 |
| cttgctgatg | acaagaccgc | aaaggactac | aacatcgagg | gtggatctgt | cctccatctt | 540 |
| gtncttgctc | tgaggggtgg | ttactagtct | aaacctgatg | | | 580 |

<210> SEQ ID NO 106
<211> LENGTH: 987
<212> TYPE: DNA
<213> ORGANISM: Brassica napus
<220> FEATURE:
<221> NAME/KEY: misc_feature
<223> OTHER INFORMATION: Ceres CLONE ID no. 975672
<220> FEATURE:
<221> NAME/KEY: misc_feature
<223> OTHER INFORMATION: Encodes the protein at SEQ ID NO: 44

<400> SEQUENCE: 106

| | | | | | |
|---|---|---|---|---|---|
| attccatcaa | cttcagacac | acagatctct | tctcaatcac | attacttctg | gttctcccac | 60 |
| catgaggaaa | gggagaggct | cttccgccgt | tccacccgcc | cttcccggat | ctgtgaagga | 120 |
| gccgaggtac | agaggcgtta | ggaagagacc | ttggggccgt | ttcgccgccg | agatccgtga | 180 |
| cccctttgaaa | aaatcccgag | tctggctcgg | cacgttcgac | tccgcggagg | aagccgcacg | 240 |
| cgcctacgac | gcagccgctc | gtaacctccg | cggtccaaag | gccaagacca | acttccaaat | 300 |
| cgactgttct | ccttcctctc | ctctccaacc | actccatcat | cggaaccaga | tcgatccctt | 360 |
| tatggaccac | cggttatacg | gcggagagca | ggaggttgtt | atcatcagcc | ggccggcgag | 420 |
| tagcagcatg | agcagcaccg | ttaagtcgtg | cagcggagtg | agaccagcgt | cttcttccgt | 480 |
| ggcgaaggcg | gcgacgaaga | gatatccacg | gactccgccg | gtggcgccgg | aggattgccg | 540 |
| cagcgactgc | gattcgtcgt | cgtcggtggt | tgaagacgga | sacgacatag | cttcgtcgtc | 600 |
| ttcgcggcgg | aaaccgccgt | ttgagtttga | tcttaatttt | ccsccgttgg | atggcgttga | 660 |
| cttattcgta | ggcgcggacg | atctccactg | caccgatctg | cgtctttgat | ctttgagcac | 720 |
| aatgacaaca | aagatgatga | agaagtgata | gggagagaga | gtttgtgtta | agatctgttg | 780 |
| ttgtaagaac | cagatctgtg | tttcattcac | ttgtctgttt | cttataaaga | tcaaccttt | 840 |
| gttacatgta | acacttatat | agctgctgat | gattcttaat | tattcaaaat | ccaaagtctg | 900 |
| tagaatttat | acagtatcta | tcactgatgt | gcttatggat | ggtttggagt | atgaggctac | 960 |
| attttcataa | atacattcaa | tgtgtgt | | | | 987 |

<210> SEQ ID NO 107
<211> LENGTH: 1034
<212> TYPE: DNA
<213> ORGANISM: Zea mays
<220> FEATURE:
<221> NAME/KEY: misc_feature
<223> OTHER INFORMATION: Ceres CLONE ID no. 273307
<220> FEATURE:
<221> NAME/KEY: misc_feature
<223> OTHER INFORMATION: Encodes the protein at SEQ ID NO: 45

<400> SEQUENCE: 107

| | | | | | |
|---|---|---|---|---|---|
| ctctccttcc | ttcacggatt | cccaaatact | cgcttccaat | accaattctc | cgatccacgt | 60 |
| tcgttcccgc | accctcgcgc | tccgctgatc | cggcggcatg | cggcgccgcg | gcgtggcggc | 120 |
| ggctgatgcg | gacggtgacg | tggagttgcg | gttccgcggg | gtgcggaaga | ggccgtgggg | 180 |
| ccggtacgca | gcggagatcc | gggacccggc | gaagaaggcg | cgcgtctggc | tcggcacatt | 240 |
| cgactccgcc | gaggacgccg | cccgcgccta | cgacgccgca | gcgcggatgc | tgcgcgggcc | 300 |
| caaggccagg | accaacttcc | cgctccccgc | cgcagccgcc | ctccaccacc | ccacatgcc | 360 |
| cgctgctgcc | gccgcagcag | ctccaccata | cacaacatat | cccaccgcca | cgggcgtcgt | 420 |
| ctcgacgccg | ccggtcgcca | gaccggcttg | cagcagcctc | agctccaccg | tggagtcctt | 480 |
| cagcggcgcg | cggccgcggc | ctgtgctccc | gccgcggttc | cctccgccgt | cgattcctga | 540 |
| tggcgactgc | cgcagcgact | gtggttcctc | ggcctcggtc | gtggacgacg | actgcacgga | 600 |
| cgcggccgcc | tctgcgtcgt | gccccttccc | gctcccgttc | gacctcaacc | tgcccccagg | 660 |
| cggcggcgga | gccggcgtcg | ggttttacgc | cgatgaggag | gatgagctca | ggctcacggc | 720 |
| gctgcggctg | tgacgtcgag | ctcaatcgag | ccgctgctta | gaaagaggaa | aaggagaaaa | 780 |
| atatttggtt | cttcccttct | cttgtagccg | acacgaactc | tccatccact | cgatgttgt | 840 |
| tgtttacttg | atctgattat | gatatttgcc | tgaatcctag | tcaacttacc | tgcatgcatg | 900 |
| cctgcttgtt | ttctggcgat | tgaggattat | cgccaaacgc | caaatcttgc | agcagctgtt | 960 |
| gtactgtaat | atatcaacat | tttacttcct | tcctcttatg | aggaaagaga | cagataaagt | 1020 |
| aacttatttc | aatc | | | | | 1034 |

<210> SEQ ID NO 108
<211> LENGTH: 911
<212> TYPE: DNA
<213> ORGANISM: Triticum aestivum
<220> FEATURE:
<221> NAME/KEY: misc_feature
<223> OTHER INFORMATION: Ceres CLONE ID no. 1055099
<220> FEATURE:
<221> NAME/KEY: misc_feature
<223> OTHER INFORMATION: Encodes the protein at SEQ ID NO: 46

<400> SEQUENCE: 108

| | | | | | |
|---|---|---|---|---|---|
| aaacaaaaaa | ccaccagggg | aagaagggaa | agacacacgc | cactgtgacc | aaaccctagg | 60 |
| ccggccgcga | tgcgcaaggc | gaggccgccg | cagccccagc | cgcagccgtc | gcagcagtcg | 120 |
| ccggagatcc | ggtaccgcgg | cgtgcggaag | cgccctcgg | gccgctacgc | cgccgagatc | 180 |
| cgggaccccg | ccaagaagac | gccgatctgg | ctcggcacct | tcgactgcgc | cgaggacgcc | 240 |
| gcccgcgcct | acgactccgc | cgcccgatcc | ctccgcgggc | ccaccgcccg | caccaacttc | 300 |
| ccgcccctcct | ccgccacgca | gccgccgccg | aggcccctc | cccccgcggc | cgcggccgcg | 360 |
| gccgccacgt | ccagccagag | cagcaccgtc | gagtcctgga | gcggcggcgg | gccccgcgcc | 420 |
| cccgccaggg | cccgcagcgc | cgcccgagcg | ggcacggcca | aggaggggga | ggaggactgc | 480 |

```
cgcagctact gcggctcctc gtcctccgtc ctcctcgagg agggcgcgga cgacgcggcc     540
gcctcccgct ccccgctgcc cttcgatctg aacatgccgc cccgcagga gggggcgctt      600 gacgccgagg ccgatcagat gacctgccgg tacgacacgc tgctccgcct ctagctccac     660
gacgacgaga gcaaggattc gtgggagggg aactgggaaa aggaacgaga aaagcgcttg     720
cccccgctcc gctccggtcc gtcttccgat gatctcgtgg tgttctctct ttgttagaaa     780
tggataattc ttgccatttt ttttctttac tttctttcct tcttctttt ttttcttct      840 taccactttg attcgatatg tgaataattg agtcatgtaa gctgcgagca aggaaatctg     900
agcttttcct t                                                         911
```

<210> SEQ ID NO 109
<211> LENGTH: 160
<212> TYPE: PRT
<213> ORGANISM: Arabidopsis thaliana
<220> FEATURE:
<221> NAME/KEY: misc_feature
<223> OTHER INFORMATION: Ceres GI ID no. GI_15226675
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 109

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Glu Leu Gly
            20                  25                  30

Leu Lys Leu Phe Ile Lys Ile Phe Glu Ile Ala Pro Thr Thr Lys Lys
        35                  40                  45

Met Phe Ser Phe Leu Arg Asp Ser Pro Ile Pro Ala Glu Gln Asn Pro
    50                  55                  60

Lys Leu Lys Pro His Ala Met Ser Val Phe Val Met Cys Cys Glu Ser
65                  70                  75                  80

Ala Val Gln Leu Arg Lys Thr Gly Lys Val Thr Val Arg Glu Thr Thr
                85                  90                  95

Leu Lys Arg Leu Gly Ala Ser His Ser Lys Tyr Gly Val Val Asp Glu
            100                 105                 110

His Phe Glu Val Ala Lys Tyr Ala Leu Leu Glu Thr Ile Lys Glu Ala
        115                 120                 125

Val Pro Glu Met Trp Ser Pro Glu Met Lys Val Ala Trp Gly Gln Ala
    130                 135                 140

Tyr Asp His Leu Val Ala Ala Ile Lys Ala Glu Met Asn Leu Ser Asn
145                 150                 155                 160

<210> SEQ ID NO 110
<211> LENGTH: 1823
<212> TYPE: DNA
<213> ORGANISM: Arabidopsis thaliana
<220> FEATURE:
<221> NAME/KEY: misc_feature
<223> OTHER INFORMATION: Ceres Promoter 28176

<400> SEQUENCE: 110
gtctcttaaa aaggatgaac aaacacgaaa ctggtggatt atacaaatgt cgccttatac     60

```
atatatcggt tattggccaa aagagctatt ttaccttatg gataatggtg ctactatggt      120
tggagttgga ggtgtagttc aggcttcacc ttctggttta agccctccaa tgggtaatgg      180
taaatttccg gcaaaaggtc ctttgagatc agccatgttt tccaatgttg aggtcttata      240
ttccaagtat gagaaaggta aaataaatgc gtttcctata gtggagttgc tagatagtag      300
tagatgttat gggctacgaa ttggtaagag agttcgattt tggactagtc cactcggata      360 cttttcaat tatggtggtc ctggaggaat ctcttgtgga gtttgatatt tgcgagtata      420
atctttgaac ttgtgtagat tgtacccaaa accgaaaaca tatcctatat aaatttcatt      480
atgagagtaa aattgtttgt tttatgtatc atttctcaac tgtgattgag ttgactattg      540
aaaacatatc ttagataagt ttcgttatga gagttaatga tgattgatga catacacact      600
cctttatgat ggtgattcaa cgttttggag aaaatttatt tataatctct cataaattct      660
ccgttattag ttgaataaaa tcttaaatgt ctcctttaac catagcaaac caacttaaaa      720
atttagattt taaagttaag atggatattg tgattcaacg attaattatc gtaatgcata      780
ttgattatgt aaaataaaat ctaactaccg gaatttattc ataactcca ttgtgtgact       840 gcatttaaat atatgtttta tgtcccatta attaggctgt aatttcgatt tatcaattta      900
tatactagta ttaatttaat tccatagatt tatcaaagcc aactcatgac ggctagggtt      960
ttccgtcacc ttttcgatca tcaagagagt tttttataa aaaatttat acaattatac       1020 aatttcttaa ccaaacaaca cataattata agctatttaa catttcaaat tgaaaaaaaa      1080
aatgtatgag aattttgtgg atccattttt gtaattcttt gttgggtaaa ttcacaacca      1140
aaaaaataga aaggcccaaa acgcgtaagg gcaaattagt aaaagtagaa ccacaaagag      1200
aaagcgaaaa ccctagacac ctcgtagcta taagtaccct cgagtcgacc aggattaggg      1260
tgcgctctca tatttctcac attttcgtag ccgcaagact cctttcagat tcttacttgc      1320
aggttagata ttttctctct ttagtgtctc cgatcttcat cttcttatga ttattgtagc      1380
tgtttagggt ttagattctt agttttagct ctatattgac tgtgattatc gcttattctt      1440
tgctgttgtt atactgcttt tgattctcta gctttagatc cgtttactcg tcgatcaata      1500
ttgttcctat tgagtctgat gtataatcct ctgattaatt gatagcgttt agttttgata      1560
tcgtcttcgc atgtttttta tcatgtcgat ctgtatctgc tctggttata gttgattctg      1620
atgtatttgg ttggtgatgt tccttagatt tgatatacct gttgtctcgt ggtttgatat      1680
gatagctcaa ctggtgatat gtggttttgt ttcagtggat ctgtgtttga ttatattgtt      1740
gacgttttgg ttgttgtatg gttgatggtt gatgtatttt tgttgattct gatgtttcga      1800 ttttttgtttt tgttttgaca gct                                             1823
```

<210> SEQ ID NO 111
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0668

<400> SEQUENCE: 111

```
atagagtttt actatgcttt tggaatcttt cttctaatgt gccaactaca gagaaataca       60
tgtattacca ctaggaatcg gaccatatca tagatatcag gattagataa ctagttctcg      120
tcgctatcac ttcgcattaa gttctagtaa ttgttaaaga ttctaatttt ttactaaaca      180
aaaactaaat caacatcaaa tatgcaaagt gtgtgttgtc cacacaagtg actcaaagta      240
```

```
tacgcaggtg ggattggacc atattattgc aaatcgtttc cgaaccactc atatttcttt    300 tttctctcc tttttttatc cggagaatta tggaaccact tcatttcaac ttcaaaacta    360
attttttggt tcagtgatca aatacaaaaa aaaaaaaaaa gttatagata ttaaatagaa    420
aactattcca atcttaaaaa tacaaatgaa accataattt taatttatac aaaactattt    480
aattagctaa gggttgtctt aacgtttaga aaataaaaaa ttatgattgt ctgtttaaaa    540
ttacaatgaa tgaataaaaa aaatatgcaa tgaatgaaag aataaatttt gtacatccga    600
tagaatgaga aaatgaattt tgtacaaacc actcaagaat tcaaaacaat tgtcaaagtt    660
ttcttctcag ccgtgtgtcc tcctctccta gccgccacat ctcacacact aatgctaacc    720
acgcgatgta accgtaagcg ctgagttttt gcatttcaga tttcacttcc accaaacaaa    780
actcgccacg tcatcaatac gaatcattcc gtataaacgt ctagattctt tacagcctac    840
aatgttctct tctttggtcg gccattattt aacgctttga acctaaatct agcccagcca    900
acgaagaaga cgaagcaaat ccaaaccaaa gttctccatt ttcgtagctt ctttaagctt    960
tttcagtatc atagagacac tttttttttt ttgattagaa                         1000
```

<210> SEQ ID NO 112
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0535

<400> SEQUENCE: 112

```
ttagtgaaat tatgacatta agtaaggttt tcttagttag ctaatgtatg gctattcaat     60
tgttatgtta ggctatttta gttagtatat gaatttaggc agtctatgca aatgatttcg    120
ttttcatttt ttcatatgta aacatcaaga tcaagtaacg ccattcgagt tgatattttt    180
tttttaaatt agtgtgtgta aattttggac cgcttatttg agtttgctaa tgaagttgca    240
tatatattac gttaaaccat aggcaaacta atttgaaaca tccgattcga tttcctgtaa    300
tttttcttgg ttaattgacc aaaatcaaga tcttcagaaa taaaataaaa gacgaaagaa    360
agctgtcgca aagcagattg tgttaaaaaa aagtggattg ggctcaaacg caacttgtcc    420
agcccgtgac aattacccta tacgcaagta agagtaacgt atcactggca aaagttggta    480
ttagttacga tatctttgtc atgggggcat gcatgggcat ggcttaagag ttaagcctta    540
agaagagtcc cacactcgtg actctcatga tcacttgttg tttcttacgg gcaaatacat    600
ttaactttat tcttcattta ttcacctata ttctttggga taataacttt tctctatata    660
aaataacaaa catcgtacgt ttcatttatt tacaacaagc gatgagaatt aaaaggagac    720
cttaattgat gatactcttc ttttctctcg gttacaacgg gattattaca gataatgata    780
atctatatgg atgctgacgt ggaaaaacaa aatttggtga aacacgtcaa ttaagcacga    840
cttttccatg gctagtggct aagatcgttt catcacatgg ctatatcata taatacttgg    900
atgaattcaa aataaacgac tgagaaaatg tccacgtcac ggcgcaccgc tttggactta    960
agtctcctat aataaataca acaccaaaca ttgcattcca                         1000
```

<210> SEQ ID NO 113
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter PT0585

<400> SEQUENCE: 113

```
tgaagtcatt taatatgagt ttgacattag gtaaacctaa tctatgagat tatagaatgt      60
agcaaaacta tcaatgtttc ttttccaaaa tattttgtgg ttttttcttt tggttcatta     120
tgttttgtta tttgtgaatt attttaatat gaagtaatta tattgatttt atatgatata     180
catattattt tgatataaaa tttaacactt atccattaaa atagcatggg cataatcaaa     240
atcgggacta ttacgatgaa aaagatagtt aaattgtatg ataaaataaa atgtgtaaga     300
ttaaaatttt gggttttaga aaattactaa acaaaatata gacaaagtat gttgactatt     360
atttaaaatt taaatatcat caataagata tagttaaagt cattaagtgt atagcaaaat     420
gaaaattcta agattaaaat tcgattaaaa ttttttttac taaattaaat atttaaaaat     480
agggattatc atttactatt tacaattcta atatcatggg taaaaattga taactttttt     540
taaacccgcc tatctaggtg ggcctaacct agtttactaa ttactatatg attaacttat     600
taccactttt acttcttctt ttttggtcaa attacttat tgttttttat aaagtcaaat      660
tactctttgc attgtaaata atagtagtaa ctaaaatctt aaaacaaaat attcaacctt     720
tcccattatt ggaatggtaa tgtcttcaac accattgacc aacgttaagg aatgtctttt     780
aatattttg gaacctaaat gctaatactg tataccacaa tcacttatga gtattgaagt      840
tgagatagag gaggtacaag gagaccttat ctgcagaaga caaaaagcca tttttagcaa     900
aactaaagaa agaaaaaaga ttgaaacaca aatatgcgcc actcgtagtc caccccctatc    960
tctttggcaa aagccacttc actcttttc ccttttat                              999
```

<210> SEQ ID NO 114
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0613

<400> SEQUENCE: 114

```
ttaatactaa cattgtagaa agccacaaaa aagaaattga aatgtgagta gatgctgagt      60
cagaggtttg gtcaatacac aacagctaat tgagataata ttatacacgt cacgatgact     120
tgttttttct cctcccaact tgttaatttc tttattctta aaattaaacc atcgcaaaaa     180
cagaagaaca cagctgtttt tctcgactcc caatttctat tttgctgcta aggacatttc     240
atttcattat ttcccaattc aggactcctt agattttcct aaatttgttt tcctaacttg     300
ctctctctca ttctaacatt ttctcatttt tttagattat cttgtacttt ttagtagatt     360
attttatcag gttttacaaa catacattga cattctaaaa agggcttcta aaaattcagt     420
gtggaatgct gatatactaa aaaaaggtca tgcaaaatta tctacgattt atctaaaatt     480
agataatttg ccatatataa ctattaacta ataatcgatc ctttgatttt ttgtttagat     540
aaaacgaaac agctatatct tttttttttg ttatcggatt ttaatcgaat aaaagctgaa     600
aaataacagt tatatcttct tctttttaa ctaatgaaac agttatatct taaacaaaca      660
acagaaacag taaatatatta atgcaaatcc gcgtcaagag ataaattta acaaactaat      720
aacaattgag ataagattag cgcaaaagaa actctaattt tagagcgtgt aaacacaaac     780
acgtcttgaa agtaaacgtg aattacacgc ttctaaaacg agcgtgagtt ttggttataa     840
cgaagatacg gtgaagtgtg acacctttct acgttaattt cagtttgagg acacaactca     900
```

```
agttatgttt gatatctaag gacttgcact gtctccaaat ctgcaggaag gactttttga    960
ttggatcaat ataaatacca tctccattct cgtctccttc                         1000

<210> SEQ ID NO 115
<211> LENGTH: 351
<212> TYPE: DNA
<213> ORGANISM: Arabidopsis thaliana
<220> FEATURE:
<221> NAME/KEY: misc_feature
<223> OTHER INFORMATION: Ceres Promoter PT0625

<400> SEQUENCE: 115
gatcatgatc agtttcaact cgctgtgccc acgtgtcgag agatcggcac gtgcctgagc     60
tctcagccgc tcataaatac acttgtttag tagcaacagt atactatagt agtcctctcc    120
tgtttggctt ttagcttgca tcgatggatg gatggatgga tcgcatgaga gggcttcgcg    180
aaggtacgga accttacaca acgcgtgtcc tttctacgtg gccatcgtgt aggcgtctcg    240
ccatgctacg tgtcccggag gatgtctcga tgccaaccct tataaatact gttccattcc    300
aatcccatcg ccacagccag tgcaaatctg atcgatcaag ataatcgagc a            351

<210> SEQ ID NO 116
<211> LENGTH: 1022
<212> TYPE: DNA
<213> ORGANISM: Arabidopsis thaliana
<220> FEATURE:
<221> NAME/KEY: misc_feature
<223> OTHER INFORMATION: Ceres Promoter PT0633

<400> SEQUENCE: 116
cccgatcggc cttaatctga gtcctaaaaa ctgttatact taacagttaa cgcatgattt     60
gatggaggag ccatagatgc aattcaatca aactgaaatt tctgcaagaa tctcaaacac    120
ggagatctca aagtttgaaa gaaaatttat ttcttcgact caaaacaaac ttacgaaatt    180
taggtagaac ttatatacat tatattgtaa tttttttgtaa caaaatgttt ttattattat    240
tatagaattt tactggttaa attaaaaatg aatagaaaag gtgaattaag aggagagagg    300
aggtaaacat tttcttctat tttttcatat tttcaggata aattattgta aaagtttaca    360
agatttccat ttgactagtg taaatgagga atattctcta gtaagatcat tatttcatct    420
acttctttta tcttctacca gtagaggaat aaacaatatt tagctccttt gtaaatacaa    480
attaattttc gttcttgaca tcattcaatt ttaattttac gtataaaata aaagatcata    540
cctattagaa cgattaagga gaaatacaat tcgaatgaga aggatgtgcc gtttgttata    600
ataaacagcc acacgacgta acgtaaaat gaccacatga tgggccaata gacatggacc    660
gactactaat aatagtaagt tacattttag gatggaataa atatcatacc gacatcagtt    720
tgaaagaaaa gggaaaaaa gaaaaaataa ataaagata tactaccgac atgagttcca    780
aaaagcaaaa aaaagatca agccgacaca gacacgcgta gagagcaaaa tgactttgac    840
gtcacaccac gaaaacagac gcttcatacg tgtcccttta tctctctcag tctctctata    900
aacttagtga gaccctcctc tgttttactc acaaatatgc aaactagaaa acaatcatca    960
ggaataaagg gtttgattac ttctattgga aagaaaaaaa tctttggaaa aggcctgcag   1020
gg                                                                  1022

<210> SEQ ID NO 117
<211> LENGTH: 1000
<212> TYPE: DNA
<213> ORGANISM: Arabidopsis thaliana
```

<220> FEATURE:
<221> NAME/KEY: misc_feature
<223> OTHER INFORMATION: Ceres Promoter PT0650

<400> SEQUENCE: 117

```
catacttaat tctaaaaaaa caacacttat agtttataag cagctcttat gataaaaatc      60
tttctgagtt atagctctgt taaacttgta ttcaccccaa aaacggatgt ttcatttctt     120
atttttact tggagtattt tattgtaatt tgtaaaaaaa aatgtaaagt gggggatatc     180
atgaaaaaca acgtcacttt gtttggtcac aatatacatt tgataaaata atggtcgtcg     240
cgtgatttag ttgattttg ttttatcaac cacgtgtttc acttgatgag tagtttatat     300
agttaacatg attcggccac ttcagatttg ggtttgccca catgacat accgacatag     360
aaggttaaat ccacgtggga aatgccaata ttcaatgttt ggttttcaaa agagaatcat     420
ttctttatat gatctcaaaa gtatggaatt gaaatgacta atgagcacat gcaattggtg     480
ctatcttaaa aaccgaacgt ctttgaattt aatttgtttt tcaccaaagg tacctaatga     540
aacccttca ttaaaaaata aaggtaacaa acaaaatttt gtattggaaa aaacattttt     600
tggaatatat aatttggtaa tagaattatg agcaaaaaag aaaaagaaaa gaaagaataa     660
tgagcataat aaagccttta cagtattact aattgggccg agcagttttg ggctcttgat     720
catgtctagt aatcttaaac agacgataaa gttaactgca atttagttgg ttcaggtgag     780
ctaccaaatc caaaaatacg cagattaggt tcaccgtacc ggaacaaacc ggattatca     840
aaatccttaa gttatacgaa atcacgcttt tccttcgatt tctccgctct tctccactct     900
tcttctctgt tctatcgcag acattttgt ttatatgcat acataataat aatacactct     960
tgtcaggatt tttgattctc tctttggttt tctcggaaaa                         1000
```

<210> SEQ ID NO 118
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter PT0660

<400> SEQUENCE: 118

```
caagtcaagt tccaatattc taaggagaaa taatagtata ctaaacatac attagagagg      60
ttaaacttct ttttggattt aagtgtgtat gcataggcta tttattctta agtataacta     120
ttaactgtag ctagatttat acaagaaata cataaaactt tatgcatgtg aggtagccat     180
gaatatacgt acatgttgca atcgattata catgttgtat ttggatttct ctatacatgt     240
tttaacttgt cattctctaa gtatatacat accattaata ctgtgggcat gagtttatga     300
taagactttt cttttggaga ccagttttgt tttccttcc acctatattt gtctataggc     360
ttcacggtac actagtttac aagtgttttt atatgttcta aataaaattg agattttccg     420
gaacggtatg atctgtttgc aaataaggac gtatatataa cagtatcaaa tatatttgtt     480
gttataaggc aataatatat tttctgagat attgcgtgtt acaaaaaaga aatatttgtt     540
aagaaaaaaa aagatggtcg aaaaggggga gtaggtgggg gcggtcggct tttgattagt     600
aataaaagaa accacacgag tgacctaccg attcgactca acgagtctac cgagctaaca     660
cagattcaac tcgctcgagc ttcgttttat gacaagttgg ttttttttt ttttttaat     720
ttttcatct tcttgggttt ggttgggtca ctcttcaggt caggtgtgta aaaagaaag     780
aaagaaaaga gagattgttg tgttgtaacc cctttgacta aaatctaatg aacttttta     840
```

| acacaacaaa actccttcag atctgaaagg gttcttcttc tctcttagtc tcttcgtcct | 900 |
| tttattctcc gtcgtcgttt catgatctga ctctctggtc ttctcttctt cttcttcttc | 960 |
| ttctattttt tcttacttcg tcactgttgt gtctgaac | 998 |

<210> SEQ ID NO 119
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0665

<400> SEQUENCE: 119

| aaaaaggatg ggtaatggga cctatttcc ccaacatccc acatgcacac ttccctctcc | 60 |
| attctctcac atttatttct ttcattctaa tttatccatt ccgtgtgtaa catattcact | 120 |
| aataatctca tctcactaac tcattcattg attgtgatat gtttatctag aattagtgtt | 180 |
| ttaacactgt gtctacatat gatttccttt tcattgtatg tgaacatgtt aactcactaa | 240 |
| tcattttgta ttttcgagtt aacatgagtc tccacttcgg tagactaaag taaagatagg | 300 |
| tttgagtata ataagttta aaatttgctt taaaatcaat atttataaat aagttttat | 360 |
| cataagtgat ttttgtatgt tatattggac cttgtataaa cagactacag aagaaaatta | 420 |
| tttatgagaa cttgtaatgt tagagtggac ctcgtataaa ctaattatgt gggcttttac | 480 |
| cataaactat ttatgaaaat tattatggcc cacaccacta taactaaagc ccacatattt | 540 |
| agcagcccag tttcattgta agagacatgt tcgctctgga actagaattt tctggttttt | 600 |
| gggtatttgt tttcttatgt gtagagaaat gatggtaacg attaaatgtt gtgtattaca | 660 |
| atttacaatg gtaagacgat taatatattt acacacaatt ttgttgttgc tgtaacacgt | 720 |
| tagtgtgtgt gatgatagaa tttcataaag ctttaactac gaggggcaaa atgttaattc | 780 |
| taaatagttg acagcagaaa aagatatgta tacataatat aaggattaaa acgtaaataa | 840 |
| taataaataa ggcgagttaa attaaaaccc tgttaaaacc ctagcttgaa acacatgtat | 900 |
| aaaaacactt gcgagcgcag cttcatcgcc atcgccattc tctctctcat caaaagcttt | 960 |
| tctccttgat tttcgcattc tttagagtct aacgcaaag | 1000 |

<210> SEQ ID NO 120
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter PT0672

<400> SEQUENCE: 120

| cagccgtaaa tcctccataa atttattttg caagttttgc tcattatata atgagcggaa | 60 |
| tttatgatat aatcgtttgt aataatgtta tgttttgatc aaaatttgaa attaaaagta | 120 |
| ggtgagaact tgttatacag tgtagataag gtggatcttg aatataaaaa taaaatttat | 180 |
| aagatgtatt taaagcagaa aagcataaaa ctttagataa aataatgtaa aaatgtgtta | 240 |
| gcatcaatgt tgggatattg gccgacccga acttaatcaa tgtcggaagc cattacttct | 300 |
| ctcccaaaag acctttttcc ttcggagaac taggaacttc ctcactacct ttcgcttaac | 360 |
| gtgaaagcca taaatttcat atattcataa aaatcagaaa atctaaaact gtttagtatc | 420 |
| acctgttttt ggtatagact attggttttg tgttacttcc taaactatat gatttcgtac | 480 |
| ttcattggat cttatagaga tgaatattcg taaaagata agttatctgg tgaaacgtta | 540 |

| | |
|---|---|
| cttcagtcat gttgggtcta gatttacata ctactatgaa acattttaag ataataatta | 600 |
| tcctagccaa ctatatgttc tatattatgg gccaagaaga tatagaacta aaagttcaga | 660 |
| atttaacgat ataaattact agtatattct aatacttgaa tgattactgt tttagttgtt | 720 |
| tagaataaat agtagcgtgt tggttaagat accatctatc cacatctata tttgtgtggg | 780 |
| ttacataaaa tgtacataat attatataca tatatatgta tattttgat aaagccatat | 840 |
| attactcctt gacctctgcc cccatttcct tttactataa ataggaatac tcatgatcct | 900 |
| ctaattcagc aatcaacacc aacgaacaca acctttcca aagccaataa taaaagaaca | 960 |
| aaagctttta gtttcatcaa agacgaagct gccttagaa | 999 |

<210> SEQ ID NO 121
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0676

<400> SEQUENCE: 121

| | |
|---|---|
| aagatagtac agtttcagtg ttttgagaaa aaaagctgaa ctaaaactaa aatgtttaag | 60 |
| gacacaatat ttagtttcaa ttagataatt caacagtttg aacaattttt ttttttttt | 120 |
| tttgaagtca tttatttata caatgttta aaacgcatta agcatttagg cagccgacaa | 180 |
| acgcctattg tctaactgta aataggcgct tccacttagg ttcatattgc atatttacta | 240 |
| tatgtgtata gtgacaaaaa ccaatatttc tcttattttg gatgaaggta tagtagttgt | 300 |
| taaatgttca atataattaa gcattaatga caaataaaat aaaattaatt tagttgataa | 360 |
| aaagataatc ttataaaaag atcgatgaat agatataatg gtttactgaa ttctatagct | 420 |
| cttaccttgc acgactatgt cccaaggaga ggaagtacct taactataat tctgaacata | 480 |
| attttgtcta tcttggtgag tattatatga cctaaaccct ttaataagaa aaagtataat | 540 |
| actggcgtaa cgtaataaat taacacaatc ataagttgtt gacaagcaaa aaaacataca | 600 |
| taatttgttt aatgagatat attagttata gttcttatgt caaagtacaa ttatgcctac | 660 |
| caaaattaat taatgatttc aacaggaagt ctgagatgat gggccgacgt gtagttacgt | 720 |
| ttcttgaatt gtgagagatg gtatttatta tactgaagaa acattatttt actaaataaa | 780 |
| ttttcatttc acatcttctg taatcaatgc gggtagatga agaagttgtt aatacgatgg | 840 |
| ccaaccatat ggatctcttt tttggcgttt ctatatatag taacctcgac tccaaaggca | 900 |
| ttacgtgact caataaaatc aagtcttttg tttccttta tccaaaaaaa aaaaaagtc | 960 |
| ttgtgtttct cttaggttgg ttgagaatca tttcatttca | 1000 |

<210> SEQ ID NO 122
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter PT0678

<400> SEQUENCE: 122

| | |
|---|---|
| aattaaatga aaccgcccct aaattaggag ggatttgggt aagtggtaac acattcactg | 60 |
| gaaacatgtg aagaaaggag gatgtcaagt agctgaaaac tcagtatagt aaccaacggc | 120 |
| ttctcaccaa cctttcatta ataatttggt catccctata tttttattca acattttgtt | 180 |

```
tttcaatagc ttagagcacc ttaatacctt tcagtgtttt tttataaaaa aaacaaaaat    240
tgggattaat catcaatccc caaatgtaac gttacttag attatgttca tttttctata    300
cacacaaatc atattctttt gttttaatct tcgaaaaacg agaggacatt aaatacccct    360
aaaaaaggag gggacattac taccaacgta cattaacatg tttgatagca aacgatttat    420
tttgttcgtt ttgaaaaggg gaaagtaatg tgtaaattat gtaaagatta ataaactttt    480
atggtatagt aacattttcg aataataaga gagggaaaac actcgccatt gtcggcaatt    540
tagaaccaat attgaaggg ttttttaga gaaaaaggac ttaaagtttt agagaccta    600 acaacaactt atttagaaat agacatgctt aagttgacaa cagcgagttt attttctata    660
tcgaagaaaa atacgaactt tttcttaatt agatttcgaa tgcatgcact atcgagaatc    720
gaccgtcaca agaaaaaact aatatacata ctgtacatat ctatattcaa tattggtggg    780
gatgggttta atgtgtattt ataattcatg ataaattca cacaataagg tccatgaaac    840
tagaaggtac caaaaataag cattaatgac tctttgccac ttatatatat gattctctca    900
tagtaccatt ttattctccc aaacctatct tcttcttcct ctcttgtctc tctcgctctc    960
tctcttctac attgtttctt gaggtcaatc tattaaaa                           998

<210> SEQ ID NO 123
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0683

<400> SEQUENCE: 123
gattgaatga tgagtgtgca cccttgtatt actaataaaa aatttagcaa cagttataag     60
ctaacgtcat ccatgagtca ttcattagat tcactatttg cgttctcaaa aatcgaattg    120
ttaaaatttg agaagctcta atatacgagt caatgagatg tggcaaaagc atgtccttga    180
ccataaaatt tcgaggggtc aactcattag ataaggacaa gaatcaacca attgaaggcg    240
tcttctataa caagtttctt tattactaat attaaagtcc aatggggtga gggggagaag    300
aacttaaata aaaggaaata attggtaagt gaataaaatc taaatacgat actagatgat    360
tgatttgtgc tagtgcatgg tattagatca gatatgtgtt actattcgaa ttcaaattgg    420
catattccat gttgttgata agaaaattgt agaagtgtaa aagctgagtt actatattca    480
aactagtggt ttacataaag tgagacaaca actgtttcac aaaaatgact ataaaatagt    540
aagtagtatt aggtcaattg attttaaaat tttaatcaaa ttcaaatttg tgatataatc    600
aaatttgttt atagaaaatg ttaagaaatc aattttggca gaactaattc agtgagaaac    660
aatcatttac aaaaacaatt ttaacattat ttaacagtaa gatttgacat ttaacccgtt    720
cgtgtgaacc catcatatct aacatggctc tacccatgac gcctccatgc catggacaat    780
tttgacagat cagaagttct gaacgtggac gaggtaagaa caccatgatg atacgattgg    840
agttagttat gtcgccaccg acatcactgc caatctcatt aataaaagtg gtactaaatc    900
tctaatctct attaactata aatataacaa agaaccaaaa gaaagtttct tatctctctt    960
atctttcata atttccaaga aacacaaacc ttttctacta                         1000

<210> SEQ ID NO 124
<211> LENGTH: 1000
<212> TYPE: DNA
<213> ORGANISM: Arabidopsis thaliana
<220> FEATURE:
```

```
<221> NAME/KEY: misc_feature
<223> OTHER INFORMATION: Ceres Promoter PT0688

<400> SEQUENCE: 124
acgttcagag gcatcgcttt tgtacaaatt gaagcgggtt tgttcaatat ttaaaataac      60
acaggaaaca ttcaaatgta ttattgatgt tgcttaggtt tgtgaaatga tatgaaccat     120
atcgtatata ttactagatt tttcttatat gtttttaaggg tagtggggct gacctatcat    180
tctgtttggc attaccaatc agactatcag agtattcacc attcaggatt ccataactag    240
aaaaagaagg ggtttacatt ttctcatact gtataatttt ctactatcag agattttatc    300
gattacatta atctcatagt gattattctg atttataaaa aagttgacaa ataattaaa     360 accagtatt t tataacaaga ttgtctctct cccatggcca ttattttgac ctctgactta    420
tttaaatctt aattaacagc ataatactgt attaagcgta tttaaatgaa acaaaataaa    480
agaaaaaaag aacaaaacga aagagtggac cacatgcgtg tcaagaaagg ccggtcgtta    540
ccgttaaggt gtgtcgaact gtgattgggc cacgttaacg gcgtatccaa aagaaagaaa    600
gggcacgtgt atagatctag gaaaaaagaa agaatggacg gtttagattg tatctaggta    660
ccaggaaatg gaacgtcaca ccaaacggta cgtgtcggat cctgcccgtt gatgctgacg    720
gtcagcaact tccccttatt catgccccc  tgcccgttaa ttacgtgtaa cccttccatg     780
cgaaaatcaa accctttttt tttttgcgt tcttcttcaa cttttctttt taaatcaaac      840
cttttctttt taaatcaca ttgcatttcc taacgctcaa caaaatctct ctctactaat     900
atctctctct ctctctctct attgttgaag aagactcata atcggagatt gtttgttttt    960
ggtttgctct gtaaattgga gaagttttgt tagagatcaa                          1000

<210> SEQ ID NO 125
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0695

<400> SEQUENCE: 125
aacattttct ttaacttact cttaaatttt aatagtaagt tgatgcatgt tatgttgatc     60
cgtcttgatc acaaatattg ttttatggac gaattctttg acagtaaatg gctatagtga    120
ctcagcttgg agcatcccga tatgaaaaca aagtgcagta ttgtgtcgtg gtcatcacta    180
acgcactttc ctagaactat cgcgcgtgtt tgacctatgc aacacaccag atgtcatgaa    240
cgtatactta aatagaaaca atgatataga caattggcta tattctgtca tggaacgcaa    300
accggataac atgtctatta gattcatcgg acttgatcat ggttatgtct taatagacga    360
attctttgtt aacgattggt taaaacggct cacgttagag catcctacta tgacttcaaa    420
attgataaat attacatgga aatcacttta attttagtta gaaggtagtt aatttagata    480
ttcttattta ataaattaaa aaatagaaga aaaaagatg agaagagttt tgtttataa    540 aataagaaat atcttttatt gtaatttta a aattaaacaa atttaattta tattaaaatt    600
atctttgttt tattgttaag gcaataatta tttttttggt gggaattgtt aaaacaataa    660
ttagtatact gttaagtggt cctttaataa taagataacg tgatttaaaa aagaacgaga    720
caggctaata tagtagagag gaaaaaatac aatttaggcc caataaagcc caatatagag    780
ttgtgctcaa acacaggtct tcgccagatt tcctatgacg ccgtgtgtca atcatgacgc    840
caagtgtcat tcaagaccgt cacgtggcgt tgtttctaca cataggcgat ccatacaaat    900
```

```
cagtaacaaa cacgaaaaga gcattcatat gtacgaaagt agaaaagaag agactctttg    960
tgataaaact aagtaagaaa tagcataaaa gtaaaaggga                         1000
```

<210> SEQ ID NO 126
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0708

<400> SEQUENCE: 126

```
gtttccaaaa ctagtattct ttatttgctc tattcattat attttatat ttgtaacgtc     60 ccgaccgtct ttattaggtt tcgacaatca cttctcggaa ggtcgtccat cctgaaatta   120
ctctatccta aacatgttta actataaaat tctctcgaaa cttttgtaac gtatataacc   180
acataaattc tcttaaactt atttgcatac accattatat ttctgaaatc gatatgttac   240
aatattattt aatatttaga ttacttttac tgaatcgaat taaatatcaa atcgaaacaa   300
atctaatcta ccaaaaataa ttttgttata acatttctt gcctagttct acctcatata    360
cattttagtt aaagaaagaa atcacaacaa ttcccataat tcaataatta aatccacaaa   420
atcttggagt aagtaagaga ataaaaaga tagtatctta acataaacaa ttcaaagatg    480
ctctctcaca caattcacac acacttacaa aacaaaagac agaaacaatg ttttcattca   540
aatcaaaaga agttataaca ctagtacaaa aaaagctcaa attctaatag taactctttt   600
tatttcccaa ttacccaaag attctctctc acttcacaaa actagctttg agagtcgtgt   660
tccacaaaat ccattaaagc tgaaacggtt ttgctcacca ttcaaacaaa tacaaaattg   720
caaaacccca aattataaca aaataatata aaaattaaac cgctaaaaag agtgaaccaa   780
caaaaatcgc cgaatgtgtg tgtaatgaga aaaccgaccc atcatcccaa tcatctcttc   840
ccgtgtcact ctcttcctct cccacgtttc ttctctcttc cctttatggg ttttaacttc   900
tccttcttct tcttcttcaa tcttcagttt tcaaattcaa caacaattca cattttgatt   960
tcttcatcat ctctctctct ctcgcttctc tctcaaatcg                        1000
```

<210> SEQ ID NO 127
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0710

<400> SEQUENCE: 127

```
tagtgcgcgt ggggagaggg aatggtgaaa ccttagtggt taagttatga ggaaaatgat     60
aaaaggataa aacaatcaaa tgcagcttga aacggccata acataaagta ccttatggtg   120
gtgcgaatat ttttgtgttt ctttcactct tttattgctg aaagctacga cacttgtctt   180
aatatattgt ttccgcaagt cacatgatct acttttatt taacgtctag aaacgccgag    240
atatatgatg attagtatat cacgtctatg caaattgtta gttcgtgttt ggccaaaaga   300
tatcgagaca tgtctgaaga accgagtctg gttttgagat atttcttcaa gcattactat   360
acaatagaaa aaggagacac gcgaatatga taatagcaaa aggcataaaa aggcgaaaat   420
taaagaaaaa cgtaaagtga tttggcctca atcaacggga acgtatctta atttagagg    480 ttcttctttt acttttgaga cgagagagtt tgcgtctttg cgagctgctt tggttgacta   540
```

```
aacattatca tattgaaaac caaaatacaa cggaggaata tttgtcacag tttcactttc      600
acattgtttc cttaacgttt aatcaaccct gttcaaaatt tctatagttg taatcatcat      660
tgtttacaaa attttcgttc aaagatgatt ttaaataaaa ttgtgaaaga aaacctttc       720 tgaaataagg attggatgat agtgttaaaa gaaaaatatg aactgaggca aaagaggag       780 tggtccccgg aagattgtga atgtgtcat  ctaaaccagc cagacgtagt cacgtgttct     840
ctctagcttt atgaacttcc ttagccagca ccatcattgt gattgtagta tatatgtaac      900
cctaccttca tctctcccat tttccattct ccatatagac tcctttacaa tatacaaaac     960
ctatccaaaa gcgaagaagc caagcaaaca tattataaaa                            1000
```

<210> SEQ ID NO 128
<211> LENGTH: 1002
<212> TYPE: DNA
<213> ORGANISM: Arabidopsis thaliana
<220> FEATURE:
<221> NAME/KEY: misc_feature
<223> OTHER INFORMATION: Ceres Promoter PT0723

<400> SEQUENCE: 128

```
gtcatatctt atcaacacgt caacgatcaa aacctttagc ctattaaatt caacggctta      60
gatcaaaacg aaactaggtg ggtcccactt ttaatatcgt ggctgcataa catttcctcg      120
ataactgaag ccgttgtggt cttttctcaga atctggtgct taaacactct ggtgagttct    180
agtacttctg ctatgatcga tctcattacc atttcttaaa tttctctccc taaatattcc     240
gagttcttga ttttgataa  cttcaggttt tctcttttg  ataaatctgg tctttccatt    300 ttttttttt  tgtggttaat ttagtttcct atgttcttcg attgtattat gcatgatctg     360
tgtttggatt ctgttagatt atgttattgg tgaatatgta tgtgttttg  catgtctggt    420 tttggtctta aaaatgttca aatctgatga tttgattgaa gcttttttag tgttggtttg     480
attcttctca aaactactgt taatttacta tcatgttttc caactttgat tcatgatgac     540
acttttgttc tgctttgtta taaaattttg gttggtttga tttgtaatt  atagtgtaat    600 tttgttagga atgaacatgt tttaatactc tgttttrcga tttgtcacac attcgaatta    660
ttaatcgata atttaactga aaattcatgg ttctagatct tgttgtcatc agattatttg     720
tttcgataat tcatcaaata tgtagtcctt ttgctgattt gcgactgttt cattttttct    780
caaaattgtt ttttgttaag tttatctaac agttatcgtt gtcaaaagtc tcttttcattt    840 tgcaaaatct tctttttttt tttgtttgta actttgttt  ttaagctaca catttagtct    900
gtaaaatagc atcgaggaac agttgtctta gtagacttgc atgttcttgt aacttctatt     960
tgtttcagtt tgttgatgac tgctttgatt ttgtaggtca aa                        1002
```

<210> SEQ ID NO 129
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter PT0740

<400> SEQUENCE: 129

```
tgtggccact aaagatttac ccttaaccgg gcccatataa gcccacgtca agtggcgctt      60
atacgctctc cgtaagagag ccaacatttg gtatgtaatg ttgcaaatta ttcttcaaga     120
caataaattc aaatataatt caatattgtc caaatatagt gatgtacttc agttgtgcac     180
atagaaactc cactaaacca acttttagat agatgcattc acaaattttc aacaatgtcg     240
```

```
cgaaagtcta atccatcacc agattctaac attttaatta ttatatttaa ctatacatac    300
tctaatcagc atgagtcaaa cgtgtacaat agcccaagca tataataaga ccaaagtcaa    360
actcaaataa atgtctccaa actcaaaact tgaaaaagac ctaattatta catggtagat    420
atgactttgt cgacaagtaa accaactaat cctcgaagct accttctctt cccagttatt    480
atgtgtgatc gatttataaa tctcttcttc taataacacc tatattttc ttatgatgtg    540 aataaatata aaacttttaa ctttaaaaca tatttatccg aaatattgca cttagatttc    600
aaatagataa ataatagtac tatctaactg atattgaaaa gacctaacac ggaaaacagt    660
tttataaaaa atcccaaatg tgggtaatta tcttgatttc ttgggggaaa cagaaaatgg    720
attaagatta atcggagtcg tgtcaagcag ctcgttaata actgtagcaa gttgactgag    780
taagcatcaa cgtgtcatct ccgtaaagcc cattatttct agtctcgccg cgtcttctct    840
tccacgtagc acttcacttt ttctctcctt ttgtttcctt tggaacacaa acgtttctat    900
ttataggaat aattacgtcg tccgtatctg tgtcggaaca tagatccaaa ttaaaagcga    960
cttacttaat tacatatcgt tcgtgttttt ttcttcaaaa a                        1001
```

<210> SEQ ID NO 130
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter PT0743

<400> SEQUENCE: 130

```
tcgattggcc cgatcggccc caaaatcaag ctgagccgct tcaaacttca gcttttgaaa    60
tcacccccaa actcatgtcc tcttatcatt ataactaaag gatctttcat tttatttaac   120
tcatcgtctt gcactaccca acccaaaggt tccaactata cccgaagctt tctaaaggtc   180
caaagacttt ttttttcgag ccagactatt caagccaaga aaagccaaac cccacaagcc   240
agtacttttc aattccatat tataaactta tctgtcttgt tttagtccca ctaaaaacaa   300
cagaatttaa tttaggttga gctaaaaccc ttgacaaaag tgtatagtcg tcgattcagt   360
agcacactca tcactcatca gatttgatag ttgacctaaa gtatgactac tccatttcaa   420
ctaacaaatg aaaataaaag agacctaagg gttagaggat tgaaactata ctctcaagtc   480
ttttatcact aggctactac cagctagtta acttgatgga tttaagcaag aaaacgtaga   540
atttatattc gagcagattg tttagctaaa aaagctgggg tttgaaattg ccttttctcc   600
catataagca cgtcggttcc taaataactc tttctagcgg agagtgtctt tccaataatt   660
taataaaaat ggtgtttgta tatcaaaaaa aaagaaaaa agaaactgat cgagatagaa    720
cgtttgcagt tttataaaca atttaaaaaa caaaaaaaat taaactcaat gtattttta   780 ttaattcaca aacaataata aatcatagga tcgaatattt acacggtatc aaaacctact   840
cgccgctact atataaaaat tgaagtcaaa tatcaaccgc aattattaaa ccagcaagac   900
aataattcat aaacttaata taaacataaa taaattaatg ttacacaacg atatatggtg    960
agggttatta ctatcttctt cctctcaaaa cacatctcct aaccttaagc tttagacggc   1020
ctgc                                                                1024
```

<210> SEQ ID NO 131
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0758

<400> SEQUENCE: 131

| | | | | | |
|---|---|---|---|---|---|
| agctagccac | atcagtgacc | aaaaaagata | attaacaaac | caaataaaat | aacaaatttt | 60 |
| gatcatttgg | aataaaattt | ataaaaggaa | cgaaagcgcc | ttctcacggg | tcccatccat | 120 |
| tgaaatatat | tctctctttt | tgctctatat | aataataacg | cgtactaatt | tgtagtatat | 180 |
| attattacaa | agtcgatatt | tgattgtttt | gtgaacgttg | atatattaat | tttcttggat | 240 |
| gatgacaaaa | aaagtcatag | aaagtaacgt | gtgaacatag | cattaacaaa | atacaaacat | 300 |
| aatatataac | caaatatatg | aaaataggat | aaaatctcat | tgaatagatc | ttcttctatt | 360 |
| caaatatata | aatatttgtt | tgtctataaa | attaacagag | cattcacatt | atctaaaata | 420 |
| atagtaaaat | caaaataaaa | ctaaataaaa | ataactctgg | ttttataacg | attgatttta | 480 |
| aatattagtt | tttgttgtaa | agagatcatt | atatatgtct | gtaatatttt | tatactgagt | 540 |
| tacatgatat | ttagttatta | tagcgtaatt | aactaagata | agaaattaac | taaagtgata | 600 |
| ttctgattat | tattatttttt | gttaggacac | gtacgtggaa | aaactaaaca | ctataggtta | 660 |
| caaaacggta | taataaactc | accattactg | gaaaatgttt | gcatttgact | caataagtaa | 720 |
| cttattataa | gttactgata | taatgcatag | ttttgaaatt | cttaaataaa | ttattttggt | 780 |
| ttcgcatgaa | aatatgaaag | gagagaaatt | tattattgtc | acttatatat | atatacatcg | 840 |
| taatcatttt | ttcgtgaata | attctctctc | ccattccatt | atttctcagt | atctctcttt | 900 |
| ctttccctta | ctttattgtt | gcttttaaac | cttcaatttg | ctcataaacc | aaatatataa | 960 |
| tatcaaaaca | aacaaacaaa | aaatcagaat | tccctaata | | | 1000 |

<210> SEQ ID NO 132
<211> LENGTH: 921
<212> TYPE: DNA
<213> ORGANISM: Arabidopsis thaliana
<220> FEATURE:
<221> NAME/KEY: misc_feature
<223> OTHER INFORMATION: Ceres Promoter PT0829

<400> SEQUENCE: 132

| | | | | | |
|---|---|---|---|---|---|
| aaagttttga | attattggga | atcaatttcg | aagttttgta | attcttggg | ggctaatagg | 60 |
| atattttatt | ttcttggttt | cgtctattgt | tgttttttcta | tttatggttg | ggcttttaga | 120 |
| actctggaca | ggcccatgtc | atatgttttc | ccttctcctt | atattttttca | ttttcatttt | 180 |
| tgttaaatta | atgcataata | tccaaaaaca | atttaaattt | ttgaaggaac | cctttagtta | 240 |
| cggctccgaa | gctttcacaa | gtgagaatgt | gagatcaaag | aaggcaaatg | gaggatttta | 300 |
| aaagttaaaa | tcatcttta | tctgcaaaag | ttgacatttt | ttttgtatca | aatctaaatc | 360 |
| atcaaactct | cttaaactac | aagagcataa | caacctctat | gtaatccatg | aaataatctg | 420 |
| cttgaaggac | ataacataaa | tcattatggc | tagagtgact | aacttcaatc | aaatcctctt | 480 |
| aactctagct | cccttacaat | ggtatcgtaa | aacattatgc | attagggatt | gttgtcctag | 540 |
| gaaaataaaa | taaaaatccc | cacagaccaa | ctaccatttt | aacttaaaaa | taagcttcgt | 600 |
| ccgcgacgaa | ttgttttcca | tcctaaaaat | agaatggtgt | aatctgctaa | tggtttagtt | 660 |
| ccattaactt | gcaagttcta | ttgaaagcct | aaatgtcaat | aaagatatta | aaattcggag | 720 |
| tcaaaagaca | aatgaatcaa | aagcaacaag | acaagtcagc | tccattcttc | actacccatc | 780 |
| ttttacaata | aatcatctct | cttttcacaa | atttcaaact | actctcattg | ccctttagct | 840 |

```
ttgttataga gccaacacta cagagagact cacacacttg tttcaataat taaatctgaa        900
tttggctctt cttataaact a                                                  921

<210> SEQ ID NO 133
<211> LENGTH: 763
<212> TYPE: DNA
<213> ORGANISM: Arabidopsis thaliana
<220> FEATURE:
<221> NAME/KEY: misc_feature
<223> OTHER INFORMATION: Ceres Promoter PT0837

<400> SEQUENCE: 133
aactacaagg gagacataat atcaccatct ggttcctgtt atcatctgaa gatttcttgt         60
tttaccttcc agtgataaaa tgatccttat aatacatata gatatattaa attgctgtat        120
tttaagatta tagatatata aggtacatga gagtgtttat ttaaaaaaat tcacttggaa        180
ttcatgtttt gtgatacgtt agattggaat ccatttggga aaagaagaat catctgttct        240
tatgtctcaa attttgactt cattcacttt tcttcttgtc ttttaagaaa gcttccacaa        300
tctaactgtt cgatgtgaaa actgagattc gagtaagaaa atgtgaactg tgttatactg        360 tttttttaatt agataattta gattgcactc agataaatta ataacattcc tcgaatactt      420
ttatgtgatt ggatatatta ggtatatctg ccaaccaacc aataaactgc tatgtttaaa        480
caaattaaat aaattagtat atgtttactc aagaataaag aagatagaaa agaaaattct        540
atatgagcta aatttgctgg aggaggcatc ggacgtgggt accagacctt tccaagcaca        600
cgagtagtgc ttagccatgt catgctaaca tacaccattt ggttcataca aaatccaaat        660
caaaatctat ttttaaaatc ttttgcacac gtctttgaaa aacacctctc atactatagc       720
tacggaagct tcaatttcaa ggtttgtcta aaagctaacg att                          763

<210> SEQ ID NO 134
<211> LENGTH: 751
<212> TYPE: DNA
<213> ORGANISM: Arabidopsis thaliana
<220> FEATURE:
<221> NAME/KEY: misc_feature
<223> OTHER INFORMATION: Ceres Promoter PT0838

<400> SEQUENCE: 134
atactggtat gcttaaggtt gaagccaaga tctctgtctt acccaagtaa ccactttcta         60
ttagaaggga tcaacactaa gaatatggag atttaagcct aagggctaag gcggttctca        120
acaatacatg atgtgaatac aatcacagac gatttactga ggtttgttga taagatcttg        180
atcagtctct gcatcatctg ttcaacaatc tcaatctttg actgtttgct ttcggagcca        240
taaacagagg aatcccttat tccctgttat aggagcaata caccaagtat tatttccatg        300
gctgaaattc tcttatggaa acctaattgt tccattgaag ctgtaaaatc gaatctggtg        360
aatattctcg agcaaagccg catgctaatt atgtcaattc agaagagttt gattaggaga        420
ctcgaagcga gtttgatgat cttcttgat gttcaactcc gattgtaagg gtataattga        480
cttttcatgt attacggctc caccacctga cactaaggca ctctttgtcc atctcgttgg        540
tatcatcgga ttcggatggt aaaaataaaa agagcagagg aaacttgtta ctcatgcaag        600
cttctcaggt gccacgtcac tccattacgt gtcatcttca cacaccatct cgctcaaaac        660
cgatctcatt tttcaaacct taaggcaga agcaactgat taagttaaca ctcttgagaa        720
gctctcgatt aagcttgaac ttggaggatc a                                       751
```

<210> SEQ ID NO 135
<211> LENGTH: 669
<212> TYPE: DNA
<213> ORGANISM: Arabidopsis thaliana
<220> FEATURE:
<221> NAME/KEY: misc_feature
<223> OTHER INFORMATION: Ceres Promoter PT0848

<400> SEQUENCE: 135

```
tctctttaaa tcagttaact aaccgtttat atatttacga taaggtttga agagattatt      60
gataaaataa tacatttcat aatcccgcgt tcaaccgttt aaagtaacat ttaagttgac     120
tatatctaat ttttttttcca ttaaatatgg agctggtaaa ctttatcaac ttctaaaaag    180
tgtaacaaca aaaattaggt caatcacaat tctgttttt ttattatttt ggattgactt     240
ccaattgcaa atagtcttag tgatcaccat tatcatacat atacatca agtaggtttc      300
atcatgatat accacaaagt atttgacaag ccatatggtt ttggatcaaa aagtcggtcc    360
aaaattaatg ttttatgtgc aagaaccgac ccattgtaca cacgtgttaa catcttcaag    420
actttcatct ctattttct tttggtcatt aagatacca ttgatccgaa tctgttacat      480
tcccacctac ttttttaatt tttactatcc actccaaatt aaacacaacc gatgatttta    540
ataattggaa gcttttaaaa atatttcaaa acaagcctct ttgtgtttgt ctatatat     600
acacgtaata agaaggtgaa tgaatctcac agcttacttg ttctaaggct tccaataacg    660
aaaacagta                                                            669
```

<210> SEQ ID NO 136
<211> LENGTH: 702
<212> TYPE: DNA
<213> ORGANISM: Arabidopsis thaliana
<220> FEATURE:
<221> NAME/KEY: misc_feature
<223> OTHER INFORMATION: Ceres Promoter PT0863

<400> SEQUENCE: 136

```
cgggaaacga caatctgatc tctagtccag tcgattggcc cgatcggccg attataaact     60
tacatgagac aagtataaat aattattata aacttattaa gtttaagatc aaggcttttg    120
tgcaatgtat caatgaatgt tagatgtgat atgatgaaag caatgtttta aacacataca    180
tagtcattga tcggaatgtg tgttattaga aatgcatgcc taagccgata gggttatcta    240
tgtttggtct tggacattat agccaaattt cgaatctaat tcttccaata tatattttt    300
tttttttgct tagggccact actagtattg cttatcaatt ttaagagctc atgaaaatgc    360
aacaatatag tagttgcaaa tccttgtttc aagagaaatc aaagggccac ttgtgaattg    420
aataataata atatttgcaa ataaccttc actaaaccat accaacaaaa ccacacagat    480
ttggcaaaga cataaccttt gggagacgtg aaaaggctca aaatttgaca attgtcctta    540
caaattcgct cattagtgca attgtgagat ttgtttgcat ccaaatccaa ttcataactc    600
acactcgtct caaattcgaa aaggcctgca gggccagtgc actgggatcc aacaatgtcc    660
tccgactcgt ccaagatcaa gaggaagcgg aaccgcaccg cg                      702
```

<210> SEQ ID NO 137
<211> LENGTH: 435
<212> TYPE: DNA
<213> ORGANISM: Arabidopsis thaliana
<220> FEATURE:
<221> NAME/KEY: misc_feature
<223> OTHER INFORMATION: Ceres Promoter PT0879

<400> SEQUENCE: 137

```
ttctaggaag actggtcaag ctaagctgtt tctgtttttt gttttttgtac tttacttttt    60 gtttgctagt gggaactggg tttattgggc cttgaagttg ataaaagatg aataaaagac   120
atatcgccta aagcccatat gagaagcaga agacaaaaac ctccaacttt gggcataaat   180
tttgattata gttaaaagtc cagacccaat ttggcacctg gcttagttac gattctaagg   240
catgacacct gcctaatatg tttattacag aaaataaaga gaatcagcta ggtgtccctt   300
attgaacaca ttaacaaact ccaacgacac tacgtgtctt cgtgactctt actatatcca   360
aaaacctata gctaaagctg aattttccat gattagtata gtcccaacca aaaaaatact   420
gaagaaggca taagc                                                   435

<210> SEQ ID NO 138
<211> LENGTH: 397
<212> TYPE: DNA
<213> ORGANISM: Arabidopsis thaliana
<220> FEATURE:
<221> NAME/KEY: misc_feature
<223> OTHER INFORMATION: Ceres Promoter PT0886

<400> SEQUENCE: 138
agtgtatttg aaaacgacat tgaagaatta atatattttt ttttaatttt agttttttat    60
agtacaaata ttaaaacaaa caatcctacc atatcataac atttgtaaat aacattttaa   120
gttttgtttt gagttttaat taattttcta tgacaaaaaa atgaagtcaa tagactaagt   180
gaatcatata gtataaataa acacaattta aatagtttca ataaattta gaaagaataa   240 aacaaataga aatcagaagg tgtctgtttc ctcctcgcaa catacgatca aagagaaaca   300 acttgacccct ttacattgct caagagctca tctcttccct ctacaaaaat ggccgcacgt   360
ctccaacctt ctcccaactc cttcttccgc catcatc                           397

<210> SEQ ID NO 139
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0007

<400> SEQUENCE: 139
agcagaacaa ctatatttat tgtgtcacat aaatctgaga tcatttataa ccaccaaaga    60
acctatacac agtaaatgac aaatgtatct ccctctatct ctattgccca tatgtagatg   120
ctaaagtaag atttctcttt tttttaatgt acttttttt gtataaagta tattccataa   180
gaaaaaggaa aagcttgttt atggatcaat tgaccccaaa aaagttttt agatcaaagc   240 ccaatataaa aaaaaacac agtagtgaca caaaggaact taaataaacc atgaattgat   300
ctataaacag tagagatcga taaggcgaac attttccatg tgaagtgtct tctttcatct   360
ataatatttt tgacatccaa taatttcctc tataatatca ttcacataat tgatagaaac   420
attatgttag aattgtccac atcatttgag ctgtaatata ttctgtttta acaaattata   480
tggtagttgc ttaatcttat gtccatcttc ttctatgcat cgttttcgcg cctagttgtc   540
cagtccattt caactaccta cctctaattc ttatcttaaa acaacatttt ttaatttaag   600
tattatgctc aaagactaac tagatagaaa accgttatta acattaaac gaattaaaag   660 tcttacatgg aaaatgtagg tttataaacc acgagttatg attgacaata aaaaaaatgc   720
aaatcatcaa tcaaaagaga cttgagtgcg actctatatc aaccattgca attaaaatta   780
```

| | |
|---|---|
| tctatcacaa aaattttaga cagattaagt taatttagtc taaattcact aatttatttt | 840 |
| ctataattag taattaacta tatttattta tttacacatt ttctgataat ttagaaattt | 900 |
| gcatgaataa caaatataag attttggaaa ttagtagcaa atttaattaa taattatttt | 960 |
| tgcctaaatg aaccaaacta taaaacctcc acatacacca gtcatcaaat ttacagagac | 1020 |
| aaca | 1024 |

```
<210> SEQ ID NO 140
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0008

<400> SEQUENCE: 140
```

| | |
|---|---|
| ctcgagagat gaagtcttag taatgtttga acaaacaata atcacgtttt ccatcaaatt | 60 |
| cgagcattta aagtttatat tactacatgc cccaagatga taccgtccat ctcatccgaa | 120 |
| aatatttctg aaattgcgct aagacaacaa tgtttgctca aattcgatca tttaaagttt | 180 |
| acaaatctct catcaatctt acaaacttct cacactaaac agaggtacat attttcttat | 240 |
| aaagacaaaa ggttcgaaca gctggcttct caactcgagt tgtttgtcag ggcctctctt | 300 |
| cactaactac aagttggtac ttcaaatatt ggtggctagc ttcacgtgat attgtctaca | 360 |
| aattaaaccc atgaaaaagc tgcattaatt gttccaagtg aaccctgagg agtgtcaata | 420 |
| gtctttgctt tagtgtgatc attaaaccaa atctctaaat tcctaatttg tactaacatt | 480 |
| tggaacgtat ttcctactct tctccctgct ccaactccca aaaataagat tagttagatt | 540 |
| tctataacta atatacatgt atactcccaa aaacagtaaa accatattaa taaagctaat | 600 |
| tttgcataga tttatttcgg taaaccggcg gttcaagttg ggaaaaaaa agacaaacgg | 660 |
| tctaaagtca tccaaagaca aaaaaccaaa gacaagttga gagagacgag accaatcaca | 720 |
| acattgcttc gtagattgcg tgacatcatc cttgacggct actttcattt gtgtcttatt | 780 |
| tggataaaac gcacgtgttt aattcacgaa ccttcatagc aataagaaat ttccattact | 840 |
| ttcatatttt caactttttt tattacccat tacatgctta aaatattaat tcacaagtct | 900 |
| ttgtcaaaat tcaatatttt ccaggttcat gaacccttttt tatctcaatc tactctataa | 960 |
| tatctcccta taaattacaa caaaacctct ttattttttca | 1000 |

```
<210> SEQ ID NO 141
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0019

<400> SEQUENCE: 141
```

| | |
|---|---|
| gatataagta gaatcatttt ttgccgccgt ttctcgctaa cacaccgaaa actgaatcaa | 60 |
| atctcctagc tcttctacgc aaaatcgagt gcatcgacaa tggcggaacg tggtgtcgaa | 120 |
| cgtggtggag atcgcggcga tttcggacgt ggattcggtg gtcgcggcgg tggaagaggt | 180 |
| ggtccgagag gtcgtggtcg ccgtgcaggt cgtgctccag aggaggagaa atgggtgcca | 240 |
| gtgactaagc ttggtcgtct cgtaaaggaa ggtaagatca caaagattga gcagatctac | 300 |
| ctccattctc tcccagtcaa ggagtaccag atcatagatt tactcgtcgg tccttcattg | 360 |
| aaagacgaag tgatgaaaat catgccggtt caaaaacaaa ccagagccgg tcagagaacg | 420 |

```
agattcaagg ccttcatcgt cgtcggagat agtaacggtc acgtcggatt aggagtcaaa      480
tgctccaagg aagttgcgac ggcgatcaga ggcgcgatca ttctcgcgaa attgtctgtg      540
gttccgatac gaagaggtta ttggggtaac aagattggaa aaccacatac ggttccgtgt      600
aaggtaaccg ggaaatgtgg atctgttact gtacgtatgg ttccagctcc gagaggttct      660
ggtattgtgg cggctagagt tcctaagaag gttcttcaat tcgctggaat tgatgatgtc      720
tttacttctt ctagaggatc caccaaaact cttggaaact tcgtcaaggt atgtactttc      780
acaatggctg ttttggtttg atgaactctg aattaggcag tgaaaaagta atcattacca      840
gttaagtgaa tttatattga agattaggat ttagctgatt gtattggttt gagcatgtga      900
gtttgtgttt aagattgctt gaattgaaat gctttaggtt gtttgattac gctaaattct      960
gactaatgta attcaaattg ttgttgtttt ttttggtc                              999
```

<210> SEQ ID NO 142
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0028

<400> SEQUENCE: 142

```
gtcagtgaag tcgattggta gtacttgaaa cacttggttg gtttcatgta tttggcctat       60
atataaacaa acatcgtaat tatatacgga ttttttcgg aattttacgc catatctgta      120
agtatatata acatgcatgt cgttttcaaa ttcatatgat gaacgatcca cgtaagtgct      180
actactccta caatattgca tgagagagat atgtatttat aaattttatt ttgaagaaga      240
aataagaggg aaggttactt gggtggatcg atgtgaaaac aaaagaagaa aaagcgaaac      300
ccactaagcc attacatgat atcgaccttc ttatctttt cctctttatt ttattttct      360 catcttcttt ttgtcaggac tttttctac ttaatgaaac ctccaaacta tctaactaat      420
acactcccat gtagaataaa gaaaattata taagatattg ttgatatttt gtaactagaa      480
aatatatttg ctctgtaatt tttcgtaagt taaatcaaca ttttaaagta gaaacaaata      540
ttactgcaaa aagtaggatc attatttttg tccaaaatct cagttagcta tagggttgta      600
gtaaaaacaa aacacattct tgatttgccc caaaaaataa agagagagaa gaatattgtt      660
caaaagtggt ctcttctctc tctaattatg ttttcactaa acccaattag attcaaacag      720
tctacaaagt ccaaaagata aacatgggac aacaattcga tgcaaaaaat cctcttttca      780
tgctcttttt ttattctcta gtcttttaaa ttactaataa aaactcacaa atccaccaaa      840
cccattctct acaactcacc ttcatctaga tttaccact cccaccgaga aacacaagaa      900
aaaaaatata catatataaa tatacaagac aacacatgat gctgatgcaa tatacacaac      960
aaagtattaa atcttagata ttgtgggtct ccctttcttc tattcatttt cttattcatt     1020
aaaa                                                                  1024
```

<210> SEQ ID NO 143
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0039

<400> SEQUENCE: 143

```
ccgttcgagt atttgaaaat tcgggtaca cccgcctaaa taggcggacc ttatctagta     60
tatatataca tttgaactat attgtttact ttttagttga tttaggctat gtcatgacat    120
tgacataaat ctacctgtta tttatcacgt gtaattcgtg taaagtgtaa actagaaagt    180
tcaaatacgt atttgttttt gttctgttat ataggattgt catagttgta aatctacaat    240
ttattacaac atgaataagt acacaagcaa tgtaattgga tttaattgct aaactcttta    300
catggtcaat ctaaatttga taagaaatac gtcacatatt actaagactg atagtttttt    360
tgttgtcacc aattattttt gttaaattga cgaaaacaat tccaaaaact caaatgtaca    420
aaatcataca gtctcacaaa catctcatag agaaagatat aaatctccca tatgggaacg    480
ataacacgag gtcgaaatac tattcgtaaa actaaacgc cttagttata aatcgttagt     540
tgtaaccgcg gtcgagaata catacagatc cacgaaacta ctactacaca tgctgctgaa    600
ttggaatttg gaaaagacca tcttctttag gaagagctca cccaatgagt gacaaaggtg    660
tcggtggctt gttttctacc catatgtata catcaaatgg tagtttcatt aacgtttggt    720
tttgagaaaa gtaagacttt ggctagtagc taggttcgta tataataaac tcttttgaga    780
aagttcatca ctggtggaaa atgttaaacc ggttttttct catttttttcc gccatgttaa    840 ccaccggttt aaaaagaccg taacacattg aaagattaat aagggtatat ttgtaattac    900
ggtttgctgg caattttttaa ttattatttt aattagagaa aatagagaag ccctatcaat    960
gtacatggta tatatataaa aggcaaaacc ctagaaaacg atactattcg actcagccgt   1020
cctt                                                                1024

<210> SEQ ID NO 144
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0050

<400> SEQUENCE: 144
aatctgatct ctagtccagt cgattggtac ttgagggaaa catcatattt ttaaaccttg     60
tctcagtaag ctaacacaca ccccttgtga ttacttatcc atgtttatcc acaagaatgc    120
agttggattg agatattttc ttctttgttg aaatcaggcc tcaaggtgtt catgtggtct    180
gcaaaaaaat tcccaaaaat aaagatagtg acatctgaaa tcgataatgg attagacgaa    240
gagtttcgtg ttattccttg gtatgggcgg gtttggggac agatatttttg gcacagacga    300 ggactaggcc actgtggtcc tgcagcatta ggtgtcccct tccatgtcctg cattacattt    360 tattgatgga ttcatcaccc tatctactac aacggctaca caaactatga agagttttgt    420
ttactaataa atgcccaagt gaggggtcga tcgaacccgg gacacgtttt tcagtttacc    480
atatagaatt atccttggaa cccttgatac tccatagaac atcaccacct ctgttgtcat    540
ctcaggaatc caggttcaaa cctagtctct ctctccctag tgggaggtat atggccactg    600
ggccaatgat gacaaaatgc aaaaaaaata aaatacattt gggttcatta tctaaaatat    660
ctcttgtgtt tgtaagtttt ggttgcacac tcgtgtggtt gaagtgtgtg tgagaggtac    720
tatacaatac actctgcttt tgttttgtac ctatctcttt ctcttctcca catatccaag    780
actttgggga taaagctgag atcattggtt gccatttggt tgtgtagaag caatcaccca    840
tttgctttat ccgaggttga taaatttcct cgggttctcc ttctgacacg tatgacaaat    900
tctaatagta tattcctcgt agatattacc tatatattct caatagttgc aggtacttaa    960
```

```
ggctttgtct tggcatcctc gtcctcttca gcaaaactcg tctctcttgc actccaaaaa    1020
gcaa                                                                  1024

<210> SEQ ID NO 145
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0086

<400> SEQUENCE: 145
cttatccttt aacaatgaac aggtttttag aggtagcttg atgattcctg cacatgtgat      60
cttggcttca ggcttaattt tccaggtaaa gcattatgag atactcttat atctcttaca     120
tacttttgag ataatgcaca agaacttcat aactatatgc tttagtttct gcatttgaca     180
ctgccaaatt cattaatctc taatatcttt gttgttgatc tttggtagac atgggtacta     240
gaaaaagcaa actacaccaa ggtaaaatac ttttgtacaa acataaactc gttatcacgg     300
aacatcaatg gagtgtatat ctaacggagt gtagaaacat ttgattattg caggaagcta     360
tctcaggata ttatcggttt atatggaatc tcttctacgc agagtatctg ttattcccct     420
tcctctagct ttcaatttca tggtgaggat atgcagtttt ctttgtatat cattcttctt     480
cttctttgta gctggagtc aaaatcggtt ccttcatgta catacatcaa ggatatgtcc      540
ttctgaattt ttatatcttg caataaaaat gcttgtacca attgaaacac cagctttttg     600
agttctatga tcactgactt ggttctaacc aaaaaaaaaa aaatgtttaa tttacatatc     660
taaaagtagg tttagggaaa cctaaacagt aaaatatttg tatattattc gaatttcact     720
catcataaaa acttaaattg caccataaaa ttttgttttta ctattaatga tgtaatttgt    780
gtaacttaag ataaaaataa tattccgtaa gttaaccggc taaaaccacg tataaaccag     840
ggaacctgtt aaaccggttc tttactggat aaagaaatga aagcccatgt agacagctcc     900
attagagccc aaaccctaaa tttctcatct atataaaagg agtgacatta gggttttgt      960 tcgtcctctt aaagcttctc gttttctctg ccgtctctc                            999

<210> SEQ ID NO 146
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0088

<400> SEQUENCE: 146
tcgattggga ttactacttc atctagtaag gttctgaaaa cgtttgttgt tgataaggaa      60
gattcgtctc aggttattac tgttgatctt caaggtttgt gattgtgacg cttatacatg     120
tgctgaaact gtggtgttta tttattgaaa acaaaaaaaa agtctctctt gtagtttcat     180
tgtactaaat agaaaacaag aaacgttttt ttctttaatc ttctacattg ataatattgg     240
atcaaaggat tgtttctgca agacacaaca caaacatact tatactagtt tacttctact     300
aagtactaac tacatacccca tacacacact tgcacctaga ctttacttct agacatcatt    360
accctaaggt agaaccaagc ttacaagcaa gttttaccga caactcttac attacaactc     420
tagtctgtag tctttaacgt agacttacta actagtcatt agtggtttaa ttttttaaat     480
tttcatccat atgttttgt tgtagatata aactaaagtc ggtcacattt ataattgtc       540 attatgtccg cgtaaaagtc aattcagcta ttggacattt atgaaatgta agattttctc     600
```

```
tctcatttcc ccgtgcgtga agacatgcat tggtttttct gtaataatca acaaatccaa     660
accccttttc gatctttatt tggacattgt tagagacaaa atttctctat agtcttttc      720 ctaatttgat accatgtttt tgtttctgca caaatttact cactggttta actaactatc     780
cacttattta tgattttacc attaggcgtc agctagccct agtcaaattt gtaaacaagc     840
caagctatct acataaatcg agatgtcatt aacgttaatc gtcgttaatt cgaatttgaa     900
aacatagata gctttagcag tacaatgggc aatggtaaga agaatagcaa aaggcccaat     960
atttggtttg cagaaattaa agccttaaaa aaaagcccac agatatttgt caagaaccc    1020 taat                                                                1024

<210> SEQ ID NO 147
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0092

<400> SEQUENCE: 147
aaagattgag ttgagagaga tggtggagac gcagaacaga caaagggagt ttaccatata     60
gtgctctaaa gggcaatgag attgcagtga tgtggctatc cggggaatca tcgcaggtta    120
ttccttccca tgagcaacaa tcaatggatg ggttccaatt cagaggagaa acagaagaag    180
aaacgtttcc agagaaccac agtagggatt ctcgatcttg cgagttgcag agagcctctg    240
aaactgcaat agaaaggaca ctgatgaaaa gaacacactg aaggagtatg ccaatcatgt    300
gaaaactcag agcttgtatt ggtcttgtgg ttgatgaagt tctcacaaaa cctttggctt    360
tgaatctccc ctcattagtc atggtgagaa caagaacaag acgagaaaca gacaaagaag    420
atgaaaaaac ttgttggcca gtgttgacta aggggaata gccccagaca taacaaaatt     480
agacttgtcg tacatcttta atattttttt atctgtttct ttgtcctgac gctttcatta    540
ttcctgtgat caattttctc ataccattgg tccatcgtta atcctttctt aatttcattt    600
tctacgtaac atgagaggag accaagtcct atgagaacag ttgacgtaac agtggttgtt    660
aagttaagtt aaaaagagga agctagtgag agtgaccgtt aggtagagaa gtgagatctt    720
taaccactct tctttctctc tctctctgct ttttttcgtcg tctttcacat ctactgttcg    780
caaactctct tatgcttcca ataatggtga taccaattga gacttgcagg agaatctcct    840
cttctccaca ctctatcaac tggtcagcca tggaatggtc gtttcagttt caatattcct    900
ggattctttt taaggattcc tgtttctctt ctgttcctgg tatattctta acgacgaaat    960
tagtatcgga tcctggtaat acattttgaa gcttttaagt accattgcac tgggatccaa   1020
caat                                                                1024

<210> SEQ ID NO 148
<211> LENGTH: 1020
<212> TYPE: DNA
<213> ORGANISM: Arabidopsis thaliana
<220> FEATURE:
<221> NAME/KEY: misc_feature
<223> OTHER INFORMATION: Ceres Promoter YP0096

<400> SEQUENCE: 148
gaggtcagtg agtcgattgg tgcaaaattg aaaaattgaa gggtgaaaca aatttaaaga     60
taatatctat taaatcctct aatttttaaaa atttagcaaa aattgtattt tcttatggat    120
```

```
ctgttagttc acacgtatct taattagtac caaatcatat ctaatgatta gtgataaaac      180
tagttagata tctatatgtg tctttaccat ttaacttgaa tccttcttct ttttttttacg    240 taaacaactt gaatccttcg ttaatacata aatttaaagc attttttctt taattctatt     300
gatcggtata tatttactat aagttttagc tcatatgcaa tttcaaatga tatgcttta      360 aattttgtct aggtgtgata gttgtatctt taacataaat cttatagcaa aattatactt     420
gatattctaa atttatctat ttgctcttgt gaacctcata ttagtctaga gaaactttga     480
aatcctttca attagttgta tgtccaatac attttttacta acatttatta gtcttttaa    540 ttaagattat tgttagaaaa aaaaagattt tttaaaaata ataatatgt tttagataca      600 atgtgagtta ggcttcttat attttaaaaa ataaatttat ttcatactta aaaatagttt    660
ggaatttcaa tttatttggc tgaataccat aaaatatgtc aatttgaacc ttatacccat     720
tgactatttg gtgttagaaa cccttttaaca aaaaaaaact atttggtgtt agatatcaaa    780
ataaaaaaag tttaaccatt ggtttctat attgaattgg atattgttac atgtattaaa     840 gttttttttgg tttaattttg aaacgttgat agaaactatt aagtttaagt ttggtagtat    900
atttatttgt ggaaaattta attgccatta aatataacgt caactttttt tggttttttt     960
tgagaagtta cgttgtgatt ttgatttcct atataaaagt tagattacgt cattttttaa    1020
```

<210> SEQ ID NO 149
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0097

<400> SEQUENCE: 149

```
ttcatcttta tatttaagag tttaaaaact gcaacttttg ttttttcttc actaagtctt       60
atggccacag ttaattaaaa gcagatgaaa ggtggtccaa tggaaaagga gaatgtgatt      120
gggctagttg ggagagttct gatgtctagt gttgggtaca cgtgtccgtc agttacacat     180
agcattaaat cagacggcat gtcattattc aaatctagtt cacatagtac gactaatagc    240
tgataaatta atgattatac agcatatgaa ttatgaattc aaaaaaaaaa aaaaattgaa    300
aatgttaagg agatgctata ttttacaaaa ttcatcgcaa tgctttctac taatttgcta    360
agtggtcttc tccagttagt cttgtcgatt ccaagcgata ttattaaatc ttgaagcatc     420
gctcaaagca ttatagctta agataaccaa attgttatta aaacaccta gtgaaatttt     480 taaattaaaa caatttgat atctttgtaa tatctaatac tactctttct gtgtctaaaa      540
ggattaattt tcaaaaattt cacacatatt aaaaaaaaaa aaaattact agctaaacaa      600 ttttcaataa tctaaaaca atagtaactt aataattttt ttttattttc aaaatagtcc     660
ttcaagttta caattcattt tagtattata atcaacaaaa tttgtattaa aaagttggaa    720
aattaatctt tgtggaacaa aaaaatctag aaatcatttt ttagaattag agagaggttt    780
gataaaaaaa aataaaaaaa aatagagaga ggtagtacat actaaacgat gtgatactac    840
tattgacaaa atcttaattc tcagtttagt agaataaact agaaggaatg aatgaagtaa    900
atgcgaatcc aactactaac aaaccctact tagtcatcat attttcccat atgaaatccc    960
tatataaacc catcatcatc tcccactttt ttcatatcca                         1000
```

<210> SEQ ID NO 150
<211> LENGTH: 1004
<212> TYPE: DNA

```
<213> ORGANISM: Arabidopsis thaliana
<220> FEATURE:
<221> NAME/KEY: misc_feature
<223> OTHER INFORMATION: Ceres Promoter YP0101

<400> SEQUENCE: 150
ttctcgttct ctagaatatt gctggaccgg attaggtcaa tattattggg ccagattaga      60
tattgaattg tcgacgttgc ttacgttacg ttatatcttg tttaagaatt aaacctatcg     120
acttagtctt aattaagaaa acattgcctt aaattctctg gtctgcgacc gttttttga     180
ccgttaaccc ctaattaaag aaacaaaata attatagaaa gagcactgaa atgtgattat     240
tttaacagta ctcttatgag aaaattcgta cttttagtt tttttttgt acaaatctct      300
aagaaaaaca ctactactaa ttaagaaacg tttcaaacaa ttttattttc gttggctcat    360
aatctttctt tctcggtccg ggactaaccg ttggcaaaaa aaaaaaaaaa gttgacaata   420
attattaaag cgtaaatcat acctctcaaa taaaaacttg aatttggaaa caaagacaac   480
taaaaaactc gaatttaaga gaattcctaa aatcaagtga agtatcatca cttggtaaaa   540
tttcataacc gttggcttct atttctatgt gtgccttggt ttgcaggaga taatatttca   600
tttccaacca atgatattcg tacacatagt caaacaaatg tttgtctttg ttattatatt   660
gagaaagaaa caagaaagag agagagagat agataagacg aaggaagtga agcttccaag   720
cgcccaccgt taaaaatctc gtgtgcaagt ttcaaataca agtggccggt ggtctccata   780
atttgatcgt catccaatta aaaggaaga aaaagcgtgt tttatacaag aaaactcatt     840
aaaatagcaa gtctagaaat atctcaacac taatctacca cgtctattac acacacacac   900
acacacactt gatcttaatt tatttttcaag attcaagaaa atacccattc cattaccaca   960
acttgaccac acgcctatat ataaaacata aaagcccttt cccc                    1004

<210> SEQ ID NO 151
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0102

<400> SEQUENCE: 151
atttggttga taacgttttc actcgactaa ttatatactt cagaaggata gtaatagaat     60
accaaaataa ttaaatgatt ggttagtgcc ttagtggaga cttttaacc gattctaata   120
gactaatgat gtagctaagc atttatttgg gatcatcact gtttgaaaac gtgaaatgtg  180
ataaaagtta tgaaacgatt aaaatataaa ataaccgtac aaaacattat gtaccgtttt   240
tttctctgtt cttttggcga tttggtttag ttcgttacac tctaaatgtt attgcagata   300
tatatataat gatgcatttg catctgagga acatataatt ccggttaaca cttccaaatc   360
ttatatccgt ctaggtaggg attttataaa tcatttgtgt catcatgcgt tatgcttgtc   420
ggctttgacc ataacgcaga gatatagaac tagcttttac ttaacttta gatttattat    480
ttgatctaga gttaagtgga gatatatagt gtttttgtta gattattggt ggatgtgaga   540
gtttgtcttt agtttcaagt tgagaatata aggcaagagg agactctgag gcaatcagag   600
gttttgattg gcaaaatatc caaaggccc aaaccaagtc gaagcccatc tcgtacaaaa    660
aaagaaagag atctgtaaga aaaaatattc tttgatattc ttacaaaaat aagtgtaaaa   720
cttttattag tcaaaatctt caatctttaa aaactctcat cactcctacg aaagcgcgtg   780
agagttatga gacattcctt aatagcatta ctcacaagtc acaagttcaa aacgtctgac   840
```

| | |
|---|---|
| tgaaacagaa acaagccttt gttgaagtct tgaagaagag acattagtac tcgtcgtata | 900 |
| gccataaaag gtaatatacg aaatttcttc gctaatctct tcaccttcct ctacgcgttt | 960 |
| cactttcact ttataaatcc aaatctccct tcgaaaacat | 1000 |

<210> SEQ ID NO 152
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0103

<400> SEQUENCE: 152

| | |
|---|---|
| gttttgaaga acaatctgga tcgaaatcta acataaggtc atcgtattca agttacgcag | 60 |
| tcaaggactt gacatcatcc tactctggtc tgaggttacc acttccaaag atgggatttt | 120 |
| tcgactcggt atgcttccta agaaattcgt tttattgaac ctagcaaata tcttgtaatg | 180 |
| taagattcct gagatgatga agaaaaaaca aacttttgtt acagcaggag aacggagaga | 240 |
| aagaaaacag agaaccaaat gctcttgaag caaacagaag aagaagacac aaatccaaac | 300 |
| ttgagacttc ttctacacca gaaaaccgca gcattctggg acaacgcaaa acacgaaagt | 360 |
| gaaacgggca atgatatata tgtcttgggt gcgttacaag gcatcgtttg caactgttga | 420 |
| gttggataag tcaactgtct tcttttcctt tggttgtagt agctgccttt ttttccttt | 480 |
| gttgctttaa gaaatagccc gaaaaaaaga atgttctaca tttcggagca gaaaactaac | 540 |
| cgaatgagtt tttggtcgga tcatcggatc gatcagatat attttgagtt acgaactgtt | 600 |
| ataaaaaaag ccataatttt gtgttgagtt tgcaaaatac cttataactt gttatttgag | 660 |
| attgcacctc catatatatt aattcgtaag agtatttatt aagtaagctt tagtataaat | 720 |
| cctttttttcc tttaaagtaa gttaatgttc tactaaataa tagtaaagtt gaagaaccgc | 780 |
| tccgtttta caccatgcac gtgttatcta acaaagaaaa tatggtacac ctaatgctga | 840 |
| atgcaaagga caacacaatg aaactaactt gactctgtgt tatagaaacc catagacatc | 900 |
| tgcatacatc ctagtatttg tataaattgg actcaaattc ctgaggacaa tcatagcaaa | 960 |
| caatcacatc atcgcaatat acataaacaa aagaggaaga aaaa | 1004 |

<210> SEQ ID NO 153
<211> LENGTH: 1003
<212> TYPE: DNA
<213> ORGANISM: Arabidopsis thaliana
<220> FEATURE:
<221> NAME/KEY: misc_feature
<223> OTHER INFORMATION: Ceres Promoter YP0107

<400> SEQUENCE: 153

| | |
|---|---|
| taacaatcct tgggaacatt gcatccatag atatccggtt aagatcgatc tttgaactca | 60 |
| taaaaactag tagattggtt ggttggtttc catgtaccag aaggcttacc ctattagttg | 120 |
| aaagttgaaa ctttgttccc tactcaattc ctagttgtgt aaatgtatgt atatgtaatg | 180 |
| tgtataaaac gtagtactta aatgactagg agtggttctt gagaccgatg agagatggga | 240 |
| gcagaactaa agatgatgac ataattaaga acgaatttga aaggctctta ggtttgaatc | 300 |
| ctattcgaga atgttttttgt caaagatagt ggcgattttg aaccaaagaa acatttaaa | 360 |
| aaatcagtat ccggttacgt tcatgcaaat agaaagtggc ctaggatctg attgtaattt | 420 |
| tagacttaaa gagtctctta agattcaatc ctggctgtgt acaaaactac aaataatcta | 480 |

```
ttttagacta tttgggcctt aactaaactt ccactccatt atttactgag gttagagaat    540
agacttgcga ataaacacat tccccgagaa atactcatga tcccataatt agtcggaggg    600
tatgccaatc agatctaaga acacacattc cctcaaattt taatgcacat gtaatcatag    660
tttagcacaa ttcaaaaata atgtagtatt aaagacagaa atttgtagac ttttttttgg    720
cgttaaaaga agactaagtt tatacgtaca ttttatttta agtggaaaac cgaaattttc    780
catcgaaata tatgaattta gtatatatat ttctgcaatg tactattttg ctattttggc    840
aactttcagt ggactactac tttattacaa tgtgtatgga tgcatgagtt tgagtataca    900
catgtctaaa tgcatgcttt gtaaaacgta acgaccaca aaagaggatc catacaaata    960
catctcatag cttcctccat tattttccga cacaaacaga gca                     1003
```

<210> SEQ ID NO 154
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0110

<400> SEQUENCE: 154

```
gggatgcggt tccgcttcct cttgatcttg gacgagtcgg aggacattgt tggatcccag    60
tgcaatggta atataaaaca agaaaacaag agattttata ggacaatcac taaatgacat   120
ttaattgatt aaacatttat tcattaataa ttgtatgtta ctaacttcaa catttaataa   180
ttttgtttaa gatacgttta catcagagac tattaatatt tttacaggtt gtaacttaa    240 actttgtctt gaatcgaaca tgactataga ttttgggcaa acttaaagat aacaacattt   300 ccgtttttt tcaaattatt acaaatcaaa ctgatatatt agacacaaca cgattacacg    360
taatgaaaaa agaaaaagat aaaaagataa agaagggat cgattctgtt tggtctggtt     420
tagtgagatt caaagttaag ctcttccttt caagacatgc cttcttaaac cgggaatgtg    480
aacgtttgta atgtagtccg tccagttaat gcttccaaca tcaaatccaa attctctctt    540
ctcgtcctct gacatattct ccattaatct ctggggtatt gctgttatca aatctgtaaa    600
agaaaccaaa aaaaaaagat gaaaactttg cgggtaccgg ttttgtctgc tctaagaatt    660
agaatgttaa tgagttctgt cttaccttcc accatagaaa gtgtatggct cataaatagt    720
agcaaggtgt ttggcttgtt caacagattt cttgcatata aactttagct tctgcatcat    780
cttactatcc actgaactca taccactcat caacccactc cgttcttgag catctctcca    840
caaatgatcc gagaaatcat caacggaatt gaaaagtttc atcaaacgca ccataatagg    900 atcacccttta gagtccatgc atggagatgt tttgtagtgg ttataaagaa gctccgctaa    960
gtcttcgaaa accagcgggt ttatcgccga agaagcgatc tgatacacgt ttatttcagg   1020
ttcc                                                                1024
```

<210> SEQ ID NO 155
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0111

<400> SEQUENCE: 155

```
cgattggatt tagtctatac attatagggc gcaagtttgt ggatttaaga attatataaa    60
aacttgaaat atatagtttt tatgcattct cctcttgtgt aatacataaa ccaaatatga   120
```

```
gataggttaa tctgtatttc agataatatt aaattccaaa caatatttt acttgttata      180
agaaggcaat taatatctct ctgttaatgg caagtggtac caagtagtat taaactatta     240
atgcaatgga agagtactgt tggaaattat aatcctctat cacacattca aacagatctc     300
ctgaaatctt ctcttccaaa cttgtacttc tctgatccaa atgtaggctc caaaatatag     360
acatttacca tttactaagt ccacaactcc tttcttgtct ccttcaaaaa tgactcttgt     420
gtaaccacca tatgactccg acagttcggc attgccatga tgagagctta aaaattcacc    480
ttcctgagca tttcaagtct tcactccctt agcttgacct gaaccaagat aaaatgcctt    540
tgtcgtcccg taatatccat cctgctttgg acggcatcat agttacattc gatccatcct    600
atttacaatg ttatttagt attaaaaaca tgacaataaa tttgttgtta aacatattca     660
aatacaatat gattggattt ataagtaatt gtaatatgaa atgtccttag taatatgtta    720
aaaaatacat agatacacac acgtactaaa agaggcaacg cgggagatgt cattagagga    780
agaactagga agcagagcgt tcatgcaaaa tgctaccaaa aacgttaatg caatatctca    840
actaatcagc acagtccatt tcatactgag aatgtaaaaa ccaatcagca tcgtccattt    900
tttcatctaa ttatttgtta actcttaatt ggccacaact tccaaccaca tgacgctctt    960
tctattccct ttatatattc ccatctcaaa tgttcttgga gacacaaaat atcataaaca   1020
tata                                                                 1024
```

<210> SEQ ID NO 156
<211> LENGTH: 996
<212> TYPE: DNA
<213> ORGANISM: Arabidopsis thaliana
<220> FEATURE:
<221> NAME/KEY: misc_feature
<223> OTHER INFORMATION: Ceres Promoter YP0115

<400> SEQUENCE: 156

```
gtcgattgga tgatgaacat tctacatata taattattat gtttaagcac ttagacagca      60
taaattcttt ctaattatat aaatctaacc ttgttacatt gtacatctat aaattacttg     120
aagaaataac gagttctatt tcttttaaa aattaaaaat actataccat atctcagtga      180
ttaagttgaa ccaaaaggta cggaggagaa acaagcattt gattcttcct tatttattt      240
tattcatctc tcactaatga tggtggagaa aaaagaaaa tacctaacaa acaaatatat       300
attgtcatac aaaaatattt ctatatttt agttaattag tttatattcc tcactttca       360
gggcttatat aagaaagtga gcaaacacaa atcaaaatgc agcagcaaat actatcatca     420
cccatctcct tagttctatt ttataattcc tcttcttttt gttcatagct ttgtaattat     480
agtcttattt ctctttaagg ctcaataaga ggaggtacta ttactacact tctctctact    540
tttacttgta ttttagcatt aaaatcctaa aatccgtttt aaattcaaaa ataaacttag    600
agatgtttaa tctcgattcg gttttttcggc tttaggagaa taattatatg aaattagtat     660
ggatatcttt actagtttcc attcaaatga ttctgatttc aatctaatac tctcactctt    720
taattaaact atatgtagtg taatttcaca ctgttaaatt tctaccatgt catgtatatt    780
agagttgcat agaaaattgt aaaacatcca tttgaattcg aatgaaacaa atgttttaa     840
aataaaattt tggtttttaa agaaaaaatc taaaactgaa ttatatcgtt taaccaagtt    900
gtaaaagtca taaaacgtag tatcttgtaa atcgctcttc cacggtccaa atagacttct    960
agtaataaac aagtaaaact aattttggtt tcttac                              996
```

<210> SEQ ID NO 157
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0117

<400> SEQUENCE: 157

| | | | | | | |
|---|---|---|---|---|---|---|
| gtcagtgagt | cgattggatc | acagtccttt | atgataaaac | aaactcataa | ttattccacc | 60 |
| gacaacatgc | gttttaaatt | attttttctt | aaattatatt | atattatatt | gatatcaacc | 120 |
| tagctaaaat | aattcggatg | gcgaaatcgg | acaattttta | atagaaaaaa | tgggtatgaa | 180 |
| gatagtctat | gattccgttc | ttagcgacta | gagggacctg | ctcaaatctc | ccgggtgata | 240 |
| cgcgatgtca | agctcaatag | aaccccacaa | ccgacgagac | cgagaaatcc | ttgatttggg | 300 |
| ctagaagatt | ttgaaataaa | tttaatatat | tctaagtaac | ttgcttaaat | ttttttttcaa | 360 |
| actctaaaga | cataactaac | ataaagtaaa | aaaaaaaaag | ttaatacatg | ggaagaaaaa | 420 |
| aattaaacta | atgattagct | ctctaacgtg | tttaatctcg | tatcaagttt | ttttttaaaa | 480 |
| attatattgc | tattaaaaca | ttgtactatt | gtttctattt | tgtttagcta | ttattcttgt | 540 |
| gaaatgaaaa | gttgtgttta | ttcaattact | aaatggcaat | atttatcttg | gaaaactata | 600 |
| cctctaattg | gattaggccc | tagacatcct | ctttagctta | ttgacgttaa | aattattccc | 660 |
| aaaactatta | aagtttagta | gtttgaaaga | tgcatcaaga | cctactcaga | taggtaaaag | 720 |
| tagaaaacta | cagttagtgt | gattatattt | taaaatatat | aaaacaatct | tattaaacta | 780 |
| aatattcaag | atatatactc | aaatggaaga | taaaaacatt | tagtctgtta | ccactaccag | 840 |
| cctagctagt | cactaatagt | cactttggaa | ctgagtagat | atttgcatct | tgagttacca | 900 |
| tggactcaaa | agtccaaaaa | gagaccccga | gtgaaaatgc | taccaactta | ataacaaaga | 960 |
| agcatttaca | gcggtcaaaa | agtatctata | aatgtttaca | caacagtagt | cataagcacc | 1020 |
| attg | | | | | | 1024 |

<210> SEQ ID NO 158
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0119

<400> SEQUENCE: 158

| | | | | | | |
|---|---|---|---|---|---|---|
| taccaaaaat | aaggagtttc | caaaagatgg | ttctgatgag | aaacagagcc | catccctctc | 60 |
| cttttcccct | tcccatgaaa | gaaatcggat | ggtcctcctt | caatgtcctc | cacctactct | 120 |
| tctcttcttt | cttttttttct | ttcttattat | taaccattta | attaatttcc | ccttcaattt | 180 |
| cagtttctag | ttctgtaaaa | agaaaataca | catctcactt | atagatatcc | atatctattt | 240 |
| atatgcatgt | atagagaata | aaaaagtgtg | agtttctagg | tatgttgagt | atgtgctgtt | 300 |
| tggacaattg | ttagatgatc | tgtccatttt | ttttctttttt | cttctgtgta | taaatatatt | 360 |
| tgagcacaaa | gaaaaactaa | taaccttctg | ttttcagcaa | gtagggtctt | ataaccttca | 420 |
| aagaaatatt | ccttcaattg | aaaacccata | accaaaata | gatattacaa | aaggaaagag | 480 |
| agatattttc | aagaacaaca | taattagaaa | agcagaagca | gcagttaagt | ggtactgaga | 540 |
| taaatgatat | agtttctctt | caagaacagt | ttctcattac | ccaccttctc | cttttgctg | 600 |
| atctatcgta | atcttgagaa | ctcaggtaag | gttgtgaata | ttatgcacca | ttcattaacc | 660 |

| | |
|---|---|
| ctaaaaataa gagatttaaa ataaatgttt cttctttctc tgattcttgt gtaaccaatt | 720 |
| catgggtttg atatgtttct tggttattgc ttatcaacaa agagatttga tcattataaa | 780 |
| gtagattaat aactcttaaa cacacaaagt ttctttattt tttagttaca tccctaattc | 840 |
| tagaccagaa catggatttg atctatttct tggttatgta ttcttgatca ggaaaaggga | 900 |
| tttgatcatc aagattagcc ttctctctct ctctctagat atctttcttg aatttagaaa | 960 |
| tctttattta attatttggt gatgtcatat ataggatcaa | 1000 |

<210> SEQ ID NO 159
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0120

<400> SEQUENCE: 159

| | |
|---|---|
| tagttttga tttaatctac gttttctta atcataaatg ggtaattatt agttttgca | 60 |
| aaatcaaaat ccaaaaattg ttctaaacac tgcaaccatt taaggcctat atcactcaga | 120 |
| aaatttctgg tgggagaact aatcgtttgt cctttctaaa tctcacatat tagaatttag | 180 |
| aattagtgtg ctacataaga atattagttc agctcggaac aactattttt tggtaaaaca | 240 |
| gagaacttaa acaaatgcat tatttatca acatgcattt tgaattgaat ataaaatttc | 300 |
| ataattgtaa agacataaat tacataaaat tttacatgaa aaaatagata tagaaagaaa | 360 |
| atgaaactaa ctgatgatat gctctctaaa tttttaatc tcataacaag aattcaaatt | 420 |
| aattagttca tattttggt taatataaca tttacctgtc taagttggaa ctttcatttt | 480 |
| tttctgtttt gtttagtcag tattcttaat gtgaaacgga aagttgaatt tattcaaact | 540 |
| taaattcaat agcattaatt aaaggcgaaa gctattatct ctacatgtgg ttcaaactag | 600 |
| acatccaatt taattagctt attgacgttg aaatgttttc caaaactact atagtttggc | 660 |
| aatttgaaag atgcatcaga actactcaga caggtaaaag tagaacctct agctgtgtga | 720 |
| attgtatgtt agtccataaa gaacatcttg taaacttcat acttaagata tatattacaa | 780 |
| tatatacttg aatggtagat aaaaacgatt agtctgattg ctagcatact cacaactatt | 840 |
| tggaaatgag taagatattg gcattctaga gttactacta tggagacaaa agtcgaataa | 900 |
| aagagacctc acgtgaaaat gttacagct agtaaaaaaa gcatttacac taacggtaaa | 960 |
| aaaagtatct ataaatgttt acacaaggta gtagtcatt | 999 |

<210> SEQ ID NO 160
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0121

<400> SEQUENCE: 160

| | |
|---|---|
| ttggattttt ttttgttga gtcagcagac catctaatct ctcttttcc accacagcct | 60 |
| gctttctatg aagcatttgg gcttacggtt gtggaatcaa tgacttgtgc actcccaacg | 120 |
| tttgctacct gtcatggtgg acccgcagag attatcgaaa acggagtttc tgggttccac | 180 |
| attgacccat atcatccaga ccaggttgca gctaccttgg tcagcttctt tgagacctgt | 240 |
| aacaccaatc caaatcattg ggttaaaatc tctgaaggag ggctcaagcg aatctatgaa | 300 |
| aggttggccc attctccttg acaggcttaa caatacaact tgtatcgctt caacaagatg | 360 |

```
atggcttaat aaggatttttt gcatgtatag gtacacatgg aagaagtact cagagagact    420
gcttaccctg gctggagtct atgcattctg gaaacatgtg tctaagctcg aaaggagaga    480
aacacgacgt tacctagaga tgttttactc attgaaattt cgtgatttgg ttagtgtaac    540
ccactgttat tcttttgatg tctacatcta ctttacttac attattcttt tcttcggttt    600
gcaggccaat tcaatcccgc tggcaacaga tgagaactga tcatgacagg gtaggatttt    660
atttcctgca ctttctttag atcttttgtt tgtgttatct tgaataaaaa ttgttgggtt    720
ttgtttcctt cagtggtttg attttggact tatttgtgtt aatgttgttt tggctgttct    780
cttaatatca ataacaaata aatttactgg ttggtatcta agatctaaca atagttacta    840
tttttagagg taaagacacc aaccttgtta tattggtcag agagctaaaa ccttgacttg    900
ttgggaaaac aaaactctaa tgacagaaaa tctgacatga tgccttataa ttcacagcct    960
catgttctac ataaatccta acaatagcac tttgtttct                           999
```

<210> SEQ ID NO 161
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0128

<400> SEQUENCE: 161

```
gataaactga taatggaaaa gaacaaagaa accagttttt aactatttgc atatgtaatt    60
tatttgttgc aaattatatt tagttaaaat gtttcctcta tttatatata tatatatcag    120
tcaagcacta tgtataagaa atgtcaattt ataatttttt acatgtcctt taacagaaag    180
aaaatgaatt tttacatgtc attcatagag agtcactcgt ttatttctta tatagagaat    240
aacacactca catgcatatg catgcaatat gatacatttt atgacaaaga taatcaacgg    300
aaacggtcaa gacataattt gataaacaac ttgcacgatg cacagatctg atcaaatata    360 taactctttta acatatccaa aatattcaaa aagaaaaact cgatccaaac tagcaacatc    420
acgctcacgc ggtaggctaa aaatttatta atctccaaaa gtctttctta tgaacactgc    480
aaacacaaca acttgaaaag tcatataggt ttagatgatg acgcgtattg gctatcgctt    540
accggagtgg ctcataaata caataaacaa tacgtaaaag tcaaagtcaa atatatttag    600
tcaactataa ccattaatcg ggcaaaacct ttagctgtca aaacaacgtg aaaacgatat    660
ttgtatatat catcaagaat cagtagataa gagaatgatt taatcccctg actattacaa    720
ttttggtgta ataaacagtc tctattggtt tttattcttt gttttaattt ctcatgacct    780
atagagagaa ttaggtagtt tcgaaaattg gctaatcaac ttttgaaaac tactgtctac    840
tttgcttaaa ttctctacac ttagtttcgg ataagataat tgtcggacta atagttaatc    900
ccttgacaat ctttgatatt ataaaaggtt tagttaatct cttctctata taaatattca    960
tacaccagct ttcaaaaata tataatccaa acaccaaaaa caaa                    1004
```

<210> SEQ ID NO 162
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter YP0137

<400> SEQUENCE: 162

```
gtggcacatg ctgaaacccc gagcatctct ccggaagaca cgcgtcgttc gctccaaaga    60
aaacagtcac agctgccgga gaatctccgc cgtcttcttc tgccaccgga aaaactctct   120
ccaccacttt cagtgcccac ctcgtgttat atccactgta tcctcgtagc accatatcag   180
cctaataaaa ttttatgtat caaattttaa gacatagccg aaactacact atactagaca   240
ataataatat gatttgtttc ctgaaaaatt atggtttcat gagaaacatt aatcatctat   300
aaaacaaatt agctatggca tcgaagagtt atcaatcaaa actgatgaat ctttacttaa   360
tatatacaac atatctttac cttgcggcgg agaagatcgg cgagagaagc accccagcca   420
ccgtcactaa aggattcttc agtgatgaa tcaccaaaga gaaaaaccct ccgtctcatc    480
atcttccaca caatcttctt gagaaaatct gagagataag aaggtgtag tggttttgct    540 gaagtgatcg tgtttgattt agtaaagaaa tgctttattt attgttgggg gaaacataaa   600
taaataaagt aaaagtggat gcactaaatg ctttcaccca ctaatcaccg accttccatg   660
gtttattgtg aaatacactc atagatagac atacaatacc ttatgtacgt aaataacatt   720
ttatttgtcg acacttatgt aagtaacgca tagattattt tctatgtgat tgccactctc   780
agactctcag tttcaaccaa taataacaat aactacaaca acattaatca taaacatatg   840
ctctggttta caattaaagc ttagattaag aaactgtaac aacgttacag aaaaaaaatg   900
ttatttacgt tttgtaagat tagtctctag aatcatcacc gttttttata tattaatgat   960
tctttcttat atataaaacc tttctcgaaa tacccatgaa a                      1001
```

<210> SEQ ID NO 163
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter YP0143

<400> SEQUENCE: 163

```
atacaacaga tggcagatat cgagttaaat acgtgaatca gccgttacga tattttaaaa    60
ctagaaaatt atttaaaaat attgcaaaat accatttaat ttcattgttc ataaaaaaaa   120
gaaattcaaa aacttaaaaa ctgattcaaa aatttggatt aattctcatt aacagtcttc   180
aacactacaa caacatgttt ctaatttatt ttatattta ataattaaac aatatatacg    240
tctgcacatt gttgctccga cataatctag tataaaaata gttgcagcat atgtgaaaag   300
caagcagcat ttatcactca atactttaa ttttatctgt tgtatgtatt aaggttttgt    360
agctttaaga aaacgcttat aatataaaat aacttctaaa agatatttca tgcgtataca   420
ataaatattt gtgaaaaaac atttcgaaaa cgtgtacaat atataaacta ttgtgttatc   480
ttttgacatt caaacaaatg ttgacaatgt aatttatcc atgatatgat tggccaatta    540
gctgcgaggt aaaaatccgt atacgagtaa aagtaagata aatttcgca agaagatttt     600 tagcaggaaa tctaagacaa gtgtcatgaa cgtgtcaatc aacaaacgaa aaggagaatt   660
atagaatcca gattcgacgt accacattaa taaatatcaa aacatttat gttatttat     720 ttttgctctg gcagttacac tctttttcat tgctccaata aaaaaatcac tcgcatgcat   780
gcatatatat acaccatagt aaactccgcc tcttcttcat tttaaaagta tcagtttaca   840
ctgacacaat ccttaactat tttcctttgt tcttcttcat ctttattaca cattttttc    900 aaggtaacaa ataatctttt taagtcactt ttatactctt taaatcttag attgatatat   960
gaatgcatgt taatatttca agatttatag gtctaccaaa c                      1001
```

<210> SEQ ID NO 164
<211> LENGTH: 1003
<212> TYPE: DNA
<213> ORGANISM: Arabidopsis thaliana
<220> FEATURE:
<221> NAME/KEY: misc_feature
<223> OTHER INFORMATION: Ceres Promoter YP0144

<400> SEQUENCE: 164

| | | | | | |
|---|---|---|---|---|---|
| aaacgttgca | agattattga | ttgtgagaaa | gagtgctcaa | ggtagtactg | atttctgtaa | 60 |
| agctcacggt | ggtgggaaac | gatgttcttg | gggagatggg | aaatgtgaga | aaatttgcta | 120 |
| gaggaaagaa | gcggtttatg | cgctgcgcat | aacactatta | tgtctcggga | gaacaaagat | 180 |
| ggaagcaaga | gcggtttgat | tggaccggga | ctctttagtg | gccttgtttt | tggctctact | 240 |
| tctgatcatt | ctcagtctgg | agctagcgct | gtctctgatt | gtactgattc | tgttgaacga | 300 |
| atacagtttg | agaataggca | gaagaacaag | aagatgatga | taccgatgca | ggttctagta | 360 |
| ccttcatcaa | tgaaatctcc | aagtaattca | catgaaggag | aaacaaacat | ctatgacttc | 420 |
| atggttccgg | aggagagagt | tcacggcggt | gggctagtaa | tgtctttact | tggtggctcc | 480 |
| attgatcgaa | actgaaagcc | atttatggta | aaagtgtcac | attctcagca | aaaacctgtg | 540 |
| taaagctgta | aaatgtgtgg | gaatctccga | atctgtttgt | agccggttac | gttatgctgg | 600 |
| atcaaaaact | caagatttgt | tggatattgt | tatgctggat | cggtggtgaa | accacttccc | 660 |
| ggttgctaaa | taaataaacg | ttttttgtttt | ataatctttt | tcactaaacg | gcagtatggg | 720 |
| cctttagtgg | gcttccttta | agcgaccaat | acaatcgtcg | caccggaatc | tactaccatt | 780 |
| tataggttta | ttcatgtaaa | acctcggaaa | atttgagagc | cacaacggtc | aagagacaaa | 840 |
| aacaacttga | agataaaggg | ataaggaagg | cttcctacat | gatggacaac | atttcttttcc | 900 |
| acacaaattc | tcataataaa | aatcttataa | tacaaatact | tacgtcataa | tcattcaatc | 960 |
| tagtccccat | gttttaaggt | cctgtttctt | gtctgataca | aat | | 1003 |

<210> SEQ ID NO 165
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0156

<400> SEQUENCE: 165

| | | | | | |
|---|---|---|---|---|---|
| ttggtttgca | ttgtgaagat | ttgtattaac | tatagaacat | tgaattgatg | gtgttaagtt | 60 |
| cttacacaag | cgtgcttctc | ggtttgaact | gtttcttttg | tatgttgaat | cagagcttag | 120 |
| tttataggaa | ccagagtatc | tacttagtca | ttctctgatg | ctaagtgcta | aggttctacc | 180 |
| tagttgccct | ctaggccctt | atgttattga | taacttatga | agctatttga | acacttgatt | 240 |
| cttaggagac | ctaagttggt | acagccagat | agagtgtatg | ttcttgttct | ctatgtgaca | 300 |
| ggatcaagct | gccacacata | gttcaagggt | atgctctgtg | tgggtttgct | cagattgagg | 360 |
| acaaatctat | acaaggaagt | agagtctttg | acattttgat | gttgtatgat | aagaagaaga | 420 |
| aggagagta | ataagaaag | agaaaaggga | aacagaaaca | cgtgggagaa | catcccaaag | 480 |
| aggaagcaca | cgcggatctt | catgcaaagc | tccccgattc | tcccatgtgg | tccctttctc | 540 |
| cctttgtccc | cctcctcttt | cttctttttct | cattttactc | cttttttac | cattatacaa | 600 |
| cgaatctttt | ttatcataat | ttttttggttt | tggtttattt | tccaataaca | ctttcttggt | 660 |
| tacttcccat | tctcactttt | tcatataaga | aactcacttt | gggaaactta | tgtttgagaa | 720 |

```
tgacaagtct ttttagagaa agtgatgtaa caaatctaaa gtgattatat ataaccttg      780 cacaatgttt ttgattttt gtaagattcg aatattaggt ttattattcg tagggaataa      840
acttactttc aaaagcgttc ataagttaat actttcatat atgatcataa gtacggacac      900
tattgttttt tgtttgtttg tgtttattct aaaagaaagt agcttttaat tgaaatgtcc      960
tcggaggcac agtttaaagt tcgagtgtaa cagtttctaa ggca                      1004
```

<210> SEQ ID NO 166
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0158

<400> SEQUENCE: 166

```
ttattagatt aatagattgc attgcattgc ttgtgctttc aatttacaaa ttgtctccca       60
actccatcga cacatctctt tttgtgtata taagattcag acttgttata ttttttttat      120
aaatatgtta ttagcatctt aagttaaatt gatttttat atctgcatta aggattacac       180
gactatattt gcgattgtgt gttggttaaa atataattta ggattgtctt aactacatt       240 taggattata tgactatatt tggttaaata taaaatctag ctgtgattat tagtattcaa      300
aaataagtag cctaaccaat taaaacaacg gctattgggg caaattagaa cattttagtg      360
tgtccaaaat ataatggtca ttaggtcata ttcctcctag cttcatcgca gcataattga      420
atgattgcct tatttagaag agcttttcca ctttcccaaa atctaggtgg gatcttttg       480 ttttgacctt cattttttctt gtttaccatt tttagctaaa ttatttacga ttacaaaaga     540
tatcaaaagt tggatcataa tacaatttat agacttactg tagaaaattc gtatgtacaa     600
gtacaacaaa ttcttcataa taaatttga aaattctatt acaaatgttg taagaaatag     660
aatttgaaat atatataaac taaggagaaa aaaaaagaga acatgcattg ctctagtcag    720
agtggaccaa catcaacgag ataagataac ataaaaacca actcaccata actaaaaaca     780
tcccaagaga tccaacgatt catatcaaac acaaaaacat cgaacgatca gatttaaacc     840
atctctggta tctccaaaac acaaacactt ttttttttct tttgtctgaa tggaacaaaa      900
gcatgcgaca tctctgtgtc tttatcttct ctctcctctt cttgaaaaac tgaacctta      960 attctttctt cacatctcct ttagctttct gaagctgcta                           1000
```

<210> SEQ ID NO 167
<211> LENGTH: 1005
<212> TYPE: DNA
<213> ORGANISM: Arabidopsis thaliana
<220> FEATURE:
<221> NAME/KEY: misc_feature
<223> OTHER INFORMATION: Ceres Promoter YP0188

<400> SEQUENCE: 167

```
gattggtatg aaatttcgga gaccaacaaa aaaaacttta ttgagcttgg agtgaagcta       60
tatatatggg gcaagatcat aatatgttta tatcggcctt ttcgttaact gaaaataata      120
gttttgagaa atatatcaaa tggtaaacag acatcatctt tgaaaaatac catcaatgaa      180
gttaatattg ttattggcat atggtttacc catcttaatt ttaatgcaac caaacaaaca      240
agaaacaaaa actgtataag atacaaggtg ttttacgatt ttccgtctta aaaccgaaat      300 attttttgttc ctacgacttt aaacggactt tgcttaagtt gtgtgcatgt aagctcgtcg     360
```

```
tccctcgatt gtcatcaaca ttcaccaata tcagcctcta tcacacgagt gaaggtggtg        420
attcggctta atgaaaacag agaaatattt caatatgatt cctattaaat tttaaatctt        480
ttttctcaat ctctagattt tcattaaaag catcatgatt ttttccact atgttcatat         540 atctctatca cagttttagg tacattgtag aaattggata agatacgtca tacgtctaac        600
atgaatttgg tctagcaagg aaggtttgag ataataagtg aaagaaaac acaagataat         660 aaattataat ttataaatgc tttatagtat tgaaaaataa gatgattttt tttttttta        720 ataccggatt ggctgatcca cttatgatga ctcaaatgtt attaagtttc aagacaattt        780
atgatgacac aaatcacaat gagtcaatag tagccacgaa gccagaaaaa aaaaatgtac        840 tacaaaaga taatgatagt acaaaatgat acgtcgtact gccacatgta cgacacaact         900
cgattaccaa aaagcagagc catccaacca taaaactcaa aacacacaga ttccactggc        960
gtgtgctctc ctcacttcac tcgtccttga aacttgaggt actga                      1005

<210> SEQ ID NO 168
<211> LENGTH: 1002
<212> TYPE: DNA
<213> ORGANISM: Arabidopsis thaliana
<220> FEATURE:
<221> NAME/KEY: misc_feature
<223> OTHER INFORMATION: Ceres Promoter YP0190

<400> SEQUENCE: 168
taaatagtga cattggtaag aagaaaaaaa acactattaa atagtgaaaa aatggtttat        60
aactctctta attaacatta cttattattg ctagcaccta aaatctccca caaaatattt        120
gttgtaaaac acaaatttac aaaatgattt tgttttaaa ttagtaacac atgttcatat         180
atacgttaat aagaacatac cctatatgat tttatataaa aaaatttctt tgagacgtct        240
tattcttttt tctttaataa tatgcaattg tgagagtttg gatttgaatg gtagcattag        300
aagcaaactt gaaccaaaca tatttcatga agtcaaactt gaaccaatgt gatcactaat        360
cacagtgttc gcagtgtaag gcatcagaaa atagaagaag ggacatagct atgaatcata        420
taatcttgac acatgtttta taggttttag gtgtgtatgc taacaaaaaa tgagacagct        480
ttcttctaat agacttaata tttgggctaa atgtaccaca gttgtgaatt tcttacaaaa        540
atgggccgag ctacaaaaaa ctacaggccc actctcaact cttatcaaac gacagcgttt        600
tactttttta aaagcacaca cttttttgttt ggtgtcggtg acggtgagtt tcgtccgctc       660
ttcctttaaa ttgaagcaac ggttttgatc cgatcaaatc caacggtgct gattacacaa        720
agcccgagac gaaaacgttg actattaagt taggttttaa tctcagccgt taatctacaa        780
atcaacggtt ccctgtaaaa cgaatcttcc ttccttcttc acttccgcgt cttctctctc        840
aatcacctca aaaaaatcga tttcatcaaa atattcaccc gcccgaattt gactctccga        900
tcatcgtctc cgaatctaga tcgacgagat caaaacccta gaaatctaaa tcggaatgag        960
aaattgattt tgatacgaat tagggatctg tgtgttgagg ac                        1002

<210> SEQ ID NO 169
<211> LENGTH: 995
<212> TYPE: DNA
<213> ORGANISM: Arabidopsis thaliana
<220> FEATURE:
<221> NAME/KEY: misc_feature
<223> OTHER INFORMATION: Ceres Promoter YP0212

<400> SEQUENCE: 169
agtcgattgg tacactctta atttaattag agtaagagat caacaaaaat atagaatttt        60
```

```
ctttatatcg aagtgctacg accttatata tatagaaaaa aaagcatagg tgaatctcta      120
aattgagatt gtgctgtagt aaacatatta agtttttagt ttttttaaga aatgaatctt      180
tttgttgatt aattcaaact agtagtcatt aagattccgg agattccaat ttagaaaagt      240
caaagattca aagaacaagt ccaggtccac atgttgaatc cgattcatca tccactcatc      300
cttcatatct tcctccaccg tctccgccca aaaatcaat aacataaaa atcctaaaa         360 aaacatattt gattttgaaa aaactttatc atatattata ttaattaaat agttatccga      420
tgactcatcc tatggtcagg gccttgctgt ctctgacgtc cttaattatc attattttta      480
aatttgtctc tctcagaaaa ttacgccaca atcttcctct ttccttttc cgaaaacagc       540 taatatttgt ggacctaaac taaataacgt agcctctaga ttttatataa ttactaatac      600
tatatgctac tacttgttat tatttactcc aatcatatat gataccaatc aagaatcact      660
acataagtag aaaactttgc aatgagtcca ttaattaaaa ttaagaataa acttaaaatt      720
ttatggtatt ttaagattcc ctttggattg taatgacaag aaatcagcaa attagtcgta      780
actcgtaaga ataaacaaga tcaattttta ctttcttac aaagattccg ttgtaatttt       840
agaaattttt ttttgtcact gttttttttat agattaattt atctgcatca atccgattaa    900
gaagtgtaca catgggcatc tatatatatc taacaggtaa aacgtgtatg tacatgcata     960
aggttttacg tgcttctata aatatatgtg gcagt                                 995

<210> SEQ ID NO 170
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0214

<400> SEQUENCE: 170
ccagtcgatt ggcgcctcgc atgcctatca tatttaaccg tcaataatgg atttggcggt       60
tttggtaggc cgggtcaacc ggattaaaag aaaacggttt ggagtccttc cttgcaattg      120
aattttcaca cattcgggtt ttgtgatttc tctgtcataa tgggcccggc acatatggtt      180
cataacccat gtgggcctat ggtataattt ttccaattaa aactattgtt aggtcgataa      240
aacaaaaaac aataaaaacg agtggaatac acataccaaa aagaatgtga tgaacattag      300 taatttttatt ttgatggtta atgaaaaaca aaataaatgc atcttggcat cttccgttgg    360
aaagcgcaaa tagggcagat tttcagacag atatcactat gatggggggt gagagaaaga      420
aaacgaggcg tacctaatgt aacactactt aattagtcgt tagttatagg acttttttt       480 tgtttgggcc tagttatagg atcataaggt aaaaatgaag aatgaatatt agattagtag      540
gagctaatga tggagttaag tatgcacgtg taagaactgg gaagtgaaac ctcctgtatg      600
gtgaagaaac tatacaacaa agcccttgt tggtgtatac gtattaattt ttattctttt       660
atcacaagcg atacgtatct taagacataa taaatatata tcttactcat aataaatatc      720
ttaagatata tatacagtat acacctgtat atatataata aataggcata tagtagaaat      780
taatatgagt tgttgttgtt gcaaatatat aaatcaatca aaagatttaa acccaccat       840 tcaatcttgg taagtaacga aaaaaaggg aagcaagaag aaccacagaa aagggggcta     900
acaactagac acgtagatct tcatctgccc gtccatctaa cctaccacac tctcatcttc     960
ttttccccgt gtcagtttgt tatataagct ctcactctcc ggtatatttc cccattgcac    1020
tgga                                                                  1024
```

<210> SEQ ID NO 171
<211> LENGTH: 911
<212> TYPE: DNA
<213> ORGANISM: Arabidopsis thaliana
<220> FEATURE:
<221> NAME/KEY: misc_feature
<223> OTHER INFORMATION: Ceres Promoter YP0263

<400> SEQUENCE: 171

| | | | | | |
|---|---|---|---|---|---|
| atctagctgt | ggattccacc | aaaattctgg | cagggccatg | atctaaaaac | tgagactgcg | 60 |
| cgtgttgttt | tgcagtgatt | tgtatttcat | atttgcacca | tcctacacag | tcccacttggt | 120 |
| atcgtaacca | aacataagga | gaacctaatt | acattattgt | tttaatttcg | tcaaactggt | 180 |
| ttttacctttt | tagttacata | gttgattctt | catttgtttt | agtagttatg | gagcacaata | 240 |
| atgtgcaaca | aagaaagatc | atagtggatt | aatatgttga | gaggtcagaa | attcttggtt | 300 |
| aacaaaaaaa | agttacaagg | actgagattt | tgggtgggag | aaagccatag | cttttaaaac | 360 |
| atgattgaac | ttaaaagtga | tgttatggtt | tgaggggaaa | aaggttgatg | tcaactaaga | 420 |
| tagttgaagt | aatgtcttaa | actaaagtaa | accaccggtc | caaccgtggt | ccggaagcat | 480 |
| ctctggtatg | atttatccta | aaaatcaaaa | tagtagaaac | atactttaaa | tatatacatt | 540 |
| gatcggacga | aaattgtaaa | ctagtatagt | ttcaaaaact | agttgaacag | gttatgtacc | 600 |
| ttaaacatttt | atttcaaact | taaacactaa | agaacatata | tgaatagaag | tttatataaa | 660 |
| ttactatata | tctaccataa | atctcttata | attatgatgt | cacgatgagg | aagtgttgaa | 720 |
| acgttaaaat | gccaaaatat | aagcatgcga | cggaattttg | gcagaagatt | gtagagttgt | 780 |
| aatctgtcgc | aatcattact | cgtgctagca | ttttcatttt | tcccttcatt | tgtggataac | 840 |
| gcacgatata | acattctaca | caccaacaag | attctataaa | aacgcaaagg | ttgtctccat | 900 |
| agaatatcgt | c | | | | | 911 |

<210> SEQ ID NO 172
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0275

<400> SEQUENCE: 172

| | | | | | |
|---|---|---|---|---|---|
| aaacattaat | atgtagtaac | tatgggcgta | tgctttactt | tttaaaatgg | gcctatgcta | 60 |
| taattgaatg | acaaggatta | aacaactaat | aaaattgtag | atgggttaag | atgacttatt | 120 |
| tttttactta | ccaatttata | aatgggcttc | gatgtactga | aatatatcgc | gcctattaac | 180 |
| gaggccattc | aacgaatgtt | ttaagggccc | tatttcgaca | ttttaaagaa | cacctaggtc | 240 |
| atcattccag | aaatggatat | tataggattt | agataaattttc | ccacgtttgg | tttatttatc | 300 |
| tattttttga | cgttgaccaa | cataatcgtg | cccaaccgtt | tcacgcaacg | aatttatata | 360 |
| cgaaatatat | atatttttca | aattaagata | ccacaatcaa | aacagctgtt | gattaacaaa | 420 |
| gagatttttt | tttttttggtt | ttgagttaca | ataacgttag | aggataaggt | ttcttgcaac | 480 |
| gattaggaaa | tcgtataaaa | taaatatgt | tataattaag | tgttttattt | tataatgagt | 540 |
| attaatataa | ataaaaacctg | caaaaggata | gggatattga | ataataaaga | gaaacgaaag | 600 |
| agcaatttta | cttcttttata | attgaaatta | tgtgaatgtt | atgttacaa | tgaatgattc | 660 |
| atcgttctat | atattgaagt | aaagaatgag | tttattgtgc | ttgcataatg | acgttaactt | 720 |

```
cacatataca cttattacat aacatttatc acatgtgcgt cttttttttt ttttactttg      780
taaaatttcc tcacttttaa gactttata acaattacta gtaaaataaa gttgcttggg      840
gctacaccct ttctccctcc aacaactcta tttatagata acattatatc aaaatcaaaa      900
catagtccct ttcttctata aaggttttt cacaaccaaa tttccattat aaatcaaaaa      960
ataaaaactt aattagtttt tacagaagaa aagaaaaca                            999

<210> SEQ ID NO 173
<211> LENGTH: 981
<212> TYPE: DNA
<213> ORGANISM: Arabidopsis thaliana
<220> FEATURE:
<221> NAME/KEY: misc_feature
<223> OTHER INFORMATION: Ceres Promoter YP0285

<400> SEQUENCE: 173
gggattatat atgatagacg attgtatttg cgggacattg agatgtttcc gaaaatagtc      60
atcaaatatc aaaccagaat ttgatgtgaa aacactaatt aaaacatata attgacaact     120
agactatatc atttgttaag ttgagcgttg aaagaaaatg aaagagtgta gactgtagta     180
cgtatgagtt tcccaaaaga tggtgcttga atattattgg gaagagactt tggttggttc     240
ggttgaatga agatttttac ctgccatgtt gatagagaaa ggcaaataaa tgtaggggtc     300
gatgtctaac gtaaagactg gatcaaccaa gagtcctcct cctcgtcttc accaaaaaaa     360
aagagtcctc ctcgtggaaa cttatttctt ctccagccaa gatctcatct catctcttca     420
ctctatgaaa tataaaggaa tcttatggtt tttctaaaaa ctatagtacg tctatatacc     480
aaaggaaaca atataaaatc agttaatctg ataaattttg agtaaataat aaagttaact     540
ttgtacttac ctatatcaaa ctaattcaca aaataaagta ataataacaa agaattttta     600
gtagatccac aatatacaca cacactatga gaaatcataa tagagaattt taatgatttt     660
gtctaactca tagcaacaag tcgctttggc cgagtggtta aggcgtgtgc ctgctaagta     720
catgggctct gcccgcgaga gttcgaatct ctcaggcgac gtttcttttg ttttcggcca     780
taaaggaaaa agcccaatta acacgtctcg cttataagcc cataaagcaa acaatgggct     840
gtctctgtct cactcacaca cgcgttttcc tactttttga ctatttttat aaccggcggg     900
tctgacttaa ttagggtttt ctttaataat cagacactct ctcactcgtt tcgtcaacat     960
tgaacacaga caaaaccgcg t                                              981

<210> SEQ ID NO 174
<211> LENGTH: 996
<212> TYPE: DNA
<213> ORGANISM: Arabidopsis thaliana
<220> FEATURE:
<221> NAME/KEY: misc_feature
<223> OTHER INFORMATION: Ceres Promoter YP0286

<400> SEQUENCE: 174
gaaaacaatc ataggttacg ctattatcat cgaaaggtat gtgatgcata ttcccattga      60
accagatttc catatatttt atttgtaaag tgataatgaa tcacaagatg attcaatatt     120
aaaaatgggt aactcacttt gacgtgtagt acgtggaaga atagttagct atcacgcata     180
catatatcta tgaataagtg tgtatgacat aagaaactaa aatatttacc taaagtccag     240
ttactcatac tgatttcatg catatatgta ttatttattt attttaata aagaagcgat     300 tggtgttttc atagaaaatca tgatagattg ataggtattt cagttccaca aatctagatc     360
tgtgtgctat acatgcatgt attaattttt tcccccttaaa tcatttcagt tgataatatt     420
```

```
gctctttgtt ccaactttag aaaaggtatg aaccaacctg acgattaaca agtaaacatt        480
aattaatctt tatatgagat aaaaccgagg atatatatga ttgtgttgct gtctattgat        540
gatgtgtcga tattatgctt gttgtaccaa tgctcgagcc gagcgtgatc gatgccttga        600
caaactatat atgtttcccg aattaattaa gttttgtatc ttaattagaa taacatttttt       660 atacaatgta atttctcaag cagacaagat atgtatccta tattaattac tatatatgaa        720
ttgccgggca cctaccagga tgtttcaaat acgagagccc attagtttcc acgtaaatca        780
caatgacgcg acaaaatcta gaatcgtgtc aaaactctat caatacaata atatatattt       840
caagggcaat ttcgacttct cctcaactca atgattcaac gccatgaatc tctatataaa        900
ggctacaaca ccacaaagga tcatcagtca tcacaaccac attaactctt caccactatc       960
tctcaatctc tcgtttcatt tcttgacgcg tgaaaa                                  996

<210> SEQ ID NO 175
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0337

<400> SEQUENCE: 175 taatttttt attttggaa ctaacactta ttagtttagg tttccatcac ctatttaatt           60
cgtaattctt atacatgcat ataatagaga tacatatata caaatttatg atcattttttg       120 cacaacatgt gatctcattc attagtatgc attatgcgaa aacctcgacg cgcaaaagac        180
acgtaatagc taataatgtt actcatttat aatgattgaa gcaagacgaa aacaacaaca        240
tatatatcaa attgtaaact agatatttct taaaagtgaa aaaaaacaaa gaaatataaa        300
ggacaatttt gagtcagtct cttaatatta aaacatatat acataaataa gcacaaacgt       360
ggttacctgt cttcatgcaa tgtggacttt agtttatcta atcaaaatca aaataaaagg       420
tgtaatagtt ctcgtcattt ttcaaatttt aaaaatcaga accaagtgat ttttgtttga       480
gtattgatcc attgttttaaa caatttaaca cagtatatac gtctcttgag atgttgacat      540
gatgataaaa tacgagatcg tctcttggtt ttcgaatttt gaactttaat agttttctttt     600 tttagggaaa ctttaatagt tgtttatcat aagattagtc acctaatggt tacgttgcag       660
taccgaacca attttttacc cttttttcta aatgtggtcg tggcataatt tccaaaagag       720
atccaaaacc cggtttgctc aactgataag ccggtcggtt ctggtttgaa aaacaagaaa       780
taatctgaaa gtgtgaaaca gcaacgtgtc tcggtgtttc atgagccacc tgccacctca       840
ttcacgtcgg tcatttttgtc gtttcacggt tcacgctcta gacacgtgct ctgtccccac      900
catgactttc gctgccgact cgcttcgctt tgcaaactca aacatgtgtg tatatgtaag       960
tttcatccta ataagcatct cttaccacat taattaaaaa                             1000

<210> SEQ ID NO 176
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0356

<400> SEQUENCE: 176
ttagttcatt gaaacgtcaa cttttttactt gcaaccactt tgtaggacca ttaactgcaa        60
```

| | | |
|---|---|---|
| aataagaatt ctctaagctt cacaaggggt tcgtttggtg ctataaaaac attgttttaa | 120 | |
| gaactggttt actggttcta taaatctata aatccaaata tgaagtatgg caataataat | 180 | |
| aacatgttag cacaaaaaat actcattaaa ttcctaccca aaaaaaatct ttatatgaaa | 240 | |
| ctaaaactta tatacacaat aatagtgata caaagtaggt cttgatattc aactattcgg | 300 | |
| gattttctgg tttcgagtaa ttcgtataaa aggtttaaga tctattatgt tcactgaaat | 360 | |
| cttaactttg ttttgtttcc agttttaact agtagaaatt gaattttta aaaattgtta | 420 | |
| cttacaataa aatttgaatc aatatcctta atcaaggat cttaagacta gcacaattaa | 480 | |
| aacatataac gtagaatatc tgaataact cgaaaatatc tgaactaagt tagtagtttt | 540 | |
| aaaatataat cccggtttgg accgggcagt atgtacttca atacttgtgg gttttgacga | 600 | |
| ttttggatcg gattgggcgg gccagccaga ttgatctatt acaaatttca cctgtcaacg | 660 | |
| ctaactccga acttaatcaa agattttgag ctaaggaaaa ctaatcagtg atcacccaaa | 720 | |
| gaaaacattc gtgaataatt gtttgctttc catggcagca aaacaaatag gacccaaata | 780 | |
| ggaatgtcaa aaaaagaaa gacacgaaac gaagtagtat aacgtaacac acaaaaataa | 840 | |
| actagagata ttaaaaacac atgtccacac atggatacaa gagcatttaa ggagcagaag | 900 | |
| gcacgtagtg gttagaaggt atgtgatata attaatcggc ccaaatagat tggtaagtag | 960 | |
| tagccgtcta tatcatccat actcatcata acttcaacct | 1000 | |

<210> SEQ ID NO 177
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0374

<400> SEQUENCE: 177

| | | |
|---|---|---|
| aagacacccg taaatgttgt catgtagaag aaactagaaa cgttaaacgc atcaaatcaa | 60 | |
| gaaattaaat tgaaggtaat ttttaacgcc gcctttcaaa tattcttcct aggagaggct | 120 | |
| acaagacgcg tatttctttc gaattctcca aaccattacc attttgatat ataataccga | 180 | |
| catgccgttg ataaagtttg tatgcaaatc gttcattggg tatgagcaaa tgccatccat | 240 | |
| tggttcttgt aattaaatgg tccaaaaata gtttgttccc actactagtt actaatttgt | 300 | |
| atcactctgc aaaataatca tgatataaac gtatgtgcta tttctaatta aaactcaaaa | 360 | |
| gtaatcaatg tacaatgcag agatgaccat aaaagaacat taaaacacta cttccactaa | 420 | |
| atctatgggg tgccttggca aggcaattga ataaggagaa tgcatcaaga tgatatagaa | 480 | |
| aatgctattc agtttataac attaatgttt ggcggaaaa ttttctatat attagacctt | 540 | |
| tctgtaaaaa aaaaaaatg atgtagaaaa tgctattatg tttcaaaaat ttcgcactag | 600 | |
| tataatacgg aacattgtag tttacactgc tcattaccat gaaaaccaag gcagtatata | 660 | |
| ccaacattaa taaactaaat cgcgatttct agcaccccca ttaattaatt ttactattat | 720 | |
| acattctctt tgcttctcga aataataaac ttctctatat cattctacat aataaataag | 780 | |
| aaagaaatcg acaagatcta aatttagatc tattcagctt tttcgcctga gaagccaaaa | 840 | |
| ttgtgaatag aagaaagcag tcgtcatctt cccacgtttg gacgaaataa aacataacaa | 900 | |
| taataaaata ataaatcaaa tatataaatc cctaatttgt ctttattact ccacaatttt | 960 | |
| ctatgtgtat atatataccc acctctctct tgtgtatttg | 1000 | |

<210> SEQ ID NO 178

<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter YP0377

<400> SEQUENCE: 178

| | | | | | |
|---|---|---|---|---|---|
| tataaaccat | tcctataaca | ccatatttaa | acataacaat | gaattgcttg | gatttcaaac | 60 |
| tttattaaat | ttggatttta | aattttaatt | tgattgaatt | atacccccctt | aattggataa | 120 |
| attcaaatat | gtcaactttt | tttttgtaag | atttttttat | ggaaaaaaaa | attgattatt | 180 |
| cactaaaaag | atgacaggtt | acttataatt | taatatatgt | aaaccctaaa | aagaagaaaa | 240 |
| tagtttctgt | tttcactttta | ggtcttatta | tctaaacttc | tttaagaaaa | tcgcaataaa | 300 |
| ttggtttgag | ttcaactttt | aaacacatta | atatttgtgt | gctatttaaa | aaataattta | 360 |
| caaaaaaaaa | aacaaattga | cagaaaatat | caggttttgt | aataagatat | ttcctgataa | 420 |
| atatttaggg | aatataacat | atcaaaagat | tcaaattctg | aaaatcaaga | atggtagaca | 480 |
| tgtgaaagtt | gtcatcaata | tggtccactt | ttctttgctc | tataacccaa | aattgaccct | 540 |
| gacagtcaac | ttgtacacgc | ggccaaacct | ttttataatc | atgctattta | tttccttcat | 600 |
| ttttattcta | tttgctatct | aactgattt | tcattaacat | gataccagaa | atgaatttag | 660 |
| atggattaat | tcttttccat | ccacgacatc | tggaaacact | tatctcctaa | ttaaccttac | 720 |
| ttttttttta | gtttgtgtgc | tccttcataa | aatctatatt | gtttaaaaca | aaggtcaata | 780 |
| aatataaata | tggataagta | taataaatct | ttattggata | tttcttttt | taaaaaagaa | 840 |
| ataaatcttt | tttggatatt | ttcgtggcag | catcataatg | agagactacg | tcgaaaccgc | 900 |
| tggcaaccac | ttttgccgcg | tttaatttct | ttctgaggct | tatataaata | gatcaaaggg | 960 |
| gaaagtgaga | tataatacag | acaaaacaag | agaaaaga | | | 998 |

<210> SEQ ID NO 179
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0380

<400> SEQUENCE: 179

| | | | | | |
|---|---|---|---|---|---|
| acaagtacca | ttcacttttt | tacttttcaa | tgtatacaat | catcatgtga | taaaaaaaaa | 60 |
| aatgtaacca | atcaacacac | tgagatacgg | ccaaaaaatg | gtaatacata | aatgtttgta | 120 |
| ggttttgtaa | tttaaatact | ttagttaagt | tatgatttta | ttattttttgc | ttatcactta | 180 |
| tacgaaatca | tcaatctatt | ggtatctctt | aatcccgctt | tttaatttcc | accgcacacg | 240 |
| caaatcagca | aatggttcca | gccacgtgca | tgtgaccaca | tattgtggtc | acagtactcg | 300 |
| tccttttttt | ttcttttgta | atcaataaat | ttcaatccta | aaacttcaca | cattgagcac | 360 |
| gtcggcaacg | ttagctccta | aatcataacg | agcaaaaaag | ttcaaattag | ggtatatgat | 420 |
| caattgatca | tcactacatg | tctacataat | taatatgtat | tcaaccggtc | ggtttgttga | 480 |
| tactcatagt | taagtatata | tgtgctaatt | agaattagga | tgaatcagtt | cttgcaaaca | 540 |
| actacggttt | catataatat | gggagtgtta | tgtacaaaat | gaaagaggat | ggatcattct | 600 |
| gagatgttat | gggctcccag | tcaatcatgt | tttgctcgca | tatgctatct | tttgagtctc | 660 |
| ttcctaaact | catagaataa | gcacgttggt | tttttccacc | gtcctcctcg | tgaacaaaag | 720 |
| tacaattaca | ttttagcaaa | ttgaaaataa | ccacgtggat | ggaccatatt | atatgtgatc | 780 |

```
atattgcttg tcgtcttcgt tttcttttaa atgtttacac cactacttcc tgacacgtgt    840
ccctattcac atcatcctg ttatatcgtt ttacttataa aggatcacga acaccaaaac    900
atcaatgtgt acgtcttttg cataagaaga aacagagagc attatcaatt attaacaatt    960
acacaagaca gcgagattgt aaaagagtaa gagagagag                           999
```

<210> SEQ ID NO 180
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0381

<400> SEQUENCE: 180

```
cacggtcaaa gtattgctaa catggtcatt acattgaaaa agaaaattaa ttgtctttac     60
tcatgtttat tctatacaaa taaaaatatt aaccaaccat cgcactaaca aaatagaaat    120
cttattctaa tcacttaatt gttgacaatt aaatcattga aaaatacact taaatgtcaa    180
atattcgttt tgcatacttt tcaatttaaa tacatttaaa gttcgacaag ttgcgtttac    240
tatcatagaa aactaaatct cctaccaaag cgaaatgaaa ctactaaagc gacaggcagg    300
ttacataacc taacaaatct ccacgtgtca attaccaaga gaaaaaaga gaagataagc    360 ggaacacgtg gtagcacaaa aaagataatg tgatttaaat taaaaaacaa aaacaaagac    420
acgtgacgac ctgacgctgc aacatcccac cttacaacgt aataaccact gaacataaga    480
cacgtgtacg atcttgtctt tgttttctcg atgaaaacca cgtgggtgct caaagtcctt    540
gggtcagagt cttccatgat tccacgtgtc gttaatgcac caaacaaggg tactttcggt    600
attttggctt ccgcaaatta gacaaaacag cttttttgttt gattgatttt tctcttctct    660
ttttccatct aaattctctt tgggctctta atttcttttt gagtgttcgt tcgagatttg    720
tcggagattt tttcggtaaa tgttgaaatt ttgtgggatt tttttttatt tctttattaa    780 acttttttt attgaattta taaaaaggga aggtcgtcat taatcgaaga aatggaatct    840
tccaaaattt gatattttgc tgttttcttg ggatttgaat tgctctttat catcaagaat    900
ctgttaaaat ttctaatcta aatctaagt tgagaaaaag agagatctct aatttaaccg    960
gaattaatat tctccgaccg aagttattat gttgcaggct                         1000
```

<210> SEQ ID NO 181
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0384

<400> SEQUENCE: 181

```
tttaaaaaat tggataaaac accgataaaa attcacattt gcaaattta ttcagtcgga     60 atatatattt gaaacaagtt ttgaaatcca ttggacgatt aaaattcatt gttgagagga    120
taaatatgga tttgttcatc tgaaccatgt cgttgattag tgattgacta ccatgaaaaa    180
tatgttatga aaagtataac aactttgat aaatcacatt tattaacaat aaatcaagac    240
aaaatatgtc aacaataata gtagtagaag atattaattc aaattcatcc gtaacaacaa    300
aaaatcatac cacaattaag tgtacagaaa aaccttttgg atatatttat tgtcgctttt    360
caatgatttt cgtgaaaagg atatatttgt gtaaaataag aaggatcttg acgggtgtaa    420
```

```
aaacatgcac aattcttaat ttagaccaat cagaagacaa cacgaacact tctttattat      480
aagctattaa acaaaatctt gcctattttg cttagaataa tatgaagagt gactcatcag      540
ggagtggaaa atatctcagg atttgctttt agctctaaca tgtcaaacta tctagatgcc      600
aacaacacaa agtgcaaatt cttttaatat gaaaacaaca ataatatttc taatagaaaa      660
ttaaaaaggg aaataaaata ttttttttaaa atatacaaaa gaagaaggaa tccatcatca    720
aagttttata aaattgtaat ataatacaaa cttgtttgct tccttgtctc tccctctgtc      780
tctctcatct ctcctatctt ctccatatat acttcatctt cacacccaaa actccacaca      840
aaatatctct ccctctatct gcaaattttc caaagttgca tcctttcaat ttccactcct      900
ctctaatata attcacattt tcccactatt gctgattcat tttttttttgt gaattatttc    960 aaacccacat aaaaaaatct ttgtttaaat ttaaaacca                              999
```

```
<210> SEQ ID NO 182
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter YP0385

<400> SEQUENCE: 182
actcaacaat aggacaagcc aaaaaaattc caattattgt gttactctat tcttctaaat       60
ttgaacacta atagactatg acatatgagt atataatgtg aagtcttaag atattttcat     120
gtgggagatg aataggccaa gttggagtct gcaaacaaga agctcttgag ccacgacata     180
agccaagttg atgaccgtaa ttaatgaaac taatgtgtg tggttatata ttagggaccc      240
atggccatat acacaatttt tgtttctgtc gatagcatgc gtttatatat atttctaaaa     300
aaactaacat atttactgga tttgagttcg aatattgaca ctaatataaa ctacgtacca     360
aactacatat gtttatctat atttgattga tcgaagaatt ctgaactgtt ttagaaaatt     420
tcaatacact taacttcatc ttacaacggt aaaagaaatc accactagac aaacaatgcc     480
tcataatgtc tcgaaccctc aaactcaaga gtatacattt tactagatta gagaatttga     540
tatcctcaag ttgccaaaga attggaagct tttgttacca aacttagaaa cagaagaagc     600
cacaaaaaaa gacaagggga gttaaagatt gaagtgatgc atttgtctaa gtgtgaaagg     660
tctcaagtct caactttgaa ccataataac attactcaca ctcccttttt tttcttttt      720 ttttcccaaa gtaccttttt taattccctc tataacccac tcactccatt ccctcttct      780 gtcactgatt caacacgtgg ccacactgat gggatccacc tttcctctta cccacctccc     840
ggtttatata aacccttcac aacacttcat cgctctcaaa ccaactctct cttctctctt     900
ctctcctctc ttctacaaga agaaaaaaaa cagagccttt acacatctca aaatcgaact     960
tactttaacc accaaatact gattgaacac acttgaaa                              998
```

```
<210> SEQ ID NO 183
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0396

<400> SEQUENCE: 183
catagtaaaa gtgaatttaa tcatactaag taaaataaga taaaacatgt tatttgaatt       60
tgaatatcgt gggatgcgta tttcggtatt tgattaaagg tctggaaacc ggagctccta     120
```

```
taacccgaat aaaaatgcat aacatgttct tccccaacga ggcgagcggg tcagggcact        180
agggtcattg caggcagctc ataaagtcat gatcatctag gagatcaaat tgtatgtcgg        240
ccttctcaaa attacctcta agaatctcaa acccaatcat agaacctcta aaaagacaaa        300
gtcgtcgctt tagaatgggt tcggttttttg gaaccatatt tcacgtcaat ttaatgttta        360
gtataatttc tgaacaacag aattttggat ttatttgcac gtatacaaat atctaattaa        420
taaggacgac tcgtgactat ccttacatta agtttcactg tcgaaataac atagtacaat        480
acttgtcgtt aatttccacg tctcaagtct ataccgtcat ttacggagaa agaacatctc        540
tgtttttcat ccaaactact attctcactt tgtctatata tttaaaatta agtaaaaaag        600
actcaatagt ccaataaaat gatgaccaaa tgagaagatg gttttgtgcc agattttagg        660
aaaagtgagt caaggtttca catctcaaat ttgactgcat aatcttcgcc attaacaacg        720
gcattatata tgtcaagcca attttccatg ttgcgtactt ttctattgag gtgaaaatat        780
gggtttgttg attaatcaaa gagtttgcct aactaatata actacgactt tttcagtgac        840
cattccatgt aaactctgct tagtgtttca tttgtcaaca atattgtcgt tactcattaa        900
atcaaggaaa aatatacaat tgtataattt tcttatattt taaaattaat tttgatgtat        960 tacccctttta taaataggct atcgctacaa caccaataac                           1000
```

<210> SEQ ID NO 184
<211> LENGTH: 1514
<212> TYPE: DNA
<213> ORGANISM: Arabidopsis thaliana
<220> FEATURE:
<221> NAME/KEY: misc_feature
<223> OTHER INFORMATION: Ceres Promoter p13879

<400> SEQUENCE: 184

```
tttcgatcct cttctttttt aggtttcttg atttgatgat cgccgccagt agagccgtcg         60
tcggaagttt cagagattaa aaccatcacc gtgtgagttg gtagcgaatt aacgaaaagt        120
ctaagtcaag attttttaaa aagaaattta tgtgtgaaaa gaagccgttg tgtatattta        180
tataatttag aaaatgtttc atcatttttaa ttaaaaaatt aataatttgt agaagaaga        240 agcattttttt atacataaat catttacctt ctttactgtg ttttttcttca cttacttcat        300 ttttactttt ttacaaaaaa gtgaaaagta aattacgtaa ttggtaacat aaattcactt        360
taaatttgca tatgttttgt tttcttcgga aactatatcg aaaagcaaac ggaaagaact        420
tcacaaaaaa ccctagctaa ctaaagacgc atgtgttctt cttattcttc atatatcctc        480
tgtttcttgt gttctgtttt gagtcttaca ttttcaatat ctgactctga ttactatatc        540
taaaagggaa catgaagaac ttgagaccat gttaaactgt acaatgcctt caaacatggc        600
taactaaaga tacattagat ggctttacag tgtgtaatgc ttattatctt taggtttttt        660
aaatcccttg tattaagtta tttaccaaat tatgttcttg tactgcttat tggcttggtt        720
gttgtgtgct ttgtaaacaa cacctttggc tttatttcat cctttgtaaa cctactggtc        780
tttgttcagc tcctcttgga agtgagtttg tatgcctgga acgggtttta atggagtgtt        840
tatcgacaaa aaaaaatgt agcttttgaa atcacagaga gtagttttat attcaaatta        900
catgcatgca actaagtagc aacaaagttg atatggccga gttggtctaa ggcgccagat        960
taaggttctg gtccgaaagg gcgtgggttc aaatccccact gtcaacattc tcttttttctc       1020 aaattaatat ttttctgcct caatggttca ggcccaatta tactagacta ctatcgcgac       1080
taaaataggg actagccgaa ttgatccggc ccagtatcag ttgtgtatca ccacgttatt       1140
```

```
tcaaatttca aactaaggga taaagatgtc atttgacata tgagatattt ttttgctcca   1200
ctgagatatt tttctttgtc ccaagataaa atatcttttc tcgcatcgtc gtctttccat   1260
ttgcgcatta aaccaaaaag tgtcacgtga tatgtcccca accactacga attttaacta   1320
cagatttaac catggttaaa ccagaattca cgtaaaccct ctctaaacct agaaaatatc   1380
taaaccttgg ttaatatctc agcccccttaa taaatgcga gacttcgtct acatcgttct   1440
acacatctca ctgctcacta ctctcactgt aatcccttag atcttctttt caaatttcac   1500
cattgcactg gatg                                                      1514
```

<210> SEQ ID NO 185
<211> LENGTH: 1954
<212> TYPE: DNA
<213> ORGANISM: Arabidopsis thaliana
<220> FEATURE:
<221> NAME/KEY: misc_feature
<223> OTHER INFORMATION: Ceres Promoter p326

<400> SEQUENCE: 185

```
gtgggtaaaa gtatccttct ttgtgcattt ggtattttta agcatgtaat aagaaaaacc     60
aaaatagacg gctggtattt aataaaagga gactaatgta tgtatagtat atgatttgtg    120
tggaatataa taaagttgta aaatatagat gtgaagcgag tatctatctt ttgactttca    180
aaggtgatcg atcgtgttct ttgtgatagt tttggtcgtc ggtctacaag tcaacaacca    240
ccttgaagtt ttcgcgtctc ggtttcctct tcgcatctgg tatccaatag catacatata    300
ccagtgcgga aaatggcgaa gactagtggg cttgaaccat aaggtttggc cccaatacgg    360
attccaaaca acaagcctag cgcagtcttt tgggatgcat aagactaaac tgtcgcagtg    420
atagacgtaa gatatatcga cttgattgga atcgtctaag ctaataagtt taccttgacc    480
gtttatagtt gcgtcaacgt ccttatggag attgatgccc atcaaataaa cctgaaaatc    540
catcaccatg accaccataa actcccttgc tgccgctgct ttggcttgag caaggtgttt    600
ccttgtaaag ctccgatctt tggataaagt gttccacttt ttgcaagtag ctctgacccc    660
tctcagagat gtcaccggaa tcttagacag aacctcctct gccaaatcac ttggaagatc    720
ggacaatgtc atcatttttg caggtaattt ctccttcgtt gctgctttgg cttgagcacg    780
gtgcttcttt gtaaagctcc gatctttgga taagagcgga tcggaatcct ctaggaggtg    840
ccagtccctt gacctattaa tttatagaag gttttagtgt attttgttcc aatttcttct    900
ctaacttaac aaataacaac tgcctcatag tcatgggctt caaattttat cgcttggtgt    960
atttcgttat ttgcaaggcc ttggcccatt ttgagcccaa taactaaatc tagccttttc   1020
agaccggaca tgaacttcgc atattggcgt aactgtgcag ttttaccttt ttcggatcag   1080
acaagatcag atttagacca cccaacaata gtcagtcata tttgacaacc taagctagcc   1140
gacactacta aaaagcaaac aaaagaagaa ttctatgttg tcattttacc ggtggcaagt   1200
ggacccttct ataaagagt aaagagacag cctgtgtgtg tataatctct aattatgttc   1260
accgacacaa tcacacaaac ccttctctaa tcacacaact tcttcatgat ttacgacatt   1320
aattatcatt aactctttaa attcacttta catgctcaaa aatatctaat ttgcagcatt   1380
aatttgagta ccgataacta ttattataat cgtcgtgatt cgcaatcttc ttcattagat   1440
gctgtcaagt tgtactcgca cgcggtggtc cagtgaagca atccaacgg tttaaaacct   1500 tcttacattt ctagatctaa tctgaaccgt cagatatcta gatctcattg tctgaacaca   1560
gttagatgaa actgggaatg aatctggacg aaattacgat cttacaccaa cccctcgac   1620
```

-continued

```
gagctcgtat atataaagct tatacgctcc tccttcacct tcgtactact actaccacca   1680
catttcttta gctcaaccttt cattactaat ctccttttaa ggtatgttca cttttcttcg   1740
attcatactt tctcaagatt cctgcatttc tgtagaattt gaaccaagtg tcgattttg    1800 tttgagagaa gtgttgattt atagatctgg ttattgaatc tagattccaa tttttaattg   1860
attcgagttt gttatgtgtg tttatactac ttctcattga tcttgtttga tttctctgct   1920
ctgtattagg tttctttcgt gaatcagatc ggaa                                1954
```

<210> SEQ ID NO 186
<211> LENGTH: 2016
<212> TYPE: DNA
<213> ORGANISM: Arabidopsis thaliana
<220> FEATURE:
<221> NAME/KEY: misc_feature
<223> OTHER INFORMATION: Ceres Promoter p32449

<400> SEQUENCE: 186

```
gatcggcctt cttcaggtct tctctgtagc tctgttactt ctatcacagt tatcgggtat     60
ttgagaaaaa agagttagct aaaatgaatt tctccatata atcatggttt actacaggtt   120
tacttgattc gcgttagctt tatctgcatc caaagttttt tccatgatgt tatgtcatat   180
gtgataccgt tactatgttt ataactttat acagtctggt tcactggagt ttctgtgatt   240
atgttgagta catactcatt catcctttgg taactctcaa gttaggttg tttgaattgc    300 ctctgttgtg atacttattg tctattgcat caatcttcta atgcaccacc ctagactatt   360
tgaacaaaga gctgtttcat tcttaaacct ctgtgtctcc ttgctaaatg gtcatgcttt   420
aatgtcttca cctgtctttc tcttctatag atatgtagtc ttgctagata gttagttcta   480
cagctctctt ttgtagtctt gttagagagt tagttgagat attacctctt aaaagtatcc   540
ttgaacgctt tccggttatg accaatttgt tgtagctcct tgtaagtaga acttactggg   600
accagcgaga cagtttatgt gaatgttcat gcttaagtgt cgaacgtatc tatctctact   660
atagctctgt agtcttgtta gacagttagt tttatatctc catttttttg tagtcttgct   720
agttgagata ttacctcttc tcttcaaagt atccttgaac gctcaccggt tatgaaatct   780
ctacactata gctctgtagt cttgctagat agttagttct ttagctctct ttttgtagcc   840 tagttctttta gctctccttt tgtagccttg ctacagagta agatgggata ttacctcctt   900
gaacgctctc cggttatgac caatttgttg tagctccttg taagtagaac ttaggataga   960
gtgagtcaac tttaagaaag aacctagtat gtggcataac cagattgcag gctctgtctc  1020
ggctacagta acgtaactct atagctcttt gttttgttca gaaagaacca gtgattggat  1080
gattcgtcct tagaaactgg acctaacaac agtcattggc tttgaaatca agccacaaca  1140
atgcctatat gaaccgtcca tttcatttat ccgtttcaaa ccagcccatt acatttcgtc  1200
ccattgataa ccaaaagcgg ttcaatcaga ttatgttttta atttaccaa attctttatg   1260 aagtttaaat tatactcaca ttaaaaggat tattggataa tgtaaaaatt ctgaacaatt   1320
actgattttg gaaaattaac aaatattctt tgaaatagaa gaaaaagcct ttttccttt    1380 gacaacaaca tataaaatca tactcccatt aaaaagattt taatgtaaaa ttctgaatat   1440
aagatatttt ttacaacaac aaccaaaaat atttattttt ttcctttttt acagcaacaa   1500
gaaggaaaaa cttttttttt tgtcaagaaa aggggagatt atgtaaacag ataaaacagg   1560
gaaaataact aaccgaactc tcttaattaa catcttcaaa taaggaaaat tatgatccgc   1620
atatttagga agatcaatgc attaaaacaa cttgcacgtg gaaagagaga ctatacgctc   1680
```

```
cacacaagtt gcactaatgg tacctctcac aaaccaatca aaatactgaa taatgccaac    1740
gtgtacaaat tagggtttta cctcacaacc atcgaacatt ctcgaaacat tttaaacagc    1800
ctggcgccat agatctaaac tctcatcgac caatttttga ccgtccgatg gaaactctag    1860
cctcaaccca aaactctata taagaaatc ttttccttcg ttattgctta ccaaatacaa     1920
accctagccg ccttattcgt cttcttcgtt ctctagtttt ttcctcagtc tctgttctta    1980
gatcccttgt agtttccaaa tcttccgata aggcct                              2016

<210> SEQ ID NO 187
<211> LENGTH: 667
<212> TYPE: DNA
<213> ORGANISM: Arabidopsis thaliana
<220> FEATURE:
<221> NAME/KEY: misc_feature
<223> OTHER INFORMATION: Ceres Promoter PD1367

<400> SEQUENCE: 187
acagttttct tttctcatct tacaacaagt ttccaggagg atagagacat aaacgaagct      60
cggattgtat cgttcttttt agcttttatt cacatccgaa agtcctgtag tttagattct     120
gttatcttgc ggttttgagt taatcagaaa cagagtaatc aatgtaatgt tgcaggctag     180
atctttcatc tttggaaatt tgttttttc tcatgcaatt tctttagctt gaccatgagt      240
gactaaaaga tcaatcagta gcaatgattt gatttggcta agacattt gtccacttgg      300 catcttgatt tggatggtta caacttgcaa gacccaattg gatacttgct atgacaactc     360
caactcaaga gtgtcgtgta actaagaacc ttgactaatt tgtaatttca atcccaagtc     420
atgttactat atgtttttt gtttgtatta tttctctcc tacaattaag ctctttgacg      480
tacgtaatct ccggaaccaa ctcctatatc caccattac tccacgttgt ctccaattat     540
tggacgttga aacttgacac aacgtaaacg tatctacgtg gttgattgta tgtacatatg     600
tacaaacgta caccttctc ctctttcact tcatcacttg gcttgtgaat tcattaattc     660
ctgcgaa                                                              667

<210> SEQ ID NO 188
<211> LENGTH: 1836
<212> TYPE: DNA
<213> ORGANISM: Oryza sativa
<220> FEATURE:
<221> NAME/KEY: misc_feature
<223> OTHER INFORMATION: Ceres Promoter p530c10

<400> SEQUENCE: 188
gcctctcgac cacgagttta gcacttgtgc aacatatatg cgtgcgatga acatctactg      60
atgcgccatg cgaattttag cgttcgttca tgacgcttcc aacggcacag aggctgagca    120
gcagcatgca tgcatggctc ttgtgaaaac aaaaaaggtt actggtaaat gacatgctgc    180
tgtagctagc tagcagaatg caaggcccat gcatatgcaa tgctatgcga caagtacagt    240
accagcatgt atggtagcca gctaactaat ctatcagcag aggcagcaag ctcgtgcatg    300
gtgtgatgca cttctctcca gtaatctagt ggtaattttc acccaaagcg ttgctcatat    360
ggacagtaat tagtaatatt accaaggttc acaatcccgt tacctgacca aatactactc    420
acgaatggta tctctggttt tcgttaaaac cgttggtaaa ccagcaaaaa tagacaaaat    480
ttgtcaaaat tttaaatttt agttttttt ttttaactta gccgggaaac cttgaagttt     540
gtgctgtcga gctgtcctgg gaaggacggt tttggttggg attgtgaacc ctggttactg    600
```

```
cacttcattt ttgaacagat attagtgcaa cagacaaatg ccaacgcatt tttttctgtt      660
taccggcaag ctgaagcttt tacgatcccc atacagccgt tgctgcaaac ctgccaagaa      720
agagcagcag aaacaggtgt cattttgtgg tggaaagcca agtaaagtaa acagaagatg      780
gaagatagtg aggaccaggg agtgaggcag gggacacatg gcccacgcct ccctgcacat      840
tttcgtgtat aaatacaggt ggatgcatcg ctctcccagc atccatcggt tctctgctct      900
gttcatccat agagtttcct cctcttctcc tttagtgcaa ggtagagaag agcatgtgtg      960
tgtgtgtgtg tgtgtgaact gtgaagtgca gagtgcttct gtagttctgt gttatgtcca     1020
tagtgatctt gttaggattg ttgctatgga tgcatgatgt tatggttgat ctctgaatta     1080
cagtagggac ttttctgaga tctctggatt agtgggggt gctaaatttt tttctggttg      1140
catcagcttg ggtttctggt attggtgtgg gttcttgctc tgaattttgg ttcagaatgt     1200
cgatttgttt gtgtttgttc tctgaagttg agagtagcta tgatccatcc agcacagaac     1260
tgcaggtcct gcctgccggc tgcatatcaa ggacatgcca ttttgcaagc tctgggctta     1320
tggtttctct tttggagttc ttcttcttgc atgatctgtg ttctctaaca aaggaagcaa     1380
gatttagcaa cttttattcag agacaagaaa aggatctggc aaccttttgt ttctgttta     1440 tcctactcgt aaagattgtt atttaagcaa aaatttccca aaagttttaa atataatttc     1500
catgatgtgc cactctcatg tccttgaacc tggcactcat tatgggctcc tcagaagtgc     1560
tgtagctaat gtcactaatc ttttgtatct ttgttcatag tcttgtattt tatgatgctt     1620
atccctttgt gctttccatg tttgatgtcc aaatgtcatg gcaatgtttt tgacttctag     1680
taggggtttt agtacctttt tgttagataa gtacatccaa attctgttta tttattcaaa     1740
aatcattctg tttattcact gaaaacattt gtccattcaa tggactcata aactgtctgt     1800 gttttttcagg cttgaggatc catctagaag atagca                              1836
```

<210> SEQ ID NO 189
<211> LENGTH: 3000
<212> TYPE: DNA
<213> ORGANISM: Oryza sativa
<220> FEATURE:
<221> NAME/KEY: misc_feature
<223> OTHER INFORMATION: Ceres Promoter pOsFIE2-2

<400> SEQUENCE: 189

```
gcttaacaca tgaactacca aaatatactg atcactttgt tctagtcata catacctaa       60 gtcattttat tctgcagtgt ttggattgga gggagcattc tagcatccct tgggtcgttc      120
cagcaaatgt ggttctccaa agcagagtaa gcacaacaca gtattttagg ttatgtttcc      180
cctatctcgt cacggacagc tcacaagtta atgtgattta tctcactata gatacgaaga      240
acatggagta tcctacatcc aaaggaagtg cccatgaagt tgtggagcat cgctacgatt      300
tgtgaccaaa tttgggtgca tgtgggcaat cgtattacag ccaccctgtt gttgatctat      360
atcgactatt atccgacgat atttatcatt atattatgac tagttagttt gtagattttg      420
agagggcaac ataagaagca atccagctta acctgttatg ttcttgatgg tagattctag      480
ttcatgtgtt gaatctgttc tccctgctgt agaatgtatc gagttgctgc tctctactct      540
gtacttttag aataccttt caatcatttg gagtcagctg attgttgtac tacttatacg       600
ccacctgatt agtcatgtca acaattaaac ttgagcactg gttaagttaa gagtggcctg      660
attgtagttg ataatcacat tttattcgta gacattgtat gctggatctt tatcagccac      720
cgtcagatca tcctctgtaa taaatcttca tcagacgtgt gtgccaatcg caaggaacac      780
```

```
gaaatgcatc cgaaatgtta ctctgagtta atcaatacta taattcttgg tcaaattaat      840
tatttatatc tataaagttt aaattaaatt taggaaaatg aattcatgca aatcttgtgg      900
taagttgtca atttcataaa aaatccagct tactactccc tttttaggag tgtgttgtgg      960
ctgcacactt ctgccttttg atatatacgg ttctattctc ggtgtactcc tttattatta     1020
ttaaaacaat cccagttact tggtaagtgc taatcacgaa tcaaagtcaa cataacaaat     1080
catgtgcgta cagctataac tcgattacac aaacaacaaa attcatattt gaacataaat     1140
ccagttgtag catatctggt agtataaagt tttttttttg tatagaagag ttttaatttc     1200
tgtaagtttt ggaaagcatt taatcctaga aattgtagtg tagctcaact aaaaaataaa     1260
tgaacttgaa tcgaaattgg gttgtatcat aaatctttac cactcaaacg aatatttatc     1320
ctaaaccaca aatgactctt ttcatcaagg aatgttttgt tttcagcatt ttaaaaaaaa     1380
acttttctaa tatggttttc atgtttcgtt cttttgaaat ttaacatcta tttaatttgc     1440
acggctccat aaattcaacg gatacatatt ctgaataatt actaaggagg catatatcgg     1500
ctctcttaat acaaccgctt gtttctcaaa atttattttg agttttgtct acacattctc     1560
aaggacggta caaacacact atagatgttc acaatttttt ttttctaaag ttgattgatg     1620
gacaaatgtt tgaacatata aacatataag cactgaatat ttgcttatgc aggaggtatt     1680
tatatcaagt tcgatacttt actaccatag tccctaggac actaaaatgc cttcaatgat     1740
ctgatgaagc ctaagagaga atattgatca gtggagcgac ttgcaactac acatggcaca     1800
agtagactag acacggtata tattcatatt aacttgttaa aattttacta cttaacagtt     1860
cacttgtggt gcatccatat caattcttac ttacacaata tttgtaaaaa caacctaaca     1920
ctataggatg acctagacaa cctttatgtc aatcacactt agaagatgat cgtcttttta     1980
ataaataatg tgtactacac accatgctct ccatatagat caagatctac aaacccttcc     2040
acttataaac cttaccacca aaaactcatt aagttgcttc atttatctat gctattaaga     2100
aaaaaactta tttcgtttat gccatttcta gaaatggcta gtcacactat tcacaatatt     2160
atataataaa taaagtttc aaatattcat ccaccaaaaa tcatcaagtc gtgggactta     2220
tatgttaatt agagaagtcc ctttgggtgc aatcgatttt ggaaaccta aattttttct     2280 atacatagaa gagagagatg tctagttgca attgcttttg cgatgtgcca accacccttc     2340
tagctttcat ccacgtctac ttaattgcca ttcttcttct tctttttctt cactattact     2400
acctcctatc ttagcgaatc ttcttcttct tcactattac tacctcccac cttagtgaat     2460
tcatcctcat tgttcacaat gacattgcta agttaactag gtatgctaag tacacaatta     2520
gaatataacc tagagccttt gtttccatca tacttaaaag atgacatttt tatatagata     2580
aagtgtgcta ctcacaaggc ttactatata tatgtatgat acacacaaac tccacaaccc     2640
aaaactcttt caagttgtgt ggcccatcta tgctattaaa aagcccattt agcccatcca     2700
acatgagaaa ccctagggtt ttttccctat aaaagatacc taggttattg ttgcttttcc     2760
accccgcccg ccgccgctcc ctattcctat ttaatcccat ctctcttcct catcaccgct     2820
ctcctctctc caggcaagag gtacgcactt tttgtttcgg atttgaaatc tttgcttcgt     2880
tttactatca ttggtcataa gttctttttt gaagatgttt gagaataagt ttatcattga     2940
gattatcgtc acttgtgata ggaagtacgc aacctcaagc cggacaagac gtgagcaaag     3000
```

<210> SEQ ID NO 190
<211> LENGTH: 2023
<212> TYPE: DNA
<213> ORGANISM: Oryza sativa
<220> FEATURE:
<221> NAME/KEY: misc_feature
<223> OTHER INFORMATION: Ceres Promoter pOsMEA

<400> SEQUENCE: 190

```
gagagcagaa catagtagcc gctgttttct gggggtgcaa tttgtgcaag atcgctatcc      60
ttatggacca tgcaagcacc aagcaatatt aagccaggtc caacagcggt cttggggaat     120
tcagaaatga gcttaaaaac ctccttgagc tggccagctc agccaaggag gtccatcatg     180
catgtgcatg ctcaatactt ggaattattg caaaatgatc ggtcattgac tggaagactt     240
tgcgccttc ctcagccaac cttatgtggc tgcatgcata gagtaccaac aggaaggtag      300
cgtttgttgg aataaggttt gcatccagca tgtccttgta gagcttcaaa gcctcagcac     360
cttggcccat gaaggccata tccagctaat tgcattccat gagaccacat tcttgctatc     420
catactgttg aagtgaagat gctccgagct tcggaaatgc ttccacacta tgcatacatg     480
tcaatgagca ctgtcatgac ataaacattg gccccaagt cctcctcagc gataatccta      540
tgcagccact ttcccaggga caaagctcca agctgtgcac acgctgaaag agagctagaa     600
atgatgattg gatttggtca cacgctaagt accagcattt gctcaaagag gcaattgcc      660
atctccgtcc agccattcta ggcatacct ggtattattg cttccatga ttccgattcc       720
gtggtcttct atggcatcgc attgaaggcc ttccttgcag actccatatc atttaaccta     780
cagtacaata tggtaattgc tgtcgacact ggagaattcg cagtaaatcc agacttgaga     840
ggaccatgta agcattgatc aagcagttca ttcccaaaca gactatacgg gatcagtgcc     900
agtgctcgag tttggcttca attccaaggc catcaaccca ataaacagat taactgatga     960
accaaccatg caattcgccg agcaaacata gattaagcat tgtaggcaac caaatctgga    1020
ttctccatca agtcaaagag acgccatgca gaattccaca tccccgctgt atacaccgag    1080
atcaaccggt cagaacatgc tcatactccg ccaaccctct cttcagaaca tgctcatact    1140
ccgccaaccc tctcttctct gcaagaggca tcctccccaa ttccccattg ttatatctgt    1200
tgctggtaag accgttgcca gcgtggttgt gtcagaccga acagactctg cactcgccat    1260
cctcacgaac gactccaggg cctccgaacc aggaagcccg gccggccatc agcgtgttcc    1320
acataacggt atccggcgac tgcacagtgt cgaacacctt gcgtgcgtgg tcacctctgg    1380
acagcatgaa gcgtacaggc tacagcttgg ccaatgcgga cgccacgaac gtgtcggcgg    1440
cgtaacccgc gcgtgcagcg cgccgcgcgc gggctgcgga gtcggttgga gacgacacgc    1500
cgccgccatg agagcaatga gcgaggtggc ggcgaaggcg aaggagaagt agtcgaggca    1560
agcggaagag aaggcggcag cggagaaagc gatcggggcg gcggaggagg tgggtgggag    1620
ggagggacgc gtagcggagg tcggaggagg agggagctga ggtttccggg gcggggtcg     1680
agagggtagt gtacggaggc gagggacacg gcgaggatct ggtcgaggta gcgcagtgtg    1740
aaggaaagcg cgatgaggcg gagggcgccg gcgaagagcg gcgcggcgga tagcgggagg    1800
aggcggcgcc ggcggggtct catccgattg gaaacagatt gggaaggggg aggggtagg     1860
aatacgtggc gtcggcagta ttaggtagag agagaaaccc tttccatcct tgtctcttta    1920
gccccgaagg agagagaaaa atcagaaaaa aaaaaccctc cgcgtgtggg ggaagcagag    1980
ctccggacgc tggcgccgct cgcgccaccg cacccgcacc gcc                       2023
```

<210> SEQ ID NO 191
<211> LENGTH: 2034
<212> TYPE: DNA
<213> ORGANISM: Oryza sativa
<220> FEATURE:
<221> NAME/KEY: misc_feature
<223> OTHER INFORMATION: Ceres Promoter pOsYp102

<400> SEQUENCE: 191

```
gaacgaccca aacgcgtaaa tggtggtact ggtttccctg ctttgccgag taccagcagc        60
cacgaagaac gttacacaat cgagtacaaa atctataaga gcaagtttaa tagcatagcc       120
aaatactacc tctaaatcat ctatagccaa tttaatagtt catttattca ataattactt       180
ataaacatat actacaatca ttaatatatg gtcttacttc ttatacacat aatattttgg       240
agtccgtgtt acagctggct ataaatataa gggattttgg ttggatgtgg tacatccctat      300
tataatgaat ctagacatga aacctgtcca aattcatcgt gctaggatac gccacatcta       360
accaaaatct cttatcttta gggatggaga gagtaataat taaatgaagc taggtagagt       420
ttcccggtca atacgcttgc gtgtgcttat aagagcatgg ccaacagttt cccgatactc       480
ttcccaatat cagttttgag gagttttgtt ggaaaaaatc gctccaacag tagacctaaa       540
tcaccccctaa aagcttggcg tttccaaacc cgcatatttc gttctccact tgtagggaag     600
agactcggcg cccaatcctt caaccgcatg cacttcgcgc gcgctgtgtg aaaattttcc       660
taccaggttc ttctttgtgc gttcgtctac ctgtgagtca atccatcacg ccagcagcct       720
catcttcccc gcagctgtct gggaaagcag ccatggctcc cccaagcttc cccagcgtcg       780
acattttttt ctcagcggca gcgccagacc catctccaac ccaattgggc ggaccttcgt       840
cggcgctccc ccagcaccac caccgactcg aatcggccgt cgcccctatt catctccaat       900
cgtccctcga ccctaccgca tcctgcagca cagcctgtct ctcgcgtcag actggcgctg      960
cgctccccc ggtaatgtgc aggcgacaaa ggcccatgc gatgcgacca gcagccggcg       1020
acaaccggag gtgcccagtc gctggccttc atcgaatcat cgtgcacctc ggtcggagtc     1080
gatttctgat tgttgctgct gctcaaatct ggagcttgct attgctgaga actgcttggt    1140
ggtggtactg gaaatttgtt gtttgctggc tgatgaaaac tgttgttctt tgctgctaaa    1200
aactgctgct tgctagtact gaaaagtact attgcagctg ctgaaatatc ttgctgcttg    1260
ctgctgaaaa cttcaagttg ttaacaccgt tcacactaaa aaagctgaaa ttttttttct     1320
gggctgaaaa ccccattgtt gatgattgca gaaccaatat ttttccatgt aaaatacagg    1380
agatcgtggt aataatcaag tgaaatatca ttttggggca aatactcaga tcgtacctga    1440
agccaatgga acattgttc aatgcttaaa ctgtcagtta tgatgtcaaa gagattgatc     1500
actgaatgtc ctgaaaggag ccgtgaggag gatgcagcat tgcagcgtgc gcgagcgtga    1560
gtggaggaga ggaatgacga ttctgttggt agttgtcgat gtggcctact ttttttgttt    1620
tgaggattaa attttgggaa tctcttggag ataaaaggta ttctcatacc ttaaatcctt    1680
tttagagatc taaaaaaaat gatttagggg attgaatttt gggtggctgt tggtgatgct   1740
ctaagttgca catcctgggg aaaaacctcc ctaatccatc agcaaaccga tcaaccaccc    1800
acgacaagtc gacgccaccg ttttttttt ctccctcta agtcctaacc ccacaaaaat     1860
cccgcgaact ttcgtctcac cacgcgccgc gtgcccccta caaataccaa acaacaccca    1920
ccacgtccac tcacaaacca cgcaggaaac ctcagaaaat caccgtacgc gacgcgggcc    1980
caagaaaacc ccgacagaaa ccgcgcagca gcaacaccac caccggcgtc ggag          2034
```

<210> SEQ ID NO 192
<211> LENGTH: 1877
<212> TYPE: DNA
<213> ORGANISM: Oryza sativa
<220> FEATURE:
<221> NAME/KEY: misc_feature
<223> OTHER INFORMATION: Ceres Promoter pOsYp285

<400> SEQUENCE: 192

```
ggcccgagtt aaacgatctt ccacgtgtca gcgaatccta gtcgttcgat gaatctgaat      60
ctgacttgtg gtggttggac ggccacgtgt taaaaaaggg aaacgtccgc atcacccgat     120
gctgggacat ttgcaatttc gatccagctg tagattgacc agttgttact ctcttttttt     180
taacaccata caaacgtaat actccctctg tcccaaaata taagtatttt ttttaacctc     240
ggttcagtct tcgaggtgct actttgacca ataatattta taaaaataag atgttttaaa     300
taaagagagt tgcatattat gatagctcgt ttaatgataa acaaagtacc atcaaattta     360
catgattaat cttttttaatt tatttgctat taatagttaa aatttaaaaa gtttgacttc     420
acactgttct aaaaatactt atattttggg acggagggag tacacattag agcaggtaca     480
atagcagact agtagccagc tataaacata ttttaatgag ataaagatg agagagaaca     540
gcgggctaca gatctgtagc cagctgcagc acggactcca agacattgtg tgtgtatgac     600
aggtgggacc atatattaat agtacagtaa gtaactattg tatgaattgg ctattagatt     660
agctataggt gaattgtagc tagtagtggg ctatactatt gaacttactc ttatatctct     720
caatatctcc agaaaactag gacgatatat attgatatta acaaagtcat catagatatc     780
tcgctatcga catatatatt acctatcact gaaaaaataa ttaatcataa atgcaagcac     840
atatactacg ttcaacactg aatgtaggta gattggtaga cgggttccac cgcaagaaaa     900
gcattgcacc agtgaagaaa gaaacatcgg aatttgtatg tagtttgttg tttgatgaat     960
tcttttgatt aaaaaaaact aaaatcagag ttgattcagt taatggtgtt gcctacgata    1020
tacttccata tcatgatatc actgtagact atgaatcata tctttaatta aaactaaatc    1080
aagaaattaa gtatgagacc tcaactcaat gaagaatttc tagttgaaaa acattcctag    1140
tgtgcgttcg gatggaggta gggatcttct ctccgttcat ataaaaccgg atggttcatt    1200
agaacatgat taattaagca acagttaatc taaaaataaa ttaatatttt ttaagaaatt    1260
tttgtataga gatcttttga aaaaaataca ttggttagaa agcatactaa taaaagaga    1320
aaaataagaa catagtacta tagtagaaaa tgagaacttg gagtatttga gaggatggga    1380
aataagaaga ttaagaagat gcgtaaagtg aacggttaac gcatgattga ttaattaaat    1440
attaattatt ttaaatttgg aaaataaatt agtatgattt ttaagcaaca tatatatata    1500
tatatatata tatatagaaa aacatagttt tagaaaatat aagcgtgtaa aacgatatgc    1560
aggaacgaaa cgttgagcat tcaaaatttc aaattgaaca tatgaatcaa gagagaataa    1620
aaaaagaggc cttctaggct ggcatggaca attggacatg ttttcaacta gggtttcaag    1680
cttcgagcat ccacttttgt ccttgcaaac tttatacggc aaggcccgtg aatctagccc    1740
cccacaccac cccacccgcc cgcgccgcgc ggccgcctcg cctcccctcc cttctcctcc    1800
tctccgcccc cgccgccagg ccgtccacct ccgccgtctc ctcccccatt cgcacccaag    1860
gcgctggcgc ggaaggc                                                   1877
```

<210> SEQ ID NO 193
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0565

<400> SEQUENCE: 193

```
caccaaatat agtgttattt caatactaaa atggtgttat ggttggagat gccctaaaga    60
taaacatgac gagacacgag atttattaat ttcttgatca accataactt ataacttaa   120
tattaatttc acttaataat ttccaattaa gtgaatcttt acttcaccaa aagttcctaa   180
cgaactctta ttttctagca tcaatattac catgaactag catcaatact atcatgaaaa   240
attcctactt cctatccaac tcttaataac aatgctagtc ttaacaatat tcatcaaaaa   300
cttgatatag accttctaac ttagccacga ctagtatcgg tgaataccaa aattaatgta   360
ttcatgagaa cttgagattt ctctaatgta ttcttgttac taaacaagta acaacactca   420
agaaatatca tgatcaaata ttttactcat aaactccata tttcacattt tgaaaatttt   480
aaacagcaaa tcacattgaa ttttcgtggt aaaagtattt aaaattgaaa aatagcagct   540
cctgatttca atgtataaat ttatctttat atggtttatg tctccaactt attttaaaaa   600
agagagaaag agcacccaaa aggtgaccgt ttgaaattcg aatttatttc cgtttgaaat   660
tcgaattcaa aaaagtaaa ccgaaccgag tctcgttact gactgtcaca cattgtttcc   720
ctaaaagcta attaacccat acgtggcgta ataacagg tcagtgatca atactaaata   780
acagacatac acctttaaaa ttcgtgcacg ctccaaaaca aaatctacac ttcaaaatca   840
acggtcacga tcattcctca aatttcaaaa aattatttaa cctcacttcc ttcgctttgt   900
ttttaaaacc tctctctctt tctcttctc tttcgccatt aaaactctgt ttccttttc   960
agagattctc agagaagatt cattttaccc taagaaaaaa                        1000
```

<210> SEQ ID NO 194
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0015

<400> SEQUENCE: 194

```
ttgagcctta ttgttgttat tgacttttag ccaatagaaa gagatggaaa ttcaataatt    60
atccacaaaa ttccaaatca ttggtgtaca aaaagatcta aggctgttat attttcaaaa   120
aagaaagaaa agaaatgcaa caaatatgga ttaaactgtg gtttgtaaat tgagctttgc   180
atgaaaactt tatcactatg atttcactac tccatattta ttgactaaag tggcactaat   240
gaatttctta atcatgaaat cttgtatcaa aaagtactaa aataaacatg acattggcaa   300
ttaggaaaat tctaaattag aaattagtaa aaatgaaagg tgaaagggaa agatgatgat   360
atgaattggt tggtgaccag gagaaatgta tcccgatttt tgcagacact ttcagtgtcc   420
ccattcatat aattatggcc cacctcgtta agattttca ttcaccacca taacaagatc   480
taagcttaga tttcatgtaa ttaaacatat aatatacttg ccaatactat ctaataaagt   540
atacttaagc aaaaattatt actctagtgt aaggcgatga aatataagtt tagttgaaaa   600
tttatgtcga tataacaaag tataatgaat taagaccttg gttttcgatt aacaaactaa   660
ttaaacacta gttttgccta ataaaaccgg gaatcgtatt caaaaccgaa cgacaaaaca   720
agggacaagt tgagagacaa aaccaaatca gcatctttct tccagaaatg tcatgaccac   780
atgacgtcat cttgacccct ttccattgtg atatctgtgg ataaagcgca cgtgtttaat   840
tcacgaacct tcgtagtaac gaaaaatcca caacttcat attttttaat tacccactaa   900
actaaaacaa atttggaaaa acatgaaaaa ctttttcttt tttccaggt tcgtgaacct   960
```

```
cgtaccctct atataaacct cttaaccacc ttccacata                             999
```

```
<210> SEQ ID NO 195
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0087

<400> SEQUENCE: 195
tgaattgagt aaaatgtgtt ttcaaacagt taggtggtag aaggtaaagg taataacatc     60
atgatcttac taaagaatt gttgcatact aactatcaat attctcaaca acataatata     120
atgttttttt aggtaatttt ccattttaat ttttttgtgat aaacaatta aacaactcga    180 atgatgatga taaaaaaaaa aaattaacaa ctcgaataag ttaaagtagc aatacacatg    240
tcgttcaatt caaccaataa agtaagactt atattttaa aagttgact aatagcttaa      300 taagttggaa aacttgtgta gtttcttaat tcccacgtgc agtaagaaat aaaaatgaaa   360
aaaattatta tatccttccc actctgcgac ttttctttta ttttatcaaa tattaaaaag   420
attcatatca cagtttacac attgaaatca taaacgataa ttatgtattt tgtaataaaa   480
agttagttct gaagctcata ctttggatag tcgctagtcg ctaatatgct ccttgtaata   540
attaaagtca ctacgacgca cgtcaaagcc gatatttagg gcttaattga tgcgtgtttt   600
tcttttcata taatagtaat ataaattagt actaataaag tatgatggat ggttgagaca   660
gaaaagaaaa aagatgactg tatggtcatc attacaaaga agaatgtatt cttcatgttc   720
ttaagaataa taaaatgtca cttgtaaatc aagttggtaa gcattttgag aactttgttc   780
gatgcaacgt atgatgattt atgtagacaa aagataaaac cgtatcttca actattgcca   840
agaaaagata aaacctaatc tagtcagtct ctcaacataa atacaaccca atagccaaac   900
tgtgtccaat tcggagagaa actaaactaa aacaaaacac aaaagcccaa cataagccca   960
ataaaaccca ttttataaac agaacattac taacactca                          999
```

```
<210> SEQ ID NO 196
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0093

<400> SEQUENCE: 196
atgatgaaca ttctacatat ataattatta tgtttaagca cttagacagc ataaattctt     60
tctaattata taaatctaac cttgttacat tgtacatcta taaattactt gaagaaataa    120
cgagttctat ttcttttaa aaattaaaaa tactatacca tatctcagtg attaagttga    180
accaaaaggt acggaggaga acaagcatt tgattcttcc ttatttatt ttattcatct      240 ctcactaatg atggtggaga aaaaagaaa ataccctaaca aacaaatata tattgtcata   300 caaaatatt tctatatttt tagttaatta gtttatattc ctcactttc agggcttata    360 taagaaagtg agcaaacaca aatcaaaatg cagcagcaaa tactatcatc acccatctcc   420
ttagttctat tttataattc ctcttctttt tgttcatagc tttgtaatta tagtcttatt   480
tctctttaag gctcaataag aggaggtact attactacac ttctctctac ttttacttgt   540
attttagcat taaaatccta aaatccgttt taaattcaaa aataaactta gagatgttta   600
atctcgattc ggttttcgg ctttaggaga ataattatat gaaattagta tggatatctt    660
```

```
tactagtttc cattcaaatg attctgattt caatctaata ctctcactct ttaattaaac      720
tatatgtagt gtaatttcac actgttaaat ttctaccatg tcatgtatat tagagttgca      780
tagaaaattg taaaacatcc atttgaattc gaatgaaaca aaatgtttta aaataaaatt      840 ttggtttta aaagaaaaat ctaaaactga attatatcgt ttaaccaagt tgtaaaagtc       900
ataaaacgta gtatcttgta aatcgctctt ccacggtcca aatagacttc tagtaataaa      960
caagtaaaac taattttggt ttcttactaa ttttcacaga                           1000

<210> SEQ ID NO 197
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0108

<400> SEQUENCE: 197
ttagctgaac caggaaattg atctcttata ccagtttccg ggtttagatt ggtttgatgg       60
cgatttgatt aaacccccga aattttatgt cgtagttgtg catagtatta ttattctttg      120
cggacaatag acgtatcggg accaagttct gtagcaaaat tgtataagct taagtttgat      180
gaaatttaaa ggtaatcact aaaacccaaa tgggacaata aaccggtgaa gatttagagt      240
ttttaatttt gactcatgaa tctggagaaa gagccctcgt taaaggagt gaatcaatcc       300 ataggggaaa aagttttgtc ttttaaaaa ctaagaacc aaaccttaat agaagcagct        360
caatgtgtga caactttcca ctggcactaa gataaagtga ctagcgatga gtgcaattat      420
tgaaatagta gatggtaaat attacataca agagtaaaaa tatctttatg tcaatgctta     480
attcagtgtt tctggttaac aagagaaact tctctaactt tcgtaattgg gtcttataaa     540
attttatgca attatgattt tacccttta ctactttca ttagctttca cgaatctatt      600
ttgacaagag aaatcattag aggtaaacat gctttttggt caagggcctt aacagttcca     660
ccaatcaagc tcaaaagttg tacttaaccg acatcttctg tgaaaacata taattacatg     720
tacaaatcaa aactaccta tgaaataaat agaatatatg cagttcattt ctaatttaac     780
ctcttcaact tttaaaacta tttacatttc tttatgtcat ttctagtcat tttgatgcaa    840
attgtaccat ttatggatta tcttcacaaa ttttaagtt ggtgaaaact ttttggtggg     900
tagttaaaac ttgaaataga aatttacttt accaaaataa actaatgaaa agtaatcact     960
ccactcccta aataagatt tccaacgttc ccactaagc                            999

<210> SEQ ID NO 198
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0022

<400> SEQUENCE: 198
tagttccatt acaatttcca aatgatttgt tacaaagcta caagattatt cgaaatagga      60
tttcatccat aagagagaat ggtgtggtcg acgctacaat gttgatttat tggttgtggt     120
ttgcatcttg gggatgtcaa atcctaagtt tcaagttctt gtaaaaacgt tttcaggttt     180
ctttaatata ttttaatatt aatgtaaaaa gaaagagat agcttttgta caaaaaaatt     240
tgtttaatca ctatgtagga ggatgcgatc aaattcatgg aatgatgtat tattagcttt     300
```

```
tctatcctca ctctaaaaac aatactatag tgagttaaat aatttgatca tttcaatgta    360
gattaaaatt ttattaaaag aagaaaaatt taaaagccta taacaaaata aaaaaggagg    420
ctcgaggtat gatgggtgta gcagaagagc tggcaacagc tatcgactga gtgattacga    480
actcagtact cagtgttctc agctcacaca ctctttttt gttctctttc ttttggacag    540
ctttcatttt ctctttcttt ttttctattt tgtttcaaaa ttccatccat attaaaatag    600
gcctgatcat gagaataaag gaaatactaa tgatgagttt ctcaataatg caataagatg    660
caattattat gagctatttta ctattgaaaa tgagcaaata aatgtcaaaa cacaatctgg    720
ttaagttaga gcaactccat tgtataggat tcatgtagtt tctaagaaaa caaaatgtat    780
taatatttta cttttacatc caaaaaacca acttatatga gtaatagaaa cgatcctaat    840
attaggaatt ttagagattt tctctcatct gtttcttaac ttttcaatat ttttattttt    900
taaaattgta tgagtttcta ctaagaaact actgctggag ttggtcttag cttcccaatg    960
cttctccacc tatatatatg catatctcct tcttaaaac                           999
```

<210> SEQ ID NO 199
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0080

<400> SEQUENCE: 199

```
aagcggcaat ttagtaagaa gtactcaaag tatcatttac caaaagtata tggttttggg     60
aagagttgtt agggatgtat tctttctaaa cagatgatat gacgatgttc ttgaaaacta    120
atgttaaaga cggaatctct ggcatcttca ctcgggagat atattaaacc gttgattgta    180
gttagccatg tacttagctt agtgcacaaa taatctgctg caagaaatct ttttctatta    240
taatatctct catttaaaca ttagaacata ttgtttaact tgttcttcta gaaataaaac    300
tgctaatttc ttatggtaaa ctattttcct ttagattgca caatcgaact cgaaaatcta    360
gtggagacta tgtgactatg tttatatata tgaaacctaa atcaaattat cccaataatt    420
gggagacaca aagaaaaaat tacgaaagaa acaggaaat caaatcaaaa gataaagaga    480
aggtaaaaaa aggcaagaag cactaatgtt taatatttat agttttctcc attaaagaaa    540
aagcgatgat gtgtgttctc atcttttgtg aaagtatata tattgctttt gcttttctca    600
aaagcaaaag actcatccaa caagaacaaa aaaaaaact aaagctcaat ccaaagacg     660 aagaatgcat tggatactac aacttctttt tcacttttct ttcaaattta caattatgat    720
tttcacaata cagtttattc aaaaataaat aaaaaaacga ggcatgaaaa taatgattat    780
cctcttcact tattaagcca ctcactataa gcagagcaac tccagaacat agtgagcccc    840 caaacatta aagcatgatg atgtctaatg atgatgatct tcttcgttcc atttctctaa    900
atttttggga tttctgcgaa gacccttctt ctctttctct tctctgaact tcaagattcg    960
tgtcggacaa attttttgttt ttatttttct gatgttaca                          999
```

<210> SEQ ID NO 200
<211> LENGTH: 3000
<212> TYPE: DNA
<213> ORGANISM: Arabidopsis thaliana
<220> FEATURE:
<221> NAME/KEY: misc_feature
<223> OTHER INFORMATION: Ceres Promoter PR0924

<400> SEQUENCE: 200

```
atctataacg agttaacatg ttgccagttt gaatcaagaa gcttggatga tgaatgaatg    60
gatcggtttg tggtacaatt cttaaaattg tagtagagga gacagagaaa aaacatgata   120
agactttggt atttacaact tgacggagac aagacagtaa gccaaatctg tcacaaaaac   180
actcaaactc ttttctcagt gttttgagtt taaagagaga cttattcact tcccctttcg   240
taacacttat ttgtctccca accaaacagt ttctgtcctt tcccttgtcc tcccacgtgc   300
atctttatat ctcatgactt ttcgtttcta gatcttgaat aatgtcttag tggattaggt   360
ttgttgtcgg taaattaggt gaccgttttt ttcttatatt tggaagatcg cgggatgaag   420
cagatactga gtttcagggc atacacacct aatttgaaaa tcattgttag tccaatttca   480
ctttaatctt gtttacaaaa aaattgatct gaaaatgttg atgggataag taaaaatgta   540
agttttgcta gtagtcatga tataataata gcaaaaccag atcaattttg agcaaaagga   600
agaaacaaaa aacagatcga tcccacgagc aagactaagt gtaaagtggt tcccacaaga   660
gccatatgga tatggtcctt caacttttaa agcccattac ttcagtggtc gacccgacat   720
tacgccacga gtagtcacgc acgcacgact ccgttcacgt gacattcacg ttgatatttc   780
cccctctact ctcttctgct tggttgatct aaaaaacatg aagagaccaa cctaatttca   840
tattaatata tgatatagac ttcatactca acagtcactt tcgtaatcca aatccatatc   900
ttacgaaatt agttcttaat aaaggttgtg gattaagtta taatattgtg ttaagagtta   960
agacacagca tataaccttg taccaacagt gctttattct taaatggaaa caaaacatat  1020
gtcaatgtca agcatacagc taaaatatca ttatctaata ttaagagtaa aacaagataa  1080
ttaaaaattg aaacaacacc atatttttat agctttactt atcgtatttt tctagtcttc  1140
atggtaattg tgttgcttta ttttgtttat aaatgaattt ggttcgacca gatagtctaa  1200
tatcagtttt taaacactgg ttttaataaa atcatatgtc ggcaattcaa cctgttacgt  1260
tgtatgattg tatcctagtc aaatagggga ggaggtacta gtcgtttcaa ttagtttacg  1320
taatcaatcc aaagaaacta aagctataaa agatcctcaa tttgttggtt acaataaaaa  1380
caacagttgt caaaatttat gtttataaaa agtaataact atgttccttc ccatatagag  1440
caaagtacct caggataggc aaaccgtact taatagccct tattcataat ttgatccaac  1500
tcttccccac aaaattgcaa ctgatgaagt caatacttgt atagtgagtc aagctataaa  1560
tgtctagtga tagttttgtc tcttaaaagg ttaacaaaag ttatgacaag ctgaaaaatc  1620
agagtttgct aggagtatta cttacagtta tcagtttaag tatcacattt atagtattgt  1680
atacaatgat tcttaaattc cacctttttcc gtgcgaaacc aaattttcta ttggaaacat  1740
agaatgtaaa caaaaatatg ggacgttgtc cgttccaaca ttaaccaaac ttgtctatta  1800
ctaatattcg tgttggtttg atgttggatg tctaaattcg ttgaatcatg tgtctcttga  1860
cgaaatatgc atcttcttat ttcttagtat agatgcactt tatcattctt ttagtacatg  1920
cttaattttt tttttttaaaa tatgttgatt gtcatattgc caaagtatg aattaaagac  1980 gcacatctaa cacaagttag cagccgtaaa tccttccata aatttatttt gcaagttttg  2040
ctcattatat aatgagcgga atttatgata taatcgtttg taataatgtt atgttttgat  2100
caaaatttga aattaaaagt aggtgagaac ttgttataca gtgtagataa ggtggatctt  2160
gaatataaaa ataaaattta taagatgtat ttaaagcaga aaagcataaa actttagata  2220
aaataatgta aaaatgtgtt agcatcaatg ttgggatatt ggccgacccg aacttaatca  2280
atgtcggaag ccattacttc tctcccaaaa gaccttttc cttcggagaa ctaggaactt  2340
```

```
cctcactacc tttcgcttaa cgtgaaagcc ataaatttca tatattcata aaaatcagaa    2400
aatctaaaac tgtttagtat cacctgtttt tggtatagac tattggtttt gtgttacttc    2460
ctaaactata tgatttcgta cttcattgga tcttatagag atgaatattc gtaaaaagat    2520
aagttatctg gtgaaacgtt acttcagtca tgttgggtct agatttacat actactatga    2580
aacattttaa gataataatt atcctagcca actatatgtt ctatattatg ggccaagaag    2640
atatagaact aaaagttcag aatttaacga tataaattac tagtatattc taatacttga    2700
atgattactg ttttagttgt ttagaataaa tagtagcgtg ttggttaaga taccatctat    2760
ccacatctat atttgtgtgg gttacataaa atgtacataa tattatatac atatatatgt    2820 atattttga taaagccata tattactcct tgacctctgc ccccatttcc ttttactata    2880
aataggaata ctcatgatcc tctaattcag caatcaacac caacgaacac aacctttccc    2940
aaagccaata ataaaagaac aaaagctttt agtttcatca aagacgaagc tgccttagaa    3000

<210> SEQ ID NO 201
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0388

<400> SEQUENCE: 201
agaagtattc acgcaccaag gttatatttg tagtgacata ttctacaatt atcacatttt      60
tctcttatgt ttcgtagtcg cagatggtca attttttcta taataatttg tccttgaaca     120
caccaaactt tagaaacgat gatatatacc gtattgtcac gctcacaatg aaacaaacgc     180
gatgaatcgt catcaccagc taaaagccta aacaccatc ttagttttca ctcagataaa      240
aagattattt gtttccaacc tttctattga attgattagc agtgatgacg taattagtga     300
tagtttatag taaaacaaat ggaagtggta ataaatttac acaacaaaat atggtaagaa     360
tctataaaat aagaggttaa gagatctcat gttatattaa atgattgaaa gaaaaacaaa     420
ctattggttg atttccatat gtaatagtaa gttgtgatga aagtgatgac gtaattagtt     480
gtatttatag taaaacaaat taaaatggta aggtaaattt ccacaacaaa acttggtaaa     540
aatcttaaaa aaaaaaaaag aggtttagag atcgcatgcg tgtcatcaaa ggttctttt      600 cactttaggt ctgagtagtg ttagactttg attggtgcac gtaagtgttt cgtatcgcga     660
tttaggagaa gtacgtttta cacgtggaca caatcaacgg tcaagatttc gtcgtccaga     720
tagaggagcg atacgtcacg ccattcaaca atctcctctt cttcattcct tcattttgat     780
tttgagtttt gatctgcccg ttcaaaagtc tcggtcatct gcccgtaaat ataaagatga     840
ttatatttat ttatatcttc tggtgaaaga agctaatata aagcttccat ggctaatctt     900
gtttaagctt ctcttcttct tctctctcct gtgtctcgtt cactagtttt ttttcgggg      960 agagtgatgg agtgtgtttg ttgaatagtt ttgacgatca                          1000

<210> SEQ ID NO 202
<211> LENGTH: 283
<212> TYPE: DNA
<213> ORGANISM: Arabidopsis thaliana
<220> FEATURE:
<221> NAME/KEY: misc_feature
<223> OTHER INFORMATION: Ceres Promoter PD0901

<400> SEQUENCE: 202
caaagtattt gacaagccat atggttttgg atcaaaaagt cggtccaaaa ttaatgtttt      60
```

```
atgtgcaaga accgacccat tgtacacacg tgttaacatc ttcaagactt tcatctctat      120
ttttcttttg gtcattaaga tacccattga tccgaatctg ttacattccc acctactttt     180
ttaattttta ctatccactc caaattaaac acaaccgatg attttaataa ttggaagctt     240
tttaaaatat ttctccacgt gcctctttgt gtttgtctat ata                       283
```

<210> SEQ ID NO 203
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0623

<400> SEQUENCE: 203

```
aaagttattg acattttgaa aggaccgtaa atattaccaa aaaactgacg gagttaggat      60
cggccacgta gaaagggaca agagagaaac agtcacggac tcggccagac taagtatggg     120
cctgtctgaa tccaaactca gctaagttcc aaaagcataa agagagatgt gtaatgaaat     180
gaacgtattc tagaaacgaa agcaatgtta tgctttgttt ttgagccaca tgttttgggg     240
agatggagag aatctttttt acgttttaa cctaacccac ttggcacttg gccaaaaaag      300
tgagaagaaa ctgtggcgaa tgagtaggcc acgccatgga ctttgttcct tgtccttcaa     360
aagttaaatt tatgttatgc gtggggacaa tctaagcaac gtggttcctt taaatatcgc     420
agcttcctct tttacacttt tggagcctac gtgttttgtt ttggaccggc caaatacacg     480
agtcagtcag tttagaaata atttggatgt ccaaaaatct tggagatcca ataaaataa     540 ttagcatgtt ttagttcata agaatatgaa atgtagataa actgtctata ttaatttttc     600
catagaattg gcttttatc gaggtgatgt acttaatgac tttgttgatt actactcgta     660
taacaataaa gaatatgata ctatgtgaga cttataatga atttggtgtg tgttaattaa     720
tccagttgaa acagtttaat aacaaatcag aataaaaatt gtagtaagaa aatttgaacg     780
ctgatccttc aacctagata gtgaacccttt caaatactat atgattcacg tgtaatgttt    840
ttgaccgttg gttattttg tgtgaactat attaacttat caatatcgaa aggctaaata      900
agtaaataac taaagaaag ttcaggaaac aactcgacct aatgacctat catttctgat     960
cacccgtcct ataaatacat acgtaagatc attcgttact                          1000
```

<210> SEQ ID NO 204
<211> LENGTH: 33
<212> TYPE: PRT
<213> ORGANISM: Artificial Sequence
<220> FEATURE:
<223> OTHER INFORMATION: Truncated version of Ceres CLONE ID no.
      100021733
<220> FEATURE:
<221> NAME/KEY: misc_feature
<223> OTHER INFORMATION: Ceres CLONE ID no. 100021733_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 204

```
Met Gln Ile Phe Val Lys Thr Leu Thr Gly Lys Thr Ile Thr Leu Glu
1               5                   10                  15
```

-continued

```
Val Glu Ser Ser Asp Thr Ile Asp Asn Val Lys Ala Lys Ile Gln Asp
            20                  25                  30

Lys

<210> SEQ ID NO 205
<211> LENGTH: 33
<212> TYPE: PRT
<213> ORGANISM: Artificial Sequence
<220> FEATURE:
<223> OTHER INFORMATION: Truncated version of Ceres CLONE ID no. 1036726
<220> FEATURE:
<221> NAME/KEY: misc_feature
<223> OTHER INFORMATION: Ceres CLONE ID no. 1036726_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 205

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 206
<211> LENGTH: 33
<212> TYPE: PRT
<213> ORGANISM: Artificial Sequence
<220> FEATURE:
<223> OTHER INFORMATION: Truncated version of Ceres CLONE ID no. 1482731
<220> FEATURE:
<221> NAME/KEY: misc_feature
<223> OTHER INFORMATION: Ceres CLONE ID no. 1482731_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 206

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys

<210> SEQ ID NO 207
<211> LENGTH: 80
<212> TYPE: PRT
<213> ORGANISM: Artificial Sequence
<220> FEATURE:
<223> OTHER INFORMATION: Truncated version of Ceres CLONE ID no. 1554560
<220> FEATURE:
<221> NAME/KEY: misc_feature
<223> OTHER INFORMATION: Ceres CLONE ID no. 1554560_T
<220> FEATURE:
<221> NAME/KEY: misc_feature
<222> LOCATION: (17)..(78)
```

<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 207

Met Ala Leu Ala Glu Ala Asp Asp Gly Ala Val Val Phe Gly Glu Glu
1               5                   10                  15

Gln Glu Ala Leu Val Leu Lys Ser Trp Ala Val Met Lys Lys Asp Ala
            20                  25                  30

Ala Asn Leu Gly Leu Arg Phe Phe Leu Lys Val Phe Glu Ile Ala Pro
        35                  40                  45

Ser Ala Lys Gln Met Phe Ser Phe Leu Arg Asp Ser Asp Val Pro Leu
    50                  55                  60

Glu Lys Asn Pro Lys Leu Lys Thr His Ala Met Ser Val Phe Val Met
65                  70                  75                  80

<210> SEQ ID NO 208
<211> LENGTH: 77
<212> TYPE: PRT
<213> ORGANISM: Artificial Sequence
<220> FEATURE:
<223> OTHER INFORMATION: Truncated version of Ceres CLONE ID no. 1802327
<220> FEATURE:
<221> NAME/KEY: misc_feature
<223> OTHER INFORMATION: Ceres CLONE ID no. 1802327_T
<220> FEATURE:
<221> NAME/KEY: misc_feature
<222> LOCATION: (14)..(75)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 208

Met Ala Leu Ala Glu Gly Asn Val Ile Phe Gly Glu Glu Gln Glu Ala
1               5                   10                  15

Leu Val Leu Lys Ser Trp Ala Leu Met Lys Lys Asp Ser Ala Asp Leu
            20                  25                  30

Gly Leu Arg Phe Phe Leu Lys Ile Phe Glu Ile Ala Pro Ser Ala Lys
        35                  40                  45

Gln Met Phe Ser Phe Leu Arg Asp Ser Asp Val Pro Leu Glu Lys Asn
    50                  55                  60

Pro Lys Leu Lys Asn His Ala Met Ser Val Phe Val Met
65                  70                  75

<210> SEQ ID NO 209
<211> LENGTH: 77
<212> TYPE: PRT
<213> ORGANISM: Artificial Sequence
<220> FEATURE:
<223> OTHER INFORMATION: Truncated version of Ceres CLONE ID no. 1876458
<220> FEATURE:
<221> NAME/KEY: misc_feature
<223> OTHER INFORMATION: Ceres CLONE ID no. 1876458_T
<220> FEATURE:
<221> NAME/KEY: misc_feature
<222> LOCATION: (14)..(75)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469 given in SEQ ID NO: 7

<400> SEQUENCE: 209

Met Ala Leu Ala Glu Gly Asn Val Ile Phe Gly Glu Glu Gln Glu Ala
1               5                   10                  15

Leu Val Leu Lys Ser Trp Ala Leu Met Lys Lys Asp Ser Ala Asp Leu
            20                  25                  30

Gly Leu Arg Phe Phe Leu Lys Ile Phe Glu Ile Ala Pro Ser Ala Lys
        35                  40                  45

Gln Met Phe Ser Phe Leu Arg Asp Ser Asp Val Pro Leu Glu Lys Asn
    50                  55                  60

Pro Lys Leu Lys Thr His Ala Met Ser Val Phe Val Met
65                  70                  75

<210> SEQ ID NO 210
<211> LENGTH: 79
<212> TYPE: PRT
<213> ORGANISM: Artificial Sequence
<220> FEATURE:
<223> OTHER INFORMATION: Truncated version of Ceres CLONE ID no. 1879148
<220> FEATURE:
<221> NAME/KEY: misc_feature
<223> OTHER INFORMATION: Ceres CLONE ID no. 1879148_T
<220> FEATURE:
<221> NAME/KEY: misc_feature
<222> LOCATION: (16)..(77)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 210

Met Ala Leu Ala Asp Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met
65                  70                  75

<210> SEQ ID NO 211
<211> LENGTH: 33
<212> TYPE: PRT
<213> ORGANISM: Artificial Sequence
<220> FEATURE:
<223> OTHER INFORMATION: Truncated version of Ceres CLONE ID no. 1884696
<220> FEATURE:
<221> NAME/KEY: misc_feature
<223> OTHER INFORMATION: Ceres CLONE ID no. 1884696_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 211

Met Gln Ile Phe Val Lys Thr Leu Thr Gly Lys Thr Ile Thr Leu Glu

```
1               5                   10                  15
Val Glu Ser Ser Asp Thr Ile Asp Asn Val Lys Ala Lys Ile Gln Asp
            20                  25                  30

Lys

<210> SEQ ID NO 212
<211> LENGTH: 76
<212> TYPE: PRT
<213> ORGANISM: Artificial Sequence
<220> FEATURE:
<223> OTHER INFORMATION: Truncated version of Ceres CLONE ID no. 1916866
<220> FEATURE:
<221> NAME/KEY: misc_feature
<223> OTHER INFORMATION: Ceres CLONE ID no. 1916866_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 212

Met Ala Thr Tyr Glu Gly Lys Val Phe Thr Glu Glu Gln Glu Ala Leu
1               5                   10                  15

Val Val Lys Ser Trp Thr Val Met Lys Lys Asn Ala Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met
65                  70                  75

<210> SEQ ID NO 213
<211> LENGTH: 33
<212> TYPE: PRT
<213> ORGANISM: Artificial Sequence
<220> FEATURE:
<223> OTHER INFORMATION: Truncated version of Ceres CLONE ID no. 1950105
<220> FEATURE:
<221> NAME/KEY: misc_feature
<223> OTHER INFORMATION: Ceres CLONE ID no. 1950105_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 213

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 214
<211> LENGTH: 79
<212> TYPE: PRT
<213> ORGANISM: Artificial Sequence
```

```
<220> FEATURE:
<223> OTHER INFORMATION: Truncated version of Ceres CLONE ID no. 1990746
<220> FEATURE:
<221> NAME/KEY: misc_feature
<223> OTHER INFORMATION: Ceres CLONE ID no. 1990746_T
<220> FEATURE:
<221> NAME/KEY: misc_feature
<222> LOCATION: (16)..(77)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 214

Met Ala Leu Ala Glu Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met
65                  70                  75

<210> SEQ ID NO 215
<211> LENGTH: 79
<212> TYPE: PRT
<213> ORGANISM: Artificial Sequence
<220> FEATURE:
<223> OTHER INFORMATION: Truncated version of Ceres CLONE ID no. 2033803
<220> FEATURE:
<221> NAME/KEY: misc_feature
<223> OTHER INFORMATION: Ceres CLONE ID no. 2033803_T
<220> FEATURE:
<221> NAME/KEY: misc_feature
<222> LOCATION: (16)..(77)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 215

Met Ala Leu Ala Glu Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met
65                  70                  75

<210> SEQ ID NO 216
<211> LENGTH: 33
<212> TYPE: PRT
<213> ORGANISM: Artificial Sequence
<220> FEATURE:
<223> OTHER INFORMATION: Truncated version of Ceres CLONE ID no. 2034916
<220> FEATURE:
<221> NAME/KEY: misc_feature
<223> OTHER INFORMATION: Ceres CLONE ID no. 2034916_T
```

```
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 216

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 217
<211> LENGTH: 33
<212> TYPE: PRT
<213> ORGANISM: Artificial Sequence
<220> FEATURE:
<223> OTHER INFORMATION: Truncated version of Ceres CLONE ID no. 513071
<220> FEATURE:
<221> NAME/KEY: misc_feature
<223> OTHER INFORMATION: Ceres CLONE ID no. 513071_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 217

Met Gln Ile Phe Val Lys Thr Leu Thr Gly Lys Thr Ile Thr Leu Glu
1               5                   10                  15

Val Glu Ser Ser Asp Thr Val Asp Asn Val Lys Ala Lys Ile Gln Asp
            20                  25                  30

Lys

<210> SEQ ID NO 218
<211> LENGTH: 33
<212> TYPE: PRT
<213> ORGANISM: Artificial Sequence
<220> FEATURE:
<223> OTHER INFORMATION: Truncated version of Ceres CLONE ID no. 522921
<220> FEATURE:
<223> OTHER INFORMATION: Ceres CLONE ID no. 522921_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 218

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys
```

```
<210> SEQ ID NO 219
<211> LENGTH: 76
<212> TYPE: PRT
<213> ORGANISM: Artificial Sequence
<220> FEATURE:
<223> OTHER INFORMATION: Truncated version of Ceres CLONE ID no. 546001
<220> FEATURE:
<221> NAME/KEY: misc_feature
<223> OTHER INFORMATION: Ceres CLONE ID no. 546001_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 219

Met Thr Thr Thr Leu Glu Arg Gly Phe Ser Glu Glu Gln Glu Ala Leu
1               5                   10                  15

Val Val Lys Ser Trp Asn Val Met Lys Lys Asn Ser Gly Glu Leu Gly
            20                  25                  30

Leu Lys Phe Phe Leu Lys Ile Phe Glu Ile Ala Pro Ser Ala Gln Lys
        35                  40                  45

Leu Phe Ser Phe Leu Arg Asp Ser Thr Val Pro Leu Glu Gln Asn Pro
    50                  55                  60

Lys Leu Lys Pro His Ala Val Ser Val Phe Val Met
65                  70                  75

<210> SEQ ID NO 220
<211> LENGTH: 76
<212> TYPE: PRT
<213> ORGANISM: Artificial Sequence
<220> FEATURE:
<223> OTHER INFORMATION: Truncated version of Ceres CLONE ID no. 651581
<220> FEATURE:
<221> NAME/KEY: misc_feature
<223> OTHER INFORMATION: Ceres CLONE ID no. 651581_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 220

Met Glu Ser Glu Gly Lys Ile Val Phe Thr Glu Gln Glu Ala Leu
1               5                   10                  15

Val Val Lys Ser Trp Ser Val Met Lys Lys Asn Ser Ala Asp Leu Gly
            20                  25                  30

Leu Lys Leu Phe Ile Lys Ile Phe Glu Ile Ala Pro Thr Ala Lys Lys
        35                  40                  45

Leu Phe Ser Phe Leu Arg Asp Ser Pro Ile Pro Ala Glu Gln Asn Pro
    50                  55                  60

Lys Leu Lys Pro His Ala Met Ser Val Phe Val Met
65                  70                  75

<210> SEQ ID NO 221
<211> LENGTH: 77
<212> TYPE: PRT
<213> ORGANISM: Artificial Sequence
```

```
<220> FEATURE:
<223> OTHER INFORMATION: Truncated version of Ceres CLONE ID no. 839727
<220> FEATURE:
<221> NAME/KEY: misc_feature
<223> OTHER INFORMATION: Ceres CLONE ID no. 839727_T
<220> FEATURE:
<221> NAME/KEY: misc_feature
<222> LOCATION: (14)..(75)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 221

Met Ser Ala Ala Glu Gly Ala Val Val Phe Ser Glu Glu Lys Glu Ala
1               5                   10                  15

Leu Val Leu Lys Ser Trp Ala Ile Met Lys Lys Asp Ser Ala Asn Leu
            20                  25                  30

Gly Leu Arg Phe Phe Leu Lys Ile Phe Glu Ile Ala Pro Ser Ala Arg
        35                  40                  45

Gln Met Phe Pro Phe Leu Arg Asp Ser Asp Val Pro Leu Glu Thr Asn
    50                  55                  60

Pro Lys Leu Lys Thr His Ala Val Ser Val Phe Val Met
65                  70                  75

<210> SEQ ID NO 222
<211> LENGTH: 76
<212> TYPE: PRT
<213> ORGANISM: Artificial Sequence
<220> FEATURE:
<223> OTHER INFORMATION: Truncated version of Public GI ID no. 11095158
<220> FEATURE:
<221> NAME/KEY: misc_feature
<223> OTHER INFORMATION: Public GI ID no. 11095158_T
<220> FEATURE:
<221> NAME/KEY: misc_feature
<222> LOCATION: (13)..(76)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 222

Met Gly Thr Leu Asp Thr Lys Gly Phe Thr Glu Glu Gln Glu Ala Leu
1               5                   10                  15

Val Val Lys Ser Trp Asn Ala Met Lys Lys Asn Ser Ala Glu Leu Gly
            20                  25                  30

Leu Lys Leu Phe Leu Lys Ile Phe Glu Ile Ala Pro Ser Ala Gln Lys
        35                  40                  45

Leu Phe Ser Phe Leu Lys Asp Ser Lys Val Pro Leu Glu Gln Asn Thr
    50                  55                  60

Lys Leu Lys Pro His Ala Met Ser Val Phe Leu Met
65                  70                  75

<210> SEQ ID NO 223
<211> LENGTH: 71
<212> TYPE: PRT
<213> ORGANISM: Artificial Sequence
<220> FEATURE:
<223> OTHER INFORMATION: Truncated version of Public GI ID no. 12963875
<220> FEATURE:
<221> NAME/KEY: misc_feature
<223> OTHER INFORMATION: Public GI ID no. 12963875_T
```

```
<220> FEATURE:
<221> NAME/KEY: misc_feature
<222> LOCATION: (8)..(69)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 223

Met Ser Ser Phe Ser Glu Glu Gln Glu Ala Leu Val Val Lys Ser Trp
1               5                   10                  15

Gly Ser Met Lys Lys Asp Ala Gly Glu Trp Gly Leu Lys Phe Phe Leu
            20                  25                  30

Lys Ile Phe Glu Ile Ala Pro Ser Ala Lys Lys Met Phe Ser Phe Leu
        35                  40                  45

Lys Asp Ser Asn Val Pro Leu Asp Gln Asn Pro Lys Leu Lys Ile His
    50                  55                  60

Ala Lys Ser Val Leu Val Met
65                  70

<210> SEQ ID NO 224
<211> LENGTH: 84
<212> TYPE: PRT
<213> ORGANISM: Artificial Sequence
<220> FEATURE:
<223> OTHER INFORMATION: Truncated version of Public GI ID no. 14701800
<220> FEATURE:
<221> NAME/KEY: misc_feature
<223> OTHER INFORMATION: Public GI ID no. 14701800_T
<220> FEATURE:
<221> NAME/KEY: misc_feature
<222> LOCATION: (21)..(82)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 224

Met Ala Leu Val Glu Gly Asn Asn Gly Val Ser Gly Gly Ala Val Ser
1               5                   10                  15

Phe Ser Glu Glu Gln Glu Ala Leu Val Leu Lys Ser Trp Ala Ile Met
            20                  25                  30

Lys Lys Asp Ser Ala Asn Ile Gly Leu Arg Phe Phe Leu Lys Ile Phe
        35                  40                  45

Glu Val Ala Pro Ser Ala Ser Gln Met Phe Ser Phe Leu Arg Asn Ser
    50                  55                  60

Asp Val Pro Leu Glu Lys Asn Pro Lys Leu Lys Thr His Ala Met Ser
65                  70                  75                  80

Val Phe Val Met

<210> SEQ ID NO 225
<211> LENGTH: 76
<212> TYPE: PRT
<213> ORGANISM: Artificial Sequence
<220> FEATURE:
<223> OTHER INFORMATION: Truncated version of Public GI ID no. 15226675
<220> FEATURE:
<221> NAME/KEY: misc_feature
<223> OTHER INFORMATION: Public GI ID no. 15226675_T
<220> FEATURE:
<221> NAME/KEY: misc_feature
<222> LOCATION: (13)..(74)
```

```
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 225

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Glu Leu Gly
            20                  25                  30

Leu Lys Leu Phe Ile Lys Ile Phe Glu Ile Ala Pro Thr Thr Lys Lys
        35                  40                  45

Met Phe Ser Phe Leu Arg Asp Ser Pro Ile Pro Ala Glu Gln Asn Pro
    50                  55                  60

Lys Leu Lys Pro His Ala Met Ser Val Phe Val Met
65                  70                  75

<210> SEQ ID NO 226
<211> LENGTH: 76
<212> TYPE: PRT
<213> ORGANISM: Artificial Sequence
<220> FEATURE:
<223> OTHER INFORMATION: Truncated version of Public GI ID no. 15824736
<220> FEATURE:
<221> NAME/KEY: misc_feature
<223> OTHER INFORMATION: Public GI ID no. 15824736_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 226

Met Ala Thr Tyr Glu Gly Lys Val Phe Thr Glu Glu Gln Glu Ala Leu
1               5                   10                  15

Val Val Lys Ser Trp Thr Val Met Lys Lys Lys Thr Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met
65                  70                  75

<210> SEQ ID NO 227
<211> LENGTH: 76
<212> TYPE: PRT
<213> ORGANISM: Artificial Sequence
<220> FEATURE:
<223> OTHER INFORMATION: Truncated version of Public GI ID no. 30909306
<220> FEATURE:
<221> NAME/KEY: misc_feature
<223> OTHER INFORMATION: Public GI ID no. 30909306_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
``` given in SEQ ID NO: 7

<400> SEQUENCE: 227

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Asp Leu Gly
            20                  25                  30

Leu Lys Leu Phe Ile Lys Ile Phe Glu Ile Ala Pro Thr Ala Lys Lys
        35                  40                  45

Leu Phe Ser Phe Leu Arg Asp Ser Pro Ile Pro Ala Glu Gln Asn Pro
    50                  55                  60

Lys Leu Lys Pro His Ala Met Ser Val Phe Val Met
65                  70                  75

<210> SEQ ID NO 228
<211> LENGTH: 73
<212> TYPE: PRT
<213> ORGANISM: Artificial Sequence
<220> FEATURE:
<223> OTHER INFORMATION: Truncated version of Public GI ID no. 37903656
<220> FEATURE:
<221> NAME/KEY: misc_feature
<223> OTHER INFORMATION: Public GI ID no. 37903656_T
<220> FEATURE:
<221> NAME/KEY: misc_feature
<222> LOCATION: (10)..(71)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 228

Met Glu Gly Lys Val Phe Thr Glu Glu Gln Glu Thr Leu Val Val Lys
1               5                   10                  15

Ser Trp Gly Val Met Lys Lys Asn Ala Ala Glu Leu Gly Leu Lys Phe
            20                  25                  30

Phe Leu Lys Ile Phe Glu Ile Ala Pro Ser Ala Gln Lys Leu Phe Ser
        35                  40                  45

Phe Leu Arg Asp Ser Asp Ile Pro Leu Glu Lys Asn Pro Lys Leu Lys
    50                  55                  60

Pro His Ala Met Ser Val Phe Val Met
65                  70

<210> SEQ ID NO 229
<211> LENGTH: 76
<212> TYPE: PRT
<213> ORGANISM: Artificial Sequence
<220> FEATURE:
<223> OTHER INFORMATION: Truncated version of Public GI ID no. 62548111
<220> FEATURE:
<221> NAME/KEY: misc_feature
<223> OTHER INFORMATION: Public GI ID no. 62548111_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 229

Met Ala Thr Tyr Glu Gly Lys Val Phe Thr Glu Glu Gln Glu Ala Leu

-continued

```
1               5                   10                  15

Val Val Lys Ser Trp Thr Val Met Lys Lys Asn Ala Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met
65                  70                  75
```

NUCLEOTIDE SEQUENCES AND POLYPEPTIDES ENCODED THEREBY USEFUL FOR MODIFYING PLANT CHARACTERISTICS IN RESPONSE TO COLD

This application is a divisional of U.S. application Ser. No. 16/659,220, filed Oct. 21, 2019 (pending), which application divisional of U.S. application Ser. No. 16/275,629, filed Feb. 14, 2019 (now U.S. Pat. No. 10,508,284), which application is a divisional of U.S. application Ser. No. 15/362,633, filed Nov. 28, 2016, (now U.S. Pat. No. 10,240,166), which application is a divisional of Ser. No. 11/779,266 (abandoned) filed Jul. 17, 2007 which application is a Continuation-In-Part of application Ser. No. 11/778,060, filed_Jul. 15, 2007 (abandoned), which is a Continuation-In-Part of application Ser. No. 11/248,547, filed on Oct. 12, 2005, and this application is also a Continuation-In-Part of application Ser. No. 11/248,547 filed on Oct. 12, 2005 (now U.S. Pat. No. 7,244,879), the entire contents of which are hereby incorporated by reference and for which priority is claimed under 35 U.S.C § 120.

FIELD OF THE INVENTION

The present invention relates to isolated polynucleotides, polypeptides encoded thereby, and the use of those products for making transgenic plants with improved tolerances to environmental stresses such as low or chilling temperatures.

BACKGROUND OF THE INVENTION

Plants are constantly exposed to a variety of biotic (i.e. pathogen infection and insect herbivory) and abiotic (i.e. high or low temperature, drought, flood and salinity) stresses. To survive these challenges to their sessile life, plants have developed elaborate mechanisms to perceive external signals and to manifest adaptive responses with proper physiological and morphological changes (Bohnert et al. 1995). Plants exposed to cold or chilling conditions typically have low yields of biomass, seeds, fruit and other edible products. The term "chilling sensitivity" is used for the description of physiological and developmental damages in the plant caused by low, but above freezing, temperatures. Important agricultural crop plants such as corn, soybean, rice and cotton have tropical ancestors that make them chilling sensitive. In some countries or agricultural regions of the world chilling temperatures are a significant cause of crop losses and a primary factor limiting the geographical range and growing season of many crop species. Another example is that chilling conditions can cause significant concern in early spring planting of corn or canola. Poor germination and reduced growth of chilling sensitive crops in the spring results in less ground coverage, more erosion and increased occurrence of weeds leading to less nutrient supply for the crop.

Typically, chilling damage includes wilting, necrosis or ion leakage from cell membranes, especially calcium leakage, and decreased membrane fluidity, which consequently impacts membrane dependent processes such as: photosynthesis, protein synthesis, ATPase activity, uptake of nitrogen, etc. (see Levitt J (1980) Chilling injury and resistance. In Chilling, Freezing, and High Temperature Stresses: Responses of Plant to Environmental Stresses, Vol 1., TT Kozlowsky, ed, Academic Press, New York, pp 23-64; Graham and Patterson (1982) *Annu Rev Plant Physiol* 33: 347-372; Guy (1990) *Annu Rev Plant Physiol Plant Mol Biol* 41: 187-223; and Nishida and Murata (1996) *Annu Rev Plant Physiol Plant Mol Biol* 47: 541-568). In addition, cold temperatures are often associated with wet conditions. The combination of cold and wet can result in hypoxic stress on the roots, causing an even more severe reduction of growth rate but, more critically, can be lethal to the plants, especially sensitive plant species such as corn and cotton.

Yet it has been observed that environmental factors, such as low temperature, can serve as triggers to induce cold acclimation processes allowing plants responding thereto to survive and thrive in low temperature environments. It would, therefore, be of great interest and importance to be able to identify genes that regulate or confer improved cold acclimation characteristics to enable one to create transformed plants (such as crop plants) with improved cold tolerance characteristics such as faster germination and/or growth and/or improved nitrogen uptake under cold conditions to improve survival or performance under low or chilling temperatures.

In the fields of agriculture and forestry efforts are constantly being made to produce plants with an increased growth potential in order to feed the ever-increasing world population and to guarantee the supply of reproducible raw materials. This is done conventionally through plant breeding. The breeding process is, however, both time-consuming and labor-intensive. Furthermore, appropriate breeding programs must be performed for each relevant plant species.

Progress has been made in part by the genetic manipulation of plants; that is by introducing and expressing recombinant nucleic acid molecules in plants. Such approaches have the advantage of not usually being limited to one plant species, but instead being transferable among plant species. There is a need for generally applicable processes that improve forest or agricultural plant growth potential. Therefore, the present invention relates to a process for increasing the growth potential in plants under low temperature, chilling or cold conditions, characterized by expression of recombinant DNA molecules stably integrated into the plant genome.

SUMMARY OF THE INVENTION

The present invention, therefore, relates to isolated polynucleotides, polypeptides encoded thereby and the use of those products for making transgenic plants with improved cold tolerance.

The present invention also relates to processes for increasing the growth potential in plants due to cold acclimation, recombinant nucleic acid molecules and polypeptides used for these processes and their uses, as well as to plants with an increased growth potential due to improved cold acclimation. Unless otherwise defined, all scientific and technical terms used herein have the same meaning as commonly understood by one of ordinary skilled in the art to which this invention belongs.

BRIEF DESCRIPTION OF THE FIGURES

FIG. 1 and the other alignment figures provided herein were generated using the program MUSCLE (Edgar (2004) Nuc. Acids Res. 32(5):1792-1797).

FIG. 2 is an alignment of ME02779.

FIG. 3 is an alignment of truncated mutant of ME02779.
FIG. 4 is an alignment of ME03944.
FIG. 5 is an alignment of ME05304.
FIG. 6 is an alignment of truncated mutant of ME05304.
FIG. 7 is an alignment of ME03186.

DETAILED DESCRIPTION OF THE INVENTION

1. Definitions

Figure 1:
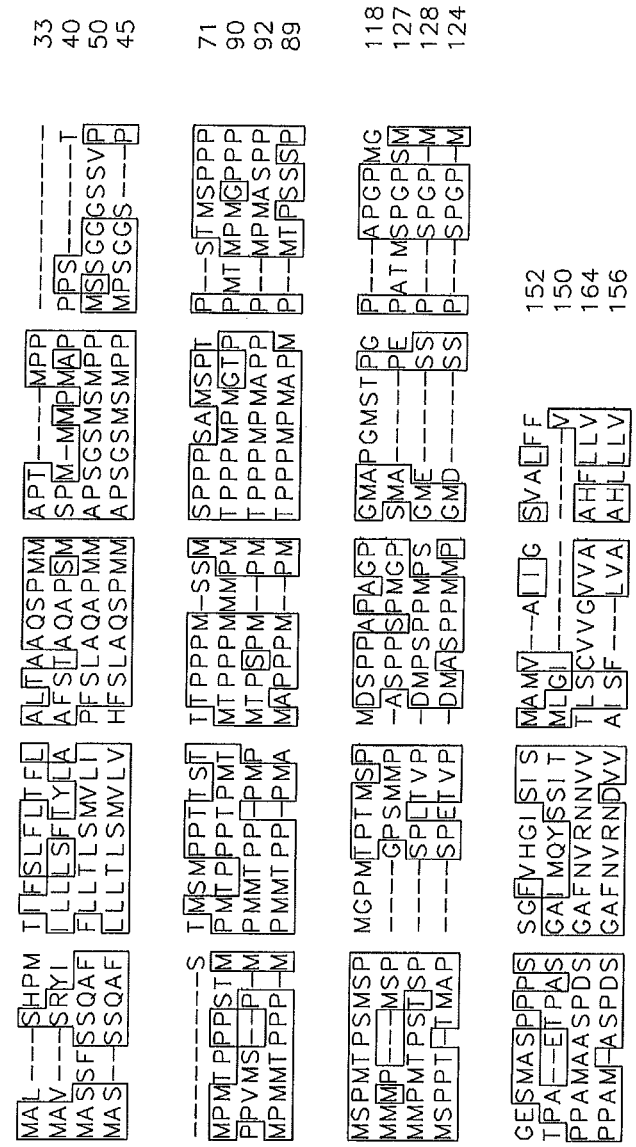
FIG. 1 is an alignment of ME01451. In all the alignment figures shown herein, a dash in an aligned sequence represents a gap, i.e., a lack of an amino acid at that position. Identical amino acids or conserved amino acid substitutions among aligned sequences are identified by boxes.

The following terms are utilized throughout this application:

Amino acid: As used herein, "amino acid" refers to one of the twenty biological occurring amino acids and to synthetic amino acids, including D/L optical isomers.

Cell type-preferential promoter or Tissue-preferential promoter: As used herein, these phrases refer to a promoter that drives expression preferentially in a target cell type or tissue, respectively, but may also lead to some transcription in other cell types or tissues as well.

Cold: Plant species vary in their capacity to tolerate low temperatures. Chilling-sensitive plant species, including many agronomically important species, can be injured by cold, above-freezing temperatures. At temperatures below the freezing-point of water most plant species will be damaged. Thus, "cold" can be defined as the temperature at which a given plant species will be adversely affected as evidenced by symptoms such as decreased photosynthesis and membrane damage (measured by electrolyte leakage). Since plant species vary in their capacity to tolerate cold, the precise environmental conditions that cause cold stress can not be generalized. However, cold tolerant plants are characterized by their ability to retain their normal appearance or recover quickly from low temperature conditions. Such cold tolerant plants produce higher biomass and yield than plants that are not cold tolerant. Differences in physical appearance, recovery and yield can be quantified and statistically analyzed using well known measurement and analysis methods.

Plant seeds vary considerably in their ability to germinate under cold conditions. Seeds of many plant species will not germinate at temperatures less than 10° C. Once seeds have imbibed water they become very susceptible to disease, water and chemical damage. Seeds that are tolerant to cold stress during germination can survive for relatively long periods under which the temperature is too low to germinate. Since plant species vary in their capacity to tolerate cold during germination, the precise environmental conditions that cause cold stress during germination can not be generalized. However, plants that tolerate cold during germination are characterized by their ability to remain viable or recover quickly from low temperature conditions. Such cold tolerant plants germinate, become established, grow more quickly and ultimately produce more biomass and yield than plants that are not cold tolerant. Differences in germination rate, appearance, recovery and yield can be quantified and statistically analyzed using well known measurement and analysis methods.

Constitutive Promoter: Promoters referred to herein as "constitutive promoters" actively promote transcription under most, but not necessarily all, environmental conditions and states of development or cell differentiation. Examples of constitutive promoters include the cauliflower mosaic virus (CaMV) 35S transcript initiation region, the 1' or 2' promoter derived from T-DNA of *Agrobacterium tumefaciens* and other transcription initiation regions from various plant genes, such as the maize ubiquitin-1 promoter, known to those of skill.

Control Plant: "Control plant" refers to a plant that does not contain the exogenous nucleic acid present in the transgenic plant of interest, but otherwise has the same of similar genetic background as such a transgenic plant. A suitable control plant can be a non-transgenic segregant from a transformation experiment, or a transgenic plant that contains an exogenous nucleic acid other than the exogenous nucleic acid of interest.

Domain: "Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

Down-regulation: "Down-regulation" refers to regulation that decreases production of expression products (mRNA, polypeptide, or both) relative to basal or native states.

Endogenous: The term "endogenous," within the context of the current invention refers to any polynucleotide, polypeptide or protein sequence which is a natural part of a cell or organism regenerated from said cell.

Exogenous: "Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

Expression: As used herein, "expression" refers to the process of converting genetic information of a polynucleotide into RNA through transcription, which is catalyzed by an enzyme, RNA polymerase, and into protein, through translation of mRNA on ribosomes.

Functionally Comparable Proteins: This phrase describes those proteins that have at least one characteristic in common. Such characteristics include sequence similarity, biochemical activity, transcriptional pattern similarity and phenotypic activity. Typically, the functionally comparable proteins share some sequence similarity or at least one biochemical. Within this definition, homologs, orthologs and analogs are considered to be functionally comparable. In addition, functionally comparable proteins generally share at least one biochemical and/or phenotypic activity.

Functionally comparable proteins will give rise to the same characteristic to a similar, but not necessarily the same, degree. Typically, comparable proteins give the same characteristics where the quantitative measurement due to one of the comparables is at least 20% of the other; more typically, between 30 to 40%; even more typically, between 50-60%; even more typically between 70 to 80%; even more typically between 90 to 100% of the other.

Heterologous polypeptide: "Heterologous polypeptide" as used herein refers to a polypeptide that is not a naturally occurring polypeptide in a plant cell, e.g., a transgenic *Panicum* plant transformed with and expressing the coding sequence for a nitrogen transporter from a *Zea* plant.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

Inducible Promoter: An "inducible promoter" in the context of the current invention refers to a promoter which is regulated under certain conditions, such as light, chemical concentration, protein concentration, conditions in an organism, cell, or organelle, etc. A typical example of an inducible promoter which can be utilized with the polynucleotides of the present invention is rd29a, the promoter from an *Arabidopsis* gene and which is induced by cold or dehydration (Baker et al. (1994) *Plant Mol. Biol.* 24:701). Examples of environmental conditions that may affect transcription by inducible promoters include anaerobic conditions, elevated temperature and/or the presence of light.

Isolated nucleic acid: "Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

Masterpool: The "master pools" discussed in these experiments are a pool of seeds from five independent transformation events of the same exogenous nucleotide sequence.

Modulation: As used herein, "Modulation" of the level of a compound or constituent refers to the change in the level of the indicated compound or constituent that is observed as a result of expression of, or transcription from, an exogenous nucleic acid in a plant cell. The change in level is measured relative to the corresponding level in control plants.

Misexpression: The term "misexpression" refers to an increase or a decrease in the transcription of a coding region into a complementary RNA sequence as compared to the wild-type. This term also encompasses expression of a gene or coding region for a different time period as compared to the wild-type and/or from a non-natural location within the plant genome.

Nucleic acid and polynucleotide: "Nucleic acid" and "polynucleotide" are used interchangeably herein, and refer to both RNA and DNA, including cDNA, genomic DNA, synthetic DNA, and DNA or RNA containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

Operably linked: As used herein, "operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

Percentage of sequence identity: "Percentage of sequence identity," as used herein, is determined by comparing two optimally aligned sequences over a comparison window defined by the length of the longest sequence, where the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman (1981) *Add. APL. Math.* 2:482, by the homology alignment algorithm of Needleman and Wunsch (1970) *J. Mol. Biol.* 48:443), by the search for similarity method of Pearson and Lipman (1988) *Proc. Natl. Acad. Sci.* (*USA*) 85: 2444, by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BESTFIT are preferably employed to determine their optimal alignment. Typically, the default values of 5.00 for gap weight and 0.30 for gap weight length are used. The term "substantial sequence identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

Query nucleic acid and amino acid sequences were searched against subject nucleic acid or amino acid sequences residing in public or proprietary databases. Such searches were done using the Washington University Basic Local Alignment Search Tool Version 1.83 (WU-Blast2) program. The WU-Blast2 program is available on the internet from Washington University. A WU-Blast2 service for *Arabidopsis* can also be found on the internet. Typically the following parameters of WU-Blast2 were used: Filter options were set to "default," Output format was set to "gapped alignments," the Comparison Matrix was set to "BLOSUM62," Cutoff Score (S value) was set to "default," the Expect (E threshold) was set to "default," the Number of best alignments to show was set to "100," and the "Sort output" option was set to sort the output by "pvalue."

Plant Promoter: A "plant promoter" is a promoter capable of initiating transcription in plant cells and can drive or facilitate transcription of a nucleotide sequence or fragment thereof of the instant invention. Such promoters need not be of plant origin. For example, promoters derived from plant viruses, such as the CaMV35S promoter or from *Agrobacterium tumefaciens*, such as the T-DNA promoters, can be plant promoters. A typical example of a plant promoter of plant origin is the maize ubiquitin-1 (ubi-1) promoter known to those of skill.

Polypeptide: "Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

Progeny: As used herein, "progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

Regulatory region: As used herein, "regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell*, 1:977-984 (1989).

Specific Promoter: In the context of the current invention, "specific promoters" refers to promoters that have a high preference for being active in a specific tissue or cell and/or at a specific time during development of an organism. By "high preference" is meant at least a 3-fold, preferably 5-fold, more preferably at least 10-fold still more preferably at least a 20-fold, 50-fold or 100-fold increase in transcription in the desired tissue over the transcription in any other tissue. Typical examples of temporal and/or tissue specific promoters of plant origin that can be used with the polynucleotides of the present invention, are: SH-EP from *Vigna mungo* and EP-C1 from *Phaseolus vulgaris* (Yamauchi et al. (1996) *Plant Mol Biol.* 30:321-9); RCc2 and RCc3, promoters that direct root-specific gene transcription in rice (Xu et al. (1995) *Plant Mol. Biol.* 27:237) and TobRB27, a root-specific promoter from tobacco (Yamamoto et al. (1991) *Plant Cell* 3:371).

Stringency: "Stringency" as used herein is a function of probe length, probe composition (G+C content), salt concentration, organic solvent concentration and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m$-5° C. to $T_m$-10° C. Medium or moderate stringency conditions are those providing $T_m$-20° C. to $T_m$-29° C. Low stringency conditions are those providing a condition of $T_m$-40° C. to $T_m$-48° C. The relationship of hybridization conditions to $T_m$ (in ° C.) is expressed in the mathematical equation $$T_m = 81.5 - 16.6(\log_{10}[Na^+]) + 0.41(\% \ G+C) - (600/N) \quad (1)$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m = 81.5 + 16.6 \log \{[Na^+]/(1+0.7[Na^+])\} + 0.41(\% \ G+C) - 500/L 0.63(\% \ \text{formamide}) \quad (2)$$

where L is the length of the probe in the hybrid (P. Tijessen, "Hybridization with Nucleic Acid Probes" In Laboratory Techniques in Biochemistry and Molecular Biology, P. C. vand der Vliet, ed., c. 1993 by Elsevier, Amsterdam.) The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used (Bonner et al., (1973) *J. Mol. Biol.* 81:123), stringency conditions can be adjusted to favor detection of identical genes or related family members.

Equation (2) is derived assuming equilibrium. Therefore, hybridizations according to the present invention are most preferably performed under conditions of probe excess and for sufficient time to achieve equilibrium. The time required to reach equilibrium can be shortened by using a hybridization buffer that includes a hybridization accelerator such as dextran sulfate or another high volume polymer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

Superpool: As used in the context of the current invention, a "superpool" refers to a mixture of seed from 100 different "master pools." The master pools are of 5 different events with the same exogenous nucleotide sequence transformed into them. Thus, while the superpool contains an equal amount of seed from 500 different events, it only represents 100 transgenic plants with a distinct exogenous nucleotide sequence transformed into them.

$T_0$: As used in the current application, the term "$T_0$" refers to the whole plant, explant or callus tissue inoculated with the transformation medium.

$T_1$: As used in the current application, the term $T_1$ refers to either the progeny of the $T_0$ plant, in the case of whole-plant transformation, or the regenerated seedling in the case of explant or callous tissue transformation.

$T_2$: As used in the current application, the term $T_2$ refers to the progeny of the $T_1$ plant. $T_2$ progeny are the result of self-fertilization or cross pollination of a $T_1$ plant.

$T_3$: As used in the current application, the term $T_3$ refers to second generation progeny of the plant that is the direct result of a transformation experiment. $T_3$ progeny are the result of self-fertilization or cross pollination of a $T_2$ plant.

Up-regulation: "Up-regulation" refers to regulation that increases the level of an expression product (mRNA, polypeptide, or both) relative to basal or native states.

Vector: "Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

2. Important Characteristics of the Polynucleotides of the Invention

The genes and polynucleotides of the present invention are of interest because when they are misexpressed (i.e. when expressed at a non-natural location or in an increased or decreased amount) they produce plants with improved low temperature, chilling or cold tolerance as discussed below and as evidenced by the results of various experiments. These traits can be used to exploit or maximize plant products. For example, the genes and polynucleotides of the present invention are used to increase the expression of genes that render the plant more tolerant to low temperature, chilling or cold conditions. As a consequence, such transgenic plants do better and grow faster under low temperature, chilling or cold conditions, leading to reduced costs for the farmer and, better yield under low temperatures.

3. The Polynucleotides and Polypeptides of the Invention

The polynucleotides of the invention and the proteins expressed thereby are set forth in the Sequence Listing. Such Sequence Listing consists of functionally comparable proteins.

Functionally comparable proteins are those proteins that have at least one characteristic in common. Such characteristics can include sequence similarity, biochemical activity and phenotypic activity. Typically, the functionally comparable proteins share some sequence similarity. Within this definition homologs, orthologs and analogs are considered to be functionally comparable.

Also, these comparables generally share at least one biochemical and/or phenotypic activity. For example, biochemical activity comparables are proteins that act on the same reactant to give the same product.

Another class of comparables is phenotypic comparables that both give the same physical characteristic, such as increased low temperature, chilling or cold tolerance. Proteins can be considered phenotypic comparables even if the proteins give rise to the same physical characteristic, but to a different degree.

4. Use of the Polynucleotides and Polypeptides to Make Transgenic Plants

To use the sequences of the present invention or a combination of them or parts and/or mutants and/or fusions and/or variants of them, recombinant DNA constructs are prepared which comprise the polynucleotide sequences of the invention inserted into a vector and which are suitable for transformation of plant cells. The construct can be made using standard recombinant DNA techniques (see Sambrook et al., Molecular Cloning: A Laboratory Manual, Second Edition, Cold Spring Harbor Laboratory Press, 1989, New York) and can be introduced to the species of interest by *Agrobacterium*-mediated transformation or by other means of transformation as referenced below.

The vector backbone can be any of those typical in the art such as plasmids, viruses, artificial chromosomes, BACs, YACs and PACs and vectors of the sort described by
(a) BAC: Shizuya et al. (1992) *Proc. Natl. Acad. Sci. USA* 89: 8794-8797; Hamilton et al. (1996) *Proc. Natl. Acad. Sci. USA* 93: 9975-9979;
(b) YAC: Burke et al. (1987) *Science* 236:806-812;
(c) PAC: Sternberg N. et al. (1990) *Proc Natl Acad Sci USA.* January; 87:103-7;
(d) Bacteria-Yeast Shuttle Vectors: Bradshaw et al. (1995) *Nucl Acids Res* 23: 4850-4856;
(e) Lambda Phage Vectors: Replacement Vector, e.g., Frischauf et al. (1983) *J. Mol Biol* 170: 827-842; or Insertion vector, e.g., Huynh et al., In: Glover N M (ed) DNA Cloning: A practical Approach, Vol. 1 Oxford: IRL Press (1985); T-DNA gene fusion vectors: Walden et al. (1990) *Mol Cell Biol* 1: 175-194; and
(g) Plasmid vectors: Sambrook et al., infra.

Typically, the construct comprises a vector containing a sequence of the present invention with any desired transcriptional and/or translational regulatory sequences such as promoters, UTRs, and 3' end termination sequences. Vectors can also include origins of replication, scaffold attachment regions (SARs), markers, homologous sequences, introns, etc. The vector may also comprise a marker gene that confers a selectable phenotype on plant cells. The marker typically encodes biocide resistance, particularly antibiotic resistance, such as resistance to kanamycin, bleomycin, or hygromycin, or herbicide resistance, such as resistance to glyphosate, chlorosulfuron or phosphinotricin.

A plant promoter is used that directs transcription of the gene in all tissues of a regenerated plant and may be a constitutive promoter, such as the Cauliflower Mosaic Virus 35S. Alternatively, the plant promoter directs transcription of a sequence of the invention in a specific tissue (tissue-specific promoters) or is otherwise under more precise environmental or developmental control (inducible promoters). Typically, preferred promoters to use in the present invention are cold inducible promoters. Many cold-inducible genes, including the cis-elements which confer cold induction, have been identified (Shinozaki et al. (2003) *Curr. Opin. Plant Biol.* 6:410). Examples of such cold-inducible genes include RD29A (Yamaguchi-Shinozaki and Shinozaki (1994) *Plant Cell* 6:251) and CBF/DREB1 (Stockinger et al. (1997) *PNAS* 94:1035. Another preferred embodiment of the present invention is to use seedling specific promoters, endosperm specific promoters and leaf specific promoters. Various plant promoters, including constitutive, tissue-specific and inducible, are known to those skilled in the art and can be utilized in the present invention.

Alternatively, misexpression can be accomplished using a two component system, whereby the first component consists of a transgenic plant comprising a transcriptional activator operatively linked to a promoter and the second component consists of a transgenic plant that comprises sequence of the invention operatively linked to the target-binding sequence/region of the transcriptional activator. The two transgenic plants are crossed and the sequence of the invention is expressed in their progeny. In another alternative, the misexpression can be accomplished by having the sequences of the two component system transformed in one transgenic plant line.

Transformation

Nucleotide sequences of the invention are introduced into the genome or the cell of the appropriate host plant by a variety of techniques. These techniques for transforming a wide variety of higher plant species are well known and described in the technical and scientific literature. See, e.g. Weising et al. (1988) *Ann. Rev. Genet.* 22:421; and Christou (1995) *Euphytica*, v. 85, n. 1-3:13-27.

Processes for the transformation of monocotyledonous and dicotyledonous plants are known to the person skilled in the art. A variety of techniques is available for the introduction of DNA into a plant host cell. These techniques include transformation of plant cells by injection, microinjection, electroporation of DNA, PEG, use of biolistics, fusion of cells or protoplasts, and via T-DNA using *Agrobacterium tumefaciens* or *Agrobacterium rhizogenes* or other bacterial hosts, as well as further possibilities.

In addition, a number of non-stable transformation methods that are well known to those skilled in the art may be desirable for the present invention. Such methods include, but are not limited to, transient expression and viral transfection.

Seeds are obtained from the transformed plants and used for testing stability and inheritance. Generally, two or more generations are cultivated to ensure that the phenotypic feature is stably maintained and transmitted.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The nucleic acids of the invention can be used to confer the trait of increased tolerance to low temperature, chilling or cold conditions without reduction in fertility on essentially any plant, including chilling sensitive crop plants such as corn, soybean, rice and cotton.

The nucleotide sequences according to the invention encode appropriate proteins from any organism, in particular from plants, fungi, bacteria or animals.

The process according to the invention can be applied to any plant, preferably higher plants, pertaining to the classes of Angiospermae and Gymnospermae. Plants of the subclasses of the Dicotylodenae and the Monocotyledonae are particularly suitable. Dicotyledonous plants belong to the orders of the Magniolales, Illiciales, Laurales, Piperales Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, Santales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales. Monocotyledonous plants belong to the orders of the Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales. Plants belonging to the class of the Gymnospermae are Pinales, Ginkgoales, Cycadales and Gnetales.

The process is preferably used with plants that are important or interesting for agriculture, horticulture, biomass for bioconversion and/or forestry. Examples are tobacco, oilseed rape, sugar beet, potatoes, tomatoes, cucumbers, peppers, beans, peas, citrus fruits, avocados, peaches, apples, pears, berries, plumbs, melons, eggplants, cotton, soybean, sunflowers, roses, poinsettia, petunia, guayule, cabbages, spinach, alfalfa, artichokes, corn, wheat, rice, rye, barley, grasses such as switch grass or turf grass, millet, hemp, bananas, poplars, eucalyptus trees and conifers.

Homologs Encompassed by the Invention

It is well known in the art that one or more amino acids in a native sequence can be substituted with other amino acid(s), the charge and polarity of which are similar to that of the native amino acid, i.e. a conservative amino acid substitution, resulting in a silent change. Conservative substitutes for an amino acid within the native polypeptide sequence can be selected from other members of the class to which the amino acid belongs. Amino acids can be divided into the following four groups: (1) acidic (negatively charged) amino acids, such as aspartic acid and glutamic acid; (2) basic (positively charged) amino acids, such as arginine, histidine, and lysine; (3) neutral polar amino acids, such as serine, threonine, tyrosine, asparagine, and glutamine; and (4) neutral nonpolar (hydrophobic) amino acids such as glycine, alanine, leucine, isoleucine, valine, proline, phenylalanine, tryptophan, cysteine, and methionine.

In a further aspect of the present invention, nucleic acid molecules of the present invention can comprise sequences that differ from those encoding a protein or fragment thereof selected from the group consisting of SEQ ID NOs: 2-5, 7, 9-18, 20-32, 34-38, 40 and 42-46 due to the fact that the different nucleic acid sequence encodes a protein having one or more conservative amino acid changes.

Polypeptides

Polypeptides described herein include cold tolerance-modulating polypeptides. Cold tolerance-modulating polypeptides can be effective to modulate cold tolerance levels when expressed in a plant or plant cell. Such polypeptides typically contain at least one domain indicative of cold tolerance-modulating polypeptides, as described in more detail herein. Cold tolerance-modulating polypeptides typically have an HMM bit score that is greater than 20, as described in more detail herein. In some embodiments, cold tolerance-modulating polypeptides have greater than 80% identity to SEQ ID NOs: 2, 7, 9, 20, 34, 40, and 42, as described in more detail herein.

In some embodiments, a cold tolerance-modulating polypeptide is truncated at the amino- or carboxy-terminal end of a naturally occurring polypeptide. A truncated polypeptide may retain certain domains of the naturally occurring polypeptide while lacking others. Thus, length variants that are up to 5 amino acids shorter or longer typically exhibit the cold tolerance-modulating activity of a truncated polypeptide. In some embodiments, a truncated polypeptide is a dominant negative polypeptide. SEQ ID NOs 7 and 40 set forth the amino sequences of cold tolerance-modulating polypeptides that are truncated at the 3' end relative to the naturally occurring polypeptides SEQ ID NOs 9 and 34, respectively. Expression in a plant of such a truncated polypeptide confers a difference in the level of cold tolerance in a tissue of the plant as compared to the corresponding level in tissue of a control plant that does not comprise the truncation.

A. Functional Homologs Identified by Reciprocal BLAST

In some embodiments, one or more functional homologs of a reference cold tolerance-modulating polypeptide defined by one or more of the pfam descriptions indicated above are suitable for use as cold tolerance-modulating polypeptides. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a cold tolerance-modulating polypeptide, or by combining domains from the coding sequences for different naturally-occurring cold tolerance-modulating polypeptides ("domain swapping"). The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of cold tolerance-modulating polypeptides. Sequence analysis can involve BLAST, Reciprocal BLAST, or PSI-BLAST analysis of nonredundant databases using a cold tolerance-modulating polypeptide amino acid sequence as the reference sequence. Amino acid sequence is, in some instances, deduced from the nucleotide sequence. Those polypeptides in the database that have greater than 40% sequence identity are candidates for further evaluation for suitability as a cold tolerance-modulating polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in cold tolerance-modulating polypeptides, e.g., conserved functional domains.

Conserved regions can be identified by locating a region within the primary amino acid sequence of a cold tolerance-modulating polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at the Wellcome Trust Sanger Institute and HMMI janelia farm research campus. A description of the information included at the Pfam database is described in Sonnhammer et al., *Nucl. Acids Res.*, 26:320-322 (1998); Sonnhammer et al., *Proteins*, 28:405-420 (1997); and Bateman et al., *Nucl. Acids Res.*, 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Figure 7:
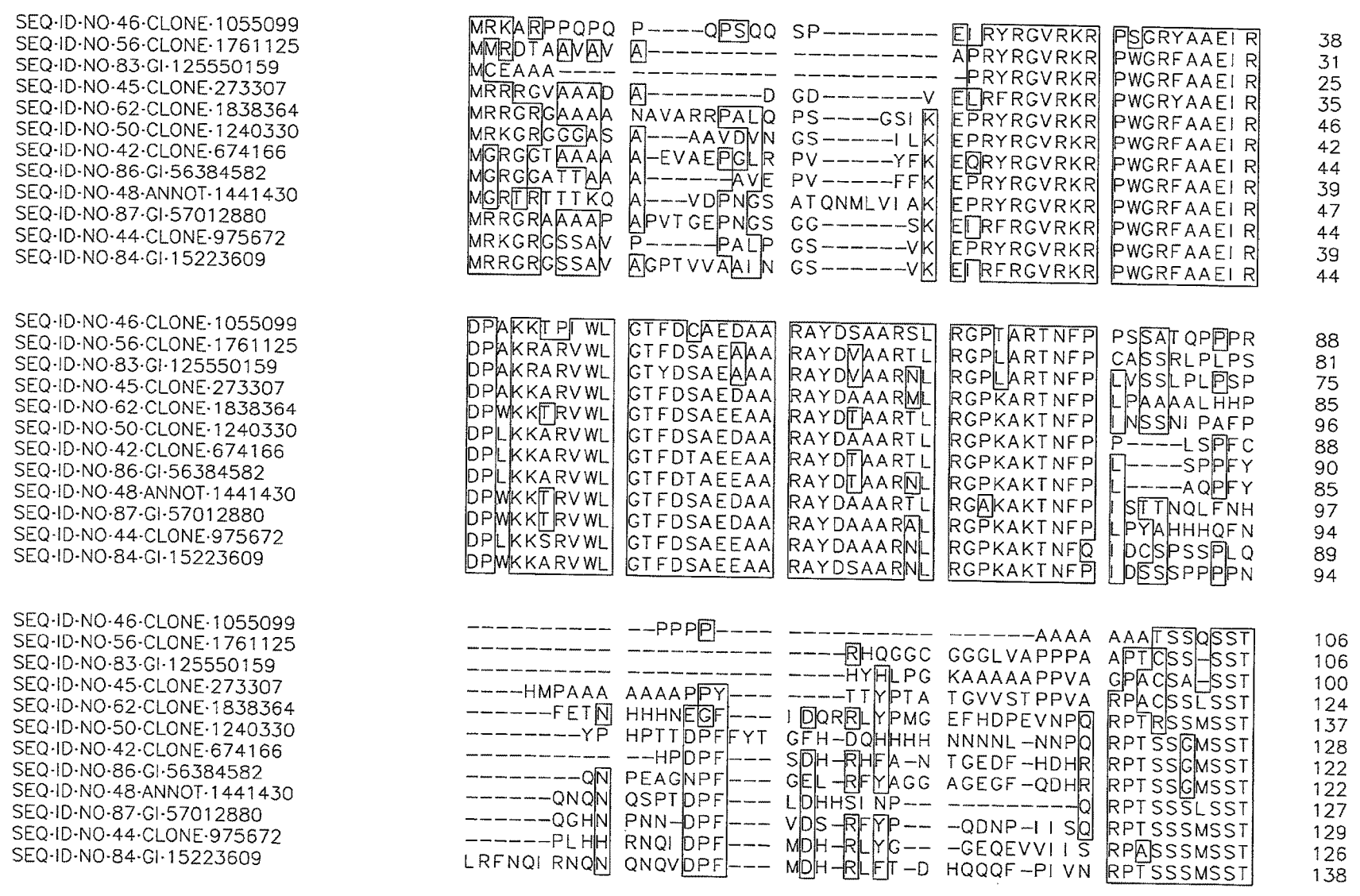

Amino acid sequences of functional homologs of the polypeptide set forth in SEQ ID NOs 2, 7, 9, 20, 34, 40 and 42 are provided in FIGS. 1-7, respectively. In some cases, a functional homolog of SEQ ID NOs 2, 7, 9, 20, 34, 40 and 42 has an amino acid sequence with at least 80% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in the Sequence Listing.

The identification of conserved regions in a cold tolerance-modulating polypeptide facilitates production of variants of cold tolerance-modulating polypeptides. Variants of cold tolerance-modulating polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in any one of FIGS. 1-7. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at all positions marked by dashes, such a polypeptide has a length that is the sum of the amino acid residues in all conserved regions and all dashes.

B. Functional Homologs Identified by HMMER

In some embodiments, useful cold tolerance-modulating polypeptides include those that fit a Hidden Markov Model based on the polypeptides set forth in any one of FIGS. 1-7. A Hidden Markov Model (HMM) is a statistical model of a consensus sequence for a group of functional homologs. See, Durbin et al., *Biological Sequence Analysis: Probabilistic Models of Proteins and Nucleic Acids*, Cambridge University Press, Cambridge, UK (1998). An HMM is generated by the program HMMER 2.3.2 with default program parameters, using the sequences of the group of functional homologs as input. The multiple sequence alignment is generated by ProbCons (Do et al., Genome Res., 15(2):330-40 (2005)) version 1.11 using a set of default parameters: -c, —-consistency REPS of 2; -ir, —-iterative-refinement REPS of 100; -pre, —-pre-training REPS of 0. ProbCons is a public domain software program provided by Stanford University.

The default parameters for building an HMM (hmmbuild) are as follows: the default "architecture prior" (archpri) used by MAP architecture construction is 0.85, and the default cutoff threshold (idlevel) used to determine the effective sequence number is 0.62. HMMER 2.3.2 was released Oct. 3, 2003 under a GNU general public license, and is available from various sources on the World Wide Web such as the HMMER page on the HHMI janelia farm research campus website; the Eddy Lab Home page on the HHMI janelia farm research campus website; and HMMER 2.3.2 download available on the Fish & Richardson website. Hmmbuild outputs the model as a text file.

The HMM for a group of functional homologs can be used to determine the likelihood that a candidate cold tolerance-modulating polypeptide sequence is a better fit to that particular HMM than to a null HMM generated using a group of sequences that are not structurally or functionally related. The likelihood that a subject polypeptide sequence is a better fit to an HMM than to a null HMM is indicated by the HMM bit score, a number generated when the candidate sequence is fitted to the HMM profile using the HMMER hmmsearch program. The following default parameters are used when running hmmsearch: the default E-value cutoff (E) is 10.0, the default bit score cutoff (T) is negative infinity, the default number of sequences in a database (Z) is the real number of sequences in the database, the default E-value cutoff for the per-domain ranked hit list (domE) is infinity, and the default bit score cutoff for the per-domain ranked hit list (domT) is negative infinity. A high HMM bit score indicates a greater likelihood that the subject sequence carries out one or more of the biochemical or physiological function(s) of the polypeptides used to generate the HMM. A high HMM bit score is at least 20, and often is higher.

The cold tolerance-modulating polypeptides discussed below fit the indicated HMM with an HMM bit score greater than 20 (e.g., greater than 30, 40, 50, 60, 70, 80, 90, 100, 200, 300, 400, or 500). In some embodiments, the HMM bit score of a cold tolerance-modulating polypeptide discussed below is about 50%, 60%, 70%, 80%, 90%, or 95% of the HMM bit score of a functional homolog provided in one of Table 7. In some embodiments, a cold tolerance-modulating polypeptide discussed below fits the indicated HMM with an HMM bit score greater than 20, and has a domain indicative of an cold tolerance-modulating polypeptide. In some embodiments, a cold tolerance-modulating polypeptide discussed below fits the indicated HMM with an HMM bit score greater than 20, and has 80% or greater sequence identity (e.g., 75%, 80%, 85%, 90%, 95%, or 100% sequence identity) to an amino acid sequence shown in any one of FIGS. 1-7.

Polypeptides are shown in Table 7 that have HMM bit scores greater than 20 when fitted to an HMM generated from the amino acid sequences set forth in FIGS. 1-7, respectively.

In another aspect, biologically functional equivalents of the proteins or fragments thereof of the present invention can have about 10 or fewer conservative amino acid changes, more preferably about 7 or fewer conservative amino acid changes and most preferably about 5 or fewer conservative amino acid changes. In a preferred embodiment, the protein has between about 5 and about 500 conservative changes, more preferably between about 10 and about 300 conservative changes, even more preferably between about 25 and about 150 conservative changes, and most preferably between about 5 and about 25 conservative changes or between 1 and about 5 conservative changes.

Inhibition of Expression of a Cold Tolerance-Modulating Polypeptide

Polynucleotides and recombinant constructs described herein can be used to inhibit expression of a cold tolerance-modulating polypeptide in a plant species of interest. See, e.g., Matzke and Birchler, *Nature Reviews Genetics* 6:24-35 (2005); Akashi et al., *Nature Reviews Mol. Cell Biology* 6:413-422 (2005); Mittal, *Nature Reviews Genetics* 5:355-365 (2004); Dorsett and Tuschl, *Nature Reviews Drug Discovery* 3: 318-329 (2004); and *Nature Reviews RNA interference collection*, October 2005 at nature.com/reviews/focus/mai. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Antisense technology is one well-known method. In this method, a nucleic acid segment from a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid segment need not be the entire sequence of the gene to be repressed, but typically will be substantially complementary to at least a portion of the sense strand of the gene to be repressed. Generally, higher homology can be used to compensate for the use of a shorter sequence. Typically, a sequence of at least 30 nucleotides is used, e.g., at least 40, 50, 80, 100, 200, 500 nucleotides or more.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al., *Proc. Natl. Acad. Sci. USA*, 92(13):6175-6179 (1995); de Feyter and Gaudron, Methods in Molecular Biology, Vol. 74, Chapter 43, "Expressing Ribozymes in Plants", Edited by Turner, P. C., Humana Press Inc., Totowa, N.J. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence of a cold tolerance-modulating polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand of the coding sequence of the cold tolerance-modulating polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region of an mRNA encoding a cold tolerance-modulating polypeptide, and the other strand of the stem portion of the double stranded RNA comprises a sequence that is similar or identical to the sequence that is complementary to the 3' or 5' untranslated region, respectively, of the mRNA encoding the cold tolerance-modulating polypeptide. In other embodiments, one strand of the stem portion of a double stranded RNA comprises a sequence that is similar or identical to the sequence of an intron in the pre-mRNA encoding a cold tolerance-modulating polypeptide, and the other strand of the stem portion comprises a sequence that is similar or identical to the sequence that is complementary to the sequence of the intron in the pre-mRNA. The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron. A double stranded RNA can have zero, one, two, three, four, five, six, seven, eight, nine, ten, or more stem-loop structures. A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

Constructs containing regulatory regions operably linked to nucleic acid molecules in sense orientation can also be used to inhibit the expression of a gene. The transcription product can be similar or identical to the sense coding sequence of a cold tolerance-modulating polypeptide. The transcription product can also be unpolyadenylated, lack a 5' cap structure, or contain an unsplicable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding a cold tolerance-modulating polypeptide. In some embodiments, the sense or antisense sequence is identical or complementary to a sequence of the regulatory region that drives transcription of the gene encoding a cold tolerance-modulating polypeptide. In each case, the sense sequence is the sequence that is complementary to the antisense sequence.

The sense and antisense sequences can be any length greater than about 12 nucleotides (e.g., 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence encoding a cold tolerance-modulating polypeptide described herein. The sense sequence complementary to the antisense sequence can be a sequence present within the mRNA of the cold tolerance-modulating polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have any arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., *Plant Physiol.*, 141: 1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences, or the left and right border-like sequences of the P-DNA, flank or are on either side of the nucleic acid. See, US 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, 1997, *Antisense Nucleic Acid Drug Dev.*, 7:187-195; Hyrup et al., *Bioorgan. Med. Chem.*, 4:5-23 (1996). In addition, the deoxyphosphate backbone can be replaced with, for example, a phosphorothioate or phosphorodithioate backbone, a phosphoroamidite, or an alkyl phosphotriester backbone.

In some embodiments, nucleic acid based inhibition of gene expression does not require transcription of the nucleic acid.

IDENTIFICATION OF USEFUL NUCLEOTIDE SEQUENCES

The nucleotide sequences of the invention were identified by use of a variety of screens under low temperature, chilling or cold conditions recognized by those skilled in the art to be predictive of nucleotide sequences that provide plants with improved tolerance to low temperature, chilling or cold conditions. One or more of the following screens were, therefore, utilized to identify the nucleotide (and amino acid) sequences of the invention.

1. Cold Germination Superpool Screen 0.5× MS Media is prepared and the pH adjusted to 5.7 using 10N KOH. Seven g/l of Phytagar is added prior to autoclaving.

Individual superpool and control seeds are sterilized in a 30% bleach solution for 5 minutes. Seeds are then rinsed repeatedly with sterile water to eliminate all bleach solution. Seeds are sown on media plates in a monolayer, including wild-type and positive controls. Plates are wrapped in aluminum foil and placed at 4° C. for three days to stratify. At the end of this time, the foil is removed and plates are transferred to an 8° C. Percival with fluorescent bulbs emitting a light intensity of ~100 µEinsteins.

Approximately 10 days after transfer to 8° C., seeds are examined microscopically to identify those that have germinated (defined as cotyledon emergence and expansion). Seedlings with more expanded and greener cotyledons compared to the wild-type population in the same plate are collected. DNA from these candidate seedlings is extracted and the transgene amplified using PCR. The PCR product is sequenced to determine the identity of the transgene and consequently the ME line from which the candidate is derived.

2. Cold Germination Assay

Independent transformation events of the ME lines identified in the Superpool screen are assayed in two generations to validate the cold tolerance phenotype. Media is prepared and seeds sterilized as described above for the Cold Germination Superpool Screen.

Two events with 27 seeds from each event are sown in a latin square layout on square Petri dishes together with 27 wild-type control seeds. Following 3 days of stratification at 4° C., plates are transferred to 8° C. in the light and grown as above. Approximately 10 days after transfer, plates are imaged on a flat-bed scanner. Plate images are analyzed using WinRhizo software to determine the area of each seedling. Subsequently, plates are transferred to 22° C. for several days of growth and then sprayed with Finale™ to identify transgenic seedlings. Seedling area and transgene status data are entered into a database. Events are considered positive for the low temperature, chilling or cold-tolerant phenotype if the seedling area of the transgenic plants within an event is significantly different by a one-tailed student's t-test than the seedling area of the pooled non-transgenic seedlings across all the events for that ME line.

References

Levitt (1980) Chilling injury and resistance. In T T Kozlowsky, ed, Chilling, Freezing, and High Temperature Stresses: Responses of Plant to Environmental Stresses, Vol 1. Academic Press, New York, pp 23-64.

Graham and Patterson (1982) *Annu Rev Plant Physiol* 33: 347-372.

Guy (1990) *Annu Rev Plant Physiol Plant Mol Biol* 41: 187-223.

Nishida and Murata (1996) *Annu Rev Plant Physiol Plant Mol Biol* 47: 541-568.

EXAMPLES

Summary

| | |
|---|---|
| Trait area(s) | Cold |
| Sub-trait Area | Cold - germination and vigor |
| Coding sequence | 1. Vector Construct Sequence Identifier 14298746 |
| Species of Origin | corresponding to Clone 30087 - ME01451; encodes a 164 amino acid protein of unknown function from *Arabidopsis*. |
| | 2. Vector Construct Sequence Identifier 14298770 corresponding to Clone 30469 - ME02779 encodes a 78 amino acid protein with identity to the N-terminal half of an *Arabidopsis* class I nonsymbiotic hemoglobin. |

-continued

|  |  |
|---|---|
|  | 3. Vector Construct Sequence Identifier 14301197 corresponding to Clone 271922 - ME03944 encodes a 92 amino acid 60s ribosomal protein L37a protein from *Arabidopsis*.<br>4. Vector Construct Sequence Identifier 14296769 corresponding to Clone 2403 - ME05304 encodes a truncated ubiquitin-like protein from *Arabidopsis*.<br>5. Vector Construct Sequence Identifier 14301334 corresponding to Clone 674166 - ME03186 from *Glycine max* encodes a 210 amino acid protein with similarity to the ethylene-responsive element binding protein (ERF) family. |
| Species in which Clone was Tested | *Arabidopsis thaliana* |
| Promoter | 35S, a strong constitutive promoter |
| Insert DNA type | cDNA |

Introduction

How plants respond to stress in the environment dictates their ability to survive and reproduce. There are probably many mechanisms by which plants regulate the temperatures under which they will germinate (Lu and Hills, 2003). Finding genes that result in stress tolerance when over-expressed has proved difficult because of the large amount of cross-talk and regulation among gene families.

Over-expression of these genes could be useful for increasing low temperature, chilling or cold tolerance in crops. If successfully deployed, low temperature, chilling or cold tolerant genes could enhance crop productivity following intermittent or sustained low temperature, chilling or cold periods that occur early in the growing season when seeds are germinating. Assuming conservation of processes controlling vegetative physiology across species, these genes and proteins are likely to function similarly in other species.

Assays described here focus on low temperature, chilling or cold tolerance in germinating seedlings. The ability to germinate and grow under low temperature, chilling or cold, and wet conditions would allow a longer growing season and mitigate damage caused by unexpected low temperature, chilling or cold periods. If this trait is recapitulated in crops overexpressing these genes, the result could be very valuable in agriculture in many crops and environments and make a significant contribution to sustainable farming. Furthermore, low temperature, chilling or cold tolerance may be modulated by expressing these clones under the control of a low temperature, chilling or cold inducible promoter.

Materials and Methods

Generation and Phenotypic Evaluation of T1 Events.

Wild-type *Arabidopsis* Wassilewskija (Ws) plants were transformed with a Ti plasmid containing different Clones in the sense orientation relative to the 35S promoter, by *Agrobacterium*-Mediated Transformation. The Ti plasmid vector used for this construct, CRS 338, contains the Ceres-constructed, plant selectable marker gene phosphinothricin acetyltransferase (PAT) which confers herbicide resistance to transformed plants. Ten independent transformation events were selected and evaluated for their qualitative phenotype in the $T_1$ generation by selecting Finale™-resistant plants and observing their physical characteristics.

Screening for Low Temperature, Chilling or Cold Germination Candidates.

All superpools (n=91) were screened for cold germination by plating seeds on MS media and germinating them at 8° C. Candidates were chosen based on a comparison to wild-type controls. The candidates were processed as follows.

Process Flow:

Procedure for 1) identifying the candidate from a cold germination superpool screen, 2) confirming the phenotype in the second and third generations and 3) determining the lack of significant negative phenotypes.

1. Superpools screened for Cold Germination
2. Cold tolerant candidates identified
3. Independent events tested for Cold Germination and Finale™ resistance in two generations
4. For all candidates, at least 2 Events were significantly tolerant to cold in 2 generations
5. Tested positive events for negative phenotypes Growth Conditions and Planting Schema Under Cold Germination.

Up to five independent T2 transformation events were evaluated for each line under cold conditions. Subsequently, T3 generation seeds for up to five events were evaluated under cold germination conditions. In these assays, the seedling area (a measure of timing of germination and cotyledon expansion) for transgenic plants within an event was compared to the seedling area for non-transgenic segregants pooled across all plates for that line.

Preparation of plates and seed sowing were performed by sowing seeds on 0.5× MS plates and grown at 8° C. Plates were scored on day 10, and analyzed for cotyledon area. After the Cold Germination Assay was complete, plates were transferred to 22° C. and insert-containing plants were identified by spraying the seedlings with Finale™. Transgenic plants are Finale™ resistant.

Screening for Negative Phenotypes.

The events described in this report were analyzed for negative phenotypes. None of the events had (a) reduction in germination of more than 25%, (b) delay in onset of flowering more than 4 days in 50% or more of plants relative to in-flat control, (c) reduction in fertility as evidenced by visual observation of reduction in silique fill or silique number, (d) a reduction in seed dry weight by 25% or more relative to control, or (e) more than 30% reduction in rosette diameter at maturity.

RESULTS

Example 1: ME01451

TABLE 1-1

| Construct | Event/Generation | Plant Stage | Assay | Result |
|---|---|---|---|---|
| 35S::30087 | -01/$T_2$ Finale resistant plants | Seedling | Cold Germination | Significant at p ≤.05 |
| 35S::30087 | -05/$T_2$ Finale resistant plants | Seedling | Cold Germination | Significant at p ≤.05 |
| 35S::30087 | -01/$T_3$ Finale resistant plants | Seedling | Cold Germination | Significant at p ≤.05 |
| 35S::30087 | -05/$T_3$ Finale resistant plants | Seedling | Cold Germination | Significant at p ≤.05 |

Ectopic expression of Clone 30087 under the control of the 35S promoter induces the following phenotypes:
  Early germination at 8° C. resulting in larger seedlings after 10 days of growth in the cold.
  Plants from Events-01 and -05 which are heterozygous or homozygous for Clone 30087 do not show any negative phenotypes under long-day conditions.
  The gene corresponding to Clone 30087 is up-regulated in developing seedlings, seeds and siliques and down-regulated in drought, heat and ABA.

Two Events of ME01451 Showed Significant Early Germination Under Cold Conditions in Both Generations.

All five events of ME01451 were sown as described in the Cold Germination Assay in both the $T_2$ and the $T_3$ generations. Two events, -01 and -05, were significant in both generations at p=0.05 using a one-tailed t-test assuming unequal variance (Table 1-2). ME01451 transgenic seedlings were significantly larger than the pooled non-transgenic segregants.

TABLE 1-2

T-test comparison of seedling area between transgenic seedlings and pooled non-transgenic segregants after 10 days at 8° C.

| Line | Events | Transgenic | | | Pooled Non-Transgenics | | | t-test |
|---|---|---|---|---|---|---|---|---|
| | | Avg | SE | N | Avg | SE | N | p-value |
| ME01451 | ME01451-01 | 0.0086 | 0.0005 | 25 | 0.0067 | 0.0006 | 54 | 0.00702 |
| ME01451 | ME01451-01-99 | 0.0106 | 0.0006 | 22 | 0.0079 | 0.0010 | 14 | 0.01374 |
| ME01451 | ME01451-05 | 0.0104 | 0.0006 | 18 | 0.0067 | 0.0006 | 54 | 0.00002 |
| ME01451 | ME01451-05-99 | 0.0125 | 0.0007 | 25 | 0.0079 | 0.0010 | 14 | 0.00035 |

Two Events of ME01451 Show 3:1 and 15:1 Segregation for Finale™ Resistance.

Events -01 and -05 segregated 15:1 and 3:1 (R:S), respectively, for Finale™ resistance in the $T_2$ generation (data not shown).

Qualitative Analysis of the $T_1$ Plants:

The physical appearance of all ten $T_1$ plants was identical to the controls.

Qualitative and Quantitative Analysis of the $T_2$ Plants:

Events -01 and -05 of ME01451 exhibited no statistically relevant negative phenotypes.
  Germination
    No detectable reduction in germination rate.
  General morphology/architecture
    Plants appeared wild-type in all instances.
  Days to flowering
    No observable or statistical differences between experimentals and controls.
  Rosette area 7 days post-bolting
    No observable or statistical differences between experimentals and controls.
  Fertility (silique number and seed fill)
    No observable or statistical differences between experimentals and controls Example 2: ME02779

TABLE 2-1

| Construct | Event/Generation | Plant Stage | Assay | Result |
|---|---|---|---|---|
| 35S::30469 | -01/$T_2$ Finale resistant plants | Seedling | Cold Germination | Significant at p ≤.05 |
| 35S::30469 | -03/$T_2$ Finale resistant plants | Seedling | Cold Germination | Significant at p ≤.05 |
| 35S::30469 | -01/$T_3$ Finale resistant plants | Seedling | Cold Germination | Significant at p ≤.05 |
| 35S::30469 | -03/$T_3$ Finale resistant plants | Seedling | Cold Germination | Significant at p ≤.05 |

Ectopic expression of Clone 30469 under the control of the 35S promoter induces the following phenotypes:
  Early germination at 8° C. resulting in larger seedlings after 10 days at 8° C.
  Plants from Events -01 and -03 which are heterozygous or homozygous for Clone 30469 do not show any negative phenotypes under long-day conditions.
  The gene corresponding to Clone 30469 is down-regulated in ABA, heat, and germinating seeds and up-regulated in high nitrogen and most cold and drought treatments.

Clone 30469 encodes a class I nonsymbiotic hemoglobin. These proteins can play a role in acclimation to hypoxic conditions, possibly explaining the cold tolerance phenotype (Hunt et al., 2001). Clone 30469 is a splice variant of a gene that encodes a longer protein.

Two Events of ME02779 Showed Significant Early Germination Under Cold Conditions in Both Generations.

Five events of ME02779 were sown as described in the Cold Germination Assay in both the $T_2$ and the $T_3$ generations. Two events, -01 and -03 were significant in both generations at p=0.05 using a one-tailed t-test assuming unequal variance (Table 2-2). ME02779 transgenic seedlings were significantly larger than the pooled non-transgenic segregants.

TABLE 2-2

T-test comparison of seedling area between transgenic seedlings and pooled non-transgenic segregants after 10 days at 8° C.

| Line | Events | Transgenic | | | Pooled Non-Transgenics | | | t-test |
|---|---|---|---|---|---|---|---|---|
| | | Avg | SE | N | Avg | SE | N | p-value |
| ME02779 | ME02779-01 | 0.0077 | 0.0007 | 12 | 0.0040 | 0.0014 | 3 | 0.01738 |
| ME02779 | ME02779-01-99 | 0.0051 | 0.0005 | 21 | 0.0034 | 0.0002 | 29 | 0.00077 |
| ME02779 | ME02779-03 | 0.0111 | 0.0007 | 19 | 0.0085 | 0.0007 | 40 | 0.00433 |
| ME02779 | ME02779-03-99 | 0.0052 | 0.0006 | 20 | 0.0034 | 0.0002 | 29 | 0.00293 |

Two Events of ME02779 Show 3:1 Segregation for Finale™ Resistance.

Events -01 and -03 segregated 3:1 (R:S) for Finale™ resistance in the $T_2$ generation (data not shown).

Qualitative Analysis of the $T_1$ Plants:

The physical appearance of nine of the ten $T_1$ plants was identical to the controls except for Event -09, which exhibited small rosettes and reduced fertility.

Qualitative and Quantitative Analysis of the $T_2$ Plants:

Events -01 and -03 of ME02779 exhibited no statistically relevant negative phenotypes.

Germination
  No detectable reduction in germination rate.
General morphology/architecture
  Plants appeared wild-type in all instances.
Days to flowering
  No observable or statistical differences between experimentals and controls.
Rosette area 7 days post-bolting
  No observable or statistical differences between experimentals and controls.
Fertility (silique number and seed fill)
  No observable or statistical differences between experimentals and controls Example 3: ME03944

Ectopic expression of Clone 271922 under the control of the 35S promoter induces the following phenotypes:

Early germination at 8° C. resulting in larger seedlings after 10 days at 8° C.

Plants from Events -02 and -06 which are heterozygous or homozygous for Clone 271922 do not show any negative phenotypes under long-day conditions.

The gene corresponding to Clone 271922 shows little differential regulation in transcription profiling experiments on wildtype.

Clone 271922 encodes a 60s ribosomal protein L37a.

Two Events of ME03944 Showed Significant Early Germination Under Cold Conditions in Both Generations.

Four events of ME03944 were sown as described in the Cold Germination Assay in both the $T_2$ and the $T_3$ generations. Two events, -02 and -06, were significant in both generations at p≤0.05 using a one-tailed t-test assuming unequal variance (Table 3-2). The $T_3$ lines are indicated as -99 which indicates that the seeds are the bulked progeny from several $T_2$ plants. ME03944 transgenic seedlings were significantly larger than the pooled non-transgenic segregants.

TABLE 3-1

| Construct | Event/Generation | Plant Stage | Assay | Result |
|---|---|---|---|---|
| 35S::271922 | -02/$T_2$ Finale resistant plants | Seedling | Cold Germination | Significant at p ≤.05 |
| 35S::271922 | -06/$T_2$ Finale resistant plants | Seedling | Cold Germination | Significant at p ≤.05 |
| 35S::271922 | -02/$T_3$ Finale resistant plants | Seedling | Cold Germination | Significant at p ≤.05 |
| 35S::271922 | -06/$T_3$ Finale resistant plants | Seedling | Cold Germination | Significant at p ≤.05 |

TABLE 3-2

| | | Transgenic | | | Pooled Non-Transgenics | | | t-test |
|---|---|---|---|---|---|---|---|---|
| Line | Events | Avg | SE | N | Avg | SE | N | p-value |
| ME03944 | ME03944-02 | 0.0115 | 0.0004 | 23 | 0.0069 | 0.0006 | 35 | 3.4023E−08 |
| ME03944 | ME03944-02-99 | 0.0070 | 0.0008 | 15 | 0.0051 | 0.0004 | 29 | 0.0173 |
| ME03944 | ME03944-06 | 0.0106 | 0.0006 | 18 | 0.0069 | 0.0006 | 35 | 2.7850E−05 |
| ME03944 | ME03944-06-99 | 0.0077 | 0.0007 | 21 | 0.0051 | 0.0004 | 29 | 0.0011 |

T-test comparison of seedling area between transgenic seedlings and pooled non-transgenic segregants after 10 days at 8° C.

Two Events of ME03944 Show 3:1 Segregation for Finale™ Resistance.

Events -02 and -06 segregated 3:1 (R:S) for Finale™ resistance in the $T_2$ generation (data not shown).

Qualitative Analysis of the $T_1$ Plants:

The physical appearance of five of the six $T_1$ plants was identical to the controls. Event -03 exhibited a small rosette and curled leaves.

Other Characteristics:

Seedlings from ME03944-06 exhibited elongated hypocotyls. This phenotype co-segregated with Finale™ resistance.

Qualitative and Quantitative Analysis of the $T_2$ Plants:

Events -02 and -06 of ME03944 exhibited no statistically relevant negative phenotypes.

Germination
      No detectable reduction in germination rate.
   General morphology/architecture
      Plants appeared wild-type in all instances.
   Days to flowering
      No observable or statistical differences between experimentals and controls.
   Rosette area 7 days post-bolting
      No observable or statistical differences between experimentals and controls.
   Fertility (silique number and seed fill)
      No observable or statistical differences between experimentals and controls

Example 4: ME05304

TABLE 4-1

| Construct | Event/Generation | Plant Stage | Assay | Result |
|---|---|---|---|---|
| 35S::2403 | -01/$T_2$ Finale resistant plants | Seedling | Cold Germination | Significant at p ≤.05 |
| 35S::2403 | -04/$T_2$ Finale resistant plants | Seedling | Cold Germination | Significant at p ≤.05 |
| 35S::2403 | -01/$T_3$ Finale resistant plants | Seedling | Cold Germination | Significant at p ≤.05 |
| 35S::2403 | -04/$T_3$ Finale resistant plants | Seedling | Cold Germination | Significant at p ≤.05 |

Ectopic expression of Clone 2403 under the control of the 35S promoter induces the following phenotypes:

Early germination at 8° C. resulting in larger seedlings after 10 days at 8° C.

Plants from Events -01 and -04 which are heterozygous or homozygous for Clone 2403 do not show any negative phenotypes under long-day conditions.

The gene corresponding to Clone 2403 shows little differential regulation in transcript profiling experiments on wildtype.

Clone 2403 encodes a truncated ubiquitin-like protein.

Two Events of ME05304 Showed Significant Early Germination Under Cold Conditions in Both Generations.

Four events of ME05304 were sown as described in the Cold Germination Assay in both the $T_2$ and the $T_3$ generations. Two events, -01 and -04 were significant in both generations at p≤0.05 using a one-tailed t-test assuming unequal variance (Table 4-2). The $T_3$ lines are indicated as -99 which indicates that the seeds are the bulked progeny from several $T_2$ plants.

TABLE 4-2

T-test comparison of seedling area between transgenic seedlings and pooled non-transgenic segregants after 10 days at 8° C.

| Line | Events | Transgenic Avg | SE | N | Pooled Non-Transgenics Avg | SE | N | t-test p-value |
|---|---|---|---|---|---|---|---|---|
| ME05304 | ME05304-01 | 0.0142 | 0.0009 | 20 | 0.0079 | 0.0006 | 39 | 0.0000 |
| ME05304 | ME05304-01-99 | 0.0061 | 0.0005 | 17 | 0.0049 | 0.0003 | 27 | 0.0213 |
| ME05304 | ME05304-04 | 0.0101 | 0.0007 | 15 | 0.0079 | 0.0006 | 39 | 0.0099 |
| ME05304 | ME05304-04-99 | 0.0067 | 0.0005 | 22 | 0.0049 | 0.0003 | 27 | 0.0014 |

Two Events of ME05304 Show 3:1 Segregation for Finale™ Resistance.

Events -01 and -04 segregated 3:1 (R:S) for Finale™ resistance in the $T_2$ generation (data not shown).

Qualitative Analysis of the $T_1$ Plants:

The physical appearance of seven of the ten $T_1$ plants was identical to the controls. The other three events exhibited the following phenotypes: late flowering (Events -01, -02 and -08), dark green rosette leaves (Events -01 and -08) and shorter petioles (Events -02 and -08). Event -01 did not reproduce the late-flowering phenotype in the $T_2$ generation.

Qualitative and Quantitative Analysis of the $T_2$ Plants:

Events -01 and -04 of ME05304 exhibited no statistically relevant negative phenotypes.

Germination
  No detectable reduction in germination rate.
General morphology/architecture
  Plants appeared wild-type in all instances.
Days to flowering
  No observable or statistical differences between experimentals and controls.
Rosette area 7 days post-bolting
  No observable or statistical differences between experimentals and controls.
Fertility (silique number and seed fill)
  No observable or statistical differences between experimentals and controls.

Example 5: ME03186

TABLE 5-1

| Construct | Event/Generation | Plant Stage | Assay | Result |
|---|---|---|---|---|
| 35S::674166 | -04/$T_3$ Finale resistant plants | Seedling | Cold Germination | Significant at p ≤.05 |
| 35S::674166 | -04/$T_4$ Finale resistant plants | Seedling | Cold Germination | Significant at p ≤.05 |
| 35S::674166 | -05/$T_2$ Finale resistant plants | Seedling | Cold Germination | Significant at p ≤.05 |
| 35S::674166 | -05/$T_3$ Finale resistant plants | Seedling | Cold Germination | Significant at p ≤.05 |

Ectopic expression of Clone 674166 under the control of the 35S promoter results in early germination at 8° C. resulting in larger seedlings after 10 days at 8° C.

Plants from Events -04 and -05 which are hemizygous or homozygous for Clone 674166 do not show any negative phenotypes under long-day conditions.

Two Events of ME03186 Showed Significant Early Germination Under Cold Conditions in Both Generations.

Two events, -04 and -05 were significant in two generations at p≤0.05 using a one-tailed t-test assuming unequal variance (Table 5-2). '-99' signifies that seeds were pooled from several plants.

TABLE 5-2

T-test comparison of seedling area between transgenic seedlings and control non-transgenic segregants after 10 days at 8° C.

| Events | Event-Gen | Transgenic Avg | SE | N | Control Non-Transgenics[a] Avg | SE | N | t-test p-value |
|---|---|---|---|---|---|---|---|---|
| ME03186-04-99[b] | 04-T3 | 0.0045 | 0.0003 | 35 | 0.0030 | 0.0002 | 31 | 1.37E−05 |
| ME03186-04-99 | 04-T3 | 0.0092 | 0.0003 | 48 | 0.0051 | 0.0005 | 12 | 3.72E−10 |
| ME03186-04-99-03 | 04-T4 | 0.0107 | 0.0002 | 70 | 0.0083 | 0.0005 | 34 | 2.72E−05 |
| ME03186-04-99-04 | 04-T4 | 0.0120 | 0.0004 | 62 | 0.0083 | 0.0005 | 34 | 3.61E−08 |
| ME03186-04-99-07 | 04-T4 | 0.0107 | 0.0003 | 69 | 0.0083 | 0.0005 | 34 | 4.91E−05 |
| ME03186-04-99-08 | 04-T4 | 0.0110 | 0.0003 | 69 | 0.0083 | 0.0005 | 34 | 5.53E−06 |
| ME03186-05[b] | 05-T2 | 0.0051 | 0.0005 | 22 | 0.0038 | 0.0005 | 6 | 0.0332 |

TABLE 5-2-continued

T-test comparison of seedling area between transgenic seedlings and control non-transgenic segregants after 10 days at 8° C.

| Events | Event-Gen | Transgenic Avg | SE | N | Control Non-Transgenics[a] Avg | SE | N | t-test p-value |
|---|---|---|---|---|---|---|---|---|
| ME03186-05 | 05-T2 | 0.0067 | 0.0003 | 53 | 0.0054 | 0.0005 | 9 | 0.0106 |
| ME03186-05-04 | 05-T3 | 0.0050 | 0.0003 | 50 | 0.0037 | 0.0003 | 9 | 0.0008 |

[a]Transgenic seedlings were compared to non-transgenic segregants within a seed line except for the T$_4$ generation of Event-04. Since these seed lines were homozygous, they were compared to pooled non-transgenic segregants from another T$_4$ generation event that was grown in the same flat as the T$_4$ generation of Event -04.
[b]These events were sown twice. The first time was to identify ME03186 as a hit. They were repeated the second time with two generations to identify ME03186 as a candidate.

Two Events of ME03186 Show 3:1 Segregation for Finale™ Resistance.

Event -05 segregated 3:1 (R:S) for Finale™ resistance in the T$_2$ generation. T$_2$ generation seed was not available for Event -04. However, the T$_3$ generation seeds that were pooled from several T$_2$ plants segregated approximately 2:1 in a manner consistent with a single insert (see Table 5-2).

Qualitative and Quantitative Analysis of the T$_2$ Plants (Screening for Negative Phenotypes):
Events -04 and -05 of ME03186 exhibited no statistically significant negative phenotypes.
  Germination
    No detectable reduction in germination rate.
  General morphology/architecture
    Plants appeared wild-type in all instances.
  Days to flowering
    No observable or statistical differences between experimentals and controls.
  Rosette area 7 days post-bolting References Hunt et ak, (2001) *Plant Mol Biol* 47: 677-692.
Lu and Hills (2002) *Plant Physiol.* 129:1352-8

Example 6: Clone 1055099 (SEQ ID NO: 46)—ME 24967

In the same manner as Example 5, transgenics made with a construct of 35S—Clone 1055099 were screened for cold tolerance. Clone 1055099 (SEQ ID NO: 46) is a wheat functional homolog of clone 674166 (SEQ ID NO: 42), and showed the following results in the seedling cold tolerance assay.

TABLE 6-1

Cold Germination Assay results for ME24967.

| | p-values | | Avg. Seedling Area | | | Sample No. | | |
|---|---|---|---|---|---|---|---|---|
| Event | Internal[a] | Pooled[b] | Transgenic | Internal | Pooled | Transgenic | Internal | Pooled |
| ME03186-04-99[c] | 0.00224438 | 0.00224438 | 0.0032 | 0.0017 | 0.0017 | 30 | 40 | 40 |
| ME24967-02 | 0.12660455 | 0.45511103 | 0.0053 | 0.0071 | 0.0054 | 29 | 5 | 83 |
| ME24967-03[d] | 0.01488322 | 0.04610112 | 0.0069 | 0.0031 | 0.0054 | 31 | 3 | 83 |
| ME24967-05[d] | 0.08783497 | 3.0406E−08 | 0.0115 | 0.0092 | 0.0054 | 23 | 12 | 83 |
| ME24967-10 | 0.40686041 | 0.25206736 | 0.0049 | 0.0053 | 0.0054 | 28 | 6 | 83 |
| ME24967-11 | 0.19290195 | 0.40123421 | 0.0051 | 0.0038 | 0.0054 | 5 | 25 | 83 |
| ME24967-12 | 0.3021565 | 0.00329335 | 0.0032 | 0.0050 | 0.0054 | 27 | 2 | 83 |
| ME24967-13 | 0.24672812 | 0.31347649 | 0.0060 | 0.0077 | 0.0054 | 23 | 7 | 83 |
| ME24967-14 | 0.17548824 | 0.29369895 | 0.0050 | 0.0032 | 0.0054 | 26 | 5 | 83 |
| ME24967-15 | 0.29278326 | 0.38586196 | 0.0057 | 0.0048 | 0.0054 | 22 | 11 | 83 |
| ME24967-16 | | 0.05451794 | 0.0041 | 0.0018 | 0.0054 | 34 | 1 | 83 |
| ME24967-17 | 0.27484717 | 0.13660585 | 0.0044 | 0.0058 | 0.0054 | 26 | 6 | 83 |

[a]Internal controls are segregating non-transgenic seedlings within an Event.
[b]Pooled controls are all of the segregating non-transgenic seedlings from all of the Events within a line.
[c]ME03186 is a positive control to verify that the experimental conditions were appropriate.
[d]These events show significantly improved seedling area for at least internal or pooled controls.

Example 7: Determination of Functional Homologs by Reciprocal BLAST

A candidate sequence was considered a functional homolog of a reference sequence if the candidate and reference sequences encoded proteins having a similar function and/or activity. A process known as Reciprocal BLAST (Rivera et al., *Proc. Natl. Acad. Sci. USA*, 95:6239-6244 (1998)) was used to identify potential functional homolog sequences from databases consisting of all available public and proprietary peptide sequences, including NR from NCBI and peptide translations from Ceres clones.

Before starting a Reciprocal BLAST process, a specific reference polypeptide was searched against all peptides from its source species using BLAST in order to identify polypeptides having BLAST sequence identity of 80% or greater to the reference polypeptide and an alignment length of 85% or greater along the shorter sequence in the alignment. The reference polypeptide and any of the aforementioned identified polypeptides were designated as a cluster.

The BLASTP version 2.0 program from Washington University at Saint Louis, Mo., USA was used to determine BLAST sequence identity and E-value. The BLASTP version 2.0 program includes the following parameters: 1) an E-value cutoff of 1.0e-5; 2) a word size of 5; and 3) the -postsw option. The BLAST sequence identity was calculated based on the alignment of the first BLAST HSP (High-scoring Segment Pairs) of the identified potential functional homolog sequence with a specific reference polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

The main Reciprocal BLAST process consists of two rounds of BLAST searches; forward search and reverse search. In the forward search step, a reference polypeptide sequence, "polypeptide A," from source species SA was BLASTed against all protein sequences from a species of interest. Top hits were determined using an E-value cutoff of $10^{-5}$ and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID NOs: 2, 7, 9, 20, 34, 40 and 42 are shown in FIGS. 1-7, respectively. The BLAST percent identities and E-values of functional homologs to SEQ ID NOs: 2, 7, 9, 20, 34, 40 and 42 are shown in the Sequence Listing. The BLAST sequence identities and E-values given in the Sequence Listing were taken from the forward search round of the Reciprocal BLAST process.

Example 8: Determination of Functional Homologs by Hidden Markov Models

Hidden Markov Models (HMMs) were generated by the program HMMER 2.3.2. To generate each HMM, the default HMMER 2.3.2 program parameters, configured for glocal alignments, were used.

An HMM was generated using the sequences shown in each of FIGS. 1-7 as input. Additional sequences were input into the model, and the HMM bit scores for the additional sequences are shown in the Sequence Listing. The results indicate that these additional sequences are functional homologs of SEQ ID NOs: 2, 7, 9, 20, 34, 40 and 42, respectively. The bit score results are provided in Table 7.

The invention claimed is:

1. A transgenic plant cell transformed with an exogenous nucleic acid, said exogenous nucleic acid comprising a polynucleotide operably linked to heterologous promoter, said polynucleotide comprising a nucleotide sequence encoding a polypeptide that is 33 amino acids long and comprising an amino acid sequence having 95 percent or greater amino acid sequence identity to the amino acid sequence of SEQ ID NO: 40, wherein a transgenic plant produced from said transgenic plant cell and comprising said transgenic plant cell has an increased level of cold tolerance as compared to the corresponding level in tolerance to cold of a control plant that does not comprise said exogenous nucleic acid.

2. A transgenic plant comprising the transgenic plant cell of claim 1.

3. The transgenic plant of claim 2, wherein said plant is a member of a species selected from the group consisting of *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), and *Pennisetum glaucum* (pearl millet).

4. The transgenic plant of claim 2, wherein said polypeptide consists of the amino acid sequence of SEQ ID NO: 40.

5. A vegetative plant product comprising a transgenic plant tissue from the transgenic plant according to claim 2.

6. The transgenic plant cell of claim 1, wherein said polypeptide comprises an amino acid sequence that has 97 percent or greater amino acid sequence identity to the amino acid sequence of SEQ ID NO:40.

7. The transgenic plant cell of claim 1, wherein said polypeptide consists of the amino acid sequence of SEQ ID NO:40.

8. The transgenic plant of claim 2, wherein said polypeptide comprises an amino acid sequence that has 97 percent or greater amino acid sequence identity to the amino acid sequence of SEQ ID NO:40.

9. A progeny of the transgenic plant of claim 2, wherein the progeny comprises the exogenous nucleic acid.

* * * * *